US012698501B2

(12) United States Patent
Bernstein et al.

(10) Patent No.: US 12,698,501 B2
(45) Date of Patent: Aug. 4, 2026

(54) USP10 TARGETED SELF-DELIVERABLE siRNA COMPOSITIONS AND METHODS FOR PREVENTING OR INHIBITING FIBROSIS AND/OR SCARRING

(71) Applicant: The Research Foundation for the State University of New York, Albany, NY (US)

(72) Inventors: Audrey Bernstein, Fayetteville, NY (US); Alexey Wolfson, Westborough, MA (US); Sean McCauley, Rutland, MA (US)

(73) Assignee: The Research Foundation for the State University of New York, Albany, NY (US)

( * ) Notice: Subject to any disclaimer, the term of this patent is extended or adjusted under 35 U.S.C. 154(b) by 804 days.

(21) Appl. No.: 17/907,826

(22) PCT Filed: Feb. 28, 2021

(86) PCT No.: PCT/US2021/020167
§ 371 (c)(1),
(2) Date: Aug. 29, 2022

(87) PCT Pub. No.: WO2021/174171
PCT Pub. Date: Sep. 2, 2021

(65) Prior Publication Data
US 2023/0122801 A1 Apr. 20, 2023

Related U.S. Application Data

(60) Provisional application No. 62/983,233, filed on Feb. 28, 2020.

(51) Int. Cl.
*C12N 15/113* (2010.01)

(52) U.S. Cl.
CPC ...... *C12N 15/1137* (2013.01); *C12N 2310/14* (2013.01); *C12N 2310/315* (2013.01); *C12N 2310/3515* (2013.01); *C12Y 304/19012* (2013.01)

(58) Field of Classification Search
CPC ............ C12N 15/1137; C12N 2310/14; C12N 2310/315; C12N 2310/343; C12N 2310/321
USPC ..................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 7,595,387 B2 | 9/2009 | Leake et al. | |
| 9,714,424 B1 | 7/2017 | Bernstein et al. | |
| 2003/0119763 A1 | 6/2003 | Wang | |
| 2005/0255487 A1 | 11/2005 | Khvorova et al. | |
| 2011/0081362 A1* | 4/2011 | Elledge ................... | A61P 35/00 |
| | | | 514/249 |
| 2012/0171192 A1 | 7/2012 | Lou et al. | |
| 2021/0147831 A1* | 5/2021 | Zhang ...................... | C12N 9/22 |

FOREIGN PATENT DOCUMENTS

WO 2019210268 10/2019

OTHER PUBLICATIONS

Stephanie R. Gillespie, The deubiquitylase USP10 regulates integrin β1 and β5 and fibrotic wound healing, J Cell Sci. Oct. 15, 2017;130(20):3481-3495, United States.

* cited by examiner

*Primary Examiner* — Jane J Zara
(74) *Attorney, Agent, or Firm* — Peter Fallon

(57) ABSTRACT

The present disclosure provides compositions and methods for using self-deliverable siRNA (sdRNAi) directed against USP-10 for the treatment of various medical conditions, including skin scaring due to trauma wounds and surgery, corneal and retina scaring due to injury and surgery, internal organ scaring due to injury and surgery, heart tissue scaring due to heart attack and surgery, and lung, liver, and kidney fibrosis due to inflammation and injury. In embodiments, compositions including self-deliverable siRNA (sdRNAi) directed against USP-10 are suitable for use in pharmaceutical formulations and treatments resulting in significant less scar formation, and include synthetic nucleic acids such as sense and antisense oligonucleotides.

18 Claims, 57 Drawing Sheets
Specification includes a Sequence Listing.

B     MAP4K4-cy3 sdRNA
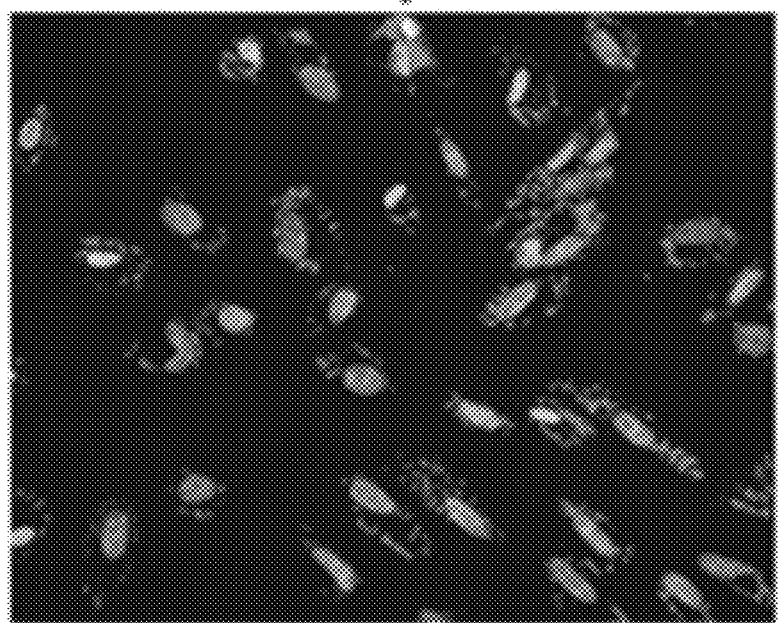
NTC sdRNA
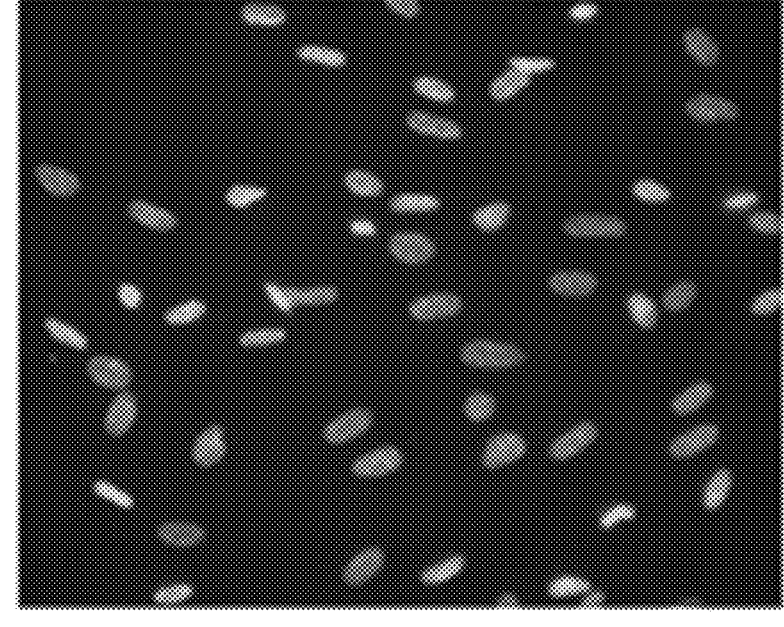
200 μm
FIG. 1B

C

5' P—
3' Chol-TEG—

- 2'-O-Methyl RNA
- 2'-Fluoro RNA
- Phosphorothioate
- 5'-Phosphate
- Cholesterol
- TEG linker

E

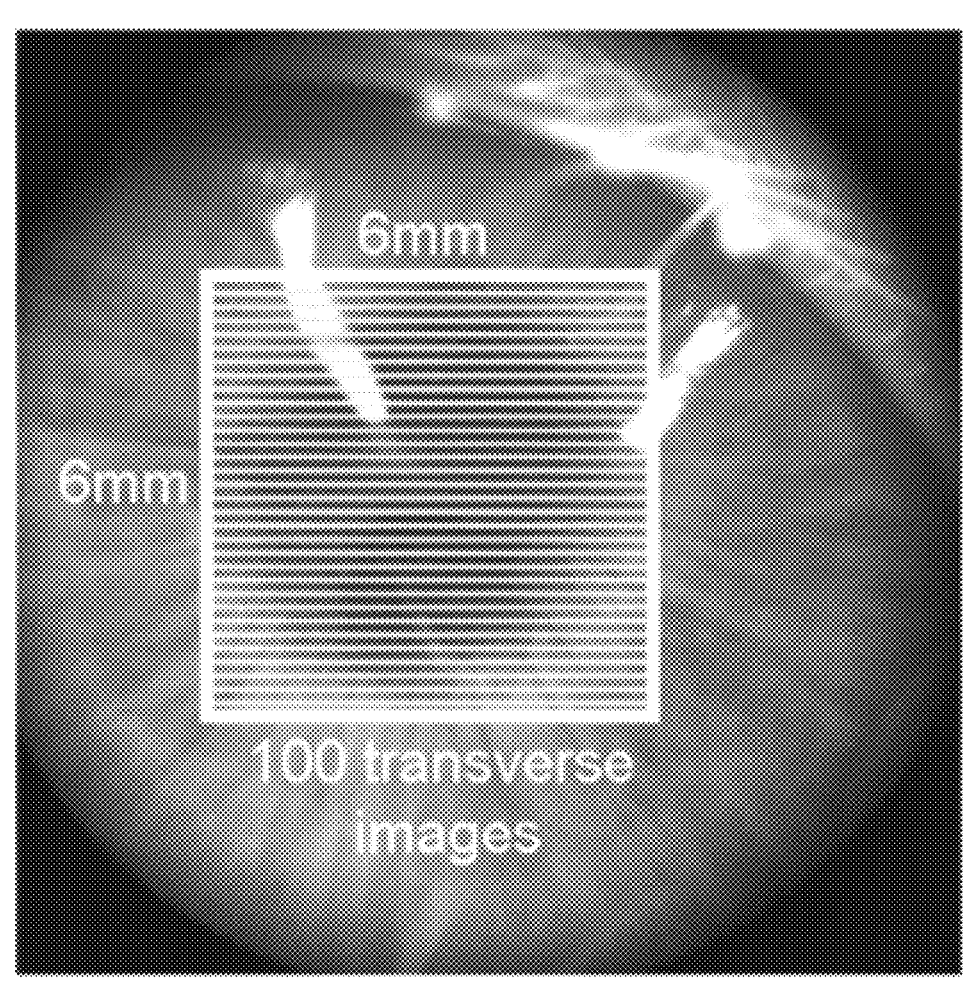
FIG. 2A

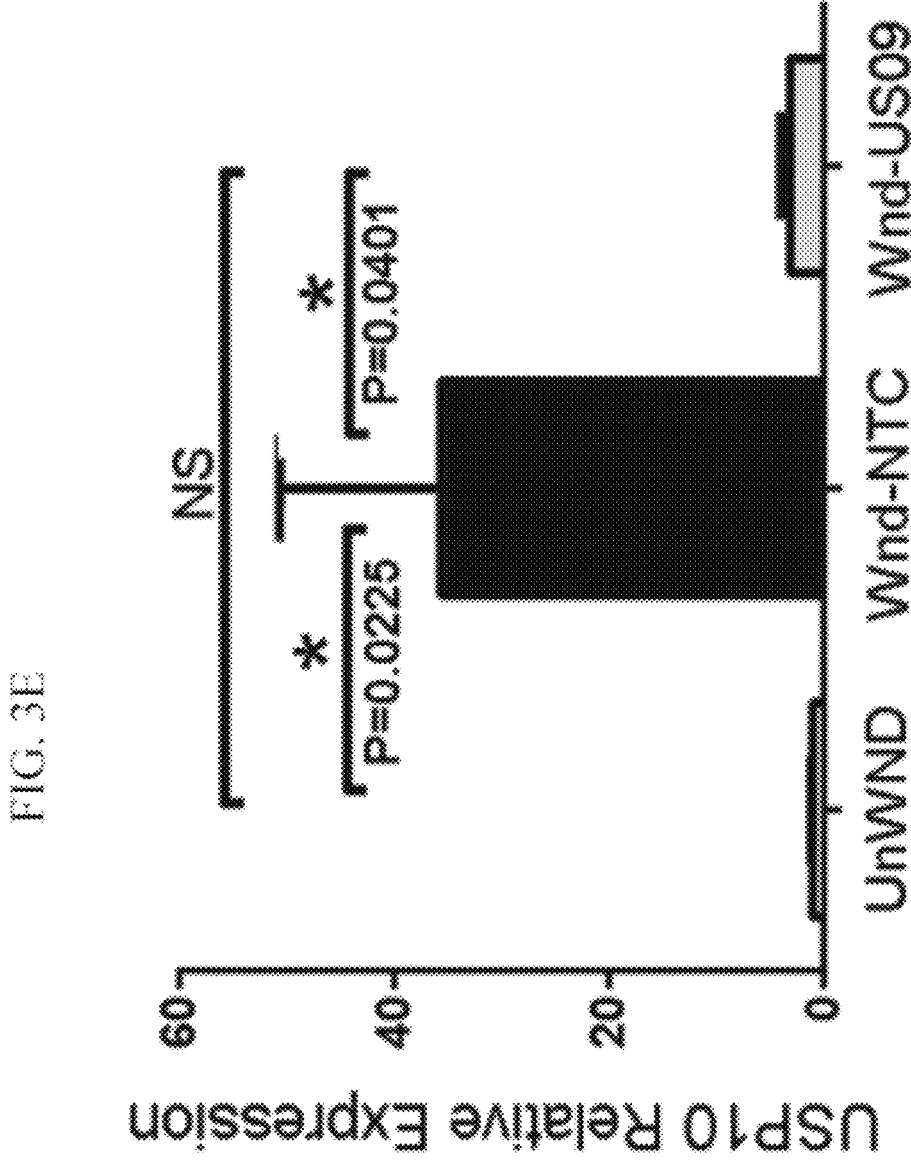
FIG. 3E

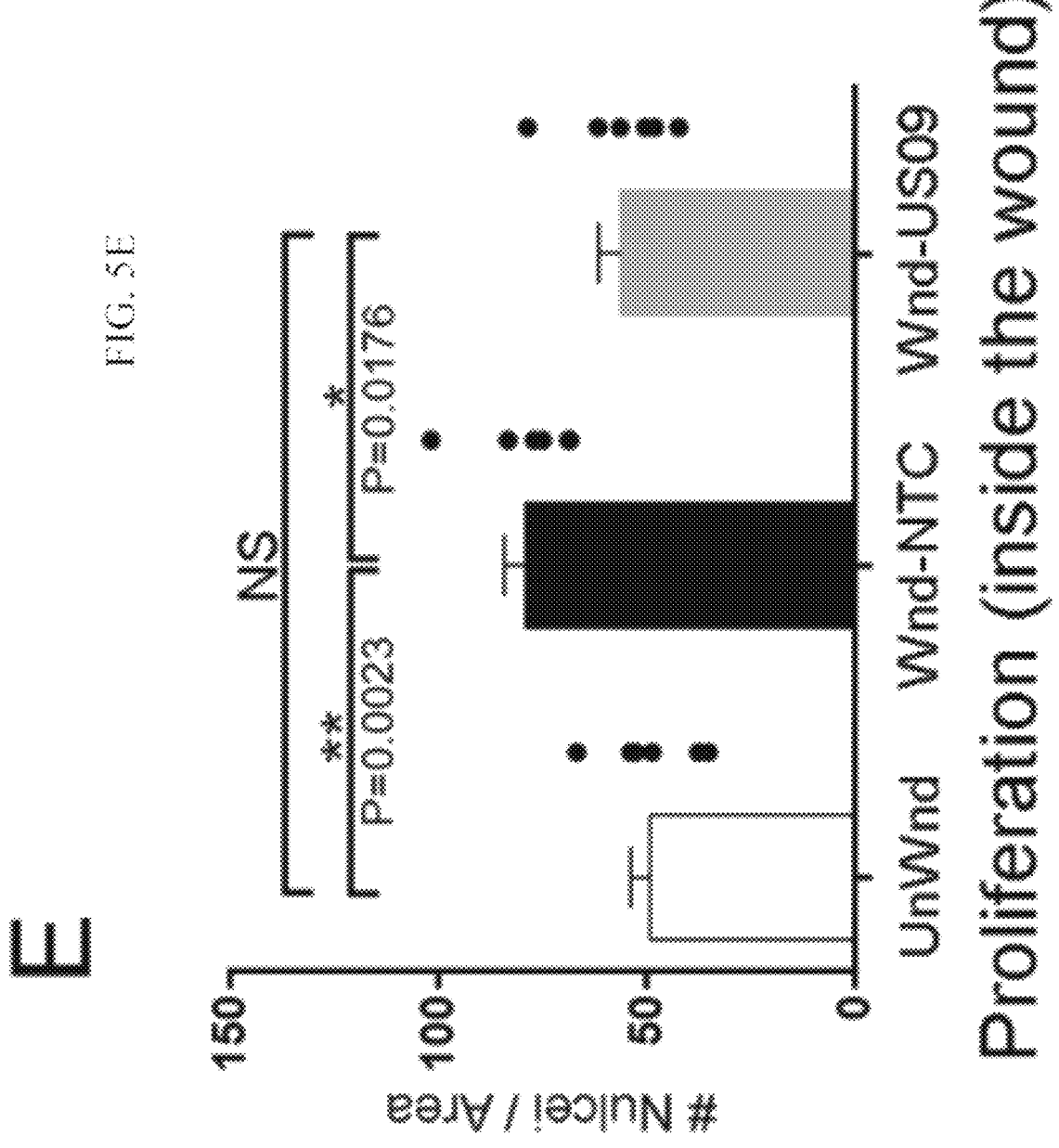

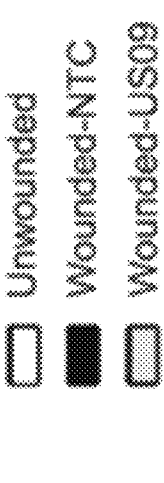
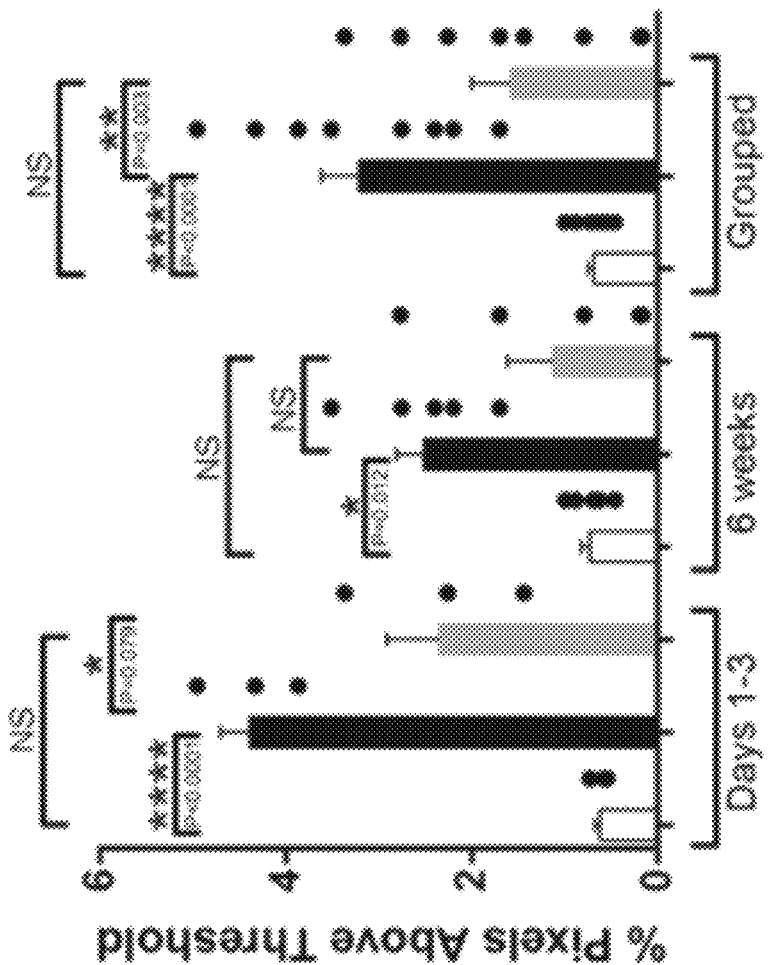
FIG. 6M

| Query | Subject Acc. | Alignme nt length | E value | Bit score | Strands | Tot. mm-matches | Species |
|---|---|---|---|---|---|---|---|
| US99 | XM_002723256.2 | 19 | 1.6 | 38.2 | Plus/Plus | 0 | PREDICTED: Oryctolagus cuniculus ubiquitin specific peptidase 10 (USP10), mRNA |
| US99 | XM_002711567.3 | 15 | 402 | 30.2 | Plus/Minus | 4 | PREDICTED: Oryctolagus cuniculus RPGRIP1 like (RPGRIP1L) |
| US99 | XM_008257302.2 | 15 | 402 | 30.2 | Plus/Minus | 4 | PREDICTED: Oryctolagus cuniculus RPGRIP1 like (RPGRIP1L) |
| US99 | XM_008271266.2 | 15 | 402 | 30.2 | Plus/Plus | 4 | PREDICTED: Oryctolagus cuniculus transmembrane protein 100 (TMEM100) |
| US99 | XM_008271265.2 | 15 | 402 | 30.2 | Plus/Plus | 4 | PREDICTED: Oryctolagus cuniculus transmembrane protein 100 (TMEM100) |
| US99 | XM_008271267.2 | 15 | 402 | 30.2 | Plus/Plus | 4 | PREDICTED: Oryctolagus cuniculus transmembrane protein 100 (TMEM100) |

FIG. 12

| ## | ID | Target Sequence | |
|---|---|---|---|
| 1 | US01 | TAAATGCCACAGAACCTATA | SEQ ID NO: 32 |
| 2 | US02 | TCGGCTGATGAACGAGTTTA | SEQ ID NO: 33 |
| 3 | US03 | GACTATCCTGTGGACTTGGA | SEQ ID NO: 34 |
| 4 | US04 | GACTTGGAGATCAGTAAAGA | SEQ ID NO: 35 |
| 5 | US05 | GGAGTTGCTAATGGACAAAT | SEQ ID NO: 36 |
| 6 | US06 | AAATGCCACAGAACCTATAG | SEQ ID NO: 37 |
| 7 | US07 | GTGGACTTGGAGATCAGTAA | SEQ ID NO: 38 |
| 8 | US08 | CAAGTCCAGCCTGTCGGAAA | SEQ ID NO: 39 |
| 9 | US09 | GCTGTCAGAAGCTGATCAAA | SEQ ID NO: 40 |
| 10 | US10 | TACTTGAGGGATGGCGGTGA | SEQ ID NO: 41 |

FIG. 13

Human USP10 sdRNA sequences. In silico design.

| ID | Target sequence | | Antisense | |
|----|-----------------|---|-----------|---|
| 1 | AUUGCCAUUAAAAGAUUUCA | SEQ ID NO: 42 | UGAAAUCUUUUAAUGGCAAU | SEQ ID NO: 52 |
| 2 | UUAGAGAGAAACUCUUUCUC | SEQ ID NO: 43 | GAGAAAGAGUUUCUCUCUAA | SEQ ID NO: 53 |
| 3 | UUGGUUGAAACAGACUGUUG | SEQ ID NO: 44 | CAACAGUCUGUUUCAACCAA | SEQ ID NO: 54 |
| 4 | ACCAGCAACAACACUUGUAA | SEQ ID NO: 45 | UUACAAGUGUUGUUGCUGGU | SEQ ID NO: 55 |
| 5 | ACUGAAAACCUUGGAGUUGC | SEQ ID NO: 46 | GCAACUCCAAGGUUUUCAGU | SEQ ID NO: 56 |
| 6 | CGGCUAAUGAAUGAGUUCAC | SEQ ID NO: 47 | GUGAACUCAUUCAUUAGCCG | SEQ ID NO: 57 |
| 7 | CCUGACAGUUAACAAGUCAA | SEQ ID NO: 48 | UUGACUUGUUAACUGUCAGG | SEQ ID NO: 58 |
| 8 | UUGGAGAUUUUAGCCCUGAU | SEQ ID NO: 49 | AUCAGGGCUAAAAUCUCCAA | SEQ ID NO: 59 |
| 9 | UCGGUCAAUGAAGAAGAGCA | SEQ ID NO: 50 | UGCUCUUCUUCAUUGACCGA | SEQ ID NO: 60 |
| 10 | UUUAGCCCUGAUUGAAUUCAA | SEQ ID NO: 51 | UUGAAUUCAUCAGGGCUAAA | SEQ ID NO: 61 |

FIG. 14

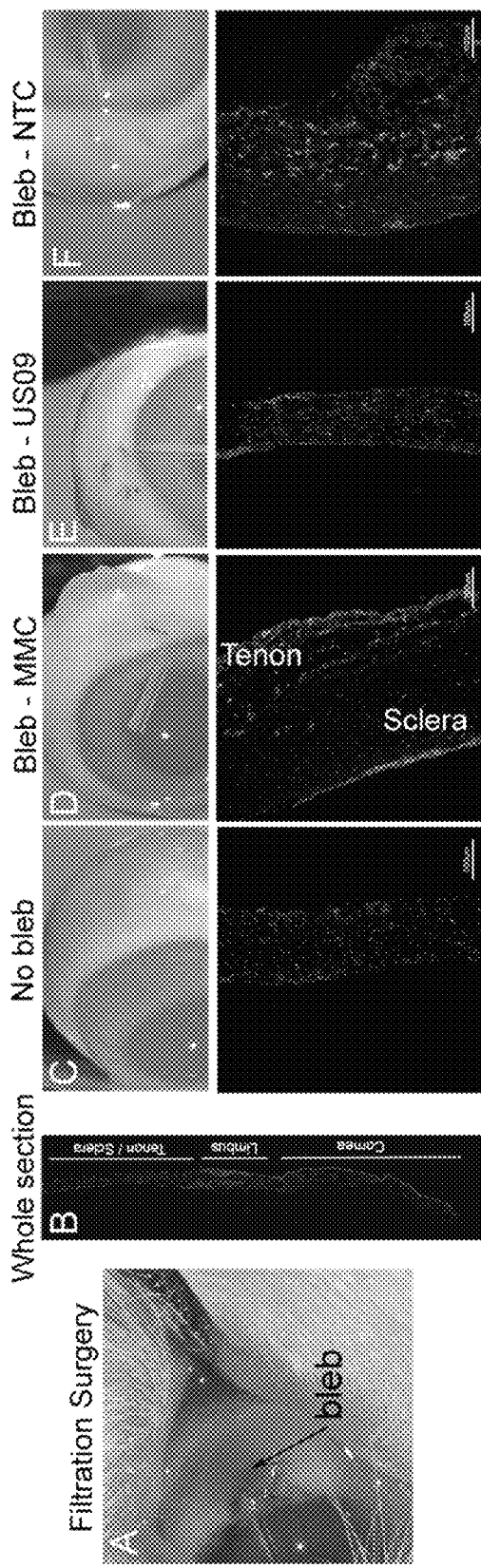
Red = α-smooth muscle actin (myofibroblasts) Blue = DAPI
MMC = Mitomycin C
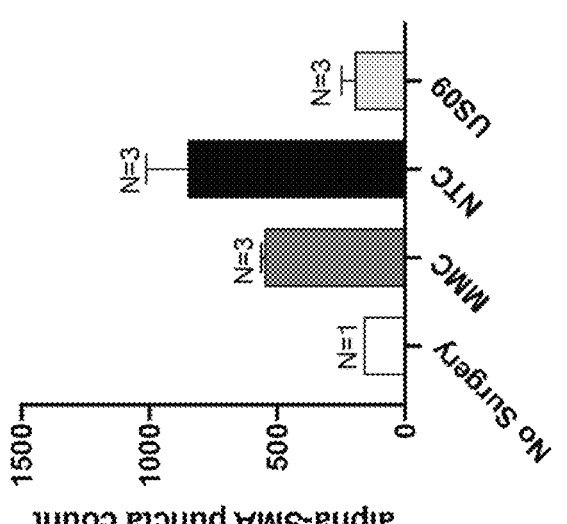
FIG. 17

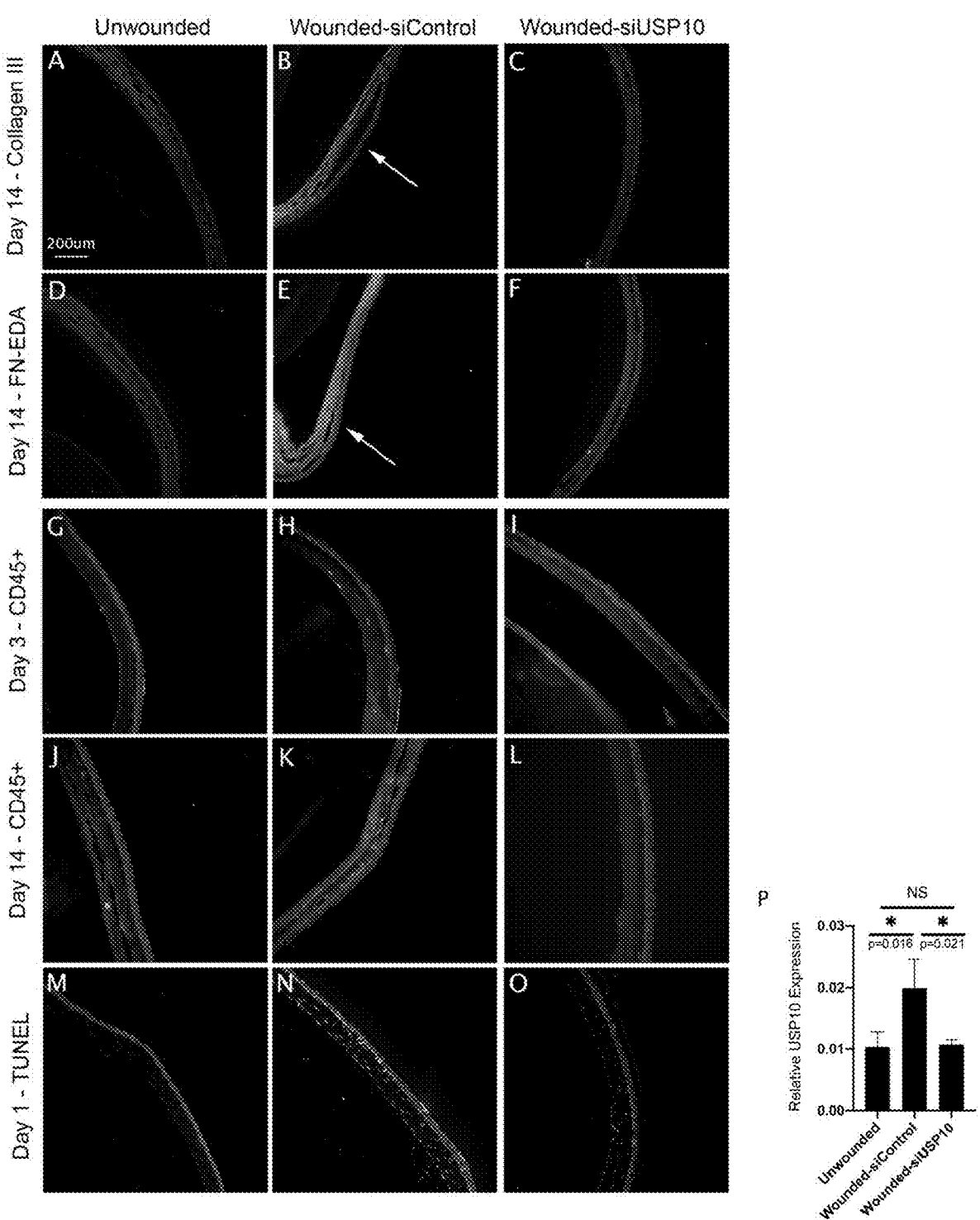
FIGS. 18 A-P

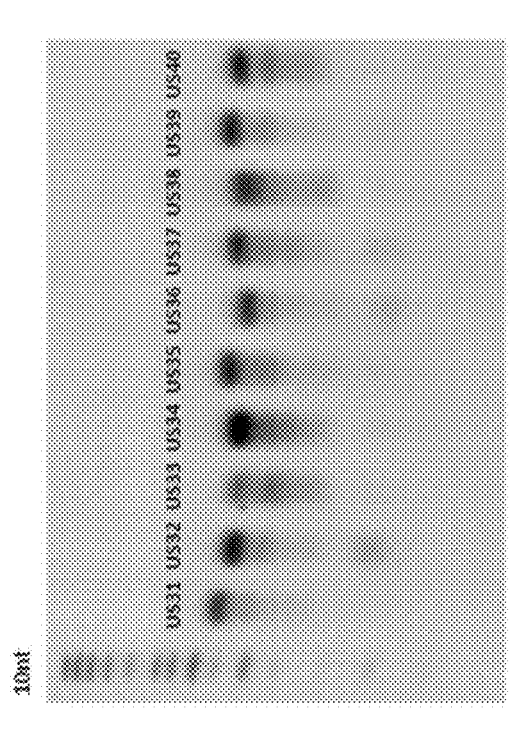
FIG. 21

Reporter screening of USP10 sdRNA compounds

Based on reporter screening, US31, US36, and US38 were chosen for dose curves in primary human corneal cells.

Dose curves of USP10 sdRNA in primary human corneal fibroblasts

Gene expression - as normalized to NTC
by concentration

| Mean | | US31 | US36 | US38 | NTC |
|---|---|---|---|---|---|
| | 2 uM | 48.233 | 32.838 | 74.375 | 100.000 |
| | 1 uM | 61.936 | 46.449 | 84.565 | 100.000 |
| | 0.5 uM | 78.376 | 64.964 | 90.577 | 100.000 |
| | 0.25 uM | 86.995 | 80.221 | 85.477 | 100.000 |
| | 0.1 uM | 95.268 | 89.864 | 103.428 | 100.000 |
| | 0.04 uM | 92.324 | 96.219 | 97.713 | 100.000 |
| | 0.016 uM | 100.997 | 96.498 | 113.745 | 100.000 |
| St Error | | | | | |
| | 2 uM | 2.983 | 1.051 | 2.446 | 4.331 |
| | 1 uM | 2.819 | 2.220 | 0.859 | 2.000 |
| | 0.5 uM | 1.104 | 3.337 | 2.261 | 9.194 |
| | 0.25 uM | 1.895 | 2.116 | 2.902 | 6.784 |
| | 0.1 uM | 4.593 | 2.986 | 2.846 | 0.826 |
| | 0.04 uM | 1.845 | 3.662 | 1.920 | 2.862 |
| | 0.016 uM | 5.489 | 0.892 | 3.416 | 2.565 |

FIG. 24

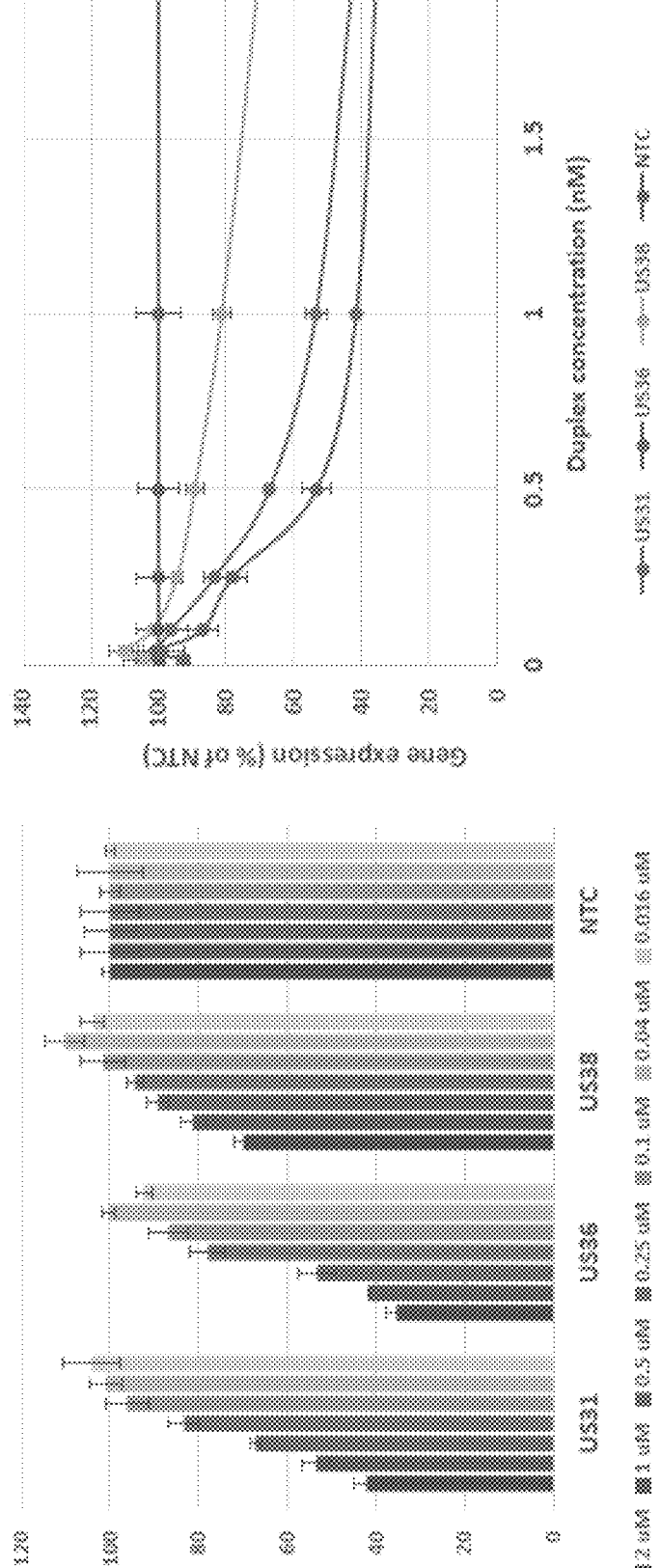
FIG. 25

Dose curves of USP10 sdRNA in HepG2 cells

Gene expression - as normalized to NTC
by concentration

| | | US31 | US36 | US38 | NTC |
|---|---|---|---|---|---|
| Mean | 2 uM | 42.115 | 35.423 | 69.937 | 100.000 |
| | 1 uM | 53.503 | 41.608 | 81.332 | 100.000 |
| | 0.5 uM | 67.259 | 53.290 | 89.300 | 100.000 |
| | 0.25 uM | 83.359 | 77.992 | 94.463 | 100.000 |
| | 0.1 uM | 96.193 | 86.840 | 101.585 | 100.000 |
| | 0.04 uM | 101.071 | 100.336 | 110.305 | 100.000 |
| | 0.016 uM | 104.239 | 92.455 | 103.912 | 100.000 |
| St Error | 2 uM | 2.890 | 2.155 | 1.947 | 1.729 |
| | 1 uM | 3.161 | 0.194 | 2.732 | 6.501 |
| | 0.5 uM | 1.180 | 4.077 | 2.488 | 5.972 |
| | 0.25 uM | 3.470 | 4.113 | 1.818 | 6.763 |
| | 0.1 uM | 4.912 | 4.480 | 4.859 | 2.118 |
| | 0.04 uM | 3.509 | 1.384 | 4.389 | 7.532 |
| | 0.016 uM | 6.283 | 1.765 | 2.621 | 0.888 |

USP10 TARGETED SELF-DELIVERABLE siRNA COMPOSITIONS AND METHODS FOR PREVENTING OR INHIBITING FIBROSIS AND/OR SCARRING

CROSS-REFERENCES TO RELATES APPLICATIONS

This application is a national phase application based on the PCT International Patent Application No. PCT/US2021/020167 filed on Feb. 28, 2021, which claims priority benefit to U.S. Provisional Application No. 62/983,233 filed Feb. 28, 2020, the contents of which are fully incorporated herein by reference.

GOVERNMENT INTEREST STATEMENT

This invention was made with government support under grant number EY024942 awarded by the National Institute of Health. The government has certain rights in the invention.

REFERENCE TO A SEQUENCE LISTING

This application contains a Sequence Listing in computer readable form, which is incorporated herein by reference.

FIELD OF THE INVENTION

The present disclosure provides siRNA (sdRNAi), such as self-deliverable siRNA, directed against USP-10 and methods for using the compositions for treatment of various human conditions, including, but not limited to, skin scarring due to trauma wounds and surgery, ocular scarring (such as corneal and retina) scarring due to injury and surgery, internal organ scarring due to injury and surgery, heart tissue scarring due to heart attack and surgery, and lung, liver, and kidney fibrosis due to inflammation and injury.

BACKGROUND

Regenerative wound healing in the eye has special importance because unlike other tissues, scarring leads to vision loss. Clinically, the global burden of ocular scarring is significant. Corneal scarring results from mechanical injury, burn, infection, or surgery (See e.g., Barrientez, et al., Corneal injury: Clinical and molecular aspects. *Exp Eye Res* 186:107709 (2019)). Other examples of ocular scarring include glaucoma filtration surgery (the bleb to relieve intraocular pressure can heal fibrotically) (See e.g., Hollo, Wound Healing and Glaucoma Surgery: Modulating the Scarring Process with Conventional Antimetabolites and New Molecules. *Dev Ophthalmol* 59:80-89 (2017) and other ocular morbidity such as proliferative vitreoretinopathy (PVR) and retinal detachment (See e.g., Morescalchi, et al., Proliferative vitreoretinopathy after eye injuries: an overexpression of growth factors and cytokines leading to a retinal keloid. *Mediators Inflamm* (2013): 269787, and Kunikata, et al., Historical, Current and Future Approaches to Surgery for Rhegmatogenous Retinal Detachment, *Tohoku J Exp Med* 248:159-168 (2019). Mitomyocin C (MMC) to improve healing and avert scarring is a standard of care for some of these indications but there is a high failure rate with the filtration surgery and cell toxicity concerns in corneal surgeries. Although there are several other therapeutic modalities being tested for the cornea including viral delivery of genes, growth factors, and stem cells derived from various sources, currently transplant of non-autologous corneal tissue is the only option available. Furthermore, there is a global shortage of tissue and limited access to this procedure for most of the world (See e.g., Fernandez-Perez, et al., Decellularization and recellularization of cornea: Progress towards a donor alternative. Methods (2019).

As a model system, the cornea is particularly interesting for wound healing studies because it is transparent, non-transplantable human tissue is readily available, and eyes are easily accessible for microscopic analysis in vivo. The human cornea includes five main layers, epithelium, Bowman's membrane, stroma, Descemet's membrane, and endothelium. Bowman's membrane beneath the epithelium that separates the epithelium from the stroma is key to the healing response. When Bowman's membrane is breached, growth factors such as TGFβ from the epithelium and tears reach the stroma, setting in place a reaction that leads to pathological myofibroblast formation. Similarly, an intact Descement's membrane prevents posterior fibrosis (See e.g., Saikia et al., Basement membranes in the cornea and other organs that commonly develop fibrosis. *Cell Tissue Res* 374:439-453 (2018)). Although myofibroblasts are integral to the healing response, timed myofibroblast apoptosis or reduced development of myofibroblasts is necessary for regenerative healing. The persistence of myofibroblasts in a healing wound leads to scarring. Chronic fibrotic conditions such as dermal, lung, liver, and kidney are also characterized by myofibroblast persistence. Thus, targeting myofibroblasts is a goal of fibrotic therapies and the transparent cornea is an interesting and accessible model system for testing even non-ocular anti-fibrotic therapies. See e.g., Wilson et al., Injury and defective regeneration of the epithelial basement membrane in corneal fibrosis: A paradigm for fibrosis in other organs? *Matrix Biol* 64:17-26 (2017).

Previous work on scarring focused on the contribution of alpha-v integrins to myofibroblast development and persistence. (See e.g., Gillespie et al., The deubiquitylase USP10 regulates integrin beta1 and beta5 and fibrotic wound healing. *J Cell Sci* 130:3481-3495 (2017) and Wang et al., Degradation of Internalized alphavbeta5 Integrin Is Controlled by uPAR Bound uPA: Effect on beta1 Integrin Activity and alpha-SMA Stress Fiber Assembly. *PLoS One* 7: e33915 (2012)). Integrins are heterodimeric transmembrane proteins that bind to the extracellular matrix (ECM) and intracellularly to the actin cytoskeleton, regulating cell adhesion, cell motility, and apoptosis. An increase in cell-surface expression of av-containing integrins (αvβ1, αvβ3, αvβ5, αvβ6, and αvβ8) throughout many organs promotes fibrosis, (See Leask, Integrin 1: A Mechanosignaling Sensor Essential for Connective Tissue Deposition by Fibroblasts. *Adv Wound Care (New Rochelle)* 2:160-166 (2013); Henderson et al., Integrin-mediated regulation of TGFbeta in fibrosis. *Biochim Biophys Acta* 1832:891-896 (2013); and Reed et al., The alphavbeta1 integrin plays a critical in vivo role in tissue fibrosis. *Sci Transl Med* 7: 288ra279 (2015)), whereas genetic silencing of av, and a blocking av peptide, prevents fibrosis in mice, (See Henderson et al., Targeting of alphav integrin identifies a core molecular pathway that regulates fibrosis in several organs. *Nat Med* 19:1617-1624 (2013) and Mamuya, et al., The roles of alphaV integrins in lens EMT and posterior capsular opacification. *J Cell Mol Med* 18:656-670 (2014)) demonstrating that lowering αv integrin levels and activity is therapeutically important. After wounding, integrins accumulate on the cell surface of myofibroblasts, increasing cell adhesion and cellular tension that promotes the expression and organization of alpha-smooth muscle actin (α-SMA) stress fibers that characterize myofibroblasts. Integrin engagement with the extracellular matrix (ECM) also activates matrix-associated endogenous TGFβ by binding to the RGD domain in its latency-associated peptide (LAP) (see e.g., Leask, Integrin 1: A Mechanosignaling Sensor Essential for Connective Tissue Deposition by Fibroblasts. *Adv Wound Care* (*New Rochelle*) 2:160-166 (2013); and Hinz, The extracellular matrix and transforming growth factor-beta1: Tale of a strained relationship. *Matrix Biol* (2015) and releasing TGFβ (See e.g, Wipff et al., Myofibroblast contraction activates latent TGF-beta1 from the extracellular matrix. *J Cell Biol* 179:1311-1323 (2007), and Wipff, Integrins and the activation of latent transforming growth factor beta1—An intimate relationship. *Eur J Cell Biol* 87:601-615 (2008). This active TGFβ creates an autocrine loop of TGFβ activity that results in pathological cell adhesion and secretion of fibrotic ECM such as collagen III, cellular fibronectin (FN-EDA) and vitronectin. (See Walraven, Therapeutic approaches to control tissue repair and fibrosis: Extracellular matrix as a game changer. *Matrix Biol* (2018)). The role of alpha-v integrin ubiquitination in generating increased cell-surface expression on myofibroblasts during stromal healing is of interest. Integrins are ubiquitinated on the intracellular C-terminus targeting them for degradation. (See e.g., Lobert, V H, and Stenmark, H (2010). Ubiquitination of alpha-integrin cytoplasmic tails. *Commun Integr Biol* 3:583-585 (2010)). The biological effects of post-translational modifications of integrins is a burgeoning field of study. Previously, using RNAseq of pathological human primary myofibroblasts a novel mechanism for post-wounding integrin accumulation has been found; the protection of integrins from intracellular proteolysis shifts the balance of integrin homeostasis resulting in integrin accumulation (See e.g., Gillespie, S R, Tedesco, L J, Wang, L, and Bernstein, A M (2017). The deubiquitylase USP10 regulates integrin beta1 and beta5 and fibrotic wound healing. *J Cell Sci* 130:3481-3495). Specifically, wounding increases the expression of the deubiquitinase (DUB), USP10 (Ubiquitin Specific Protease 10). Mechanistically, in primary human corneal myofibroblasts, USP10 removes ubiquitin from β1 and β5 (the av subunit is not ubiquitinated) (See e.g., Lobert, V H, and Stenmark, H (2010). Ubiquitination of alpha-integrin cytoplasmic tails. *Commun Integr Biol* 3:583-585; and Hsia, H C, Nair, M R, and Corbett, S A (2014). The fate of internalized alpha5 integrin is regulated by matrix-capable fibronectin. *J Surg Res* 191: 268-279) resulting in their accumulation on the cell surface, activating TGFβ. Together the augmented integrin and TGFβ activity induces myofibroblast differentiation and FN-EDA expression and organization, making USP10 a novel driver of scarring. Knockdown of USP10 with siRNA post-translationally reduced integrin expression and prevented fibrotic marker development in an ex vivo pig corneal organ culture wounding model. (See e.g., Castro, N, Gillespie, S R, and Bernstein, A M (2019). Ex Vivo Corneal Organ Culture Model for Wound Healing Studies. *J Vis Exp*).

USP10 is also a DUB for p53. (See e.g., Yuan, J, Luo, K, Zhang, L, Cheville, J C, and Lou, Z (2010). USP10 regulates p53 localization and stability by deubiquitinating p53. *Cell* 140:384-396). Much of the USP10-focused research has been centered on its role in cancer and the regulation of p53. Given the accessibility of the eye, treatment of ocular disease with siRNAs are an important new modality. (See e.g., Guzman-Aranguez, A, Loma, P, and Pintor, J (2013). Small-interfering RNAs (siRNAs) as a promising tool for ocular therapy. *Br J Pharmacol* 170:730-747).

Gene knockdown by RNA-induced gene silencing is believed to implicate a minimum of three different levels of control: (i) transcription inactivation (siRNA-guided DNA and histone methylation); (ii) small interfering RNA (siRNA)-induced mRNA degradation; and (iii) siRNA-induced transcriptional attenuation. The RNA interference (RNAi) generated by siRNA can be long lasting and effective over multiple cell divisions. Therefore, RNAi represents a potentially valuable tool that can be useful in gene function analysis, drug target validation, pathway analysis, and disease therapeutics.

Studies into the mechanism of RNAi-mediated transcript degradation pathway have revealed a number of key components in this pathway. A Type III RNase called Dicer processes long ds RNA into siRNA (19-23 bp duplexes) that subsequently partner with the RNA Interfering Silencing Complex (RISC) to mediate the degradation of target transcripts in a sequence specific manner. This phenomenon has been observed in a diverse group of organisms. Unfortunately, initial attempts to use long dsRNA to induce RNAi in mammalian cells met with only limited success due to induction of the interferon response, which results in a general, as opposed to targeted, inhibition of protein synthesis.

Moreover, when short synthetic siRNAs are introduced into mammalian cells in culture, sequence-specific degradation of target mRNA can be achieved without inducing an interferon response. These short duplexes can act catalytically at sub-molar concentrations to cleave greater than 95% of the target mRNA in a cell. A description of the mechanisms for siRNA activity, as well as some of its applications is provided in Provost et al., Ribonuclease Activity and RNA Binding of Recombinant Human Dicer, E.M.B.O.J, 2002 Nov. 1, 21(21): 5864-5874; Tabara et al., The dsRNA Binding Protein RDE-4 Interacts with RDE-1, DCR-1 and a DexH-box Helicase to Direct RNAi in *C. elegans*, Cell 2002 Jun. 28, 109(7):861-71; Ketting et al., Dicer Functions in RNA Interference and in Synthesis of Small RNA Involved in Developmental Timing in *C. elegans*, Genes and Development, 2001, 15(20):2654-9; and Martinez et al., Single-Stranded Antisense siRNAs Guide Target RNA Cleavage in RNAi, Cell 2002 Sep. 6, 110(5):563.

Despite the promise of RNAi, issues including functionality, specificity, delivery methods, and stability, should be considered when working with siRNA. Specificity refers to the ability of a particular siRNA to silence a desired target without altering the expression of other genes, and recent studies have shown that "off-targeting" (i.e., the knockdown of targets other than the intended target) is much more extensive in RNAi than originally predicted (see Jackson, A. L. et al. (2003) "Expression profiling reveals off-target gene regulation by RNAi" Nature Biotechnology 21:635-7). As off-target effects can induce undesirable phenotypes, new methods and compositions that minimize, alter, or eliminate off-target effects are considered indispensable for siRNA to become an efficacious research and/or therapeutic tool.

However, with respect to targeting an mRNA sequence of a USP-10 gene, the inventors have found that it is presently not possible to predict with high degree of confidence which of many possible candidate siRNA sequences potentially will, in fact, exhibit effective RNAi activity. Moreover, it is not possible to ensure that once an siRNA sequence targeting an mRNA sequence of a USP-10 gene is identified, that it will be in a form suitable for delivery to a subject in need thereof. Instead, individually specific candidate siRNA polynucleotide or oligonucleotide sequences should be generated and tested, such as in mammalian cell culture, to determine whether the intended interference with expression of a targeted USP-10 gene or portion thereof has occurred. Further, delivery obstacles to a subject in need thereof must be investigated and overcome.

Accordingly, there is a continuing need to provide potent siRNA duplexes targeting the USP-10 gene for scarless wound healing (such as ocular or skin) and/or the elimination or reduction of fibrosis in tissue. There further is a need to formulate such siRNA duplexes into self-deliverable siRNA compositions. There further remains a need to provide a therapeutic approach to improve the healing results of patients suffering fibrosis and/or wounds caused by injury, surgery, and many diseases.

SUMMARY

The present disclosure relates to compositions, and methods for treating or alleviating fibrosis and/or scarring. In embodiments, the present disclosure includes a synthetic nucleic acid including or consisting of SEQ ID NO: 2, 4, 6, 8, 10, 12, 14, 16, 18, or 20.

In embodiments, the present disclosure includes a synthetic nucleic acid including or consisting of SEQ ID NO: 1, 3, 5, 7, 9, 11, 13, 15, 17, or 19.

In embodiments the present disclosure includes a self-deliverable siRNA (sdRNAi) directed against USP-10 including a first synthetic nucleic acid having at least 90% sequence identity to SEQ ID NO: 2, 4, 6, 8, 10, 12, 14, 16, 18, or 20.

In embodiments, the present disclosure includes a self-deliverable siRNA (sdRNAi) directed against USP-10, including: a first synthetic nucleic acid having at least 90% sequence identity to SEQ ID NO: 2, 4, 6, 8, 10, 12, 14, 16, 18, or 20; and a second synthetic nucleic acid having at least 90% sequence identity to SEQ ID NO: 1, 3, 5, 7, 9, 11, 13, 15, 17, or 19, wherein the first synthetic nucleic acid is hybridized to the second synthetic nucleic acid.

In embodiments, the present disclosure relates to a composition including a self-deliverable siRNA (sdRNAi) directed against USP-10, and a pharmaceutically acceptable carrier.

In embodiments, the present disclosure includes a method of eliminating or reducing ocular scarring in an eye of a subject after an ocular wound including administering to the ocular wound a therapeutically effective amount of a self-deliverable siRNA (sdRNAi) directed against USP-10 to fully or substantially eliminate an upregulation of USP10 after wounding.

In embodiments, the present disclosure includes a method of eliminating or reducing ocular scarring in an eye of a subject after an ocular wound including administering to the ocular wound a therapeutically effective amount of a self-deliverable siRNA (sdRNAi) directed against USP-10 to fully or substantially knockdown USP10 after wounding.

In embodiments, the present disclosure includes a method for accelerating wound closure in an eye of a subject after an ocular wound including administering to the wound a therapeutically effective amount of a self-deliverable siRNA (sdRNAi) directed against USP-10 to fully or substantially eliminate an upregulation of USP10 after wounding.

In embodiments, the present disclosure includes a method for suppressing a production of fibrotic markers in a tissue after a wound or immune response in an eye of a subject after an ocular wound, including: administering to the wound a therapeutically effective amount of a self-deliverable siRNA (sdRNAi) directed against USP-10 to fully or substantially eliminate an upregulation of USP10 after wounding.

In embodiments, the present disclosure includes a method of eliminating or reducing fibrosis of a subject after a tissue wound including administering to the tissue wound a therapeutically effective amount of a self-deliverable siRNA (sdRNAi) directed against USP-10 to fully or substantially knockdown USP10 after wounding.

In embodiments, the present disclosure includes a method of eliminating or reducing fibrosis within a subject after a tissue wound including administering to the tissue wound a therapeutically effective amount of a self-deliverable siRNA (sdRNAi) directed against USP-10 to fully or substantially eliminate an upregulation of USP10 after wounding.

In embodiments, the present disclosure includes a method of eliminating or reducing scarring in the skin of a subject after a skin wound, comprising: administering to the skin wound a therapeutically effective amount of a self-deliverable siRNA (sdRNAi) directed against USP-10 to fully or substantially eliminate an upregulation of USP10 after wounding.

The illustrative aspects of the present disclosure are designed to solve the problems herein described and/or other problems not discussed.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIGS. 1A-1F depict USP10 sdRNA screening and in vivo corneal wounding.

FIGS. 2A-2E depict quantitative analysis after wounding by OCT.

FIGS. 3A-3E depict immunohistochemical analysis of Collagen III after wounding.

FIGS. 5A-5G depict immunohistochemical analysis of α-SMA, cell proliferation, and thickness after wounding.

FIGS. 6A-6M depict CD45+ cell infiltration after wounding.

FIGS. 8A-8B depict working model for divergent roles of USP10 as wound healing/scarring progresses.

FIG. 12 is a chart that depicts the potential off-targets of USP10 compounds were by that analyzed NCBI BLAST Sequence Analysis tool (https://blast.ncbi.nlm.nih.gov/Blast.cgi). BLASTn search parameters were optimized for short sequences. For US09 compound target sequence, six rabbit targets in total were found. However, all except for specific USP10 target were either in reverse direction or missing several critical nucleotides in seed region (see the table). For US02 compound, out of 929 targets allowing up to 4 mismatches, only one belongs to rabbit taxon, and it is the on-target sequence for USP10.

FIG. 13 depicts target sequences SEQ ID NOS: 32-41.

FIG. 14 depicts human USP10 sdRNA sequences from in silico design. Target sequences include SEQ ID NOS: 42-51, and antisense strands include SEQ ID NOS: 52-61.

Figure 15:
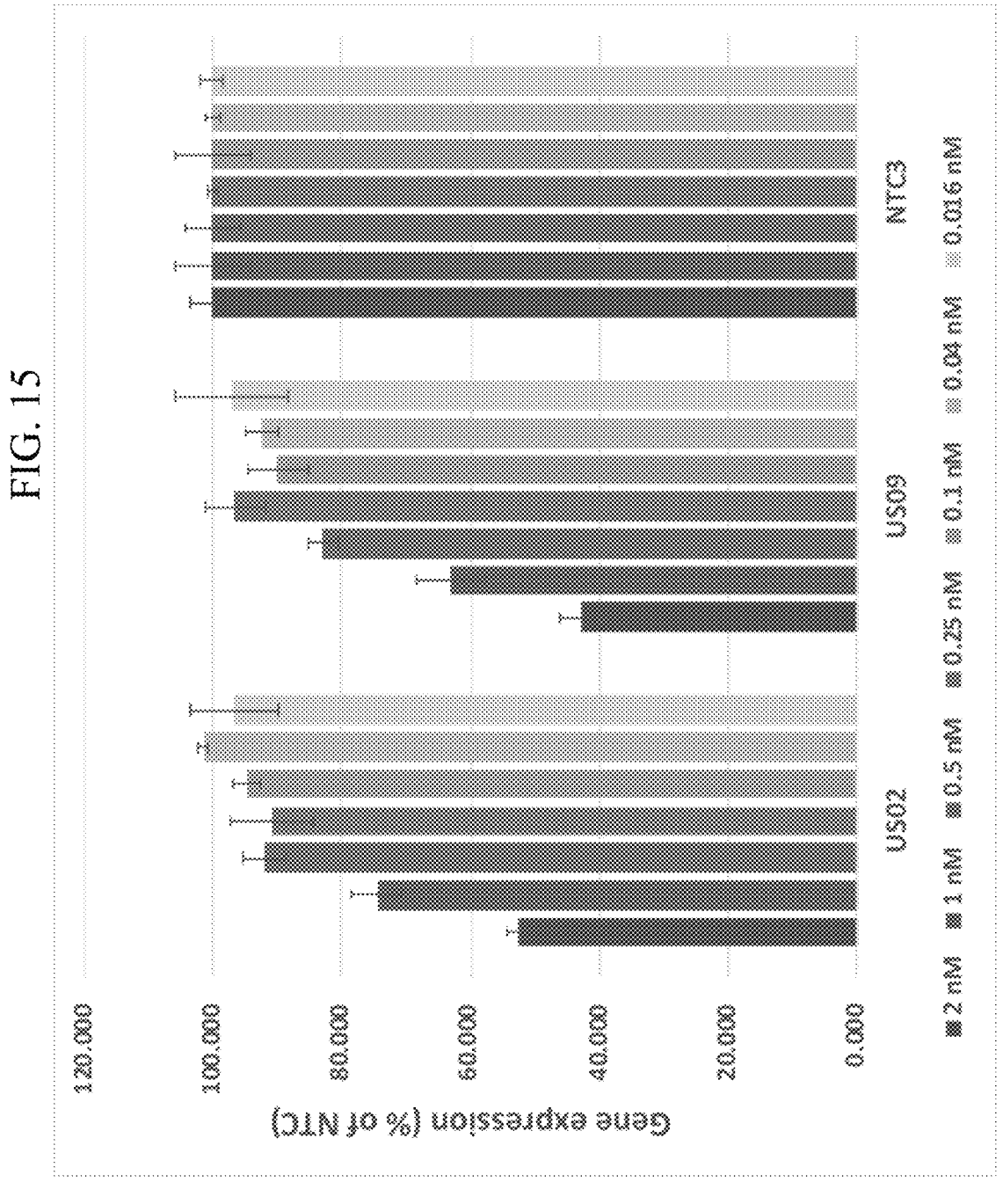

FIG. 15 depicts where primary rabbit corneal fibroblasts were treated with 0.016 nM-2.0 nM of US02, US09, and NTC (non-targeting control) for 72 hours, and USP 10 expression was analyzed by qPCR. Rabbit GAPDH served as a reference gene. Knockdown efficiency was expressed as the percentage of NTC.

Figure 16:
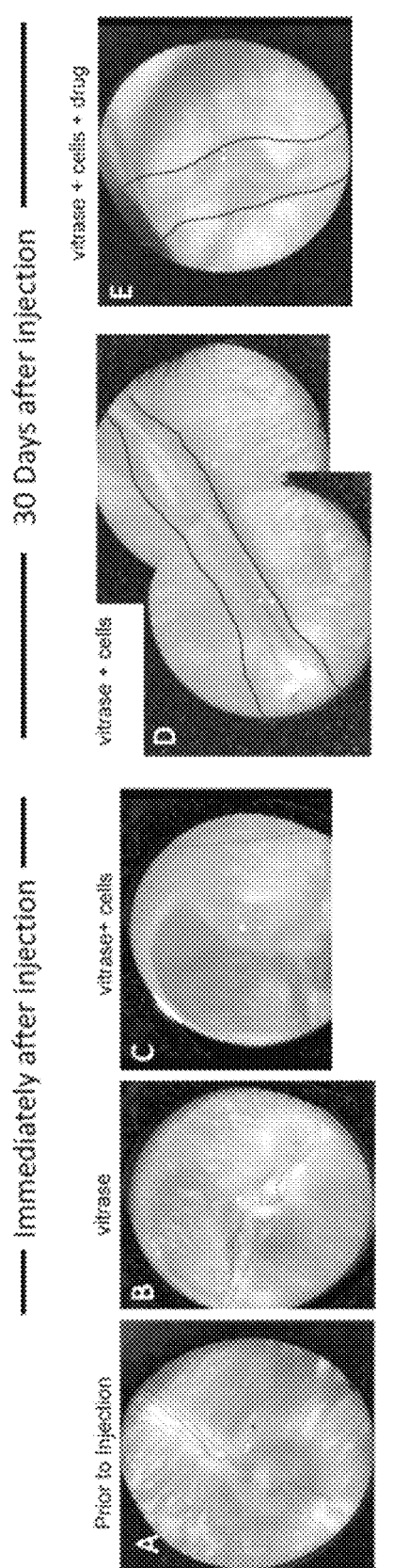

FIG. 16 depicts a PVR model of the present disclosure. Here, New Zealand White Rabbits were injected into the vitreous. The injection of cells creates a scar that detaches the retina. Vitrase "loosens" the vitreous to allow the dispersion of drugs int the vitreous. Retinal images: 10A depict prior to injection, immediately after injection FIG. 10B victrase only, FIG. 10C vitrase plus cells: 30 Days after injection FIG. 10D vitrase plus cells, FIG. 10E vitrase plus cells and USP10 siRNA. The USP10 siRNA prevents retina detachment in this model. N=2 for each condition.

FIG. 17 depicts a glaucoma filtration surgery pilot study. Here, a Pilot study comparing US09, NTC, and the current standard of care, MMC. FIG. 17A depicts a superonasal fornix-based conjunctival flap was raised behind the limbus. Drugs were injected (pipetted) into the bleb. FIG. 17B depicts frozen control section that includes Cornea, Limbus, and Tenon/Sclera. FIGS. 17C-F depict top image of enucleated rabbit eyes after sacrifice and before sectioning. Bottom Images of Tenon/sclera portion of section. Dapi (blue), α-SMA (red). Images as labeled. Of note is that in rabbits treated with US09 compared to NTC or MMC, the tissue remained "thin" similar to unwounded. α-SMA staining was also similar to unwounded tissue. N=3 rabbits in each condition.

FIGS. 18A-18P depict knockdown of USP10 in mouse cornea after wounding. To expand the data on USP10 siRNA from rabbit to another species, mouse, the USP10 knockdown experiment was performed in mice after wounding with 0.15N NaOH for 60 seconds. This is a standard chemical wounding model. Arrows denote separated epithelial in wounded siControl but not siUSP10. Panels are labeled: 18A-C) Day 14 Collagen III; 18D-F) Day 14 FN-EDA; 18G-I) Day 3 CD45+; 18J-L) Day 14 CD45+; 18M-O) Day 1 TUNEL (apoptosis); P) qRT-PCR-Relative USP10 mRNA expression at Day 3. Results are identical to knockdown of USP10 in rabbit cornea.

Figures 19A, 19B:
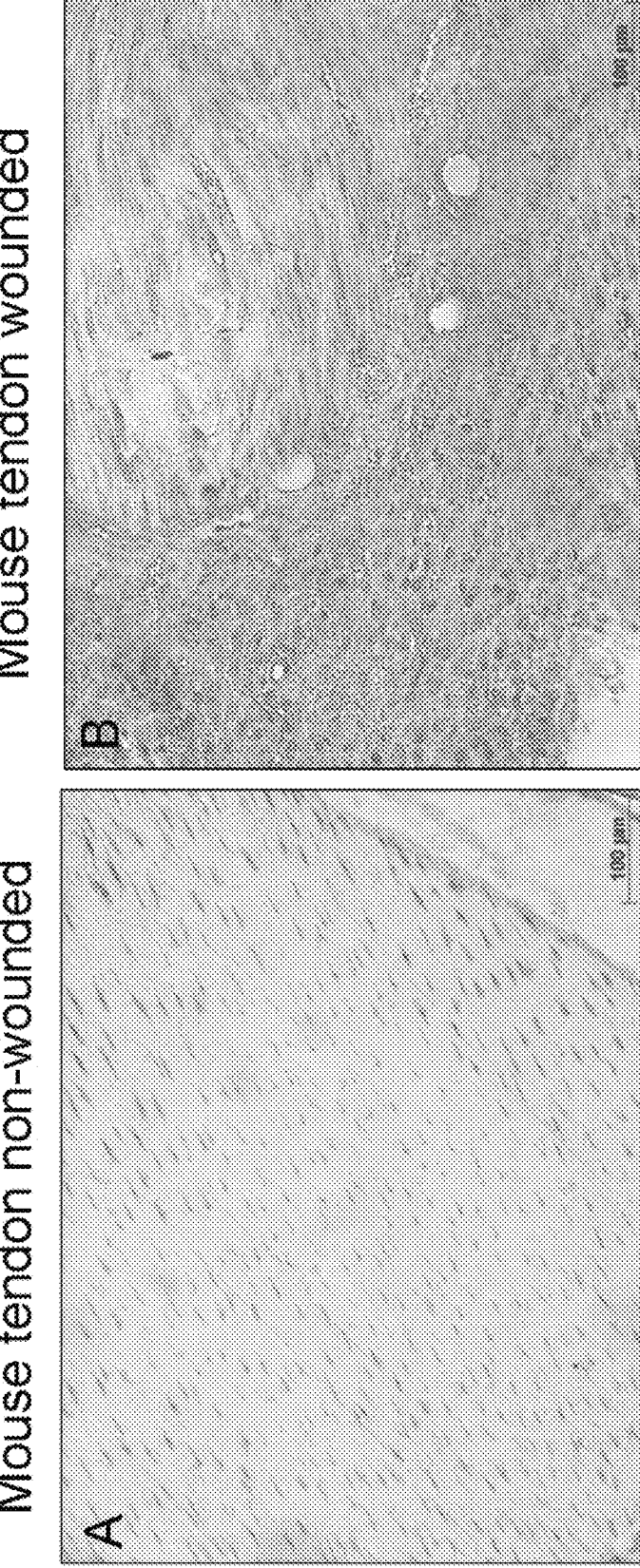

FIGS. 19A and 19B depict USP10 is increased in wounded mouse tendons. A, B) 13-week old male C57BL/6 mice remained uninjured (A) or underwent an excisional midsubstance defect (Beason et al, 2012) in the left patellar tendon using 0.75 mm biopsy punch (Shoney Scientific, Waukesha, WI) (B). Mice were sacrificed 1 week after injury, and their left patellar tendons were dissected, fixed in formalin, embedded in paraffin, and sectioned at 5 μm in the coronal orientation. USP10 is increased 3.75-fold +/−1.26 *p<0.05 in wounded tendon compared to control.

Figures 20A, 20B:
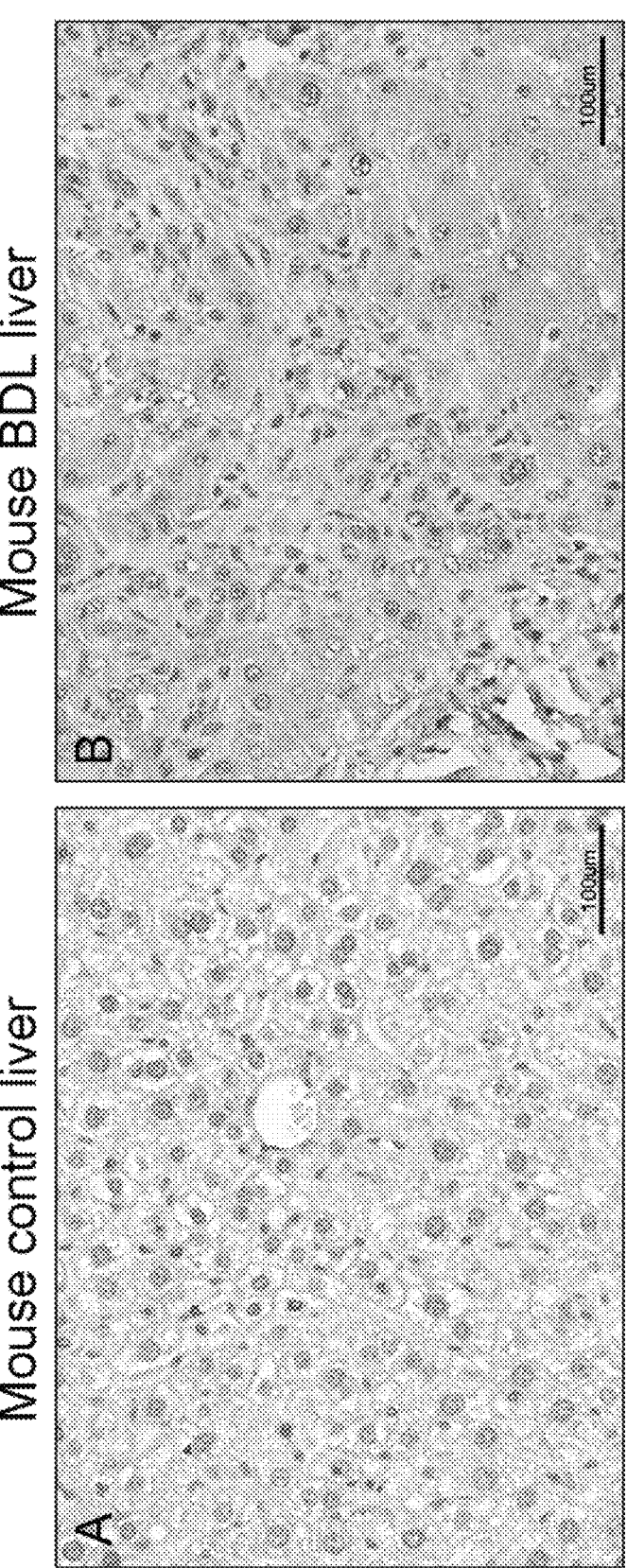

FIGS. 20A and 20B depict USP10 is upregulated in fibrotic mouse liver. The Bile duct ligation (BDL) induced cholestatic liver disease model was utilized in mice to induce acute liver injury and liver fibrosis. Compared to normal mice, fibrosis around the portal vein area is observed in the BDL model. FIGS. 20A, 20B depict mouse non-fibrotic liver control (A) and fibrotic liver (B). USP10 is increased 2.1+/−0.5. Bar=100 μm. N=3.

FIG. 21 depicts testing of sdRNA complexes targeting human USP10.

Figure 22:
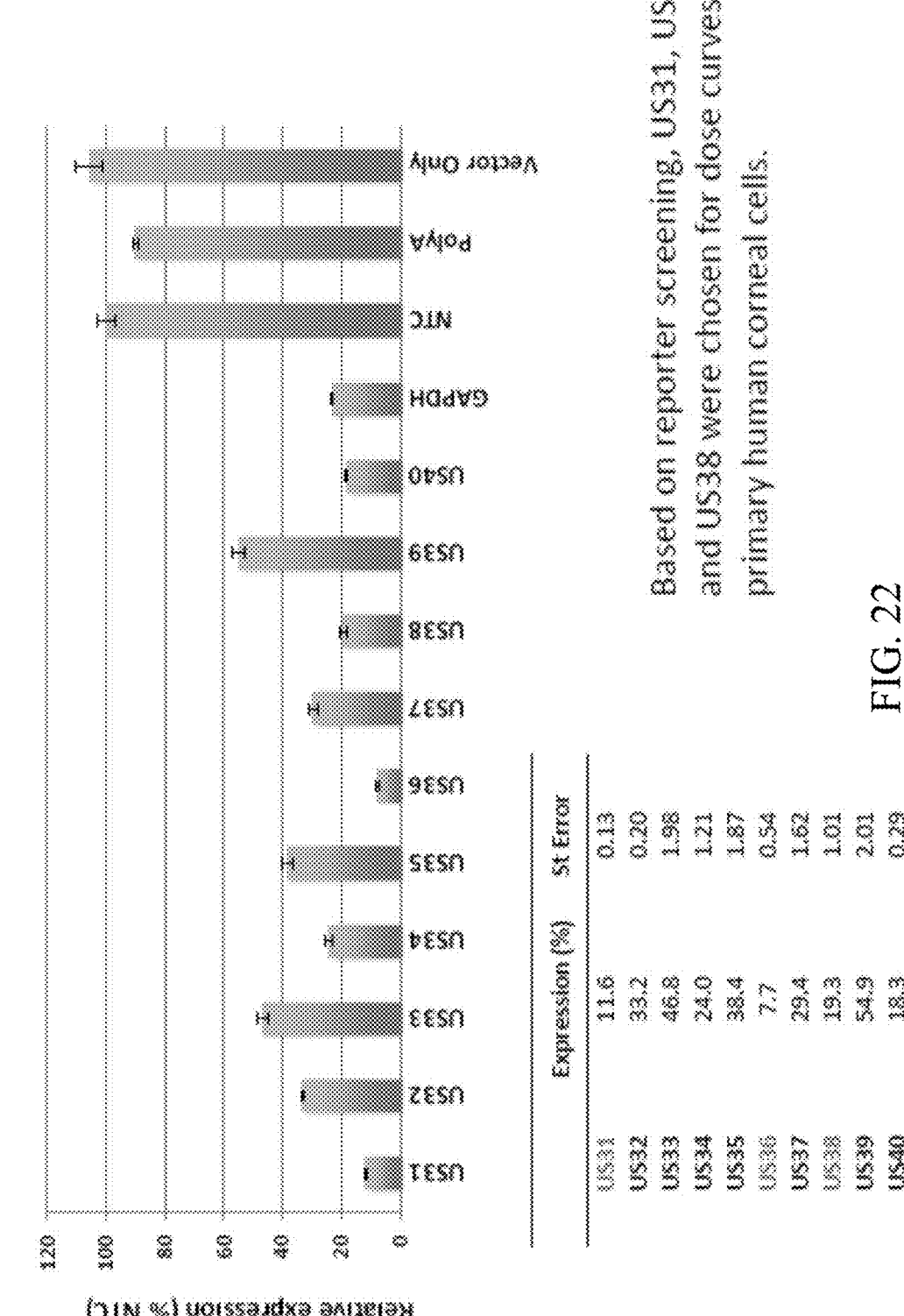

FIG. 22 depicts reporter screening of USP10 sdRNA compounds.

Figure 23:
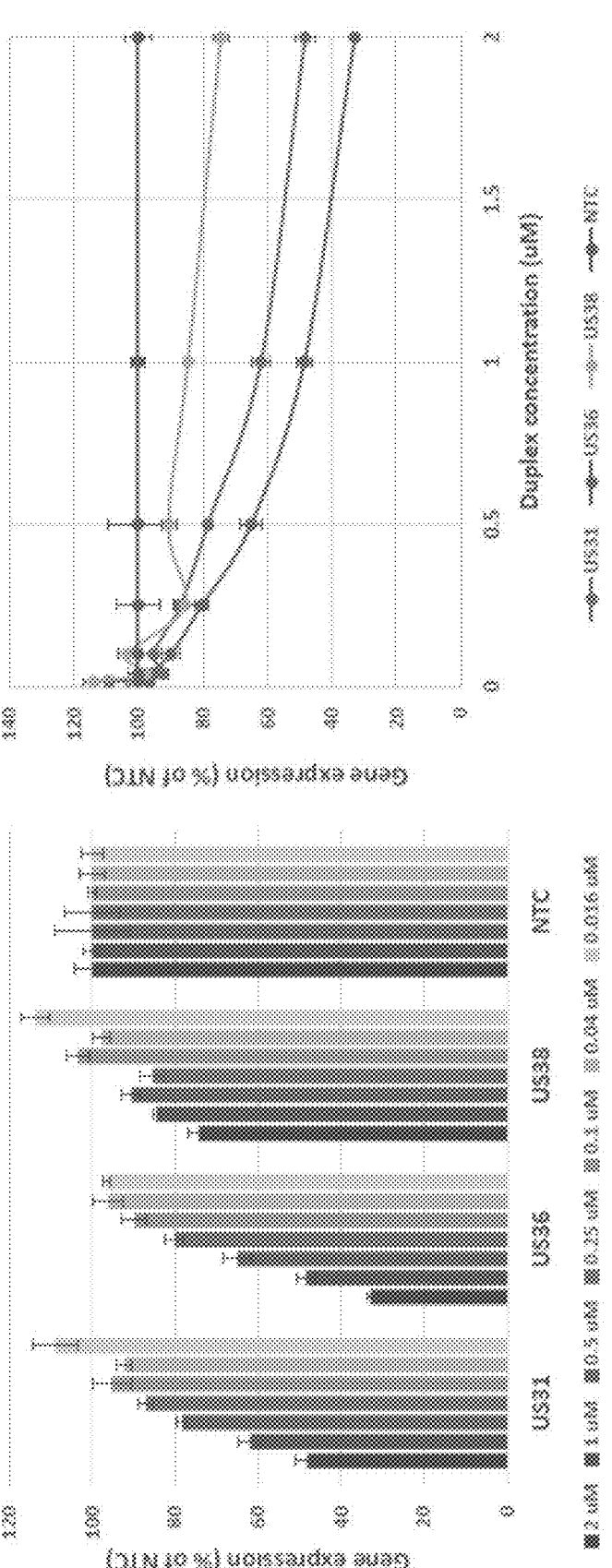

FIG. 23 depicts dose curves of USP10 sdRNA in primary human corneal fibroblasts.

FIG. 24 depicts dose curves of USP10 sdRNA in primary human corneal fibroblasts.

FIG. 25 depicts does curves of USP10 sdRNA in liver cells (HEPG2 cells).

FIG. 26 depicts does curves of USP10 sdRNA in liver cells (HEPG2 cells).

Figures 27A, 27B:
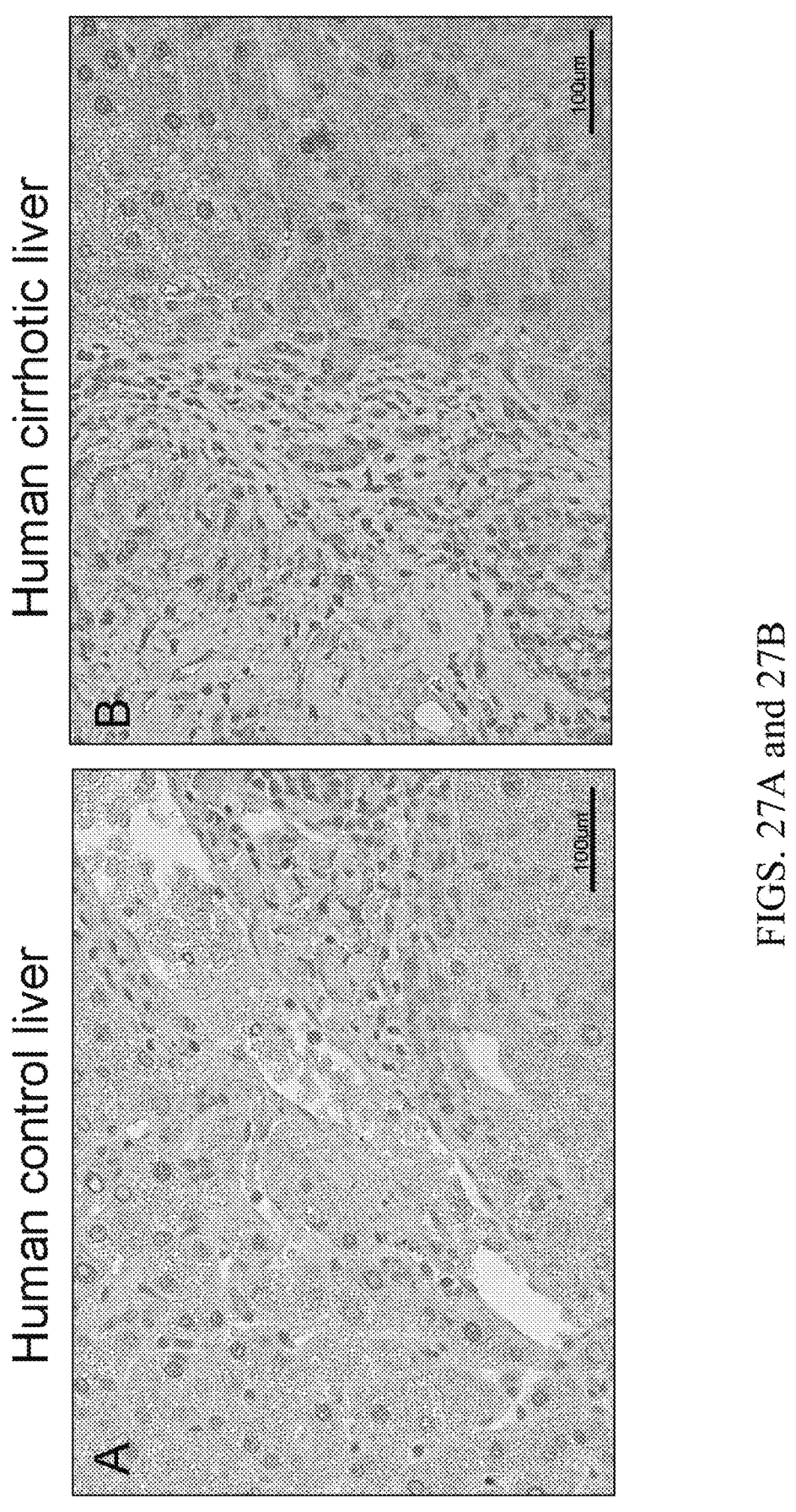

FIGS. 27A and 27B depict USP10 is upregulated in human cirrhotic liver. FIGS. 27A, 27B) Deidentified human cadaver non-fibrotic liver control (FIG. 27A) and cirrhotic liver (FIG. 27B) sections were obtained from the Biorepository and Pathology CORE at Mount Sinai Hospital, NYC. USP10 is increased 2.32+/−0.9. Bar=100 μm. N=3.

Figure 28:
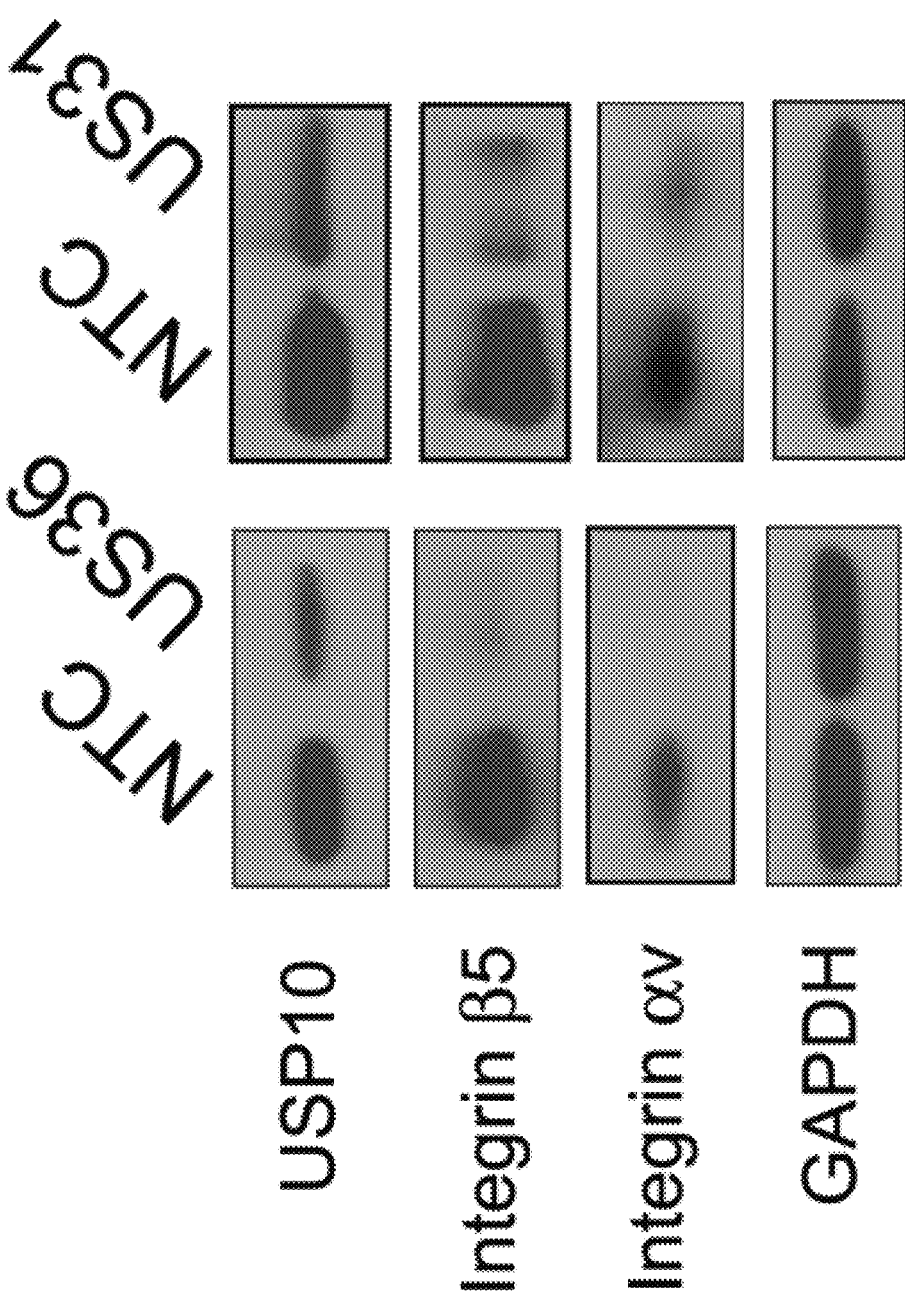

FIG. 28 depicts knockdown of human USP10 with US36 and US31 in human adult dermal cells.

DETAILED DESCRIPTION

The present disclosure provides siRNA (sdRNAi), such as self-deliverable siRNA, directed against USP-10 and methods for using the compositions for treatment of various human conditions, including, but not limited to, skin scarring due to trauma wounds and surgery, ocular scarring due to injury and surgery, internal organ scarring due to injury and surgery, heart tissue scarring due to heart attack and surgery, and lung, liver, and kidney fibrosis due to inflammation and injury. In embodiments, a composition directed against USP-10 in accordance with the present disclosure may be any chemical substance, generally a molecule, that inhibits the activity of the USP-10 targeted gene, RNA, or protein, as the case may be, in vitro or in vivo. For example, the compositions of the present disclosure can be small molecules, RNA molecules, antisense molecules, or siRNA molecules. In embodiments, compositions directed against USP10 may decrease, fully or substantially eliminate an upregulation of USP10 after wounding.

Ubiquitin specific peptidase (USP10), is an enzyme encoded by the USP10 gene. The gene encodes a cysteine protease, an enzyme that specifically cleaves ubiquitin-conjugated protein substrates. Further, the protein is a deubiquitinase that can remove conjugated ubiquitin from target proteins such as p53/TP53, BECN1, SNX3 and CFTR. In response to DNA damage, USP10 is translocated to the nucleus where it is involved in the deubiquitination of p53. The Human USP-10 gene, a source for target sequences of the present disclosure is shown in SEQ ID NO: 62.

In embodiments, the present disclosure provides a composition including an siRNA molecule that targets and binds to an mRNA molecule, or portion thereof, that codes for USP-10 protein in a mammalian cell. In embodiments, siRNA (sdRNAi) directed against USP-10, including a self-deliverable siRNA (sdRNAi) directed against USP-10 of the present disclosure, demonstrate a unique therapeutic benefit superior in subjects such as human and non-human mammals. In embodiments, the siRNA molecules are selected from the ones identified in Table 1 shown as conjugates with cholesterol such as cholesteryl-TEG (Chol-TEG). An example is the US31 in the Table 1 showing an antisense strand and a sense strand that are complimentary. In embodiments, the antisense strand may include more nucleotides than the sense strand creating an asymmetrical composition, or one or more sticky ends. In embodiments, the siRNA molecules can produce additive or synergistic effects in the cells and treatments relating to scarring and fibrosis.

pentyl, 2-ethylhexyl, isopropyl, isobutyl, isopentyl, etc. The term alkyl also encompasses alkenyl groups, such as vinyl, allyl, aralkyl and alkynyl groups. Unless otherwise specified, alkyl groups are not substituted. In embodiments, an alkyl group for a 2' modification is a methyl group with an O-linkage to the 2' carbon of a ribosyl moiety, i.e., a 2'-O-alkyl that includes a 2'-O-methyl group. In embodiments, a 2'-O-methyl group is unsubstituted: —O—CH$_3$.

TABLE 1

SELF-DELIVERABLE SIRNA (SDRNAI) DIRECTED AGAINST USP-10

| | | |
|---|---|---|
| US31 | CholTEG-$^{3'}$-ACUUUAGAAAAUUAC-$^{5'}$<br>$^{5'}$-UGAAAUCUUUUAAUGGCAAU-$^{3'}$ | (SEQ ID NO: 1 (sense))<br>(SEQ ID NO: 2 (antisense)) |
| US32 | CholTEG-$^{3'}$-AUCUUUCUCAAAGAG-$^{5'}$<br>$^{5'}$-UAGAAAGAGUUUCUCUCUAA-$^{3'}$ | (SEQ ID NO: 3 (sense))<br>(SEQ ID NO: 4 (antisense)) |
| US33 | Chol-TEG-$^{3'}$-AUUGUCAGACAAAGU-$^{5'}$<br>$^{5'}$-UAACAGUCUGUUUCAACCAA-$^{3'}$ | (SEQ ID NO: 5 (sense))<br>(SEQ ID NO: 6 (antisense)) |
| US34 | Chol-TEG-$^{3'}$-AAUGUUCACAACAAC-$^{5'}$<br>$^{5'}$-UUACAAGUGUUGUUGCUGGU-$^{3'}$ | (SEQ ID NO: 7 (sense))<br>(SEQ ID NO: 8 (antisense)) |
| US35 | Chol-TEG-$^{3'}$-AGUUGAGGUUCCAAA-$^{5'}$<br>$^{5'}$-UCAACUCCAAGGUUUUCAGU-$^{3'}$ | (SEQ ID NO: 9 (sense))<br>(SEQ ID NO: 10 (antisense)) |
| US36 | Chol-TEG-$^{3'}$-AACUUGAGUAAGUAA-$^{5'}$<br>$^{5'}$-UUGAACUCAUUCAUUAGCCG-$^{3'}$ | (SEQ ID NO: 11 (sense))<br>(SEQ ID NO: 12 (antisense)) |
| US37 | Chol-TEG-$^{3'}$-AACUGAACAAUUGAC-$^{5'}$<br>$^{5'}$-UUGACUUGUUAACUGUCAGG-$^{3'}$ | (SEQ ID NO: 13 (sense))<br>(SEQ ID NO: 14 (antisense)) |
| US38 | CholTEG-$^{3'}$-AAGUCCCGAUUUUAG-$^{5'}$<br>$^{5'}$-UUCAGGGCUAAAAUCUCCAA-$^{3'}$ | (SEQ ID NO: 15 (sense))<br>(SEQ ID NO: 16 (antisense)) |
| US39 | Chol-TEG-$^{3'}$-ACGAGAAGAAGUAAC-$^{5'}$<br>$^{5'}$-UGCUCUUCUUCAUUGACCGA-$^{3'}$ | (SEQ ID NO: 17 (sense))<br>(SEQ ID NO: 18 (antisense)) |
| US40 | Chol-TEG-$^{3'}$-AACUUAAGUAGUCCC-$^{5'}$<br>$^{5'}$-UUGAAUUCAUCAGGGCUAAA-$^{3'}$ | (SEQ ID NO: 19 (sense))<br>(SEQ ID NO: 20 (antisense)) |

DEFINITIONS

As used in the present specification, the following words and phrases are generally intended to have the meanings as set forth below, except to the extent that the context in which they are used indicates otherwise.

As used herein, the singular forms "a", "an", and "the" include plural references unless the context clearly dictates otherwise. Thus, for example, references to "a compound" include the use of one or more compound(s). "A step" of a method means at least one step, and it could be one, two, three, four, five or even more method steps.

As used herein the terms "about," "approximately," and the like, when used in connection with a numerical variable, generally refers to the value of the variable and to all values of the variable that are within the experimental error (e.g., within the 95% confidence interval [CI 95%] for the mean) or within ±10% of the indicated value, whichever is greater.

The term "alkyl" refers to a hydrocarbyl moiety that can be saturated or unsaturated. It may include moieties that are linear, branched and/or cyclic. Exemplary alkyl groups include but are not limited to moieties such as, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methyl- The phrase "2'-O-alkyl modified nucleotide" refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety includes carbons and hydrogens. In embodiments, the alkyl moiety is a methyl moiety.

The phrase "antisense strand" as used herein, refers to a polynucleotide or region of a polynucleotide that is substantially (i.e., 80% or more) or 100% complementary to a target nucleic acid of interest. In embodiments, an antisense strand may include a polynucleotide region that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. In embodiments, the phrase "antisense strand" includes the antisense region of polynucleotides that are formed from two separate strands, as well as unimolecular siRNAs that are capable of forming hairpin structures. The phrases "antisense strand" and "antisense region" are intended to be equivalent and are used interchangeably. The antisense strand can be modified with a diverse group of small molecules and/or conjugates.

The phrase "2' carbon modification" refers to a nucleotide unit having a sugar moiety, for example a moiety that is modified at the 2' position of the sugar subunit. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, 2'-O-butyl, 2-O-isobutyl, 2'-O-ethyl-O-methyl (—OCH₂CH₂OCH₃), and 2'-O-ethyl-OH (—OCH₂CH₂OH). A "2' carbon sense modification" refers to a modification at the 2' carbon position of a nucleotide on the sense strand or within a sense region of polynucleotide. A "2' carbon antisense modification" refers to a modification at the 2' carbon position of a nucleotide on the antisense strand or within an antisense region of polynucleotide.

The term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes. Complementarity is typically measured with respect to a duplex region and thus excludes, for example, overhangs. A duplex region comprises a region of complementarity between two strands or between two regions of a single strand, for example, a unimolecular siRNA. Typically, the region of complementarity results from Watson-Crick base pairing. In embodiments, perfect complementarity or 100% complementarity refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 20-mers, if only two base pairs on each strand can hydrogen bond with each other, the polynucleotide strands or regions exhibit 10% complementarity. In the same example, if 18 base pairs on each strand or each region can hydrogen bond with each other, the polynucleotide strands exhibit 90% complementarity. Substantial complementarity refers to polynucleotide strands or regions exhibiting 80% or greater complementarity.

The term "deoxynucleotide" refers to a nucleotide or polynucleotide lacking an OH group at the 2' or 3' position of a sugar moiety, and/or a 2',3' terminal dideoxy, but instead having a hydrogen at the 2' and/or 3' carbon.

The terms "deoxyribonucleotide" and "DNA" refer to a nucleotide or polynucleotide including at least one ribosyl moiety that has an H at the 2' position of a ribosyl moiety. In embodiments, a deoxyribonucleotide is a nucleotide having an H at its 2' position.

cDNA: The term "complementary deoxynucleotide" or "cDNA" means a DNA molecule that can be prepared by reverse transcription from a mature, spliced, mRNA molecule obtained from a eukaryotic or prokaryotic cell. cDNA lacks introns or intron sequences that may be present in corresponding genomic DNA. In embodiments, cDNA may refer to a nucleotide sequence that correspond to the nucleotide sequence of an mRNA from which it is derived. In embodiments, cDNA refers to a double-stranded DNA that is complementary to and derived from mRNA.

As used herein the terms "drug," "drug substance," "active pharmaceutical ingredient," and the like, refer to a compound (e.g., one or more siRNA (sdRNAi), such as self-deliverable siRNA, in accordance with the present disclosure) that may be used for treating a subject in need of treatment.

As used herein the term "excipient" or "adjuvant" refers to any inert substance.

As used herein the terms "drug product," "pharmaceutical dosage form," "dosage form," "final dosage form" and the like, refer to a pharmaceutical composition that is administered to a subject in need of treatment and generally may be in the form of tablets, capsules, sachets containing powder or granules, liquid solutions or suspensions, gels, emulsions, patches, and the like.

The term "endogenous" with respect to a polynucleotide or protein refers to a polynucleotide or protein that is naturally present in the host cell.

The term "expression" as used herein refers to the transcription and stable accumulation of sense (mRNA) or antisense RNA. Expression can also indicate translation of mRNA into a polypeptide.

The term "heterologous" with respect to a polynucleotide or protein refers to a polynucleotide or protein that is not naturally occurring in a host cell.

The term "isolated" means a substance in a form or environment that does not occur in nature. In embodiments, one or more siRNA (sdRNAi), such as self-deliverable siRNA, synthetically produced are considered isolated for purposes of the present disclosure, as are native or one or more siRNA (sdRNAi), such as self-deliverable siRNA, which have been separated, fractionated, or partially or substantially purified by any suitable technique.

The term "nucleotide" refers to a ribonucleotide or a deoxyribonucleotide or modified form thereof, as well as an analog thereof. Nucleotides include species that include purines, e.g., adenine, hypoxanthine, guanine, and their derivatives and analogs, as well as pyrimidines, e.g., cytosine, uracil, thymine, and their derivatives and analogs. In embodiments, a "nucleotide" includes a cytosine, uracil, thymine, adenine, or guanine moiety. In embodiments, nucleotides, unless otherwise specified (such as, for example, when specifying a 2' modification, 5' modification, 3' modification, nucleobase modification, or modified internucleotide linkage), include unmodified cytosine, uracil, thymine, adenine, and guanine. In embodiments, nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH₂, NHR, NR₂, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides. In embodiments, modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications that can include nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. Further, the term nucleotide also includes those embodiments or species that have a detectable label, such as for example a radioactive or fluorescent moiety, or mass label attached to the nucleotide.

The phrase "nucleotide unit" refers to a single nucleotide residue and is includes a modified or unmodified nitrogenous base, a modified or unmodified sugar, and a modified or unmodified moiety that allows for linking of two nucleotides together or a conjugate that precludes further linkage.

As used herein, the terms "isolated nucleic acid fragment", and "isolated nucleic acid molecule" are used interchangeably and are optionally single-stranded or double-stranded with synthetic, non-natural or modified nucleotide bases. This will indicate a single-stranded RNA or DNA polymer.

As used herein, the term "nucleic acid molecule" refers to any molecule containing multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As described further below, bases include C, T, U, C, and G, as well as variants thereof. As used herein, the term refers to ribonucleotides (including oligoribonucleotides (ORN)) as well as deoxyribonucleotides (including oligodeoxynucleotides (ODN)). The term shall also include polynucleosides (i.e., a polynucleotide minus the phosphate) and any other organic base containing polymer.

Nucleic acid molecules can be obtained from existing nucleic acid sources (e.g., genomic or cDNA), but include synthetic (e.g., produced by oligonucleotide synthesis). In embodiments, the terms "nucleic acid" "nucleic acid molecule" and "polynucleotide" may be used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein the term "pharmaceutically acceptable" substances refers to those substances which are within the scope of sound medical judgment suitable for use in contact with the tissues of subjects without undue toxicity, irritation, allergic response, and the like, and effective for their intended use.

As used herein the term "pharmaceutical composition" refers to the combination of one or more drug substances such as e.g., one or more siRNA (sdRNAi), such as self-deliverable siRNA, in accordance with the present disclosure and one or more excipients and one or more pharmaceutically acceptable vehicles with which the one or more siRNA (sdRNAi), such as self-deliverable siRNA, in accordance with the present disclosure is administered to a subject.

As used herein, the term "pharmaceutically acceptable salt" refers to a salt of a compound, which possesses the desired pharmacological activity of the parent compound. Non-limiting examples of pharmaceutically acceptable salts include: acid addition salts, formed with inorganic acids such as hydrochloric acid, hydrobromic acid, sulfuric acid, nitric acid, phosphoric acid, and the like; or formed with organic acids; and salts formed when an acidic proton present in the parent compound is replaced by a metal ion, for example, an alkali metal ion, an alkaline earth ion, or an aluminum ion.

As used herein the term "pharmaceutically acceptable vehicle" refers to a diluent, adjuvant, excipient or carrier with which a compound is administered.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

As used herein the term "subject" includes humans, animals or mammals. The terms "subject" and "patient" may be used interchangeably herein.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "therapeutically effective amount" as used herein refers to an amount of an agent (such as one or more siRNA (sdRNAi) or self-deliverable siRNA of the present disclosure) sufficient to achieve, in a single or multiple doses, the intended purpose of treatment. A "therapeutically effective amount" can vary depending, for example, on the compound, the severity of the disease, the age of the subject to be treated, comorbidities of the subject to be treated, existing health conditions of the subject, and/or the weight of the subject to be treated. A "therapeutically effective amount" is an amount sufficient to alter the subjects' natural state.

The term "treatment" as used herein refers to alleviation of one or more symptoms or features associated with the presence of the particular condition or suspected condition being treated, including but not limited to scarring, ocular scarring, or fibrosis. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may include additions or deletions (i.e., gaps) as compared to the reference sequence (which does not include additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Percent identity can be readily determined by any known method, including but not limited to those described in: 1) Computational Molecular Biology (Lesk, A. M., Ed.) Oxford University: NY (1988); 2) Biocomputing: Informatics and Genome Projects (Smith, D. W., Ed.) Academic: NY (1993); 3) Computer Analysis of Sequence Data, Part I (Griffin, A. M., and Griffin, H. G., Eds.) Humana: NJ (1994); 4) Sequence Analysis in Molecular Biology (von Heinje, G., Ed.) Academic (1987); and 5) Sequence Analysis Primer (Gribskov, M. and Devereux, J., Eds.) Stockton: NY (1991), all of which are incorporated herein by reference. In embodiments, sequence identity between two amino acid sequences is determined using the Needleman-Wunsch algorithm (Needleman and Wunsch, 1970, J. Mol. Biol. 48:443-453). In some embodiments, the degree of sequence identity refers to and may be calculated as described under "Degree of Identity" in U.S. Pat. No. 10,531,672 starting at Column 11, line 56. U.S. Pat. No. 10,531,672 is incorporated by reference in its entirety.

"RNA transcript" refers to the product resulting from RNA polymerase-catalyzed transcription of a DNA sequence. If the RNA transcript is a complete complementary copy of the DNA sequence, it is referred to as the primary transcript or it can be an RNA sequence derived from post-transcriptional processing of the primary transcript, referred to as mature RNA. The "Messenger RNA" or "mRNA" refers to RNA that resides within an intron and can be translated into protein by the cell.

As used herein, an "siRNA molecule" is a duplex oligonucleotide, that is a short, double-stranded polynucleotide, that interferes with the expression of a gene in a cell that produces RNA, after the molecule is introduced into the cell. For example, it targets and binds to a complementary nucleotide sequence in a single stranded (ss) target RNA molecule, such as an mRNA or a micro RNA (miRNA). The target RNA is then degraded by the cell. Such molecules are constructed by techniques known to those skilled in the art. Such techniques are described in U.S. Pat. Nos. 5,898,031, 6,107,094, 6,506,559, 7,056,704 and in European Pat. Nos. 1214945 and 1230375, which are incorporated herein by reference in their entireties.

The phrase "RNA interference" and the term "RNAi" are synonymous and refer to the process by which a polynucleotide or siRNA including at least one ribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

DETAILED DESCRIPTION OF CERTAIN EMBODIMENTS

The present disclosure provides siRNA (sdRNAi) directed against USP-10 including self-deliverable siRNA (sdRNAi) directed against USP-10 and methods for using the compositions for treatment of various human conditions, including, but not limited to, skin scarring due to trauma wounds and surgery, ocular scarring due to injury and surgery, internal organ scarring due to injury and surgery, heart tissue scarring due to heart attack and surgery, and lung, liver, and kidney fibrosis due to inflammation and injury. In embodiments, the siRNA (sdRNAi) directed against USP-10 including self-deliverable siRNA (sdRNAi) directed against USP-10 are characterized as pharmaceutically acceptable, recombinant, and/or disposed within a pharmaceutical composition. In embodiments, the siRNA (sdRNAi) directed against USP-10 including self-deliverable siRNA (sdRNAi) directed against USP-10 are characterized as a drug, and/or disposed within a drug product.

In embodiments, the present disclosure includes compositions or agents described herein that inhibit USP-10. In embodiments, the disclosure includes composition that may be combined with other compositions to inhibit USP-10. In embodiments, compositions directed against USP10 may decrease, fully or substantially eliminate an upregulation of USP10 after wounding.

In embodiments, the present disclosure includes a synthetic nucleic acid including or consisting of SEQ ID NO: 2, 4, 6, 8, 10, 12, 14, 16, 18, or 20. In embodiments, the present disclosure includes a synthetic nucleic acid including a nucleic acid sequence having at least 90%, at least 95%, at least 97%, or at least 99% sequence identity to SEQ ID NO: 2, 4, 6, 8, 10, 12, 14, 16, 18, or 20. In embodiments, the synthetic nucleic acids may be characterized as an antisense oligonucleotide. In embodiments, the synthetic nucleic acid includes one or more modified nucleic acids. For example, modified nucleic acids may include modified nucleotides, or nucleotide derivatives with modifications involving the base, the sugar, or both the base and the sugar or modified nucleosides, or nucleoside derivatives with modifications involving the base, the sugar, or both the base and the sugar.

In some embodiments, the present disclosure includes a synthetic nucleic acid comprising or consisting of SEQ ID NO: 1, 3, 5, 7, 9, 11, 13, 15, 17, or 19. In embodiments, the present disclosure includes a synthetic nucleic acid including a nucleic acid sequence having at least 90%, at least 95%, at least 97%, or at least 99% sequence identity to SEQ ID NO: 1, 3, 5, 7, 9, 11, 13, 15, 17, or 19. In embodiments, the synthetic nucleic acids may be characterized as an sense oligonucleotide. In embodiments, the synthetic nucleic acid includes one or more modified nucleic acids. For example, modified nucleic acids may include modified nucleotides or nucleosides, or nucleotide or nucleoside derivatives with modifications involving the base, the sugar, or both the base and the sugar.

In some embodiments, the present disclosure includes one or more nucleic acids including or consisting of SEQ ID NO: 1, 3, 5, 7, 9, 11, 13, 15, 17, or 19. In embodiments, the present disclosure includes a nucleic acid including a nucleic acid sequence having at least 90%, at least 95%, at least 97%, or at least 99% sequence identity to SEQ ID NO: 1, 3, 5, 7, 9, 11, 13, 15, 17, or 19. In embodiments, the nucleic acids may be characterized as an sense oligonucleotide. In embodiments, the synthetic nucleic acid includes one or more modified nucleic acids. For example, modified nucleic acids may include modified nucleotides or nucleosides, or nucleotide or nucleoside derivatives with modifications involving the base, the sugar, or both the base and the sugar or modified nucleotides, or nucleotide derivatives with modifications involving the base, the sugar, or both the base and the sugar.

In some embodiments, the present disclosure relates to a self-deliverable siRNA (sdRNAi) directed against USP-10 including a first synthetic nucleic acid having at least 90%, at least 95%, or at least 99% sequence identity to SEQ ID NO: 2, 4, 6, 8, 10, 12, 14, 16, 18, or 20. In some embodiments, the self-deliverable SIRNA (sdRNAi) directed against USP-10, further includes a second synthetic nucleic acid having at least 90%, at least 95%, or at least 99% sequence identity to SEQ ID NO: 1, 3, 5, 7, 9, 11, 13, 15, 17, or 19. In some embodiments, the self-deliverable siRNA (sdRNAi) directed against USP-10 is double stranded. In some embodiments, the self-deliverable siRNA (sdRNAi) directed against USP-10 is characterized as cholesterol-tagged. In embodiments, the first synthetic nucleic acid and the second nucleic acids are preselected and complimentary, or in some embodiments, perfectly complimentary. In embodiments, compositions directed against USP10 may decrease, fully or substantially eliminate an upregulation of USP10 after wounding.

In some embodiments, the present disclosure relates to a siRNA (sdRNAi) directed against USP-10 including a first nucleic acid having at least 90%, at least 95%, or at least 99% sequence identity to SEQ ID NO: 2, 4, 6, 8, 10, 12, 14, 16, 18, or 20. In some embodiments, the siRNA (sdRNAi) directed against USP-10, further includes a second nucleic acid having at least 90%, at least 95%, or at least 99% sequence identity to SEQ ID NO: 1, 3, 5, 7, 9, 11, 13, 15, 17, or 19. In some embodiments, the siRNA (sdRNAi) directed against USP-10 is double stranded. In some embodiments, the siRNA (sdRNAi) directed against USP-10 is characterized as self-deliverable or cholesterol-tagged. In embodiments, the first synthetic nucleic acid and the second nucleic acids are preselected and complimentary, or in some embodiments, perfectly complimentary. In embodiments, compositions directed against USP10 may decrease, fully or substantially eliminate an upregulation of USP10 after wounding.

In some embodiments, the self-deliverable siRNA (sdR-NAi) directed against USP-10 is characterized as asymmetrical. Referring to Table 1 above, 10 asymmetrical siRNA (sdRNAi) are shown including a first synthetic nucleic acid having a length of 20 nucleotides, and a second synthetic nucleic acid having a length of 15 nucleotides, wherein the second synthetic nucleic acid includes nucleotides that are complementary to the nucleic acid residues of the first synthetic nucleic acid.

In some embodiments, the present disclosure includes a self-deliverable siRNA (sdRNAi) directed against USP-10, including: a first synthetic nucleic acid having at least 90%, at least 95%, or at least 99% sequence identity to SEQ ID NO: 2, 4, 6, 8, 10, 12, 14, 16, 18, or 20; and a second synthetic nucleic acid having at least 90%, at least 95%, or at least 99% sequence identity to SEQ ID NO: 1, 3, 5, 7, 9, 11, 13, 15, 17, or 19, wherein the first synthetic nucleic acid is hybridized or bound to the second synthetic nucleic acid. In embodiments, the first synthetic nucleic acid is complementary to the second synthetic nucleic acid. In embodiments, the first synthetic nucleic acid includes about 20 nucleotides or consists of 20 nucleotides, and wherein the second synthetic nucleic acid includes about 15 nucleotide or consists of 15 nucleotides. In embodiments, the self-deliverable siRNA (sdRNAi) directed against USP-10 is characterized as asymmetrical. In embodiments, the self-deliverable siRNA (sdRNAi) directed against USP-10 is characterized as cholesterol-tagged. In embodiments, compositions directed against USP10 may decrease, fully or substantially eliminate an upregulation of USP10 after wounding.

In embodiments, the present disclosure includes a self-deliverable siRNA (sdRNAi) directed against USP-10 including a first synthetic nucleic acid having at least 90%, at least 95%, at least 99% sequence identity to SEQ ID NO: 2; and a second synthetic nucleic acid having at least 90%, at least 95%, at least 99% sequence identity to SEQ ID NO: 1, wherein the first synthetic nucleic acid hybridizes with the second nucleic acid. In some embodiments, the present disclosure includes a self-deliverable siRNA (sdRNAi) directed against USP-10 including a first synthetic nucleic acid consisting of SEQ ID NO: 2; and a second synthetic nucleic acid consisting of SEQ ID NO: 1, wherein the first synthetic nucleic acid is hybridized with the second nucleic acid. In embodiments, SEQ ID NO:1 and SEQ ID NO:2 are preselected and/or complimentary.

In embodiments, the present disclosure includes a self-deliverable siRNA (sdRNAi) directed against USP-10 including a first synthetic nucleic acid having at least 90%, at least 95%, at least 99% sequence identity to SEQ ID NO: 4; and a second synthetic nucleic acid having at least 90%, at least 95%, at least 99% sequence identity to SEQ ID NO: 3, wherein the first synthetic nucleic acid hybridizes with the second nucleic acid. In embodiments, the present disclosure includes a self-deliverable siRNA (sdRNAi) directed against USP-10 including a first synthetic nucleic acid consisting of SEQ ID NO: 4; and a second synthetic nucleic acid consisting of SEQ ID NO: 3, wherein the first synthetic nucleic acid is hybridized with the second nucleic acid. In embodiments, SEQ ID NO:3 and SEQ ID NO:4 are preselected and/or complimentary.

In embodiments, the present disclosure includes a self-deliverable siRNA (sdRNAi) directed against USP-10 including a first synthetic nucleic acid having at least 90%, at least 95%, at least 99% sequence identity to SEQ ID NO: 6; and a second synthetic nucleic acid having at least 90%, at least 95%, at least 99% sequence identity to SEQ ID NO: 5, wherein the first synthetic nucleic acid hybridizes with the second nucleic acid. In embodiments, the present disclosure includes a self-deliverable siRNA (sdRNAi) directed against USP-10 including a first synthetic nucleic acid consisting of SEQ ID NO: 6; and a second synthetic nucleic acid con-sisting of SEQ ID NO: 5, wherein the first synthetic nucleic acid is hybridized with the second nucleic acid. In embodiments, SEQ ID NO:5 and SEQ ID NO:6 are preselected and/or complimentary.

In embodiments, the present disclosure includes a self-deliverable siRNA (sdRNAi) directed against USP-10 comprising a first synthetic nucleic acid having at least 90%, at least 95%, at least 99% sequence identity to SEQ ID NO: 8; and a second synthetic nucleic acid having at least 90%, at least 95%, at least 99% sequence identity to SEQ ID NO: 7, wherein the first synthetic nucleic acid hybridizes with the second nucleic acid. In embodiments, the present disclosure includes a self-deliverable siRNA (sdRNAi) directed against USP-10 including a first synthetic nucleic acid consisting of SEQ ID NO: 8; and a second synthetic nucleic acid consisting of SEQ ID NO: 7, wherein the first synthetic nucleic acid is hybridized with the second nucleic acid. In embodiments, SEQ ID NO:7 and SEQ ID NO:8 are preselected and/or complimentary.

In some embodiments, the present disclosure includes a self-deliverable siRNA (sdRNAi) directed against USP-10 including a first synthetic nucleic acid having at least 90%, at least 95%, at least 99% sequence identity to SEQ ID NO: 10; and a second synthetic nucleic acid having at least 90%, at least 95%, at least 99% sequence identity to SEQ ID NO: 9, wherein the first synthetic nucleic acid hybridizes with the second nucleic acid. In embodiments, the present disclosure includes a self-deliverable siRNA (sdRNAi) directed against USP-10 including a first synthetic nucleic acid consisting of SEQ ID NO: 10; and a second synthetic nucleic acid consisting of SEQ ID NO: 9, wherein the first synthetic nucleic acid is hybridized with the second nucleic acid. In embodiments, SEQ ID NO:9 and SEQ ID NO:10 are preselected and/or complimentary.

In some embodiments the present disclosure includes a self-deliverable siRNA (sdRNAi) directed against USP-10 including a first synthetic nucleic acid having at least 90%, at least 95%, at least 99% sequence identity to SEQ ID NO: 12; and a second synthetic nucleic acid having at least 90%, at least 95%, at least 99% sequence identity to SEQ ID NO: 11, wherein the first synthetic nucleic acid hybridizes with the second nucleic acid. In embodiments, the present disclosure includes a self-deliverable siRNA (sdRNAi) directed against USP-10 comprising a first synthetic nucleic acid consisting of SEQ ID NO: 12; and a second synthetic nucleic acid consisting of SEQ ID NO: 11, wherein the first synthetic nucleic acid is hybridized with the second nucleic acid. In embodiments, SEQ ID NO:11 and SEQ ID NO:12 are preselected and/or complimentary.

In some embodiments, the present disclosure includes a self-deliverable siRNA (sdRNAi) directed against USP-10 including a first synthetic nucleic acid having at least 90%, at least 95%, at least 99% sequence identity to SEQ ID NO: 14; and a second synthetic nucleic acid having at least 90%, at least 95%, at least 99% sequence identity to SEQ ID NO: 13, wherein the first synthetic nucleic acid hybridizes with the second nucleic acid. In embodiments, the present disclosure includes a self-deliverable siRNA (sdRNAi) directed against USP-10 comprising a first synthetic nucleic acid consisting of SEQ ID NO: 14; and a second synthetic nucleic acid consisting of SEQ ID NO: 13, wherein the first synthetic nucleic acid is hybridized with the second nucleic acid. In embodiments, SEQ ID NO:13 and SEQ ID NO:14 are preselected and/or complimentary.

In some embodiments, the present disclosure includes a self-deliverable siRNA (sdRNAi) directed against USP-10 including a first synthetic nucleic acid having at least 90%, at least 95%, at least 99% sequence identity to SEQ ID NO:

16; and a second synthetic nucleic acid having at least 90%, at least 95%, at least 99% sequence identity to SEQ ID NO: 15, wherein the first synthetic nucleic acid hybridizes with the second nucleic acid. In embodiments, the present disclosure includes a self-deliverable siRNA (sdRNAi) directed against USP-10 comprising a first synthetic nucleic acid consisting of SEQ ID NO: 16; and a second synthetic nucleic acid consisting of SEQ ID NO: 15, wherein the first synthetic nucleic acid is hybridized with the second nucleic acid. In embodiments, SEQ ID NO: 15 and SEQ ID NO:16 are preselected and/or complimentary.

In some embodiments, the present disclosure includes a self-deliverable siRNA (sdRNAi) directed against USP-10 including a first synthetic nucleic acid having at least 90%, at least 95%, at least 99% sequence identity to SEQ ID NO: 18; and a second synthetic nucleic acid having at least 90%, at least 95%, at least 99% sequence identity to SEQ ID NO: 17, wherein the first synthetic nucleic acid hybridizes with the second nucleic acid. In embodiments, the present disclosure includes a self-deliverable siRNA (sdRNAi) directed against USP-10 including a first synthetic nucleic acid consisting of SEQ ID NO: 18; and a second synthetic nucleic acid consisting of SEQ ID NO: 17, wherein the first synthetic nucleic acid is hybridized with the second nucleic acid. In embodiments, SEQ ID NO:17 and SEQ ID NO:18 are preselected and/or complimentary.

In some embodiments, the present disclosure includes a self-deliverable siRNA (sdRNAi) directed against USP-10 including a first synthetic nucleic acid having at least 90%, at least 95%, at least 99% sequence identity to SEQ ID NO: 20; and a second synthetic nucleic acid having at least 90%, at least 95%, at least 99% sequence identity to SEQ ID NO: 19, wherein the first synthetic nucleic acid hybridizes with the second nucleic acid. In embodiments, the present disclosure includes a self-deliverable siRNA (sdRNAi) directed against USP-10 comprising a first synthetic nucleic acid consisting of SEQ ID NO: 20; and a second synthetic nucleic acid consisting of SEQ ID NO: 19, wherein the first synthetic nucleic acid is hybridized with the second nucleic acid. In embodiments, SEQ ID NO:19 and SEQ ID NO:20 are preselected and/or complimentary.

In embodiments, the siRNA molecule of the present disclosure can be made of naturally occurring ribonucleotides, i.e., those found in living cells, or one or more of its nucleotides can be chemically modified by techniques known in the art. In addition to being modified at the level of one or more of its individual nucleotides, the backbone of the oligonucleotide can be modified. Additional modifications include the use of small molecules (e.g. sugar molecules), amino acid molecules, peptides, cholesterol, and other large molecules for conjugation onto the siRNA molecule.

In embodiments, the nucleic acid compositions of the present disclosure include nucleotides or nucleosides found in nature, including guanosine, cytidine, adenosine, thymidine, and uridine, but the nucleic acid compositions are not so limited. In embodiments, nucleic acid compositions of the present disclosure modified nucleotides or nucleosides. Modified nucleotides or nucleosides include nucleotide or nucleoside derivatives with modifications involving the base, the sugar, or both the base and the sugar. Examples of modified nucleotides or nucleosides are described more fully in U.S. Pat. No. 7,595,387 entitled Modified polynucleotides for reducing off-target effects in RNA interference issued on 29 Sep. 2009 (herein incorporated by reference in its entirety).

In other embodiments of the present disclosure, any of the active agents or compositions can include a conjugate. The conjugate may include amino acids, peptides, polypeptides, proteins, sugars, carbohydrates, lipids, polymers, nucleotides, polynucleotides, and combinations thereof. In embodiments, the conjugate can be, for example, cholesterol, cholesteryl-TEG, or PEG. In embodiments, the conjugate can further include a label, such as, for example, a fluorescent label. The fluorescent label can be selected from the group consisting of TAMRA, BODIPY, Cy3, Cy5, fluorescein, and Dabsyl. Alternatively, the fluorescent label can be any fluorescent label known in the art.

In embodiments, the compositions of the present disclosure can include a duplex or duplex region including one or more mismatches. For example, a duplex region can have one or more mismatches at any one or combination of positions 2 to 20 of, for example, the antisense strand, or positions 1-15 of the sense strand. Nevertheless, the duplex region is considered in this case to include one or more mismatches where one or more mismatches can be counted among the nucleotide base pairs that are at least 80% complementary. In embodiments, a duplex region can include at least one mismatch in any of the embodiments described herein.

In embodiments, suitable modified sequences include modifications to SEQ ID NOS: 1, 3, 5, 7, 9, 11, 13, 15, 17, 19. In embodiments, the modified sequences may be a sense strand, or hybridized with another nucleic acid strand, such as an antisense strand to form a duplex. In embodiments, the sequences are characterized as:

```
                                          (SEQ ID NO: 1)
5'-[fC][mA][fU][mU][fA][mA][fA][mA][fG][mA][fU]
[mU][fU][*][mC][*][fA][CholTEG]-3'
```

```
                                          (SEQ ID NO: 3)
5'-[fG][mA][fG][mA][fA][mA][fC][mU][fC][mU][fU]
[mU][fC][*][mU][*][fA][CholTEG]-3'
```

```
                                          (SEQ ID NO: 5)
5'-[fU][mG][fA][mA][fA][mC][fA][mG][fA][mC][fU]
[mG][fU][*][mU][*][fA][CholTEG]-3'
```

```
                                          (SEQ ID NO: 7)
5'-[fC][mA][fA][mC][fA][mA][fC][mA][fC][mU][fU]
[mG][fU][*][mA][*][fA][CholTEG]-3'
```

```
                                          (SEQ ID NO: 9)
5'-[fA][mA][fA][mC][fC][mU][fU][mG][fG][mA][fG]
[mU][fU][*][mG][*][fA][CholTEG]-3'
```

```
                                          (SEQ ID NO: 11)
5'-[fA][mA][fU][mG][fA][mA][fU][mG][fA][mG][fU]
[mU][fC][*][mA][*][fA][CholTEG]-3'
```

```
                                          (SEQ ID NO: 13)
5'-[fC][mA][fG][mU][fU][mA][fA][mC][fA][mA][fG]
[mU][fC][*][mA][*][fA][CholTEG]-3'
```

```
                                          (SEQ ID NO: 15)
5'-[fG][mA][fU][mU][fU][mU][fA][mG][fC][mC][fC]
[mU][fG][*][mA][*][fA][CholTEG]-3'
```

```
                                          (SEQ ID NO: 17)
5'-[fC][mA][fA][mU][fG][mA][fA][mG][fA][mA][fG]
[mA][fG][*][mC][*][fA][CholTEG]-3'
```

```
                                          (SEQ ID NO: 19)
5'-[fC][mC][fC][mU][fG][mA][fU][mG][fA][mA][fU]
[mU][fC][*][mA][*][fA][CholTEG]-3'
```

As shown in the paragraph above, "m" refers to 2'-OMe modification in each instance, "f" refers to -2'Fluoro modification in each instance, "*" refers to a-thiophosphate modification in each instance, Chol-TEG refers to a cholesterol modification in each instance. The nucleic acid strands are written 5' to 3' in the paragraph above. In embodiments, the positioning of the Chol-TEG provides a suitable alteration for self-delivery of the molecules to a subject in need thereof. In embodiments, the present disclosure includes fully modified nucleic acid sequences, wherein each nucleotide is characterized as modified. In embodiments, the present disclosure includes partially modified nucleic acid sequences, wherein 1-5, 1-10, or 1-14 nucleotides is characterized as modified. In embodiments, the present disclosure includes non-modified nucleic acid sequences such as depicted in SEQ ID NO: 1, 3, 5, 7, 9, 11, 13, 15, 17 and 19.

In embodiments, suitable modified sequences include modifications to SEQ ID NOS: 2, 4, 6, 8, 10, 12, 14, 16, 118, 20. In embodiments, the modified sequences may be an antisense strand, or hybridized with another nucleic acid strand, such as a sense strand, to form a duplex. In embodiments, the sequences are characterized as:

```
                                          (SEQ ID NO: 2)
[5Phos][mU][fG][mA][fA][mA][fU][mC][fU][mU][fU]
[mU][fA][mA][fU][*][mG][*][fG][*][mC][*][fA][*]
[mA][*][fU]
```

```
                                          (SEQ ID NO: 4)
[5Phos][mU][fA][mG][fA][mA][fA][mG][fA][mG][fU]
[mU][fU][mC][fU][*][mC][*][fU][*][mC][*][fU][*]
[mA][*][fA]
```

```
                                          (SEQ ID NO: 6)
[5Phos][mU][fA][mA][fC][mA][fG][mU][fC][mU][fG]
[mU][fU][mU][fC][*][mA][*][fA][*][mC][*][fC][*]
[mA][*][fA]
```

```
                                          (SEQ ID NO: 8)
[5Phos][mU][fU][mA][fC][mA][fA][mG][fU][mG][fU]
[mU][fG][mU][fU][*][mG][*][fC][*][mU][*][fG][*]
[mG][*][fU]
```

```
                                          (SEQ ID NO: 10)
[5Phos][mU][fC][mA][fA][mC][fU][mC][fC][mA][fA]
[mG][fG][mU][fU][*][mU][*][fU][*][mC][*][fA][*]
[mG][*][fU]
```

```
                                          (SEQ ID NO: 12)
[5Phos][mU][fU][mG][fA][mA][fC][mU][fC][mA][fU]
[mU][fC][mA][fU][*][mU][*][fA][*][mG][*][fC][*]
[mC][*][fG]
```

```
                                          (SEQ ID NO: 14)
[5Phos][mU][fU][mG][fA][mC][fU][mU][fG][mU][fU]
[mA][fA][mC][fU][*][mG][*][fU][*][mC][*][fA][*]
[mG][*][fG]
```

```
                                          (SEQ ID NO: 16)
[5Phos][mU][fU][mC][fA][mG][fG][mG][fC][mU][fA]
[mA][fA][mA][fU][*][mC][*][fU][*][mC][*][fC][*]
[mA][*][fA]
```

```
                                          (SEQ ID NO: 18)
[5Phos][mU][fG][mC][fU][mC][fU][mU][fC][mU][fU]
[mC][fA][mU][fU][*][mG][*][fA][*][mC][*][fC][*]
[mG][*][fA]
```

```
                                          (SEQ ID NO: 20)
[5Phos][mU][fU][mG][fA][mA][fU][mU][fC][mA][fU]
[mC][fA][mG][fG][*][mG][*][fC][*][mU][*][fA][*]
[mA][*][fA]
```

As shown in the paragraph above, "m" refers to 2'-OMe modification in each instance, "f" refers to -2'Fluoro modification in each instance, "*" refers to a-thiophosphate modification in each instance. The nucleic acid strands are written 5' to 3' in the paragraph above. In embodiments, the present disclosure includes fully modified nucleic acid sequences, wherein each nucleotide is characterized as modified. In embodiments, the present disclosure includes partially modified nucleic acid sequences, wherein 1-5, 1-10, or 1-19 nucleotides is characterized as modified.

In embodiments, the present disclosure includes non-modified nucleic acid sequences such as depicted in Table II below:

TABLE II

| | |
|---|---|
| 3'-ACUUUAGAAAAUUAC-5' | (SEQ ID NO: 1 (sense)) |
| 5'-UGAAAUCUUUUAAUGGCAAU-3' | (SEQ ID NO: 2 (antisense)) |
| | |
| 3'-AUCUUUCUCAAAGAG-5' | (SEQ ID NO: 3 (sense)) |
| 5'-UAGAAAGAGUUUCUCUCUAA-3' | (SEQ ID NO: 4 (antisense)) |
| | |
| 3'-AUUGUCAGACAAAGU-5' | (SEQ ID NO: 5 (sense)) |
| 5'-UAACAGUCUGUUUCAACCAA-3' | (SEQ ID NO: 6 (antisense)) |
| | |
| 3'-AAUGUUCACAACAAC-5' | (SEQ ID NO: 7 (sense)) |
| 5'-UUACAAGUGUUGUUGCUGGU-3' | (SEQ ID NO: 8 (antisense)) |
| | |
| 3'-AGUUGAGGUUCCAAA-5' | (SEQ ID NO: 9 (sense)) |
| 5'-UCAACUCCAAGGUUUUCAGU-3' | (SEQ ID NO: 10 (anti-sense)) |
| | |
| 3'-AACUUGAGUAAGUAA-5' | (SEQ ID NO: 11 (sense)) |
| 5'-UUGAACUCAUUCAUUAGCCG-3' | (SEQ ID NO: 12 (anti-sense)) |
| | |
| 3'-AACUGAACAAUUGAC-5' | (SEQ ID NO: 13 (sense)) |
| 5'-UUGACUUGUUAACUGUCAGG-3' | (SEQ ID NO: 14 (anti-sense)) |
| | |
| 3'-AAGUCCCGAUUUUAG-5' | (SEQ ID NO: 15 (sense)) |
| 5'-UUCAGGGCUAAAAUCUCCAA-3' | (SEQ ID NO: 16 (anti-sense)) |
| | |
| 3'-ACGAGAAGAAGUAAC-5' | (SEQ ID NO: 17 (sense)) |
| 5'-UGCUCUUCUUCAUUGACCGA-3' | (SEQ ID NO: 18 (anti-sense)) |
| | |
| 3'-AACUUAAGUAGUCCC-5' | (SEQ ID NO: 19 (sense)) |
| 5'-UUGAAUUCAUCAGGGCUAAA-3' | (SEQ ID NO: 20 (anti-sense)) |

In embodiments, the composition of the present disclosure may be provided in pharmaceutical compositions that are pharmaceutically acceptable or physiologically acceptable (i.e., sufficiently non-toxic to be used in the therapeutic and prophylactic methods described herein). Accordingly, the present disclosure includes a variety of formulations, including topical creams (integrated into sunscreens) and sustained-release patches for transdermal delivery USP-10 inhibitors. In other embodiments, the pharmaceutical composition can be formulated as a topical rinse, gel, or emulsion. As will be apparent to one of ordinary skill in the art, the specific formulations can be selected based on the type of scar or fibrosis being treated. For example, an ocular rinse, gel, or emulsion can be used to treat the cornea of the eye.

In embodiments, the present disclosure includes a method for identifying the desired siRNA molecules including the steps of: (a) creating a collection of siRNA molecules designed to target a USP-10 complementary nucleotide sequence in the target mRNA molecules, wherein the targeting strands of the siRNA molecules include various sequences of nucleotides; (b) selecting the siRNA molecules that show the highest desired effect against the target USP-10 mRNA molecules in vitro; (c) evaluating the selected siRNA molecules, such as in an animal wound model; and (d) selecting the siRNA molecules that show the greatest efficacy in the model directed towards USP-10.

In embodiments, the present disclosure includes the steps of adding a pharmaceutically acceptable carrier to each of the siRNA molecules selected by step (b) to form pharmaceutical compositions and evaluating each of the pharmaceutical compositions in the animal wound model or models.

In an alternative embodiment, the siRNA molecules are examined in an in vitro organ culture assay for their USP-10 silencing activity and therapeutic efficacy.

In one embodiment, the siRNA sequences are prepared in such way that the efficacy and toxicity reactions observed in a rabbit disease model provides a good understanding about what is going to happen in humans.

In one embodiment, the present disclosure provides a composition including two or more different siRNA molecules that bind to an mRNA that codes for USP-10 protein in a mammalian cell.

In one embodiment, the siRNA molecules are combined with a pharmaceutically acceptable carrier or pharmaceutically acceptable vehicle to provide pharmaceutical compositions for administering to a subject. The subject may be any human or non-human mammal. In one aspect, the mammal is a laboratory animal, which includes dogs, cats, pigs, rabbits, non-human primates, and rodents, such as mice, rats, and guinea pigs. In another aspect, the mammal is a human.

In various embodiments of the composition, a carrier includes one or more components such as an excipient, a saline solution, a sugar solution, a polymer, a peptide, a lipid, a cream, a gel, a micellar material, a silica nanoparticle, a plasmid, and a viral vector. Other carriers include one or more of the following: a polycationic binding agent, cationic lipid, cationic micelle, cationic polypeptide, hydrophilic polymer grafted polymer, non-natural cationic polymer, cationic polyacetal, hydrophilic polymer grafted polyacetal, ligand functionalized cationic polymer, and ligand functionalized-hydrophilic polymer grafted polymer, biodegradable polyesters.

The compositions of the present disclosure are useful for treating a wound in a human or non-human mammal. A therapeutically effective amount of the composition (or compositions) is (are) administered the to the wound or to the human or mammal. The dosages, methods, and times of administration are readily determinable by a person skilled in the art, given the teachings contained herein. The wound can be in the skin (e.g., epidermis, dermis, and full thickness), eye (e.g., ocular wound such as to the cornea or retina), muscle, arterial walls, venous walls, or internal an organ such as the heart or liver. The wound may be characterized at least in part by inflammation and neovascularization. It may be caused by, among other things, trauma, an allergy, diabetic disease, inflammation, or a tumor. Trauma includes excision, incision, surgery, cuts, burns, and acute injury. In one aspect, the wound is an ulcer, such as a diabetic foot ulcer, pressure ulcer, arterial ulcer, psoriasis ulcer, and venous ulcer. In another aspect, the wound is the result of corneal replacement surgery or retina surgery. In embodiments, the treatment results in minimized scar formation compared to the scar that would be formed without treatment.

The siRNAs of the present disclosure may be administered to a cell by any method that is now known or that comes to be known and that from reading this disclosure, one skilled in the art would conclude would be useful with the present disclosure. For example, the siRNAs may be passively delivered to cells. Passive uptake of modified siRNAs can be modulated, for example, by the presence of a conjugate such as a polyethylene glycol moiety or a cholesterol moiety at the 5' terminal of the sense strand and/or, in appropriate circumstances, a pharmaceutically acceptable carrier. In embodiments, SIRNA's of the present disclosure suitable for passive uptake are characterized as self-deliverable.

The compositions are also useful for treating tissue fibrosis caused by scaring after chronic inflammation of the tissue. Such tissues include the liver, lung, kidney, and heart. A therapeutically effective amount of the compositions are administered to the human or non-human mammal or the wound.

In embodiments, the present disclosure provides a synthetic nucleic acid comprising or consisting of one or more of SEQ ID NOS: 2, 4, 6, 8, 10, 12, 14, 16, 18, or 20. In embodiments, the synthetic nucleic acid comprises one or more modified nucleic acids. In embodiments, the synthetic nucleic acid is characterized as an antisense oligonucleotide.

In embodiments, the present disclosure provides a synthetic nucleic acid comprising or consisting of one or more of SEQ ID NOS: 1, 3, 5, 7, 9, 11, 13, 15, 17, or 19. In embodiments, the synthetic nucleic acid includes one or more modified nucleic acids. In embodiments, the synthetic nucleic acid is characterized as a sense oligonucleotide.

In embodiments, the present disclosure provides a self-deliverable siRNA (sdRNAi) directed against USP-10 including a first synthetic nucleic acid having at least 90% sequence identity to SEQ ID NO: 2, 4, 6, 8, 10, 12, 14, 16, 18, or 20. In embodiments, the first synthetic nucleic acid has at least 95% sequence identity to SEQ ID NO: 2, 4, 6, 8, 10, 12, 14, 16, 18, or 20. In embodiments, the first synthetic nucleic acid has at least 99% sequence identity to SEQ ID NO: 2, 4, 6, 8, 10, 12, 14, 16, 18, or 20. In embodiments, a self-deliverable siRNA (sdRNAi) directed against USP-10 further includes a second synthetic nucleic acid having at least 90% sequence identity to SEQ ID NO: 1, 3, 5, 7, 9, 11, 13, 15, 17, or 19. In embodiments, the second synthetic nucleic acid has at least 95% sequence identity to SEQ ID NO: 1, 3, 5, 7, 9, 11, 13, 15, 17, or 19. In embodiments, the second synthetic nucleic acid has at least 99% sequence identity to SEQ ID NO: 1, 3, 5, 7, 9, 11, 13, 15, 17, or 19. In embodiments, the self-deliverable siRNA (sdRNAi) directed against USP-10 is double stranded. In embodiments, the self-deliverable siRNA (sdR-NAi) directed against USP-10 is characterized as cholesterol-tagged. In embodiments, the self-deliverable siRNA (sdRNAi) directed against USP-10 is characterized as asymmetrical. In embodiments, compositions directed against USP10 may decrease, fully or substantially eliminate an upregulation of USP10 after wounding.

In embodiments, the present disclosure provides a self-deliverable siRNA (sdRNAi) directed against USP-10, including: a first synthetic nucleic acid having at least 90% sequence identity to SEQ ID NO: 2, 4, 6, 8, 10, 12, 14, 16, 18, or 20; and a second synthetic nucleic acid having at least 90% sequence identity to SEQ ID NO: 1, 3, 5, 7, 9, 11, 13, 15, 17, or 19, wherein the first synthetic nucleic acid is hybridized to the second synthetic nucleic acid. In embodiments, the first synthetic nucleic acid is complementary to the second synthetic nucleic acid, such as substantially (i.e., 80% or more) or 100% complementary. In embodiments, the first synthetic nucleic acid comprises or consists of 20 nucleotides, and wherein the second synthetic nucleic acid comprises or consists of about 15 nucleic acids. In embodiments, the self-deliverable siRNA (sdRNAi) directed against USP-10 is characterized as asymmetrical. In embodiments, the self-deliverable siRNA (sdRNAi) directed against USP-10 is characterized as cholesterol-tagged.

In embodiments, the present disclosure provides a composition including a self-deliverable siRNA (sdRNAi) directed against USP-10, and a pharmaceutically acceptable carrier. In embodiments, the present disclosure provides a composition including a siRNA (sdRNAi) directed against USP-10, and a pharmaceutically acceptable carrier. In embodiments, the composition is formulated for topical administration, local administration into fibrotic tissue, an intravitreal route, or transcleral route.

In embodiments, the present disclosure provides a method of eliminating or reducing ocular scarring in an eye of a subject after an ocular wound including administering to the ocular wound a therapeutically effective amount of a self-deliverable siRNA (sdRNAi) directed against USP-10 to fully or substantially eliminate an upregulation of USP10 after wounding. In embodiments, the sdRNAi is US09. In embodiments, the ocular scarring occurs on a cornea. In embodiments, the sdRNAi is a fully modified asymmetric siRNA conjugated to cholesterol. In embodiments, the sdR-NAi is administered one-time. In embodiments, the sdRNAi is modified with vinyl-phosphonate. In embodiments, the present disclosure includes a method of eliminating or reducing ocular scarring in an eye of a subject after an ocular wound including administering to the ocular wound a therapeutically effective amount of a self-deliverable siRNA (sdRNAi) directed against USP-10 to decease an upregulation of USP10 after wounding. In embodiments, upregulation of USP10 is decreased 10-90 times, 20-75 times, of 30-50 times. In embodiments, compositions directed against USP10 may decrease, fully or substantially eliminate an upregulation of USP10 after wounding.

In embodiments, the present disclosure includes a method of eliminating or reducing ocular scarring in an eye of a subject after an ocular wound including administering to the ocular wound a therapeutically effective amount of a self-deliverable siRNA (sdRNAi) directed against USP-10 to fully or substantially knockdown USP10 after wounding. In embodiments, the present disclosure includes a method of eliminating or reducing ocular scarring in an eye of a subject after an ocular wound including administering to the ocular wound a therapeutically effective amount of a self-deliverable siRNA (sdRNAi) directed against USP-10 to decrease upregulation of USP10 after wounding. In embodiments, upregulation of USP10 is decreased 10-90 times, 20-75 times, of 30-50 times.

In some embodiments, the present disclosure relates to a method for accelerating wound closure in an eye of a subject after an ocular wound including administering to the wound a therapeutically effective amount of a self-deliverable siRNA (sdRNAi) directed against USP-10 to fully or substantially eliminate an upregulation of USP10 after wounding. In some embodiments, the present disclosure relates to a method for accelerating wound closure in an eye of a subject after an ocular wound including administering to the wound a therapeutically effective amount of a self-deliverable siRNA (sdRNAi) directed against USP-10 to decrease an upregulation of USP10 after wounding. In embodiments, upregulation of USP10 is decreased 10-90 times, 20-75 times, of 30-50 times.

In embodiments, the present disclosure provides a method for suppressing a production of fibrotic markers in a tissue after a wound or immune response in an eye of a subject after an ocular wound, including: administering to the wound a therapeutically effective amount of a self-deliverable siRNA (sdRNAi) directed against USP-10 to fully or substantially eliminate an upregulation of USP10 after wounding. In embodiments, the present disclosure provides a method for suppressing a production of fibrotic markers in a tissue after a wound or immune response in an eye of a subject after an ocular wound, including: administering to the wound a therapeutically effective amount of a self-deliverable siRNA (sdRNAi) directed against USP-10 to decrease an upregulation of USP10 after wounding. In embodiments, upregulation of USP10 is decreased 10-90 times, 20-75 times, of 30-50 times.

In embodiments, the present disclosure provides a method of eliminating or reducing fibrosis of a subject after a tissue wound including administering to the tissue wound a therapeutically effective amount of a self-deliverable siRNA (sdRNAi) directed against USP-10 to fully or substantially knockdown USP10 after wounding. In embodiments, the present disclosure provides a method of eliminating or reducing fibrosis of a subject after a tissue wound including administering to the tissue wound a therapeutically effective amount of a self-deliverable siRNA (sdRNAi) directed against USP-10 to decrease or knockdown USP10 after wounding. In embodiments, USP10 is decreased 10-90 times, 20-75 times, of 30-50 times.

In embodiments, the present disclosure provides a method of eliminating or reducing fibrosis within a subject after a tissue wound including administering to the tissue wound a therapeutically effective amount of a self-deliverable siRNA (sdRNAi) directed against USP-10 to fully or substantially eliminate an upregulation of USP10 after wounding. In embodiments, the present disclosure provides a method of eliminating or reducing fibrosis within a subject after a tissue wound including administering to the tissue wound a therapeutically effective amount of a self-deliverable siRNA (sdRNAi) directed against USP-10 to decrease an upregulation of USP10 after wounding.

In embodiments, the present disclosure provides a method of eliminating or reducing scarring in the skin of a subject after a skin wound, including: administering to the skin wound a therapeutically effective amount of a self-deliverable siRNA (sdRNAi) directed against USP-10 to fully or substantially eliminate an upregulation of USP10 after wounding. In embodiments, the present disclosure provides a method of eliminating or reducing scarring in the skin of a subject after a skin wound, including: administering to the skin wound a therapeutically effective amount of a self-deliverable SIRNA (sdRNAi) directed against USP-10 to decrease an upregulation of USP10 after wounding. In embodiments, the skin wound is trauma induced. In embodiments, the skin wound is made by a surgical incision, or surgical trauma. In embodiments, compositions directed against USP10 may decrease, fully or substantially eliminate an upregulation of USP10 after wounding.

The following examples illustrate certain aspects of the invention and should not be construed as limiting the scope thereof.

EXAMPLES

Example I

To understand the different functions of USP10 in wound healing, an in vivo knockdown was performed using self-deliverable RNAi technology (sdRNAi). This approach is based on the use of fully modified asymmetric siRNA conjugated to cholesterol. These cholesterol-siRNA conjugates do not require any formulation (e.g. lipids or nanoparticles) for delivery to cells and can transfect all cell types in vitro and in vivo. (See e.g., Khvorova, A, and Watts, J K (2017). The chemical evolution of oligonucleotide therapies of clinical utility. *Nat Biotechnol* 35:238-248).

The in vivo use of the self-deliverable cholesterol conjugates is especially efficient in combination with a local delivery (See e.g., Alterman et al. (2015). Hydrophobically Modified siRNAs Silence Huntingtin mRNA in Primary Neurons and Mouse Brain. *Mol Ther Nucleic Acids* 4: e266; and Byrne et al. (2013). Novel hydrophobically modified asymmetric RNAi compounds (sd-rxRNA) demonstrate robust efficacy in the eye. *J Ocul Pharmacol Ther* 29:855-864) as demonstrated in the cornea. The use of the first generation of partially modified siRNA-cholesterol conjugates demonstrated efficient and prolonged knock-down efficacy in the eye. Since full backbone modification of sdRNAs significantly enhances their in vivo activity, (See e.g., Hassler, M R, Turanov, A A, Alterman, J F, Haraszti, R A, Coles, A H, Osborn, M F, et al. (2018). Comparison of partially and fully chemically-modified siRNA in conjugate-mediated delivery in vivo. *Nucleic Acids Res* 46:2185-2196) a fully modified sdRNA was created targeting rabbit USP10. These sdRNAs are resistant to nucleases, can be delivered to target tissues by a selection of the appropriate ligand and demonstrate in vivo efficacy for months after a single treatment. Here it is demonstrated that a one-time dosing of sdRNA targeting USP10 in rabbits was sufficient to significantly reduce scarring after wounding.

The data demonstrates that knockdown of USP10 after wounding in healthy tissue significantly reduces apoptosis and subsequent immune cell infiltration. Together these data suggest that USP10 is a central regulator of integrin and apoptotic functions.

Summary of Example I

Ocular scarring after surgery, trauma, or infection leads to vision loss. The transparent cornea is an excellent model system to test anti-scarring therapies. Cholesterol-conjugated fully modified asymmetric siRNAs (self-deliverable siRNAs, sdRNAs) are a novel modality for in vivo gene knockdown, transfecting cells and tissues without any additional formulations. Myofibroblasts are a main contributor to scarring and fibrosis. Alpha-v integrins play a central role in myofibroblast pathological adhesion, over-contraction, and TGFβ activation. αv integrins are protected from intracellular degradation after wounding by upregulation of the deubiquitinase USP10, leading to integrin cell surface accumulation. Here, knockdown of USP10 with a USP10-targeting sdRNA (termed US09) was tested to see if it will reduce scarring after wounding a rabbit cornea in vivo. The wounded corneal stroma was treated once with US09 or non-targeting control sdRNA (NTC). At six weeks US09 treatment resulted in faster wound closure, limited scarring, and suppression of fibrotic markers and immune response. Specifically, Fibronectin-EDA, Collagen III, and α-smooth muscle actin (p<0.05), CD45+ cell infiltration (p<0.01) and apoptosis at 24 hours (p<0.01) and 48 hours (p<0.05) were reduced post-wounding. Corneal thickness and cell proliferation were restored to unwounded parameters. Targeting the DUB, USP10 is a novel strategy to reduce scarring. See e.g., Boumil, et al., USP-10 Targeted Self-Deliverable siRNA to Prevent Scarring in the Cornea, Molecular Therapy Nucleic Acids, Vol. 21, p1029-1043 (2020) (herein entirely incorporated by reference).

Results

Identifying USP10 Targeting siRNA for In Vivo Rabbit Studies

Figure 1A:
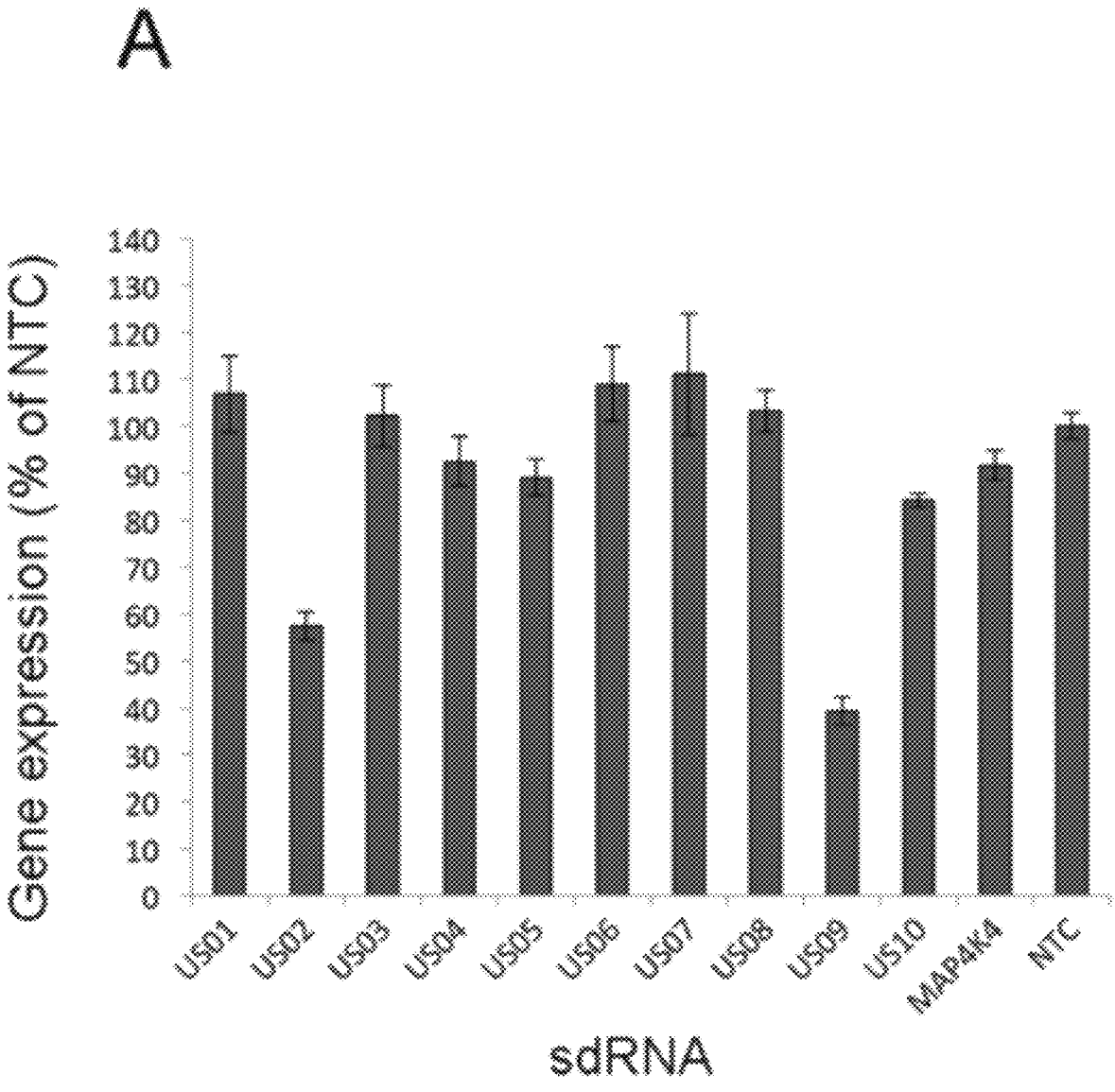
Figure 1C:
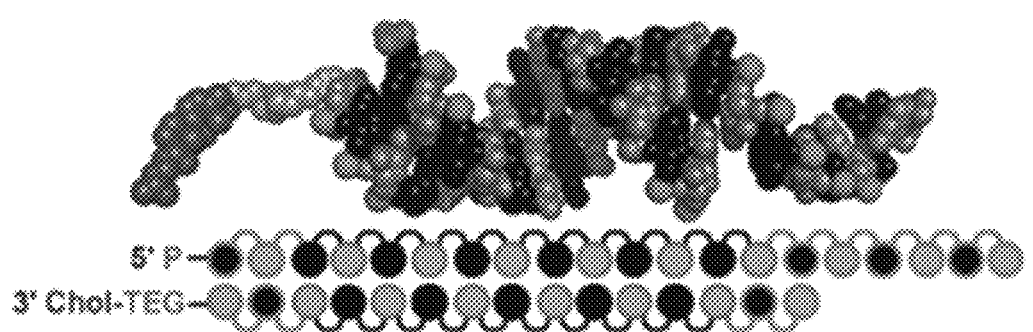
Figure 1D:
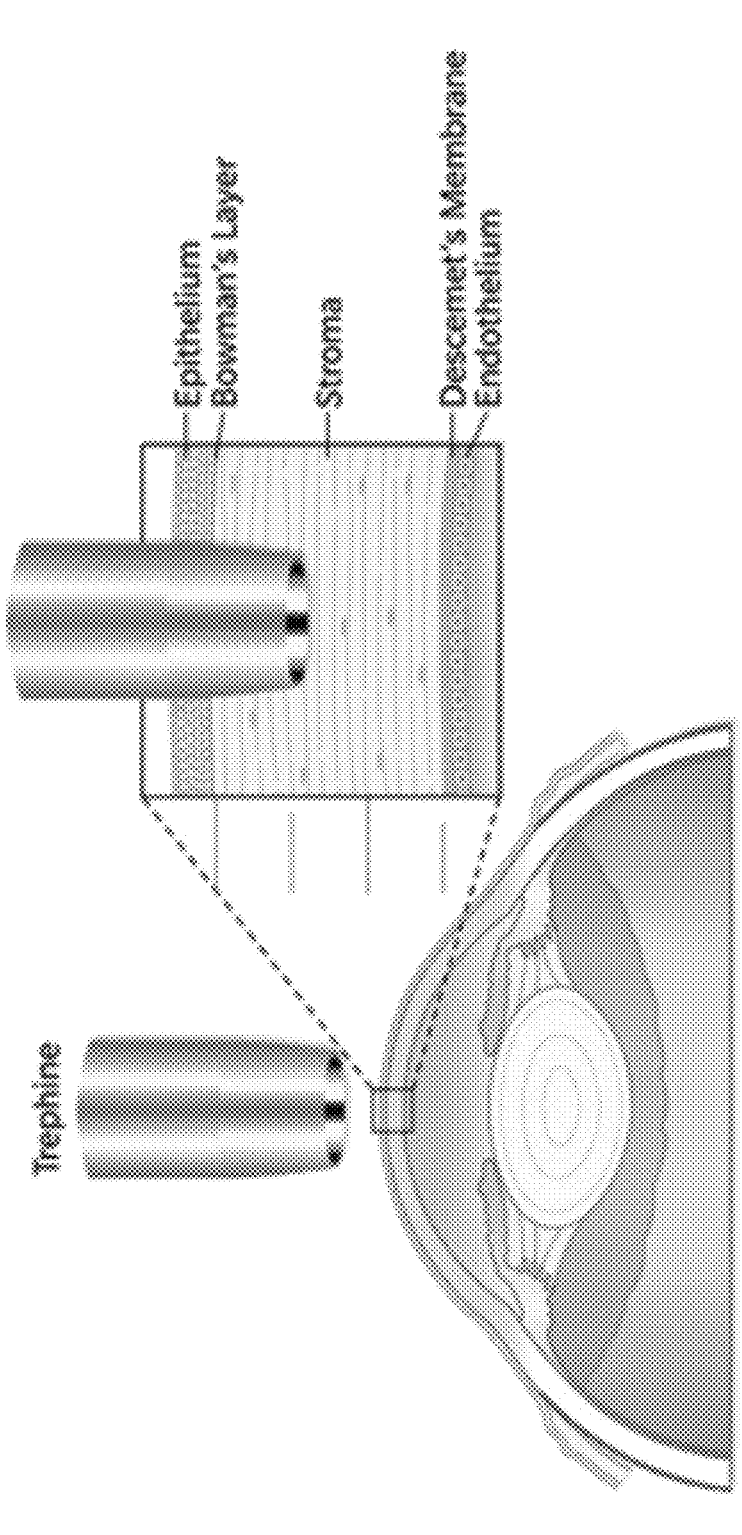

Since the public RefSeq database contained only computationally-predicted rabbit USP10 sequence, the rabbit cornea was sequenced. The resulting common "consensus" sequence for rabbit was used for sdRNA design (see Methods, Genbank MN927131). The USP10 targeting siRNA compound was selected from 10 lead candidates identified by an in silico prediction algorithm. (See e.g., Shmushkovich, et al. (2018). Functional features defining the efficacy of cholesterol-conjugated, self-deliverable, chemically modified siRNAs. Nucleic Acids Res 46:10905-10916). sdRNAs were produced and screened for knockdown of rabbit USP10 by qPCR. Of the ten, the sdRNA compound named US09 demonstrated the most effective knockdown in primary rabbit corneal fibroblasts (RCF), (See FIG. 1A). Dose response curves up to 2 $\mu$M for the best two compounds, US02 and US09, are presented in FIG. 15. More specifically, FIG. 15 depicts where primary rabbit corneal fibroblasts were treated with 0.016 nM-2.0 nM of US02, US09, and NTC (non-targeting control) for 72 hours, and USP 10 expression was analyzed by qPCR. Rabbit GAPDH served as a reference gene. Knockdown efficiency was expressed as the percentage of NTC. FIG. 1B demonstrates the efficacy of non-targeting control sdRNA (NTC) for entry into RCF (labeled with cy3, top), in contrast to non-labeled NTC which cannot be visualized (bottom). The general structure of sdRNA embodiments is depicted in FIG. 1C. For these in vivo studies US09 additionally modified with vinyl-phosphonate was used to increase the longevity of the effect. (See e.g., Haraszti, et al. (2017). 5-Vinylphosphonate improves tissue accumulation and efficacy of conjugated siRNAs in vivo. Nucleic Acids Res 45:7581-7592). Depicted in FIG. 1D is the wounding strategy. To wound the cornea, a 6 mm trephine is placed in the central rabbit cornea. A subtle twisting back and forth of the trephine demarcates a circular boundary and cuts through the anterior ⅓ of the cornea into the stroma, depicted in FIG. 1D. (See Castro, N, Gillespie, S R, and Bernstein, A M (2019). Ex Vivo Corneal Organ Culture Model for Wound Healing Studies. J Vis Exp.). The demarcated tissue is removed and the bare stroma is treated with 1 nmol US09 or 1 nmol NTC (5.6 ul of sdRNA diluted in PBS is directly pipetted onto the stroma).

Biomicroscopy slit lamp was performed on days 1,2,3 and 7 after wounding. US09 (Wnd-US09) promoted wound closure faster than NTC (Wnd-NTC). By day 2 there was an increase in wound closure with US09 treatment (p<0.01) that was significant at each day tested (p<0.05). By day 7 the US09-treated corneas were qualitatively clear compared to NTC treatment (See FIG. 1E and FIG. 1F).

Figure 10B:
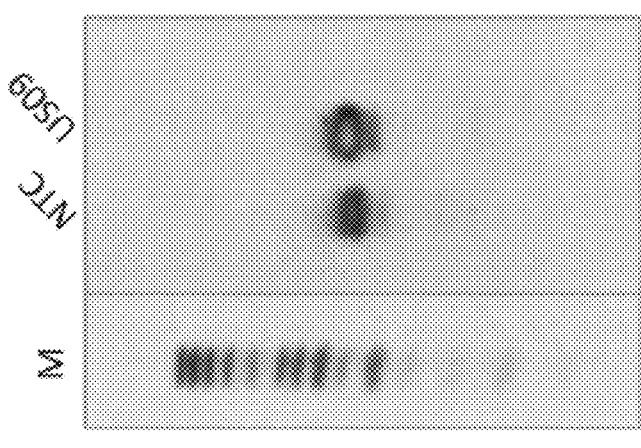
FIGS. 10A-10B depict electrophoretic gels in accordance with the present disclosure, wherein the annealed duplexes were analyzed in the native gel electrophoresis. Duplexes were mixed with 5× TBE high-density sample buffer (Novex) and loaded in the TBE 4-20% gradient gels at 10 μmol per lane. Samples were fractionated at 150V and stained with SybrGold dye (ThermoFisher) for 10 min at RT. As a reference (M), 10 nt-100 nt Low Molecular Weight Marker (Affimetrix) was used. Duplexes were formed in all the samples.
Figure 10A:
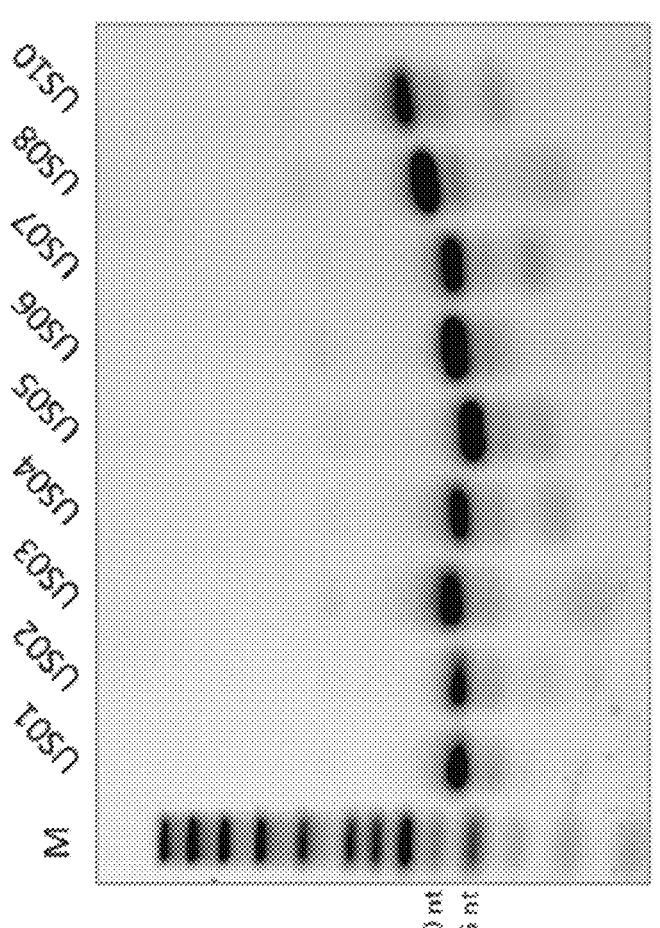

To test the ability of the sd-RNA to penetrate the wounded cornea, after nucleation of unwounded eyes from rabbits, the globes were wounded with a trephine as described above and corneas were excised and mounted on a collagen base. One nmol of non-targeting cy3-labled sdRNA (in 5.6 ul) was pipetted into the wounded stroma. Images were taken immediately at "time zero" on a dissecting scope, maintaining the sterility of the corneas. At two hours, corneas were imaged by live cell confocal microscopy and also at 24, 48, 72, and 168 (7 days). Corneas were returned to the incubator, 5% $CO_2$, 37° C., in between imaging time points. Corneas were wet with conditioned media daily. Media was changed every 48 hours without additional treatment of cy3-sdRNA. The cy3-sdRNA penetrated the bare stroma to 324 $\mu$m by 24 hr. Total depth of rabbit cornea is approximately 407 $\mu$m. (See e.g., Chan, T, Payor, S, and Holden, B A (1983). Corneal thickness profiles in rabbits using an ultrasonic pachometer. Invest Ophthalmol Vis Sci 24:1408-1410). By 48 hr the depth of the dye retreated to an average of 24 $\mu$m and remained at that depth until the final assay point of 7 days. Referring to FIGS. 10A and 10B, annealed duplexes were analyzed in the native gel electrophoresis. Duplexes were mixed with 5× TBE high-density sample buffer (Novex) and loaded in the TBE 4-20% gradient gels at 10 $\mu$mol per lane. Samples were fractionated at 150V and stained with Sybr-Gold dye (ThermoFisher) for 10 min at RT. As a reference (M), 10 nt-100 nt Low Molecular Weight Marker (Affimetrix) was used. Duplexes were formed in all the samples.

Figure 1E:
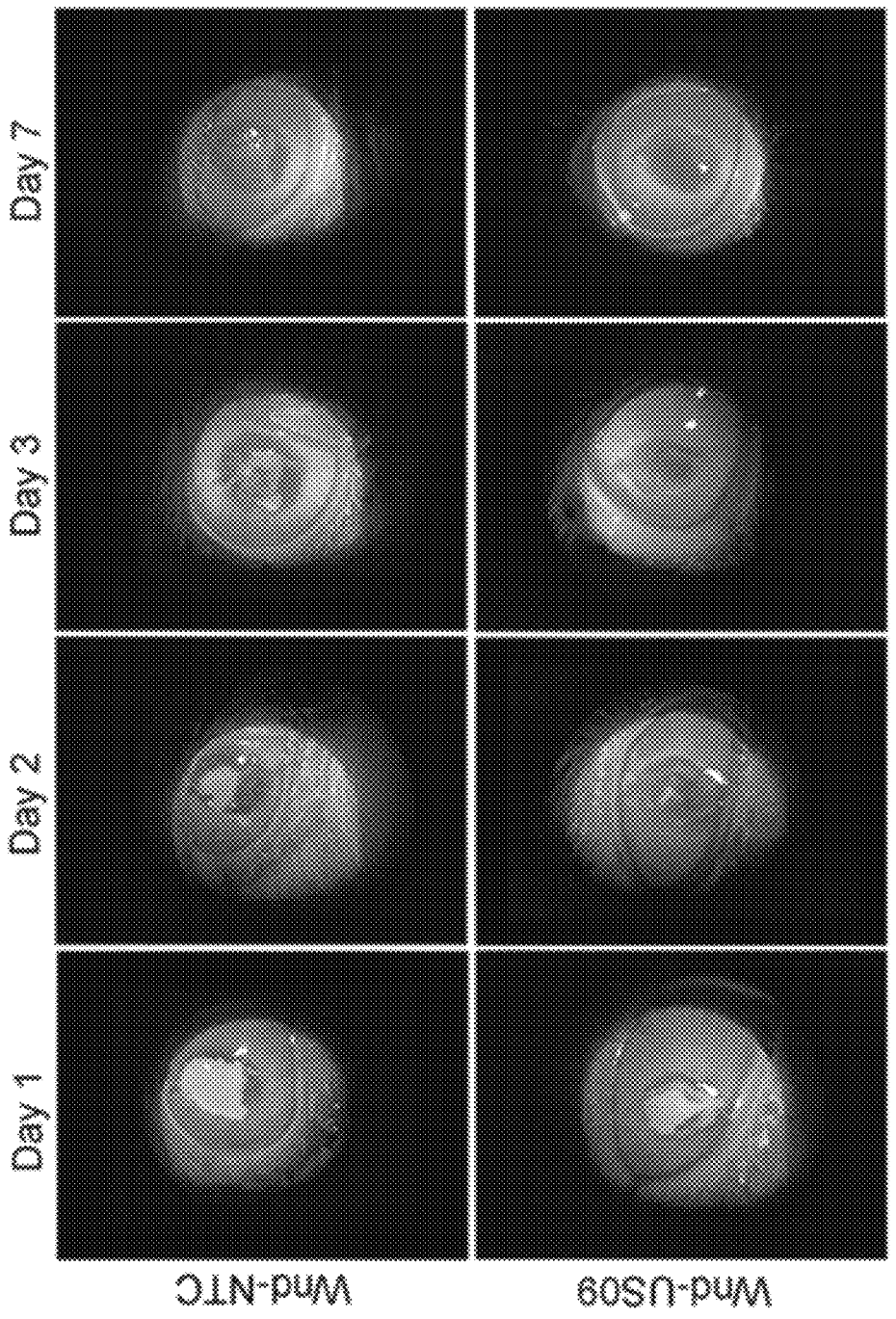
Figure 1F:
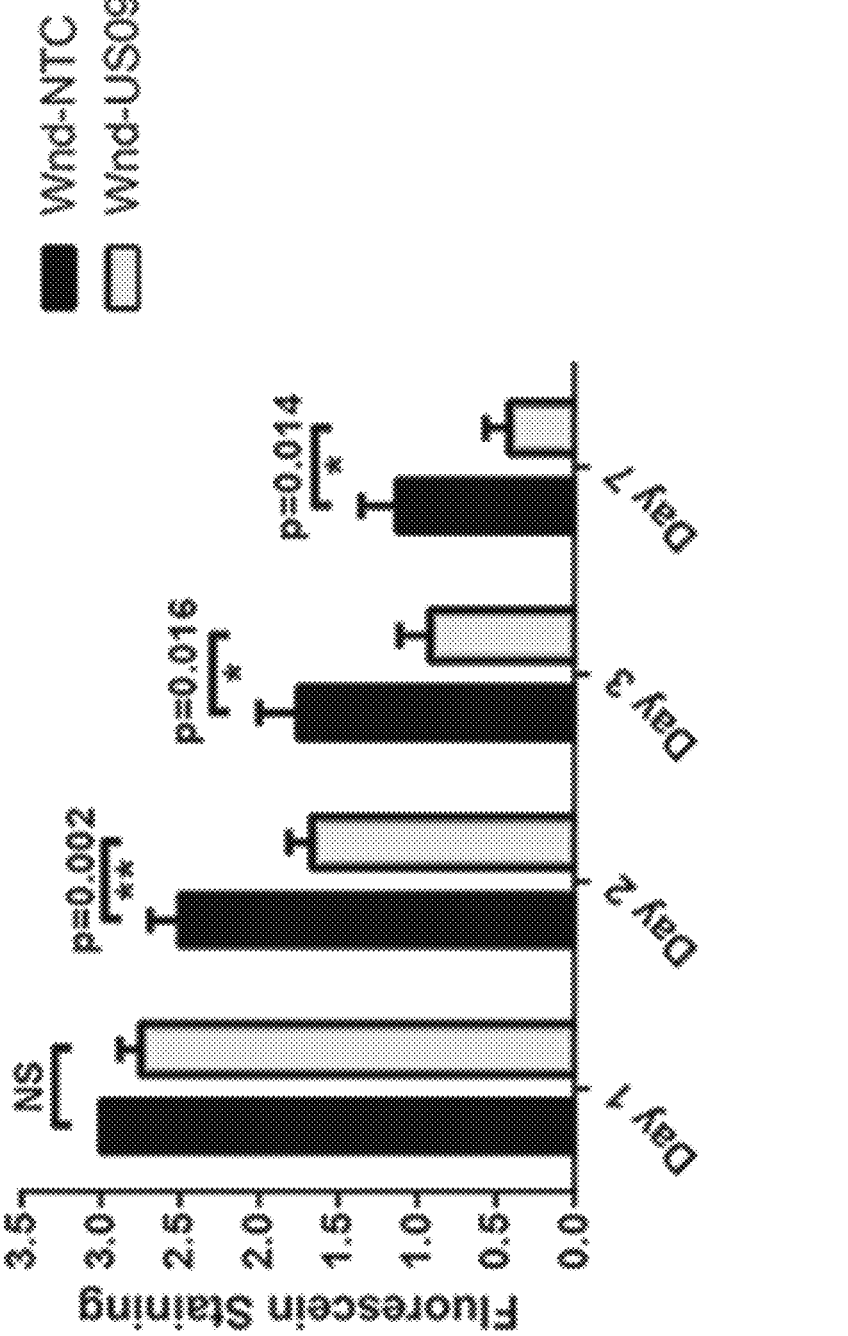

More specifically, referring to FIGS. 1A-1F, USP10 sdRNA screening and in vivo corneal wounding is depicted. FIG. 1A depicts primary rabbit corneal fibroblasts that were treated with 1 uM of each sdRNA for 72 hours, and USP10 expression was analyzed by qPCR. Rabbit GAPDH served as a reference gene. Knockdown efficiency was expressed as the percentage of non-targeting control (NTC). Referring to FIG. 1B, FIG. 1B depicts delivery of non-targeting cy3-labeled sdRNA (MAP4K4-cy3 0.25 uM) into primary rabbit corneal fibroblasts demonstrating efficient cellular uptake. Control cells were treated with the same dose of unlabeled NTC. Cells were then stained with nuclear dye Hoechst 33342 and recorded in EVOS FL imaging system (ThermoFisher Scientific). FIG. 1C depicts sdRNAs embodiments as asymmetric siRNAs, including a 20-nucleotide antisense strand and a 15-nucleotide sense strand, in which all nucleotides are either 2'F or 2'Ome modified. In embodiments, the 3' terminal backbone is phosphorothioated (six linkages in antisense and two in sense). In embodiments, the 3' end of the sense strand is conjugated to cholesterol. FIG. 1D depicts a corneal wounding strategy. The human cornea is composed of 5 main layers, epithelium, Bowman's membrane, stroma, Decement's membrane, and endothelium. Using a cylindrical blade called a trephine, a wound is made through ⅓ of the anterior portion of the cornea. The tissue within the trephine cut is excised with a blade and forceps. The bare stroma is treated with sdRNA. FIG. 1E depicts wound closure assessed by slit lamp. Wounded eyes treated with NTC (Wnd-NTC) or US09 (Wnd-US09) were treated with fluorescein drops and imaged by slit lamp on days 1,2,3, and 7 post-wounding. Images were analyzed for wound closure and rated from 0-3 (healed: no fluorescein to least healed: greatest fluorescein). FIG. 1F depicts wound closure was faster in Wnd-US09 compared to Wnd-NTC on days 2 (p<0.01), 3 (p<0.05) and 7 (p<0.05). N=6 rabbits per condition.

Figure 9A:
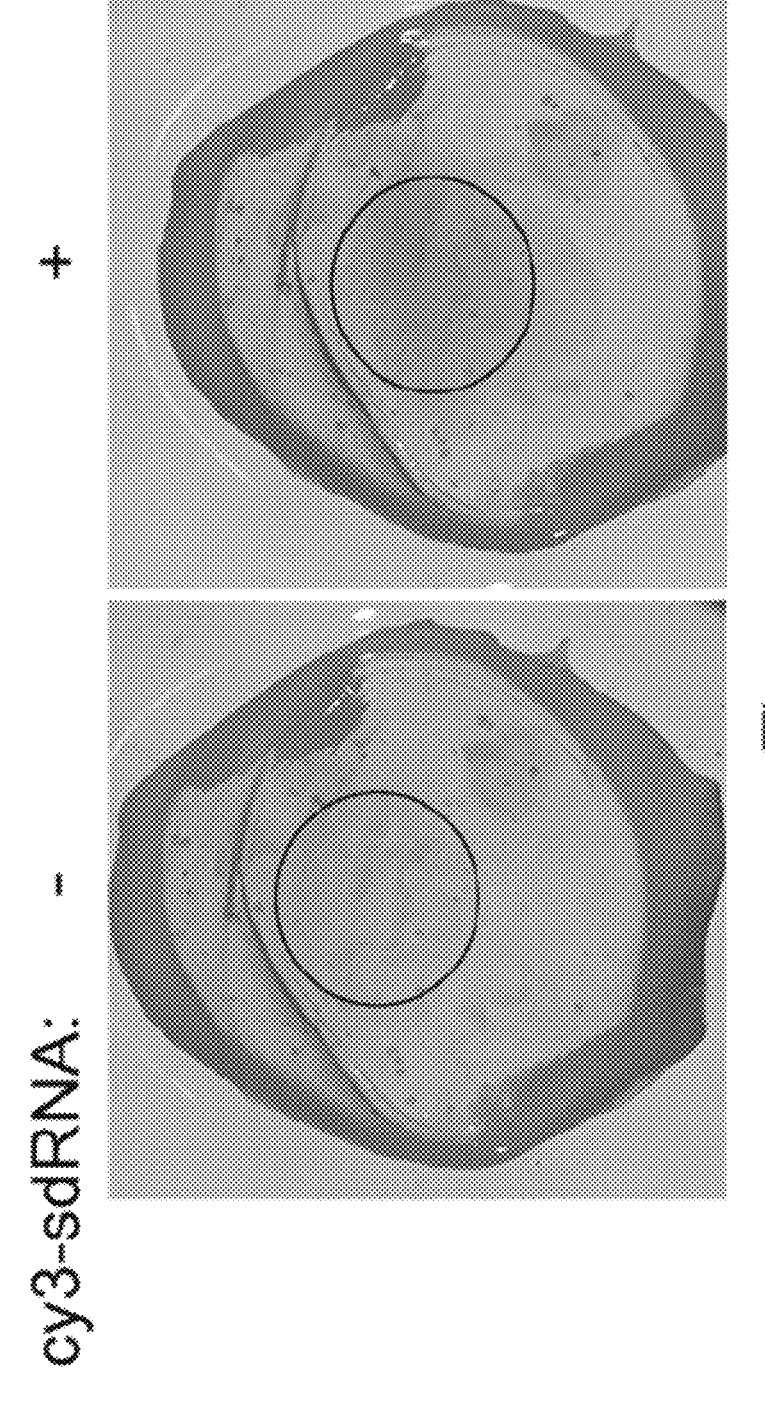
FIGS. 9A-9C depict cornea analysis in accordance with the present disclosure.
Figure 9B:
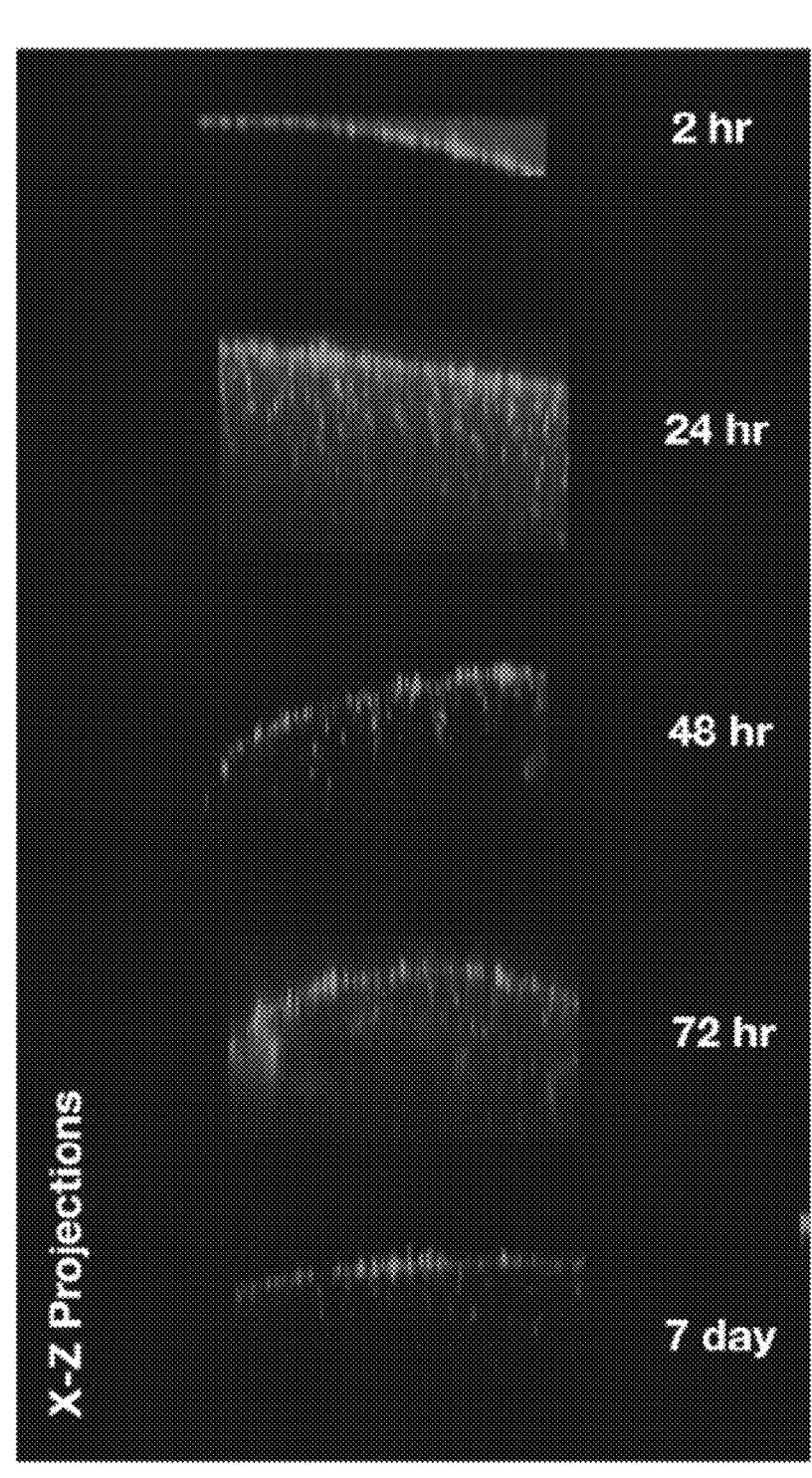
Figure 9C:
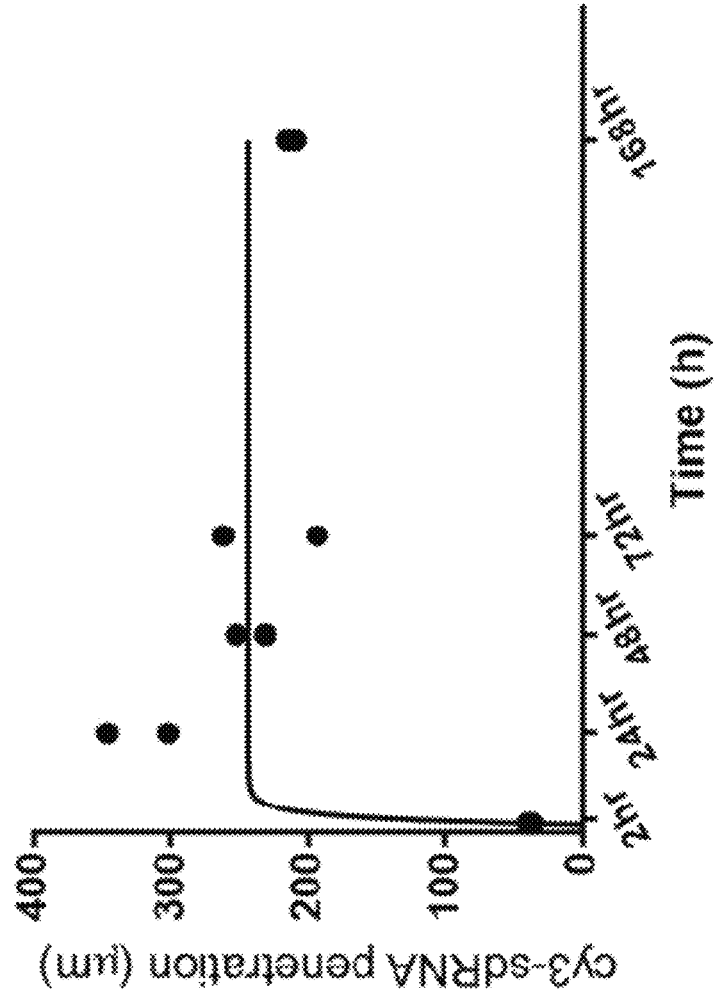

More specifically referring to FIGS. 9A-9C, eyes were enucleated from euthanized rabbits and wounded with a trephine as described in methods. Approximate circular cut is demarcated with a black circle. Corneas were excised keeping the limbus and ½ cm of sclera. Corneas were mounted on agar base as previously described for an ex vivo corneal wound healing assay. FIG. 9A depicts one nmol cy3-sdRNA in 5.6 $\mu$l was pipetted into the wound. The image was captured on a dissecting scope (Accu-scope) directly after application of the sdRNA. FIG. 9B depicts corneas were mounted on agar and cultured for 1 week. Z-stack images were captured on a Zeiss LSM780 live cell confocal at 2 hr, 24 hr, 48 hr, 72 hr, 168 hr (7 days). FIG. 9C depicts graphed data points demonstrating depth of cy3-labeled sdRNA. N=2.

Quantitative Analysis of Corneal Scarring by Optical Coherence Tomography

Figure 2B:
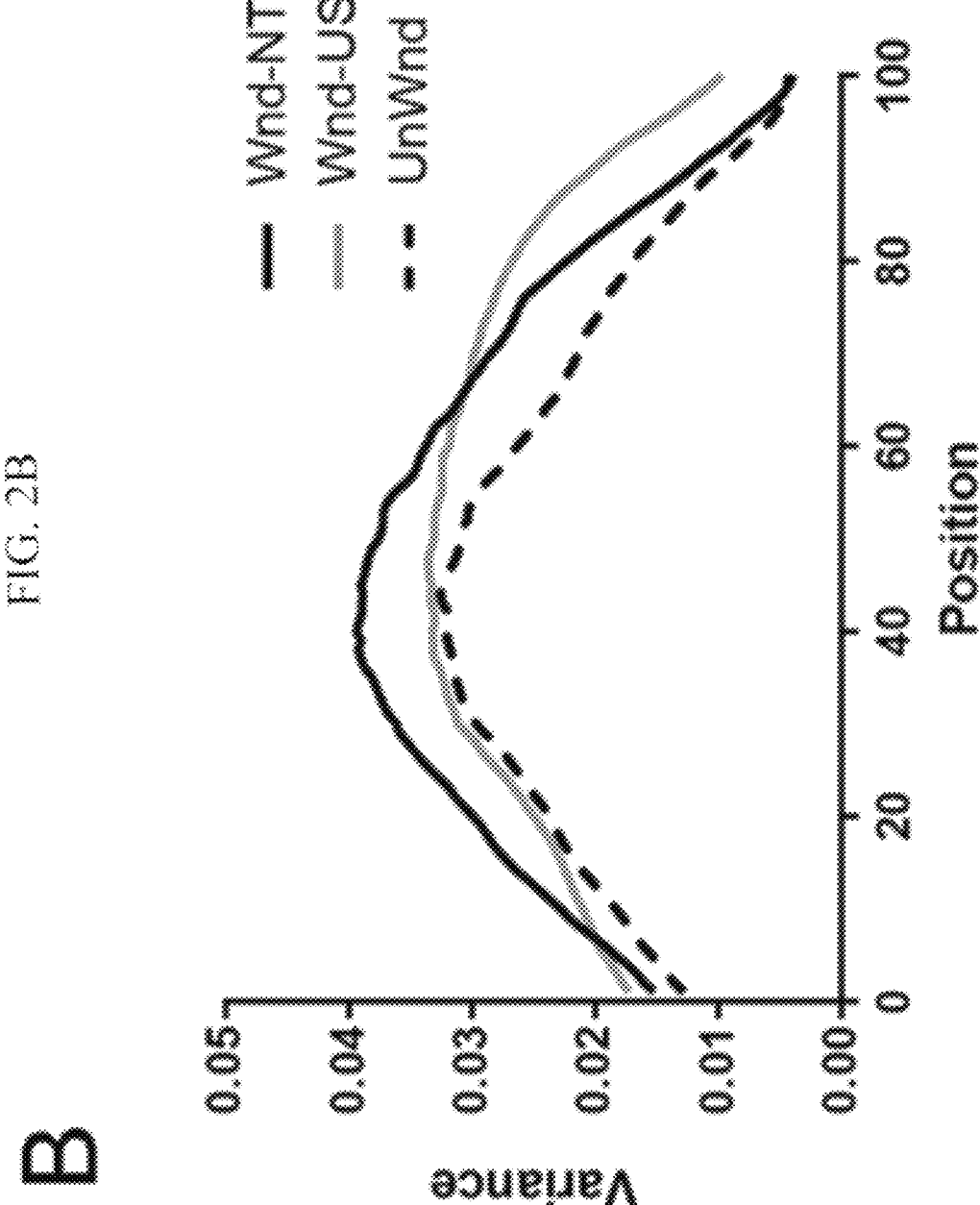
Figure 2C:
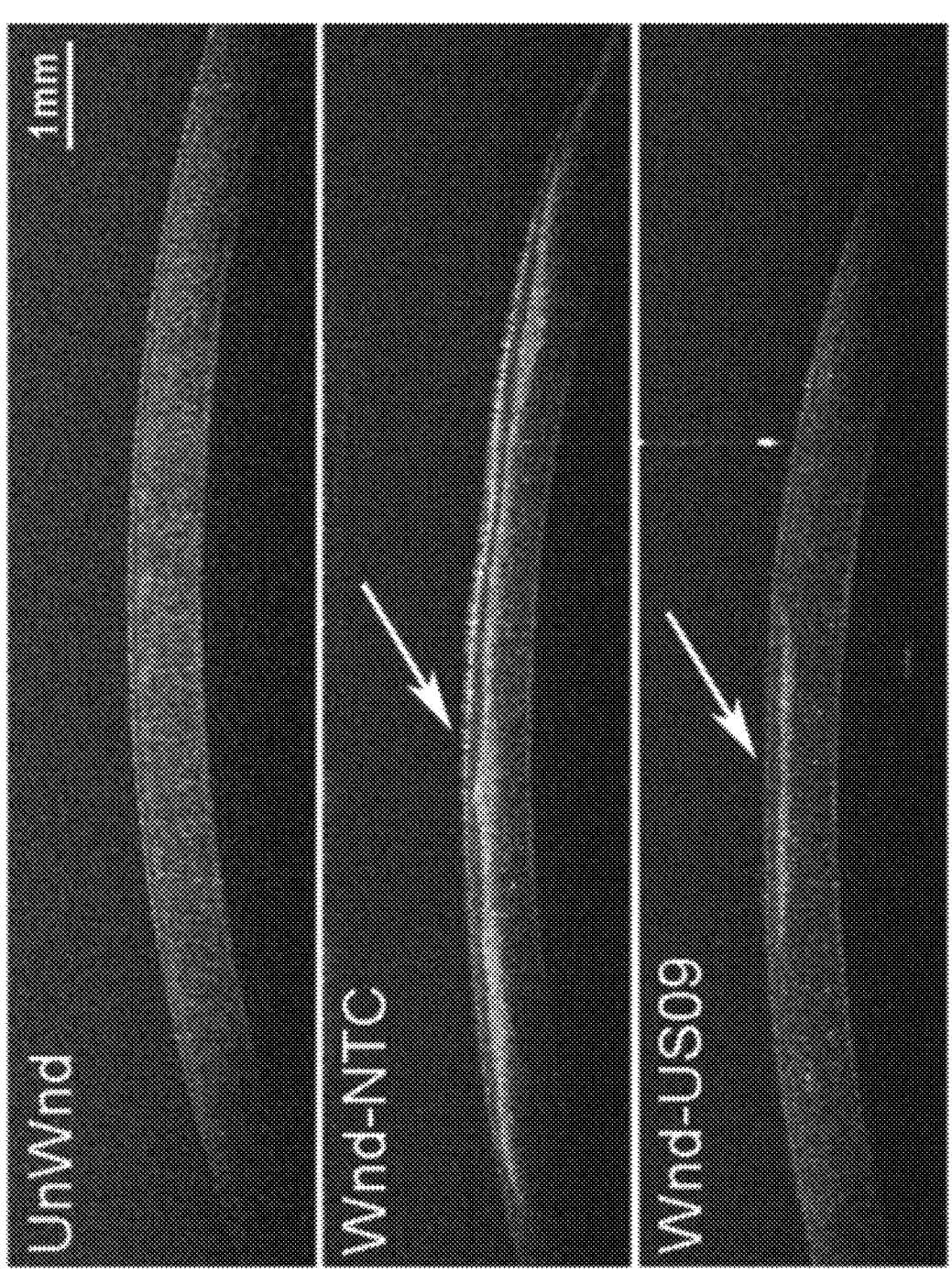
Figure 2D:
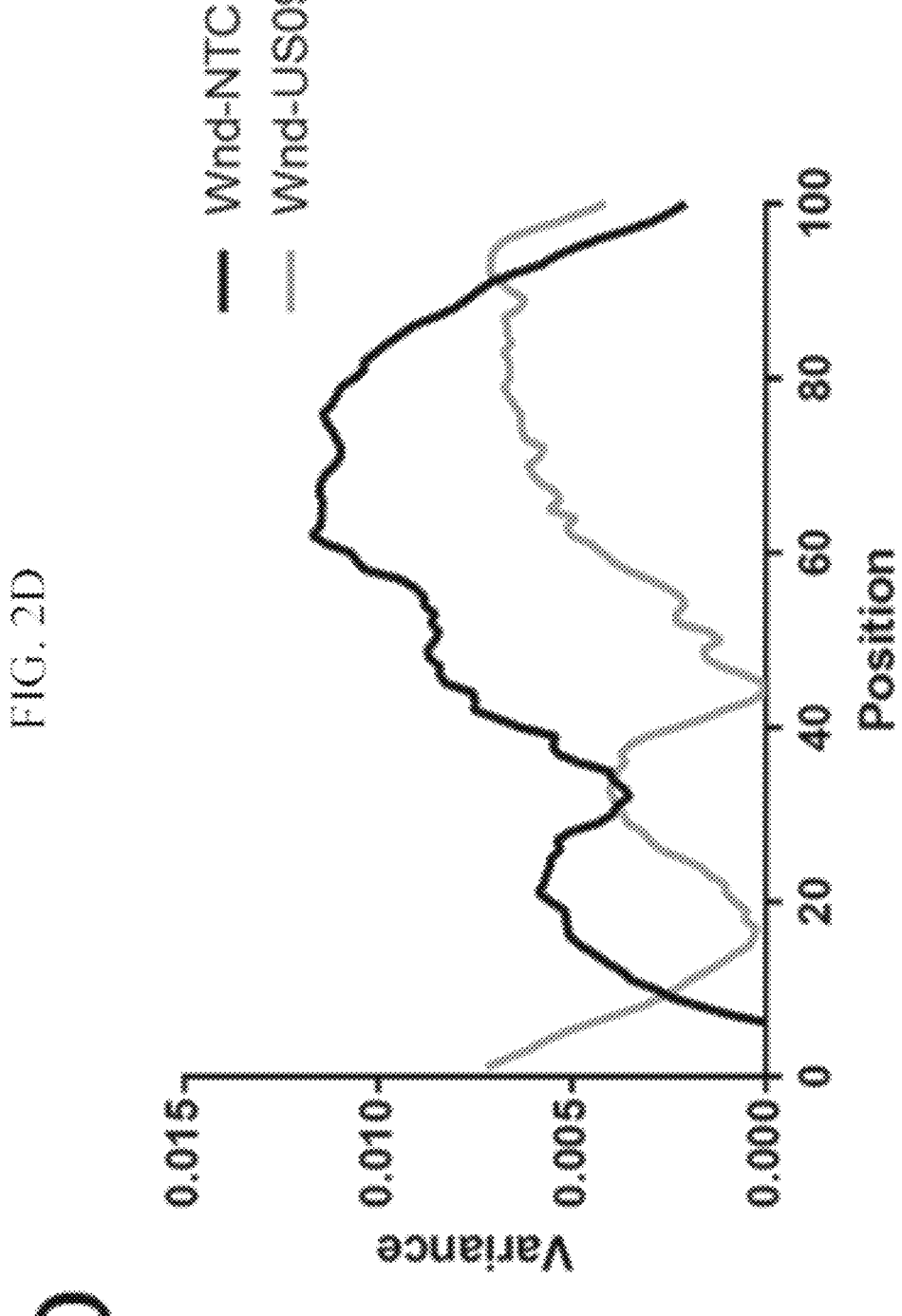

After six weeks, to quantify scarring, OCT images were analyzed for the variance of pixel intensities in the 6 mm wounded section of the cornea. Aberrations in cornea (e.g. scarring) increase non-uniformity of pixel intensities in localized areas of the cornea. To quantify this non-uniformity, the cornea in each image file was segmented into 100 equal parts (FIG. 2A). For each segment the statistical variance (ie. [st dev]$^2$) of pixel intensities was calculated. This yields 100 variances for each transverse section. Transverse sections from a dataset are averaged yielding a two-dimensional "Variance by Position" plot that was averaged for all animals in each group (FIG. 2B). OCT images of UnWnd, Wnd-NTC, and Wnd-US09 eyes are shown in FIG. 2C. Next, UnWnd variance was subtracted from Wnd-NTC and Wnd-US09 to yield a clearer model of variance between the two treatments (FIG. 2D). Finally, all points were reduced to the Mean Variance, which demonstrated a 41.5% decrease in scarring in Wnd-US09 corneas compared to Wnd-NTC (FIG. 2E).

Figure 2E:
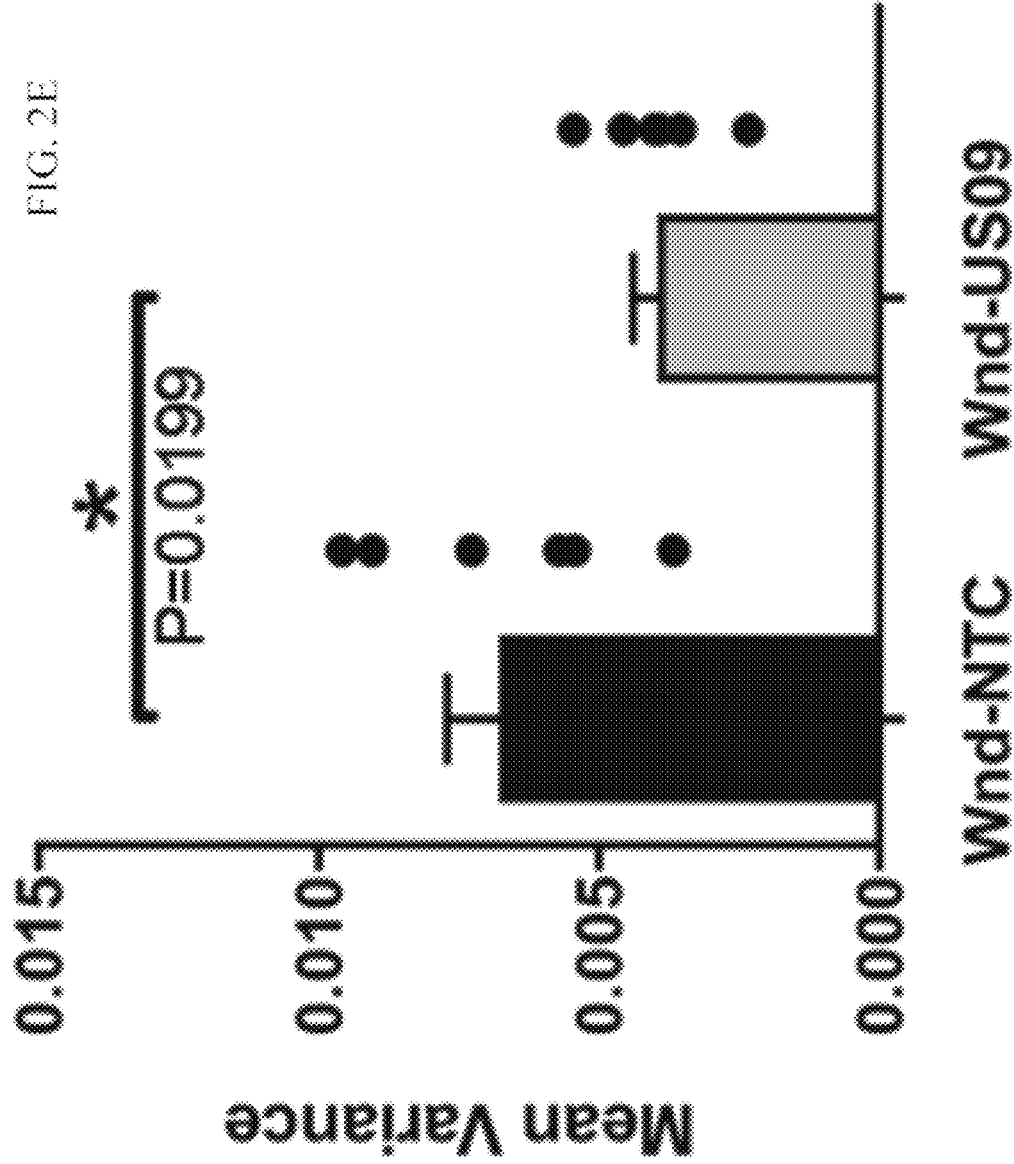

More specifically, FIGS. 2A-2E depict a quantitative analysis after wounding by OCT. At six weeks after wounding, rabbits were imaged by OCT after sedation and prior to sacrifice. 6 mm×6 mm images were captured. FIG. 2A depicts a representation of how images were partitioned into 100 optical slices in Matlab. FIG. 2B depicts the variance in each of 100 sections were quantified and averaged for all 6 animals (black: Wnd-NTC, grey: Wnd-US09, dotted line: UnWnd). FIG. 2C depicts OCT images for each condition. Arrow denotes scar. Bar=1 mm. FIG. 2D depicts variance, unwounded was subtracted from both Wnd-NTC and Wnd-US09). FIG. 2E depicts all points in both conditions were averaged to create the Mean Variance (total of 10,000 points per rabbit, six rabbits per condition). US09 promotes a 41.5% reduction in scarring (p<0.05).

Immunohistochemistry for Fibrotic Markers

After OCT analysis, rabbits were sacrificed and eyes were enucleated. The cornea was excised from the globe and cut in half through the wound. Half the cornea was frozen for sectioning and the other half was used for qPCR. In that half, the wounded portion was separated from the peripheral unwounded corneal tissue and RNA was extracted.

To assess the protein expression of classic fibrotic markers, frozen sections were immunostained for Collagen III, Fibronectin-EDA (FN-EDA, also termed cellular FN) and α-SMA, all key markers of scarring. (See e.g, Karamichos, D, Guo, X Q, Hutcheon, A E, and Zieske, J D (2010). Human corneal fibrosis: an in vitro model. *Invest Ophthalmol Vis Sci* 51:1382-1388; and Lorenzo-Martin, E, Gallego-Munoz, P, Mar, S, Fernandez, I, Cidad, P, and Martinez-Garcia, MC (2019). Dynamic changes of the extracellular matrix during corneal wound healing. *Exp Eye Res* 186:107704). For Collagen III, compared to unWnd, Wnd-NTC demonstrated a 276.2-fold increase in Collagen III immunostaining (p<0.01) which was reduced by 71.7% (p<0.05) with Wnd-US09. The comparison between UnWnd and Wnd-US09 was not significant (See FIGS. 3A-D). The increase in USP10 gene expression after wounding as assayed by qPCR was blunted by US09 (91.2%, p<0.05, FIG. 3E) even at 6 weeks. Similar to Col III, compared to unWnd, Wnd-NTC demonstrated a 8.33-fold increase in FN-EDA immunostaining (p<0.001).

Figure 3A:
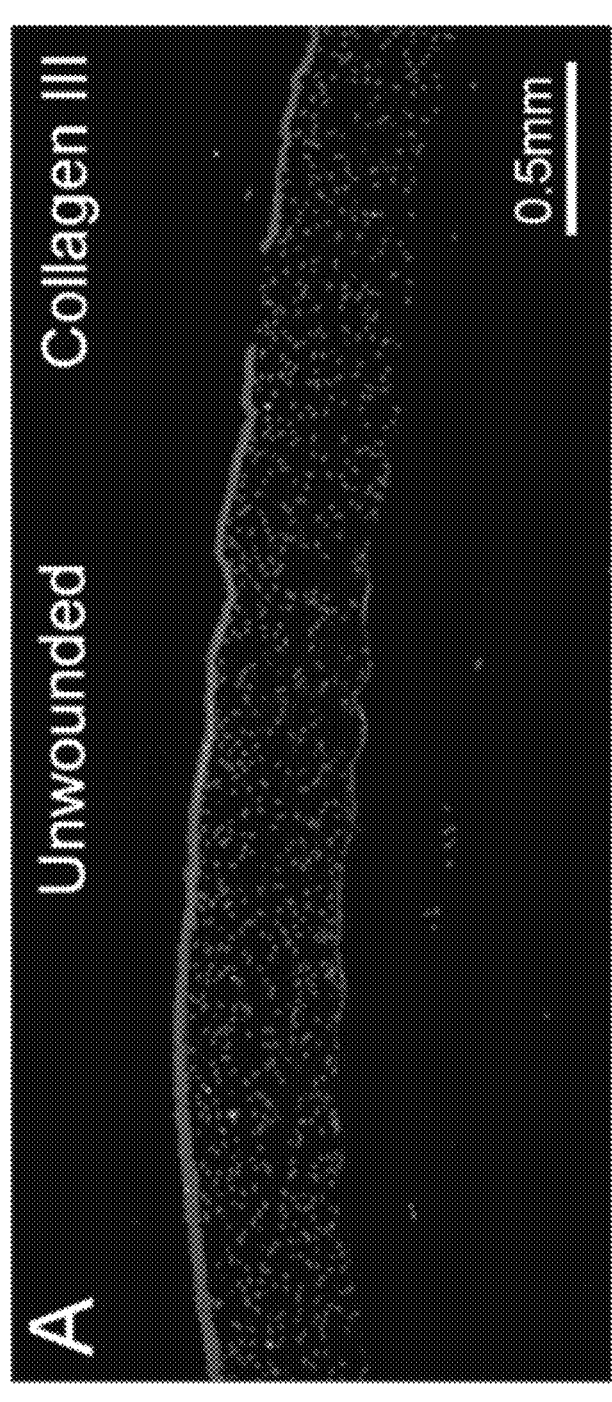
Figure 3B:
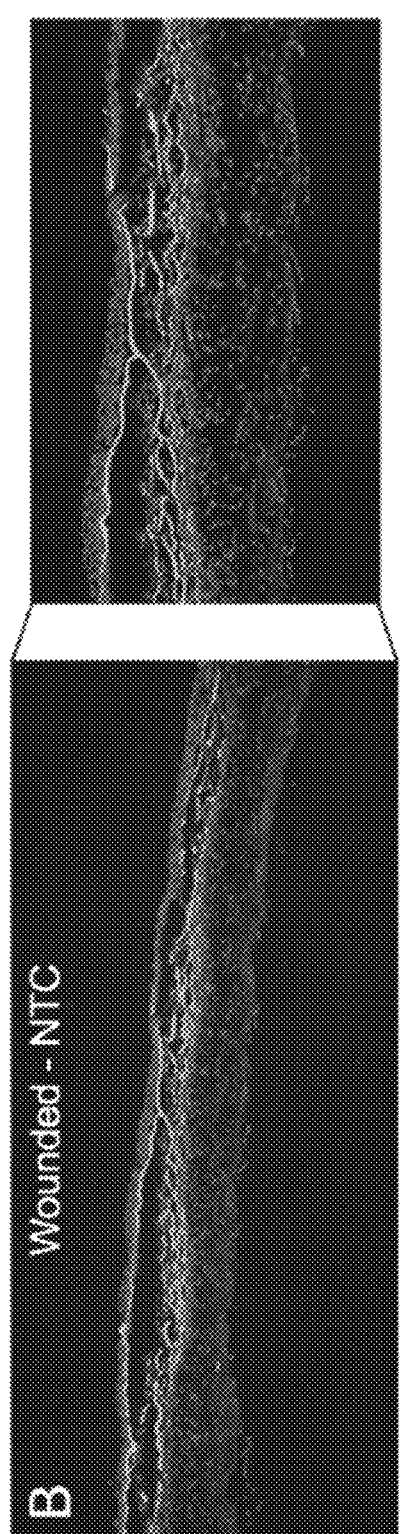
Figure 3C:
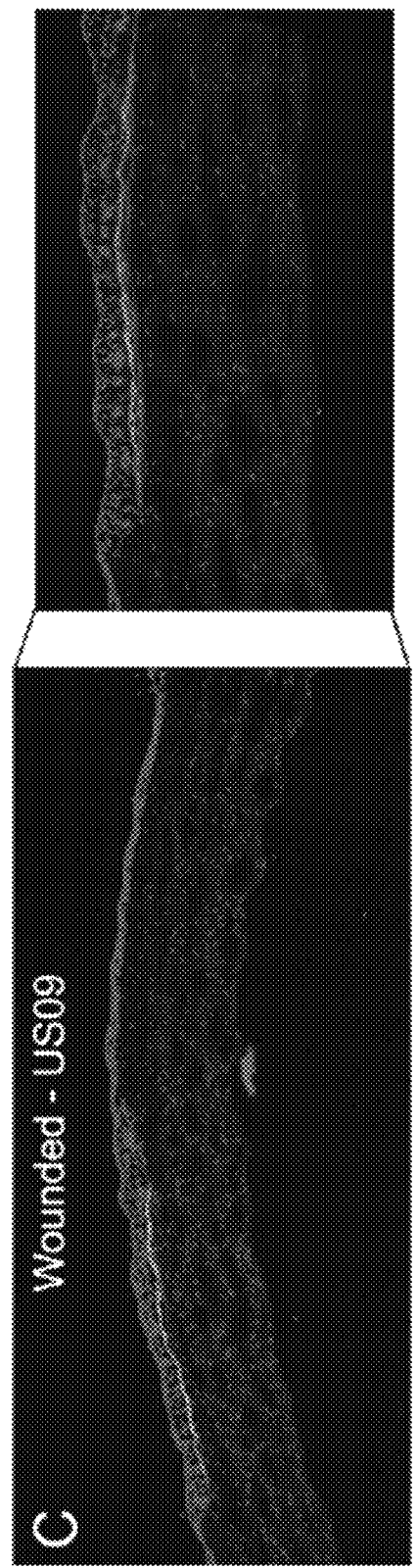
Figure 3D:
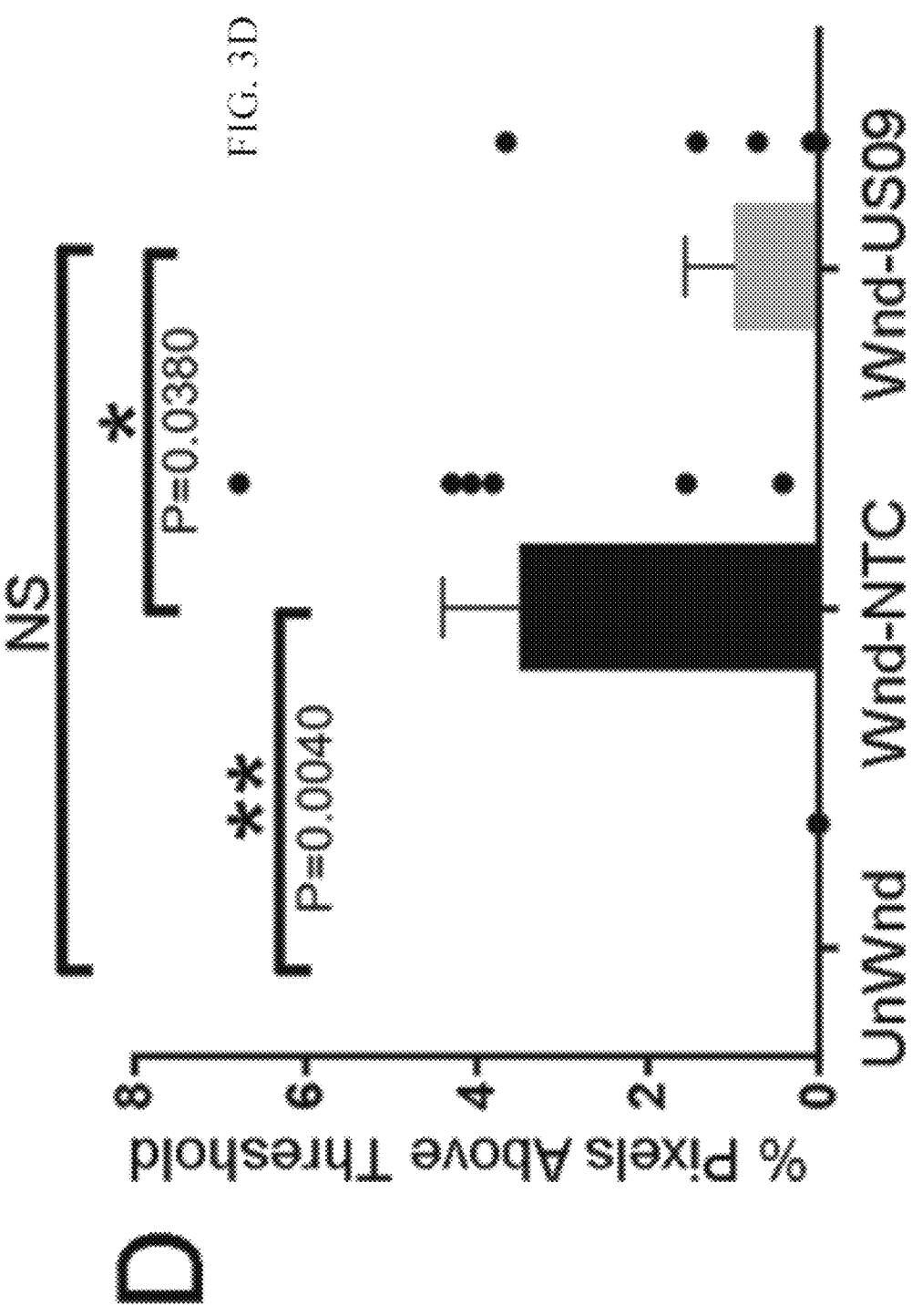

More specifically, FIGS. 3A-3E depicts Immunohistochemical analysis of Collagen III after wounding. Frozen sections of corneas six weeks after wounding were immunostained for Collagen III (green), Dapi (blue). FIG. 3A depicts Unwnd, FIG. 3B depicts Wnd-NTC with magnified inset, FIG. 3C depicts Wnd-US09 with magnified inset. Bar=0.5 mm. Referring to FIG. 3D, compared to unWnd, Wnd-NTC demonstrated a 276.2-fold increase in Collagen III immunostaining (p<0.01) which was reduced by 71.7% (p<0.05) with US09 treatment. The comparison between UnWnd and Wnd-US09 was not significant. Referring to FIG. 3E, by qPCR, compared to unWnd, Wnd-NTC demonstrated a 35.7-fold increase in USP10 gene expression (p<0.05). Compared to Wnd-NTC, USP10 expression with Wnd-US09 treatment was reduced by 91.2% (p<0.05). N=6 rabbits per condition.

Figure 4A:
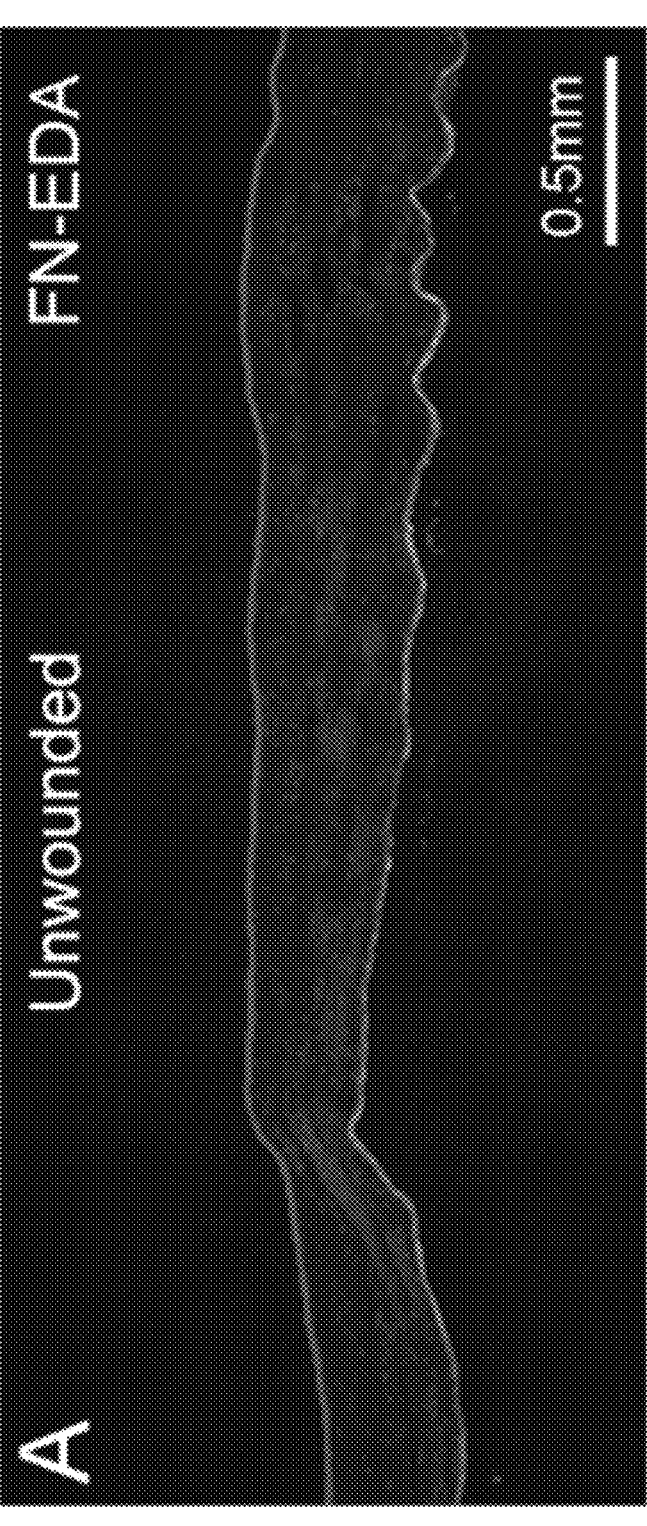
FIGS. 4A-4D depict immunohistochemical analysis of Fibronectin-EDA after wounding.
Figure 4B:
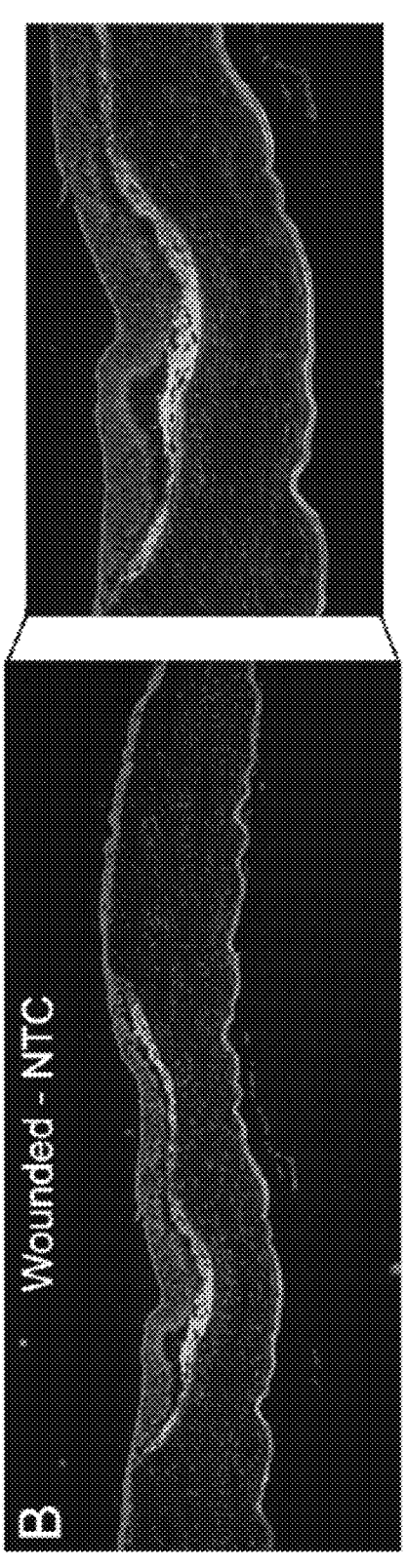
Figure 4C:
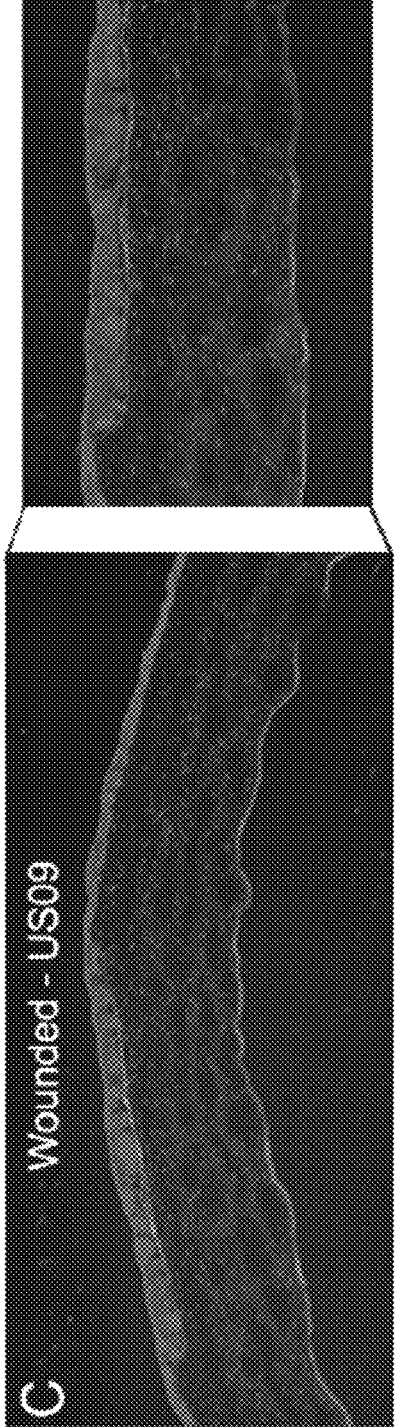
Figure 4D:
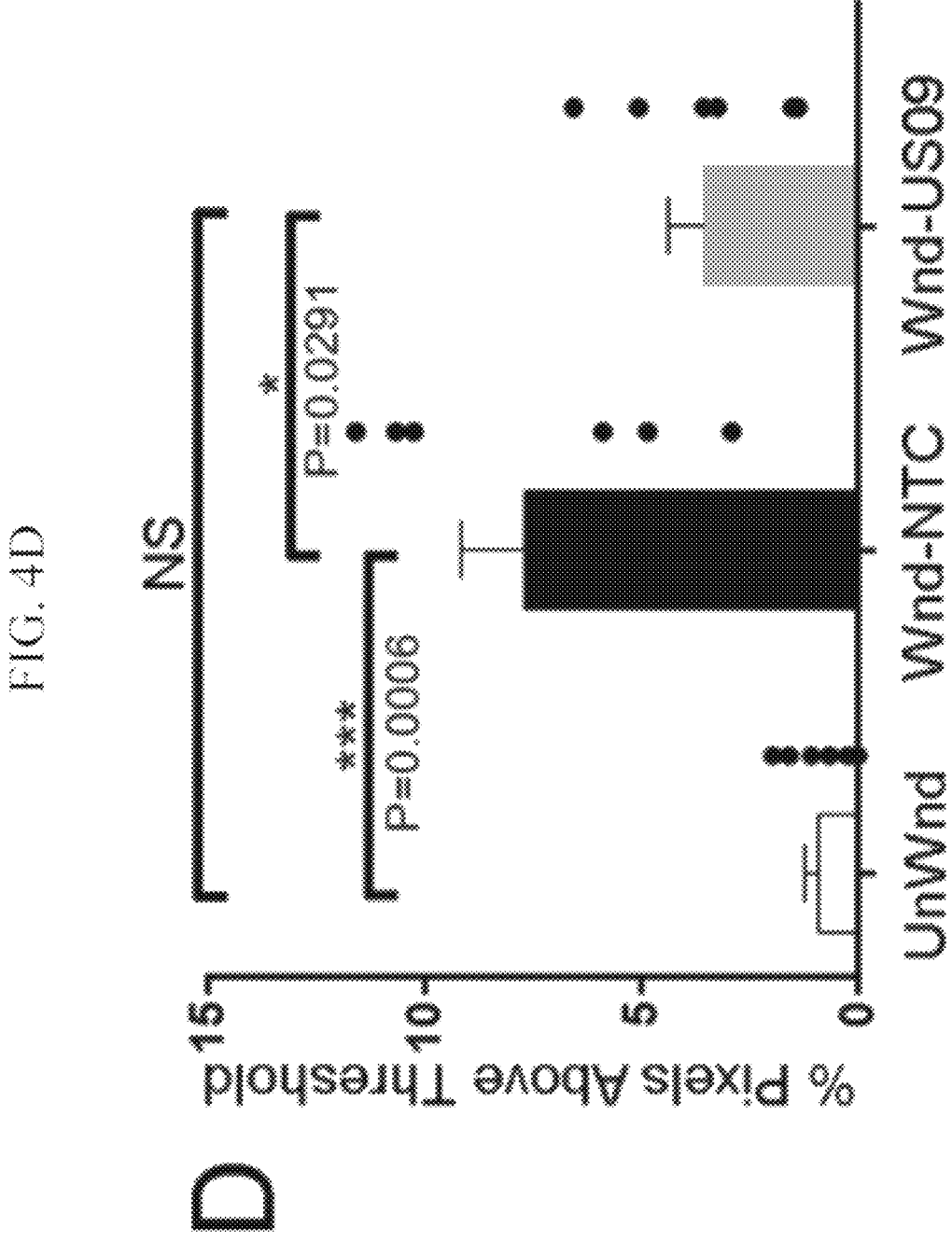

Compared to Wnd-NTC, FN-EDA immunostaining was reduced by 53.8% (p<0.05) in Wnd-US09. The comparison between UnWnd and Wnd-US09 was not significant (FIGS. 4A-D). More specifically, FIGS. 4A-4D depict immunohistochemical analysis of Fibronectin-EDA after wounding. Frozen sections of corneas six weeks after wounding were immunostained for Fibronectin-EDA (FN-EDA, green), Dapi (blue). FIG. 4A) Unwnd, FIG. 4B) Wnd-NTC with magnified inset, FIG. 4C) Wnd-US09 with magnified inset. Bar=0.5 mm. FIG. 4D) Compared to unWnd, Wnd-NTC demonstrated a 8.33-fold increase in FN-EDA immunostaining (p<0.001). Compared to Wnd-NTC, FN-EDA immunostaining after Wnd-US09 treatment was reduced by 53.8% (p<0.05). The comparison between UnWnd and Wnd-US09 was not significant. N=6 rabbits per condition.

Finally, compared to unWnd, Wnd-NTC demonstrated a 5.77-fold increase in α-SMA immunostaining (p<0.05), which was reduced by 83.6% (p<0.05) with in Wnd-US09. The comparison between UnWnd and Wnd-US09 was also not significant (FIGS. 5A-D). Next cell proliferation into the wound and corneal thickness was counted (See methods). These data demonstrate that cell proliferation into the wound in Wnd-US09 corneas is similar to UnWnd tissue, whereas Wnd-NTC is significantly increased (FIG. 5E) (p<0.01). Cell proliferation below the wound in the stroma down to the endothelial layer was invariant between conditions (FIG. 5F). Corneal thickness in Wnd-US09 treated corneas was not significantly different from UnWnd parameters (FIG. 5G), whereas Wnd-NTC corneas were thinner (p=0.5). Together these data demonstrate that a one-time treatment of self-delivery siRNA targeting USP10 after wounding significantly reduces scarring at 6 weeks.

Figure 5A:
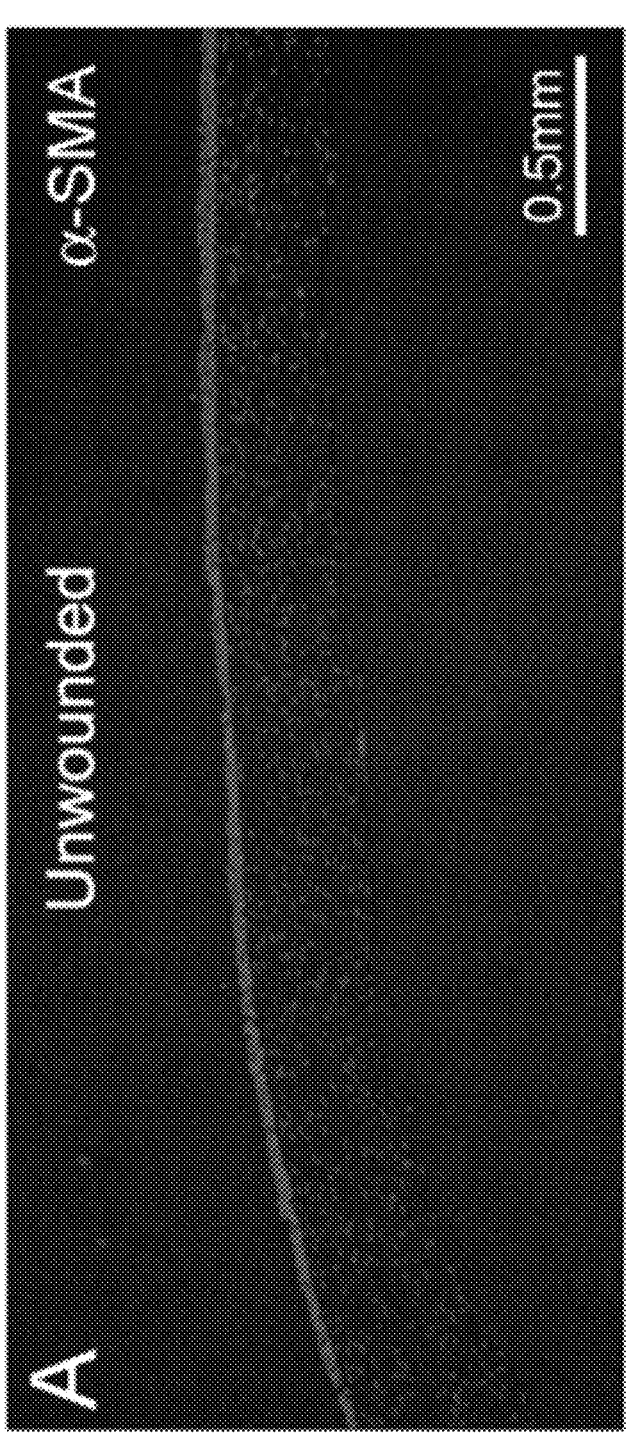
Figure 5B:
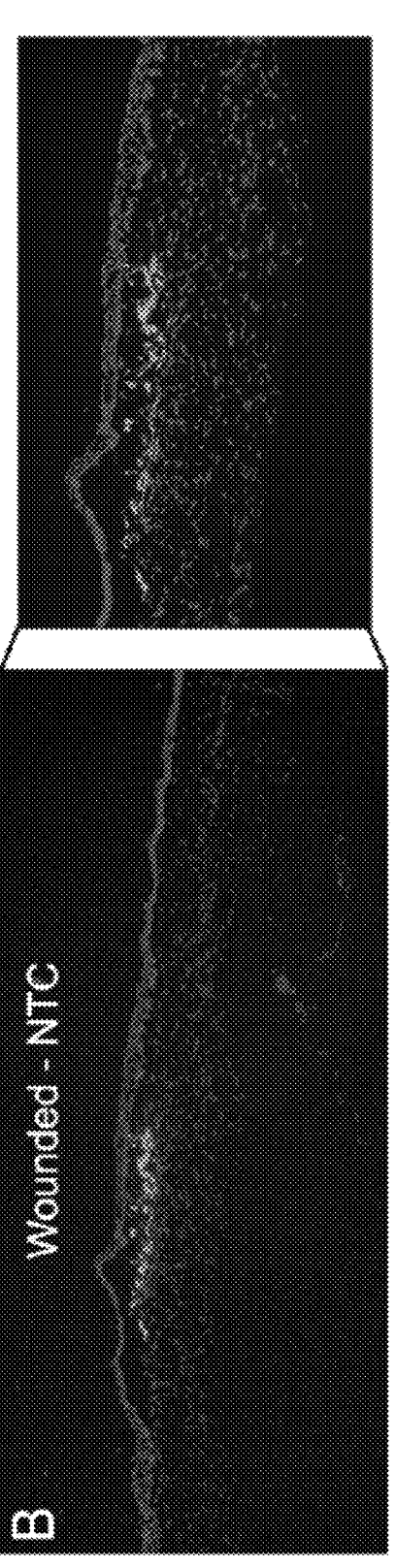
Figure 5C:
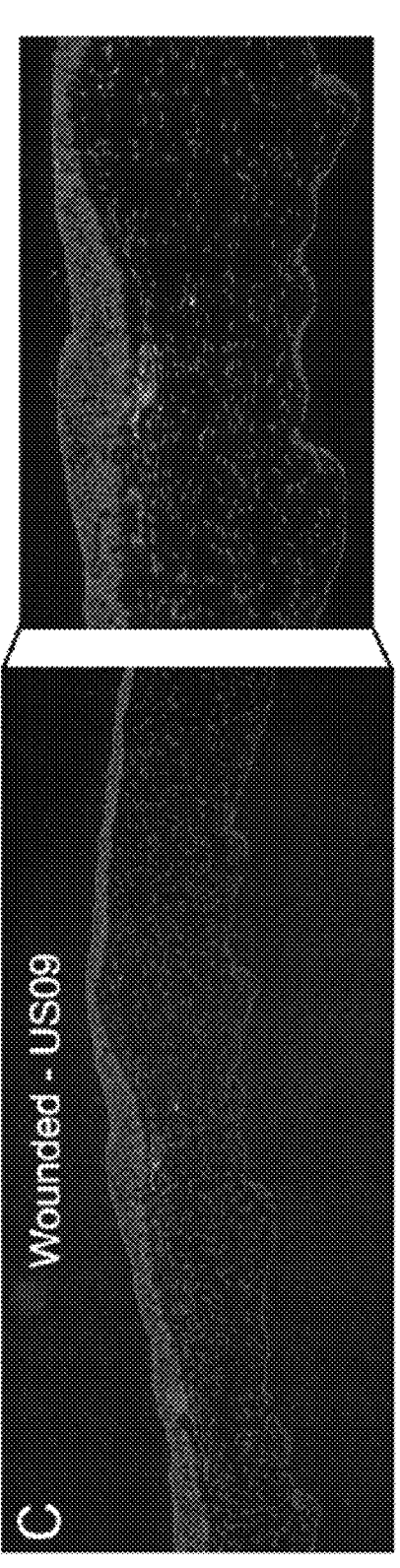
Figure 5D:
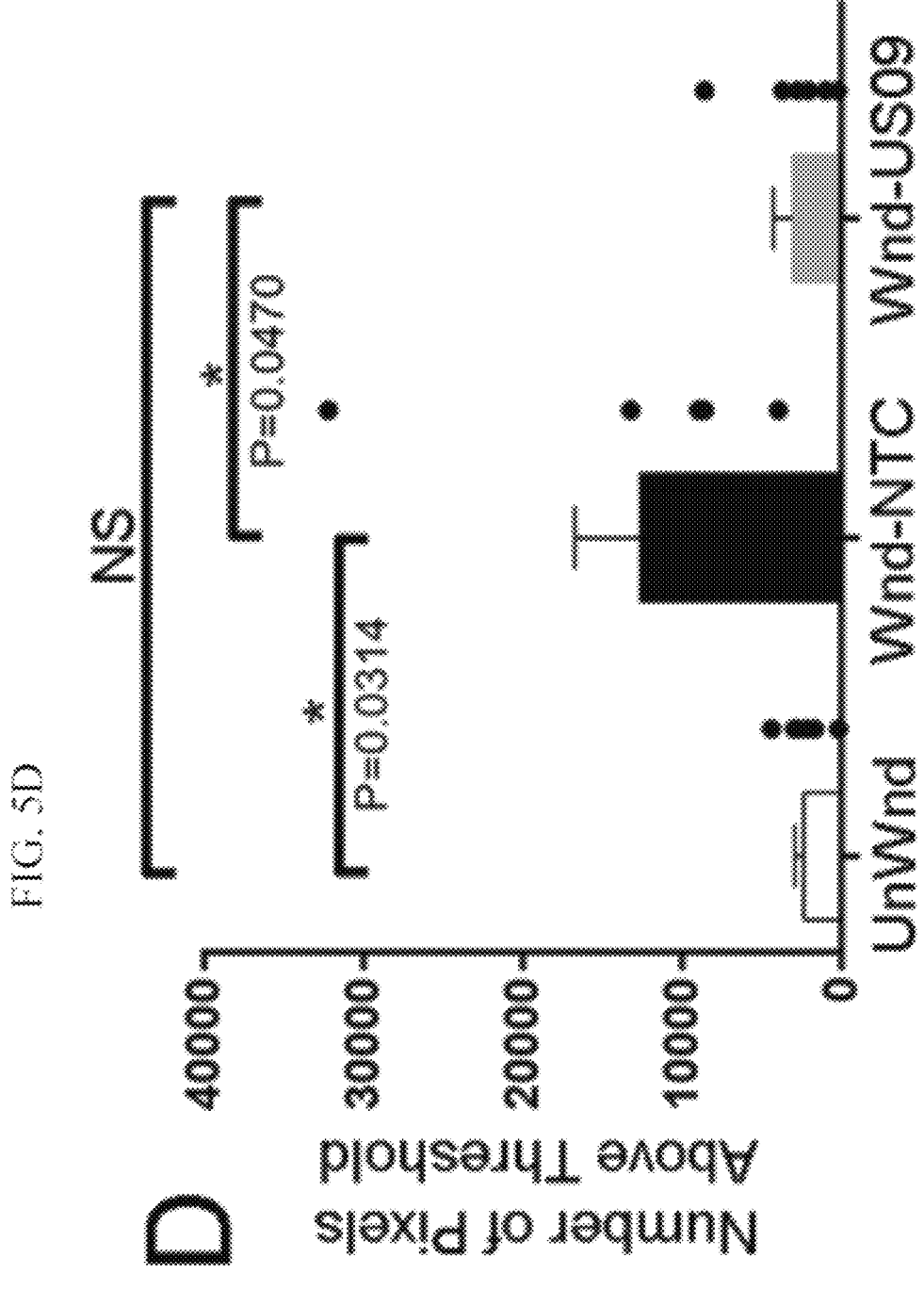
Figure 5F:
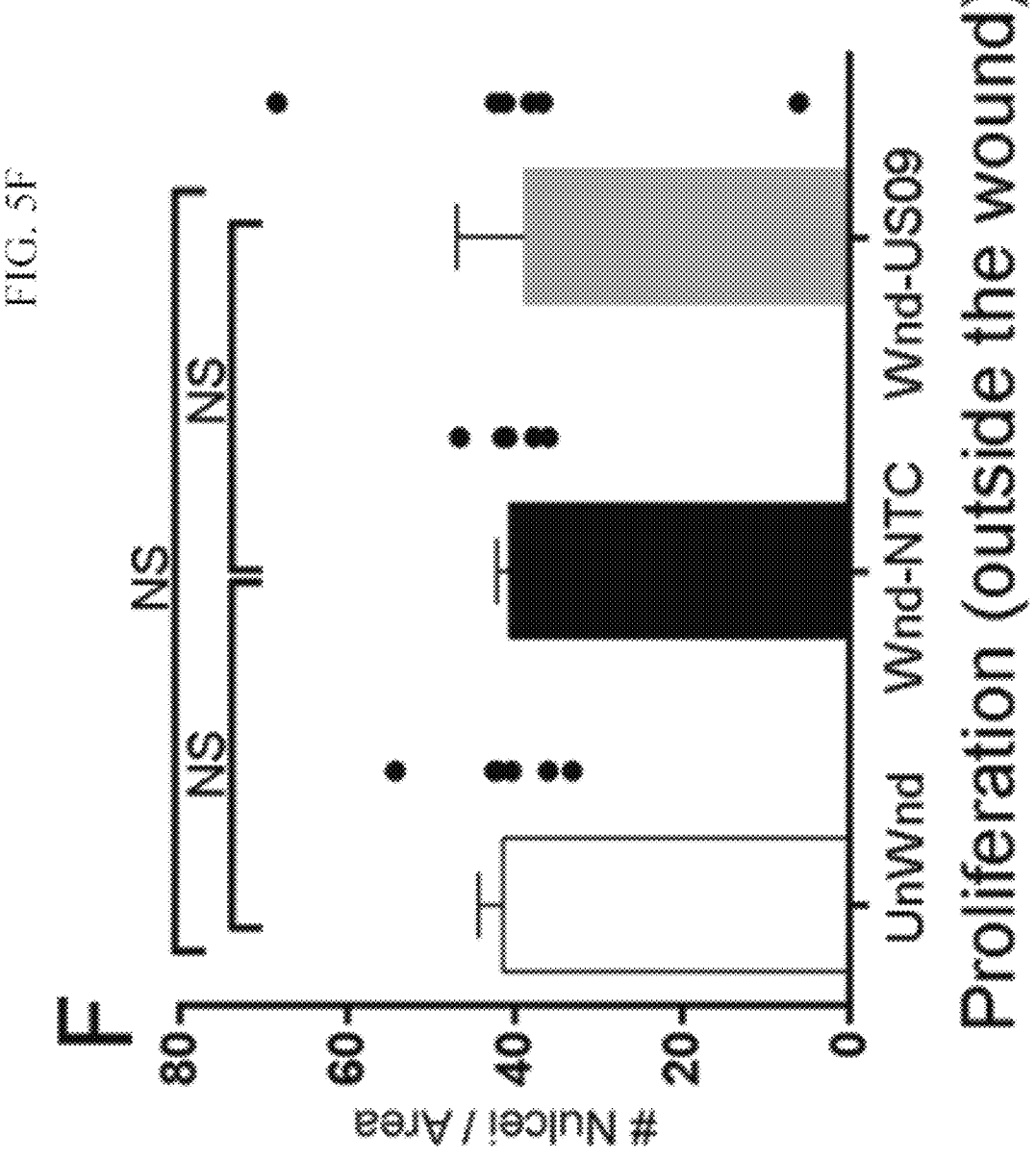
Figure 5G:

More specifically, FIGS. 5A-5G depict immunohistochemical analysis of α-SMA, cell proliferation, and thickness after wounding. Frozen sections of corneas six weeks after wounding were immunostained for α-SMA (green), Dapi (blue). FIG. 5A depicts Unwnd, FIG. 5B depicts Wnd-NTC with magnified inset, FIG. 5C depicts Wnd-US09 with magnified inset. Bar=0.5 mm. FIG. 5D depicts compared to unWnd, Wnd-NTC demonstrated a 5.77-fold increase in α-SMA immunostaining (p<0.05). Compared to Wnd-NTC, α-SMA immunostaining after Wnd-US09 treatment was reduced by 83.6% (p<0.05). The comparison between UnWnd and Wnd-US09 was not significant. FIG. 5E and FIG. 5F depict cell proliferation was analyzed by the Object Counter plugin in ImageJ software. "Inside the wound" is denoted by the anterior cornea demarcated by the Collagen III scar. "Outside the wound" is the posterior cornea beneath the scar. These counts were normalized by the total area of each portion to generate a nuclei density measurement. FIG. 5E) Compared to unWnd, Wnd-NTC demonstrated a 1.61-fold increase in cell proliferation (p<0.01). Compared to Wnd-NTC, cell proliferation after Wnd-US09 treatment was reduced by 29.9% (p<0.05). The comparison between UnWnd and Wnd-US09 was not significant. FIG. 5F) Cell proliferation below the scar, in the stroma down to the endothelium. All relationships were non-significant. FIG. 5G) Corneal thickness was measured at pixel resolution in these thresholded images as the distance across the nonzero region, and thickness is averaged across the entire cornea. Wnd-NTC demonstrated a slight but significant decrease in thickness (p=0.05). Wnd-US09 treatment restored corneal thickness to non-wounded parameters. N=6 rabbits per condition.

Immune Marker-CD45

Figures 6A, 6B, 6C:
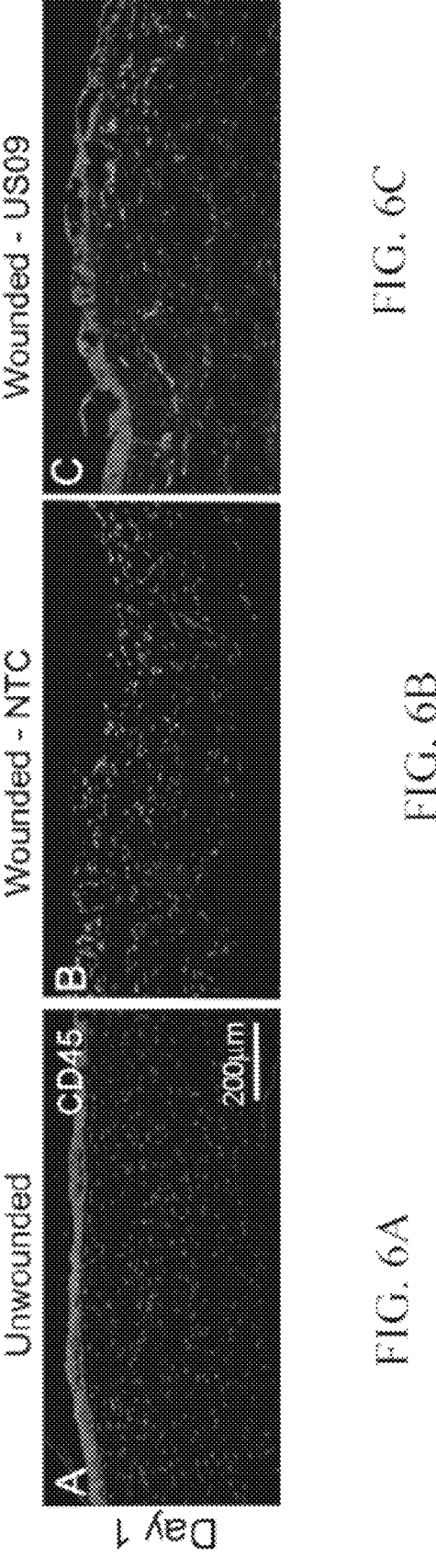
Figures 6D, 6E, 6F, 6G, 6H, 6I:
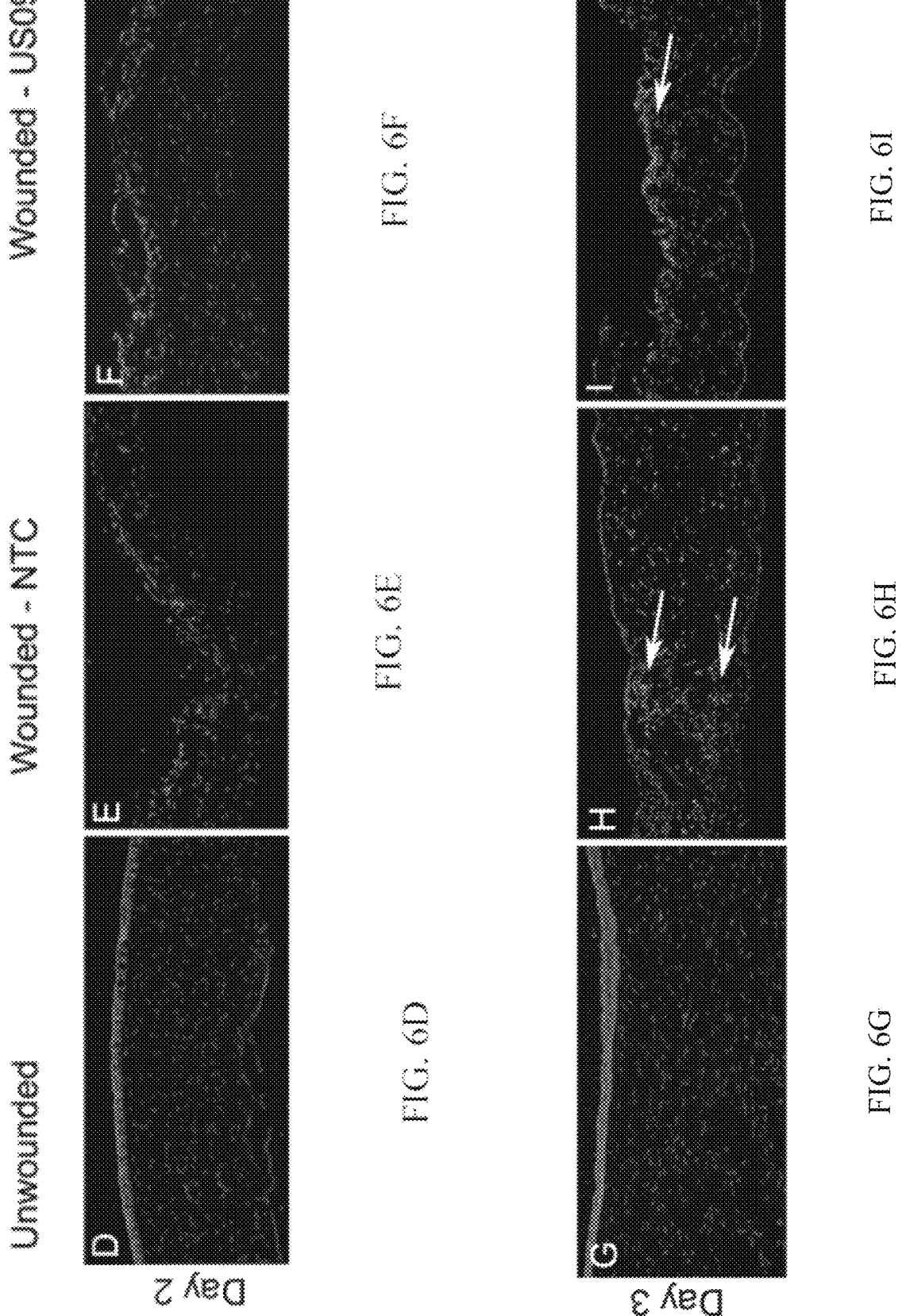
Figures 6J, 6K, 6L:
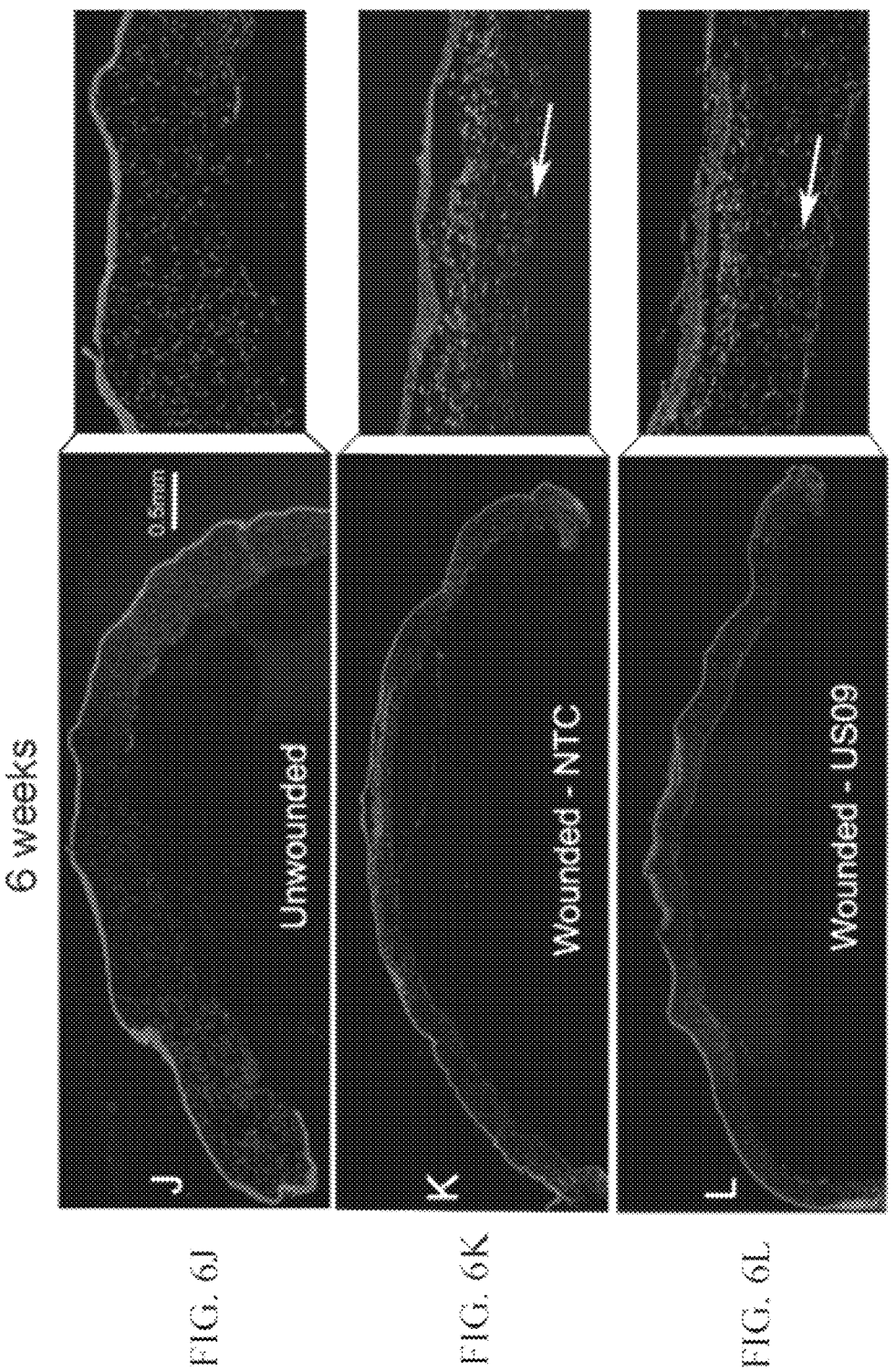

To begin to study the infiltration of immune cells into the wound, wounding experiment was repeated to analyze CD45+ staining and collected tissue at days 1, 2, and 3 to compare to six weeks. As shown in FIGS. 6A-I), by 1 day after wounding, CD45+ immune cells populate the wound in both Wnd-NTC and Wnd-US09 conditions. However, overall, by day 3 there is a clear difference between Wnd-NTC and Wnd-US09, in the Wnd-NTC tissue, there are more CD45+ cells and importantly, they are distributed throughout the stroma in and below the wound, whereas in the Wnd-US09 tissue, they are localized to the anterior stroma only (arrows). (At this early time point, the epithelium often falls off during immunostaining of wounded tissue as the tissue is not fixed and the wound margin is still fragile.) At 6 weeks, the same distribution is observed (FIG. 6J-L, with magnified panels). FIG. 6M shows the quantification of CD45+ cells in the three conditions during the first 3 days, at 6 weeks, and with the data grouped. At days 1-3, compared to unWnd, Wnd-NTC demonstrated a 7.1-fold increase in CD45+ immunostaining. Comparing Wnd-NTC to Wnd-US09, CD45+ staining was reduced by 46.2% (p<0.05). At 6 weeks, compared to unWnd, Wnd-NTC demonstrated a 3.4-fold increase in CD45+ immunostaining. Comparing Wnd-NTC to Wnd-US09, CD45+ staining was reduced by 55.2% (p=0.06). For the grouped data, compared to unWnd, Wnd-NTC demonstrated a 4.66-fold increase in CD45+ immunostaining (p=0.001), comparing Wnd-NTC to Wnd-NTC CD45+ staining was reduced by 51.0% (p<0.01). The comparison between UnWnd and Wnd-US09 was not significant. In summary, US09 reduces CD45+ cell infiltration after wounding.

More specifically, FIGS. 6A-6M depict CD45+ cell infiltration after wounding. Frozen sections of corneas days 1,2,3 and six weeks after wounding were immunostained for CD45+ (red), Dapi (blue). FIGS. 6A-C) Day 1, FIGS. 6D-F) Day 2, FIGS. 6G-I) Day 3, (Bar=200 μm) J-L) 6 weeks with magnified inset (Bar=0.5 mm). Images as labeled. M). At days 1-3, Compared to unWnd, Wnd-NTC demonstrated a 7.1-fold increase in CD45+ immunostaining. Wnd-NTC compared to Wnd-NTC, CD45+ staining was reduced by 46.2% (p<0.05). At 6 weeks, compared to unWnd, Wnd-NTC demonstrated a 3.4-fold increase in CD45+ immunostaining. Comparing Wnd-NTC to Wnd-US09, CD45+ staining was reduced by 55.2% (p=0.06). For the grouped data, compared to unWnd, Wnd-NTC demonstrated a 4.66-fold increase in CD45+ immunostaining (p=0.001), comparing Wnd-NTC to Wnd-NTC CD45+ staining was reduced by 51.0% (p<0.01). The comparison between UnWnd and Wnd-US09 was not significant. US09 reduces CD45+ cell infiltration. N=3 rabbits per condition for days 1-3, N=5 rabbits per condition for the six week time point. N=8 rabbits per condition for grouped data.

Apoptosis after Wounding

Figures 7A, 7B, 7C, 7D, 7E, 7F, 7G, 7H, 7I:
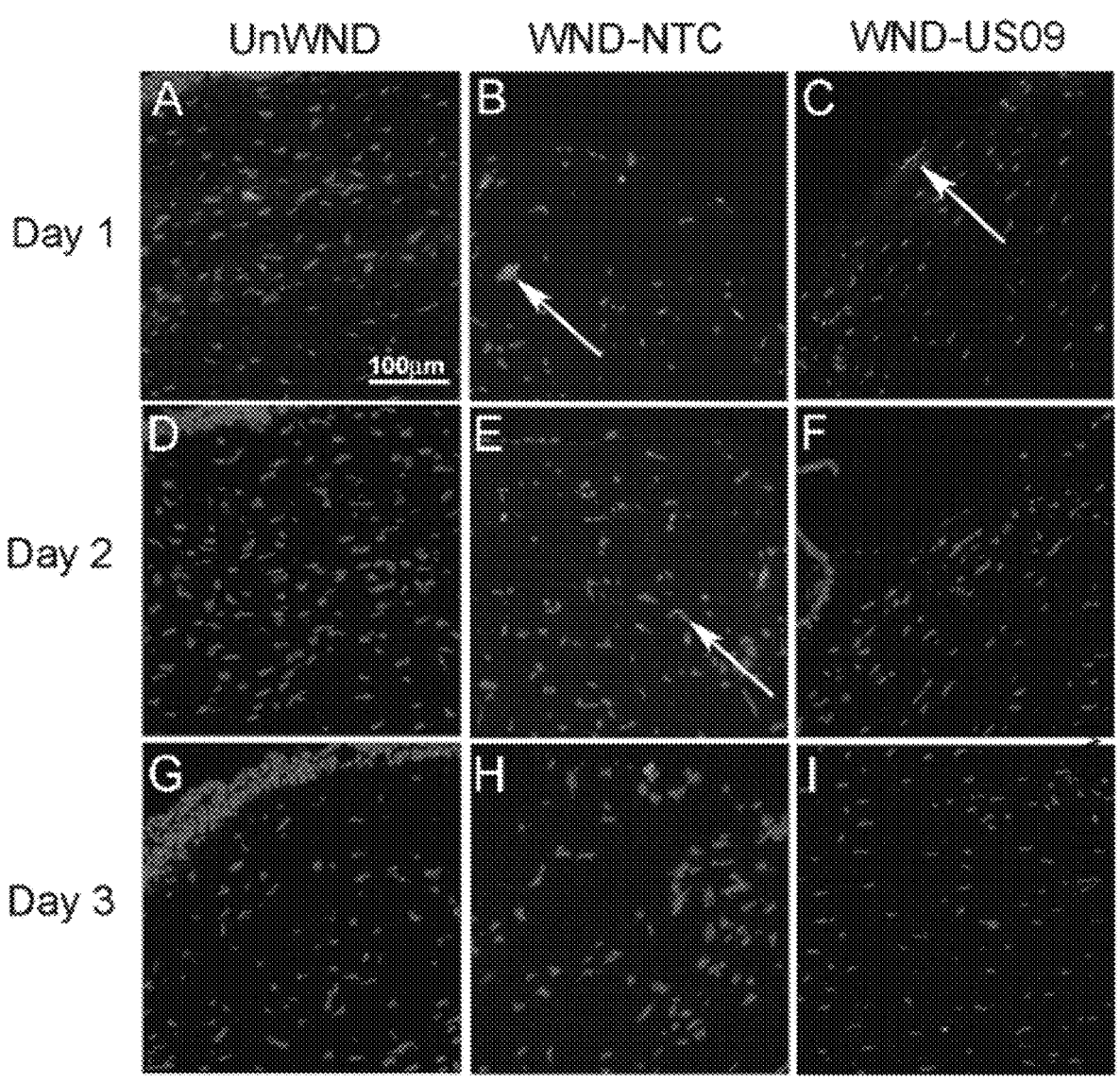
FIGS. 7A-7J depict apoptosis after wounding.
Figure 7J:
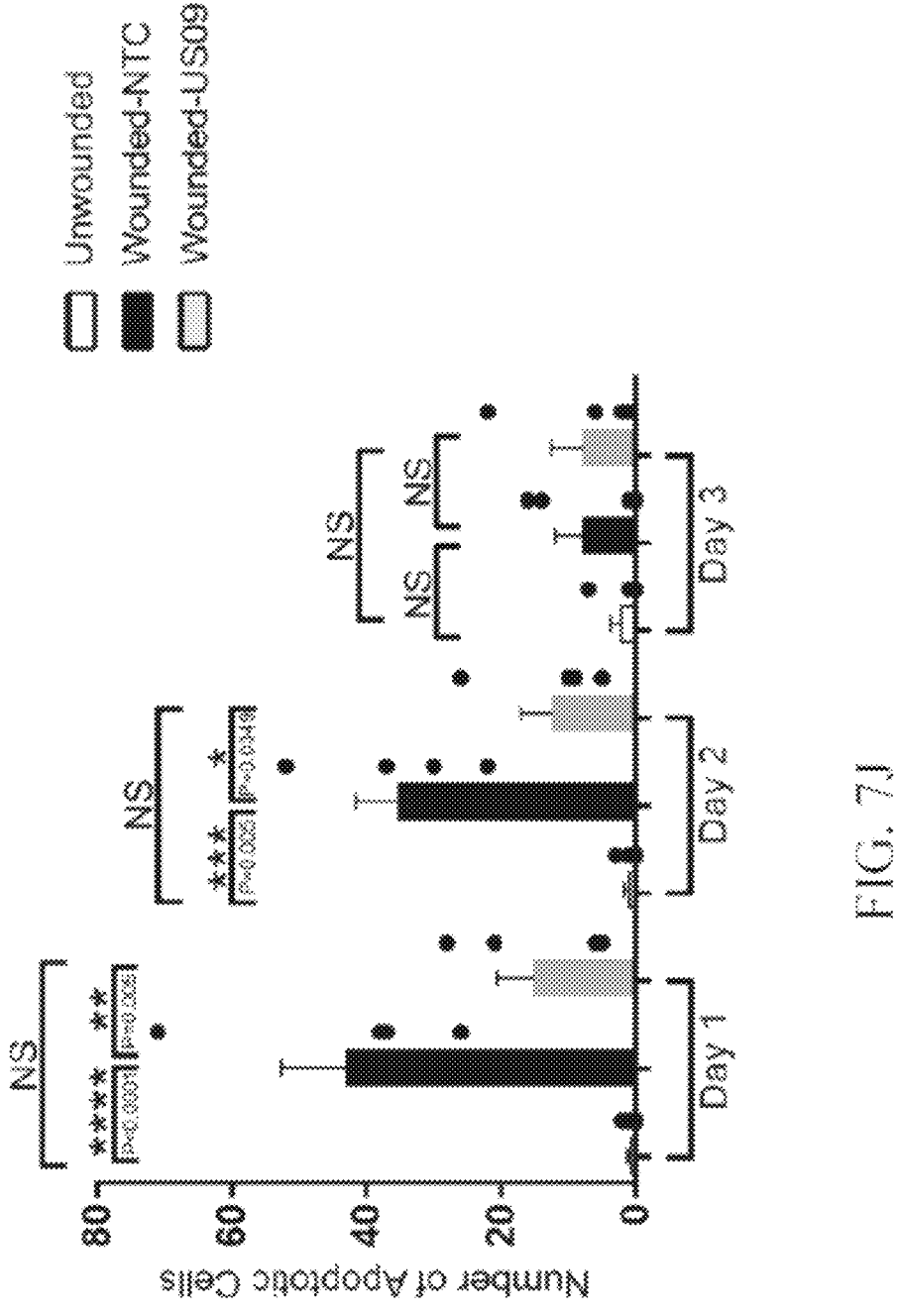

After wounding in the cornea, local cells in the stroma in and beneath the wound, apoptose. (See e.g., Wilson, S E, He, Y G, Weng, J, Li, Q, McDowall, A W, Vital, M, et al. (1996). Epithelial injury induces keratocyte apoptosis: hypothesized role for the interleukin-1 system in the modulation of corneal tissue organization and wound healing. *Exp Eye Res* 62:325-327; and Kaur, H, Chaurasia, S S, Agrawal, V, Suto, C, and Wilson, S E (2009). Corneal myofibroblast viability:

opposing effects of IL-1 and TGF beta1. *Exp Eye Res* 89:152-158). In response to wounding and apoptosis, neutrophils and macrophages (CD45+ cells) infiltrate the wound as shown in FIG. 6. It was found that US09 treatment significantly prevented apoptosis after wounding, 65.0% on day 1 (p<0.01) and 65.0% on day 2 (p<0.05) (FIG. 7). This may be a key to the anti-scarring activity of US09. Less apoptosis will attract less leukocyte infiltration with diminished scarring.

More specifically, FIGS. 7A-7J depict apoptosis after wounding. Apoptotic cells were detected with TUNEL assay on days 1, 2, and 3 after wounding (A-I). J) On day 1 US09 treatment reduced apoptosis 65.0% from 43.0+/−9.7 to 15.0+/−5.7 cells per section in the wound (p<0.01). On day 2 also 65.0% from 35.3+/−6.4 to 12.5+/−4.6 cells per section in the wound (p<0.05). Apoptosis was non-significant between conditions by day 3. Bar=100 μm. N=4 rabbits per condition per time point.

Discussion

Application of self-deliverable siRNA targeting the deubiquitinase, USP10 (US09) is a novel method to significantly reduce scarring in the cornea. This was shown by faster wound closure (FIG. 1), a decrease in the variance of pixels in OCT images (FIG. 2), a reduction in fibrotic markers to a level that was not significantly different from unwounded tissue (FIGS. 3-5), a reduction in CD45+ cells (FIG. 6), and the apoptotic response to wounding (FIG. 7). Based on the data and the known functions of USP10, USP10 plays a central role in wound healing by regulating apoptosis in a context-dependent manner; pro-apoptosis directly after wounding and anti-apoptosis (pathological myofibroblast development) later in wound healing.

The role of USP10 in myofibroblasts was identified through the utilization of a unique cellular wounding model. The extracellular protease system, uPA/uPAR generates plasminogen and plasmin on the cell surface. The receptor, uPAR is GPI-linked and it coordinates with the cytoskeleton intracellularly through binding to integrins. Whereas addition of uPA to the cell induces cell motility and high levels of uPA/uPAR/integrin binding promotes cancer cell invasion, (See e.g, Ossowski, L, and Aguirre-Ghiso, J A (2000). Urokinase receptor and integrin partnership: coordination of signaling for cell adhesion, migration and growth. *Curr Opin Cell Biol* 12:613-620) it was found that uPA or uPAR knockdown in primary human corneal fibroblasts induced an adhesive, myofibroblast phenotype with dramatically increased cell surface expression of αvβ5 and highly organized α-SMA. (See e.g, Wang, L, Pedroja, B S, Meyers, E E, Garcia, A L, Twining, S S, and Bernstein, A M (2012). Degradation of Internalized alphavbeta5 Integrin Is Controlled by uPAR Bound uPA: Effect on beta1 Integrin Activity and alpha-SMA Stress Fiber Assembly. *PLoS One* 7: e33915). Further investigation proved that it was not gene expression changes that increased integrin αvβ5 but instead a post-translational decrease in ubiquitination of integrin (5. (See Gillespie, S R, Tedesco, L J, Wang, L, and Bernstein, A M (2017). The deubiquitylase USP10 regulates integrin beta1 and beta5 and fibrotic wound healing. *J Cell Sci* 130:3481-3495).

Thus, this finding was leveraged and RNAseq on uPA siRNA treated cells was performed to find novel targets for the generation of a pathological myofibroblast phenotype without the addition of TGFβ. In support of this strategy, uPAR knockout mice develop dermal scarring, lung, and myocardial fibrosis. (See e.g., Kanno, Y, Kaneiwa, A, Minamida, M, Kanno, M, Tomogane, K, Takeuchi, K, et al. (2008). The absence of uPAR is associated with the progression of dermal fibrosis. *J Invest Dermatol* 128:2792-2797; Manetti, M, Rosa, I, Milia, A F, Guiducci, S, Carmeliet, P, Ibba-Manneschi, L, et al. (2014). Inactivation of urokinase-type plasminogen activator receptor (uPAR) gene induces dermal and pulmonary fibrosis and peripheral microvasculopathy in mice: a new model of experimental scleroderma? *Ann Rheum Dis* 73:1700-1709; and Manetti, M, Rosa, I, Fazi, M, Guiducci, S, Carmeliet, P, Ibba-Manneschi, L, et al. (2016). Systemic sclerosis-like histopathological features in the myocardium of uPAR-deficient mice. *Ann Rheum Dis* 75:474-478). From the RNAseq data it was found that the DUB, USP10 was important for myofibroblast development as it deubiquitinates β1 and β5 integrins, specifically, αvβ5 and β1 but not αvβ3, leading to an accumulation of cell surface integrin and subsequent activation of local TGFβ. Furthermore, after wounding in an ex vivo corneal wounding model, USP10 is significantly upregulated in the stroma, and USP10 siRNA reduces or eliminates fibrotic markers.

Figure 8A:
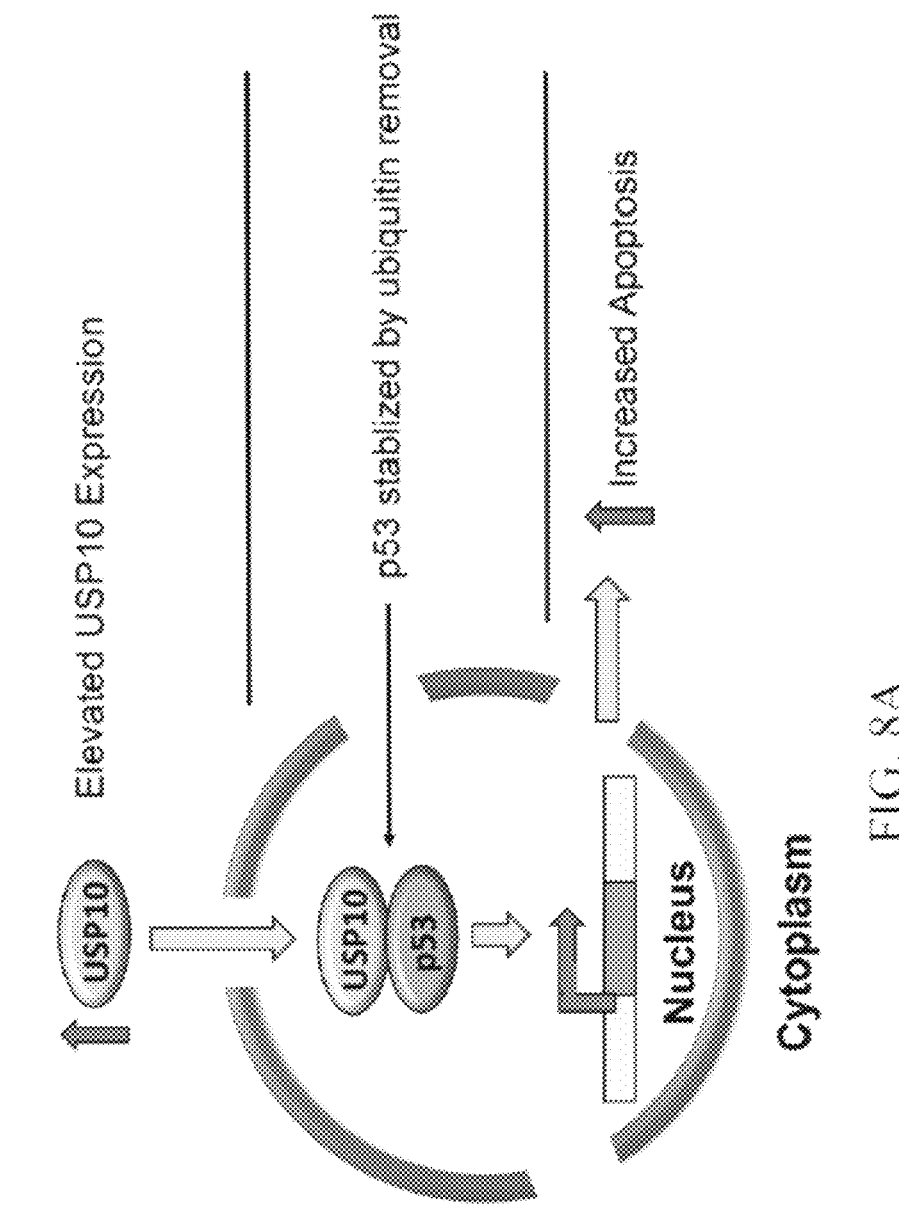
Figure 8B:
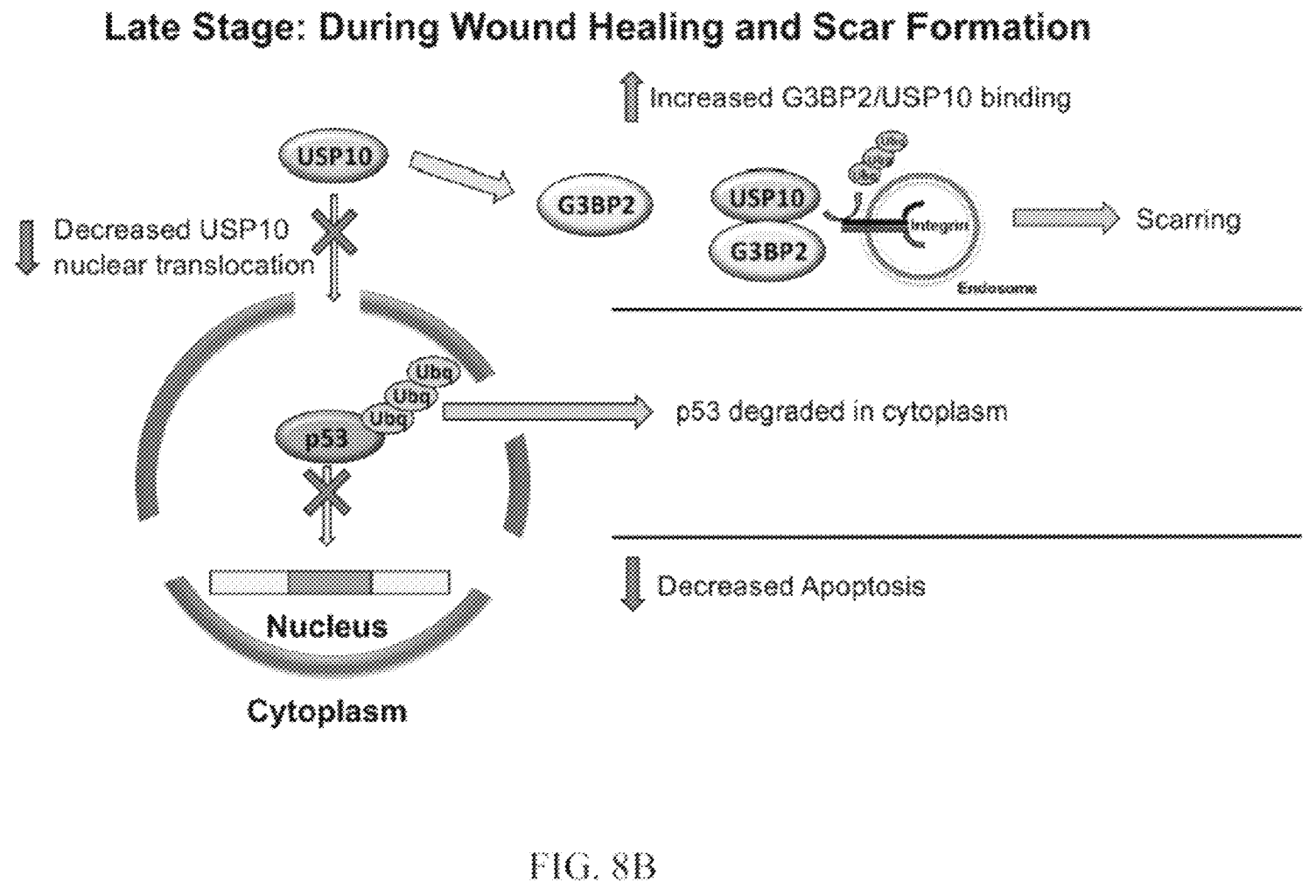

USP10 is also a DUB for p53 and thus plays a role in regulating apoptosis. Referring to FIGS. 8A-8B, FIGS. 8A and 8B depict a working model for divergent roles of USP10 as wound healing/scarring progresses. FIG. 8A depicts that immediately following a corneal stromal injury, resident keratocytes adjacent to the wound undergo apoptosis. USP10, which is upregulated in the wound (See e.g., Gillespie, S R, Tedesco, L J, Wang, L, and Bernstein, A M (2017). The deubiquitylase USP10 regulates integrin beta1 and beta5 and fibrotic wound healing. *J Cell Sci* 130:3481-3495) plays a role in apoptosis by deubiquitinating p53. p53 stabilization promotes tumor suppressor/pro-apoptotic gene expression and signaling, resulting in controlled cell death. Knockdown of USP10 by US09 treatment diminished the apoptotic response. FIG. 8B depicts USP10 deubiquitylates αv-integrins, leading to cell surface accumulation, myofibroblast persistence, and activation of TGFβ. Sustained upregulation of stress-response genes, such as the G3BP proteins (known binding partners of USP10) (See e.g, Takahashi, M, Higuchi, M, Matsuki, H, Yoshita, M, Ohsawa, T, Oie, M, et al. (2012). Stress granules inhibit apoptosis by reducing reactive oxygen species production. *Mol Cell Biol* 33:815-829) compete for interaction with available USP10 in the cytoplasm, switching USP10's function from pro-apoptotic to anti-apoptotic. This model is supported by data in prostate cancer cells and in keloid scars in which USP10 switches from a pro-apoptotic role in the nucleus to binding to stress-related proteins in the cytoplasm. (See e.g, Takayama, K I, Suzuki, T, Fujimura, T, Takahashi, S, and Inoue, S (2018). Association of USP10 with G3BP2 Inhibits p53 Signaling and Contributes to Poor Outcome in Prostate Cancer. *Mol Cancer Res* 16:846-856; and Deng, C C, Zhu, D H, Chen, Y J, Huang, T Y, Peng, Y, Liu, S Y, et al. (2019). TRAF4 promotes fibroblast proliferation in keloids by destabilizing p53 via interacting with the deubiquitinase USP10. *J Invest Dermatol*).

Other studies have demonstrated a role for G3BP2 in regulating integrin signaling molecules (Src, FAK, and ERK). (See e.g., Zhang, H, Zhang, S H, He, H W, Zhang, C X, Yu, D K, and Shao, R G (2013). Downregulation of G3BPs inhibits the growth, migration and invasion of human lung carcinoma H1299 cells by suppressing the Src/FAK-associated signaling pathway. *Cancer Gene Ther* 20:622-629). Taken together, in the early stages of wounding, USP10 promotes apoptosis and subsequent immune cell infiltration, while in the later stages of wound healing (scar formation), USP10 is directed by its binding partners to promote myofibroblast survival (inhibition of apoptosis) and differentiation (av-integrin upregulation, enhanced cellular adhesion/contractility). Knockdown USP10 gene expression after wounding, significantly reduces scarring.

FIG. 8 depicts a working model that integrates work on integrins and the current in vivo data on apoptosis and immune cell infiltration is that directly after wounding, stimulated by USP10 upregulation (See Gillespie, SR, Tedesco, LJ, Wang, L, and Bernstein, AM (2017). The deubiquitylase USP10 regulates integrin beta1 and beta5 and fibrotic wound healing. *J Cell Sci* 130:3481-3495), USP10/p53 activity in the nucleus is dominant leading to less p53 ubiquitination, stabilizing pro-apoptotic p53. (See e.g., Yuan, J, Luo, K, Zhang, L, Cheville, J C, and Lou, Z (2010). USP10 regulates p53 localization and stability by deubiquitinating p53. *Cell* 140:384-396). Local cell apoptosis induces mast cell activation and the infiltration of neutrophils and macrophages into the wound. (See e.g, Li, Z, Burns, A R, and Smith, C W (2006). Two waves of neutrophil emigration in response to corneal epithelial abrasion: distinct adhesion molecule requirements. *Invest Ophthalmol Vis Sci* 47:1947-1955; Sahu, S K, Mittal, S K, Foulsham, W, Li, M, Sangwan, V S, and Chauhan, S K (2018). Mast Cells Initiate the Recruitment of Neutrophils Following Ocular Surface Injury. *Invest Ophthalmol Vis Sci* 59:1732-1740; and Bratton, D L, and Henson, P M (2011). Neutrophil clearance: when the party is over, clean-up begins. *Trends Immunol* 32:350-357.

Activated keratocytes peripheral to the apoptotic zone proliferate to repopulate the wound margin. These cells and infiltrating bone marrow-derived fibrocytes (See e.g, Lassance, L, Marino, GK, Medeiros, CS, Thangavadivel, S, and Wilson, SE (2018). Fibrocyte migration, differentiation and apoptosis during the corneal wound healing response to injury. *Exp Eye Res* 170:177-187) differentiate into myofibroblasts in the next few days. In this second phase we propose that USP10 favors binding to cytosolic proteins such as G3BP2 and integrins directing USP10 away from nuclear p53. USP10 binding to G3PB2 in the cytosol induces p53 cytoplasmic localization, ubiquitination, and degradation. (See Takayama, KI, Suzuki, T, Fujimura, T, Takahashi, S, and Inoue, S (2018). Association of USP10 with G3BP2 Inhibits p53 Signaling and Contributes to Poor Outcome in Prostate Cancer. *Mol Cancer Res* 16:846-856). The connection between G3BP2 and USP10-mediated integrin deubiquitylation is unknown but, G3BP2 downregulation inhibits Scr/FAK/ERK signaling, suggesting a USP10/integrin/G3BP2 complex and coordination between these proteins. (See Zhang, H, Zhang, SH, He, HW, Zhang, CX, Yu, DK, and Shao, RG (2013). Downregulation of G3BPs inhibits the growth, migration and invasion of human lung carcinoma H1299 cells by suppressing the Src/FAK-associated signaling pathway. *Cancer Gene Ther* 20:622-629).

Germain to this model is a recent paper in which USP10/TRAF4 binding induced p53 ubiquitination and cytosolic degradation (like the USP10/G3BP2 interaction) leading to a fibroproliferative response and keloid formation. (See e.g., Deng, C C, Zhu, D H, Chen, Y J, Huang, TY, Peng, Y, Liu, S Y, et al. (2019). TRAF4 promotes fibroblast proliferation in keloids by destabilizing p53 via interacting with the deubiquitinase USP10. *J Invest Dermatol*). Thus, we suggest that the switching of USP10 functions from pro-apoptotic to anti-apoptotic is context dependent and depends on 3D environmental cues in the wound bed.

Directly after wounding, local apoptosis is mediated by USP10, as US09 significantly diminished TUNEL+ cells. Reduced apoptosis led to less CD45+ cell infiltration. Studies in the cornea show that blocking neutrophil invasion is the mechanism by which stem cell treatment in the cornea reduces scarring.[66] Also, less inflammatory cells reduces myofibroblast differentiation because inflammatory cells secrete growth factors, such as TGFβ. (See e.g., Laskin, DL, Malaviya, R, and Laskin, J D (2019). Role of Macrophages in Acute Lung Injury and Chronic Fibrosis Induced by Pulmonary Toxicants. *Toxicol Sci* 168:287; and Kitano, A, Okada, Y, Yamanka, O, Shirai, K, Mohan, R R, and Saika, S (2010). Therapeutic potential of trichostatin A to control inflammatory and fibrogenic disorders of the ocular surface. *Mol Vis* 16:2964-2973).

In addition, US09 may remain long enough in the ECM to prevent USP10/integrin activity in proliferating fibroblasts, reducing α-SMA organization and pathological cell adhesion. Together these USP10-mediated functions (apoptosis and integrin stabilization) appear to be a central organizer of scarring.

In general, there is little known about the regulation of myofibroblasts and cell surface integrin expression through DUB activity and the resulting link to disease. In terms of DUBs and myofibroblasts, stellate cell activation induces the DUB, UCHL1 and knockdown of UCHL1 blocks progression of CCI4-induced fibrosis in mice. (See e.g, Wilson, CL, Murphy, LB, Leslie, J, Kendrick, S, French, J, Fox, C R, et al. (2015). Ubiquitin C-terminal hydrolase 1: A novel functional marker for liver myofibroblasts and a therapeutic target in chronic liver disease. *J Hepatol* 63:1421-1428).

Furthermore, pan-inhibition of DUBs with the DUB inhibitor, PR-619 ameliorates renal fibrosis through the SMAD-4 pathway. (See e.g, Soji, K, Doi, S, Nakashima, A, Sasaki, K, Doi, T, and Masaki, T (2018). Deubiquitinase inhibitor PR-619 reduces Smad4 expression and suppresses renal fibrosis in mice with unilateral ureteral obstruction. *PLoS One* 13: e0202409). In terms of DUBs and integrins, the DUB Ataxin-3 regulation of integrin α5 is a critical component of the neurological disorder, Machado-Joseph disease. (See e.g, Neves-Carvalho, A, Logarinho, E, Freitas, A, Duarte-Silva, S, Costa Mdo, C, Silva-Fernandes, A, et al. (2015). Dominant negative effect of polyglutamine expansion perturbs normal function of ataxin-3 in neuronal cells. *Hum Mol Genet* 24:100-117; and do Carmo Costa, M, Bajanca, F, Rodrigues, AJ, Tome, RJ, Corthals, G, Macedo-Ribeiro, S, et al. (2010). Ataxin-3 plays a role in mouse myogenic differentiation through regulation of integrin subunit levels. *PLoS One* 5: e11728).

More widely, DUB biology and a focus on DUBs as drug targets is an expanding field of study. DUBs are being targeted for both cancer and neurodegenerative diseases. (See e.g, Harrigan, JA, Jacq, X, Martin, NM, and Jackson, SP (2018). Deubiquitylating enzymes and drug discovery: emerging opportunities. *Nat Rev Drug Discov* 17:57-78; and Poondla, N, Chandrasekaran, AP, Kim, K S, and Ramakrishna, S (2019). Deubiquitinating enzymes as cancer biomarkers: new therapeutic opportunities? *BMB Rep* 52:181-189). In terms of USP10, a recent discovery using a protein engineering strategy for the rational design of DUB inhibitors found a sequence that when expressed as a cDNA directly targets USP10's DUB activity. (See e.g, Zhang, W, Bailey-Elkin, BA, Knaap, RCM, Khare, B, Dalebout, TJ, Johnson, G G, et al. (2017). Potent and selective inhibition of pathogenic viruses by engineered ubiquitin variants. *PLoS Pathog* 13: e1006372). Further studies may dissect the different functions of USP10's structural domain and DUB activity and their relative contributions to scarring.

In terms of RNAi for therapies, because of the accessibility of the eye, RNAi therapy has made significant progress in clinical outcomes for eye diseases and in general, gene knockdown with eye drops or by injection rivals the success of antibody therapies that have the challenge of being quickly diluted by tears, especially for anterior surface indications. Several new RNAi therapies target disease pathways for ocular indications such as Caspase-2 for anterior ischemic optic neuropathy, hypoxia for neovascular age-related macular degeneration and diabetic retinopathy, β2-adrenergic activity for glaucoma, TRPV1 for dry eye, to name of few. (See e.g, Titze-de-Almeida, R, David, C, and Titze-de-Almeida, SS (2017). The Race of 10 Synthetic RNAi-Based Drugs to the Pharmaceutical Market. *Pharm Res* 34:1339-1363). Significant numbers of RNAi based therapies are in various stages of clinical trials for multiple indications, with the use of modified siRNA conjugates becoming a dominant therapeutic modality. (See e.g. Watts, JK, Brown, R H, and Khvorova, A (2019). Nucleic Acid Therapeutics for Neurological Diseases. *Neurotherapeutics: the journal of the American Society for Experimental Neuro Therapeutics* 16:245-247). Other RNAi for Hepatitis C and various cancers are also in clinical trials. Specific to scarring therapies for the eye is a study in rabbits for the knockdown of the MTRF (Myocardin-Related Transcription Factor) gene that is a master regulator of actin genes. RNAi to MRTF reduced scarring in the fibrotic "bleb" made during the glaucoma filtration surgery to relieve pressure in the eye. (See e.,g. Tagalakis, AD, Madaan, S, Larsen, SD, Neubig, RR, Khaw, PT, Rodrigues, I, et al. (2018). In vitro and in vivo delivery of a sustained release nanocarrier-based formulation of an MRTF/SRF inhibitor in conjunctival fibrosis. *J Nanobiotechnology* 16:97; and Fernando, O, Tagalakis, AD, Awwad, S, Brocchini, S, Khaw, PT, Hart, S L, et al. (2018). Development of Targeted siRNA Nanocomplexes to Prevent Fibrosis in Experimental Glaucoma Filtration Surgery. *Mol Ther* 26:2812-2822). Several other gene knockdown strategies for ocular scarring are also being tested in animals. The partially modified cholesterol conjugate RX109 targeting CTGF to prevent ocular scarring is in clinical trials.

In this study the fully modified siRNA conjugate was used to achieve maximal activity and longevity of the effect in vivo. (See Hassler, MR, Turanov, AA, Alterman, J F, Haraszti, RA, Coles, AH, Osborn, M F, et al. (2018). Comparison of partially and fully chemically-modified siRNA in conjugate-mediated delivery in vivo. *Nucleic Acids Res* 46:2185-2196). Regarding the possibility of off-target effects, the asymmetric (20/15) chemically modified siRNA used in this study was designed to avoid any sequence identity with other rabbit genes within the 2-18 region of the anti-sense strand. The closest rabbit sequence identified in the rabbit transcriptome has 4 mismatches in the siRNA seed region, which completely excludes the possibility of a sequence-specific off-target effect caused by an anti-sense strand of siRNA (See FIG. 12). Furthermore, since the sdRNA is delivered to cells in the asymmetric duplex form, the anti-sense strand itself can't have any off-target effects as it doesn't efficiently enter the RISC complex. The possible off-target effects caused by a sense strand are excluded by a) its length (15, too short for RISC) and b) having 2'OMe modifications in positions 2 and 14, which inhibit RNAi activity.

Improvement to total regenerative healing may be within reach with US09. Activity of the US09 can be further enhanced by the backbone modifications optimization. Although a total knockdown with siRNA may not be shown, 1) it is not always advantageous to have complete knockdown, 2) small changes in USP10 expression relate to large phenotypic changes in cells were consistently observed, and 3) the goal is this study was achieved by preventing the upregulation of USP10 after wounding, instead of knocking down USP10 below normal levels observed in unwounded tissue (FIG. 3E). Dosing US09 twice, directly after wounding and at 6, 12 or 24 hours after wounding may totally prevent apoptosis and myofibroblast differentiation by targeting a wave of infiltrating cells that are not present directly after wounding. Another option is a slower delivery mechanism by absorbing US09 to a substrate and covering the eye for a 24-hour delivery. Future studies with longer time points, 3 and 6 months will determine how the scars resolve in each condition. In summary, a novel anti-scarring method is provided through the knockdown of USP10. This strategy can be more broadly applied to prevent scarring in other, non-ocular tissues.

Methods:

Sequencing of Rabbit Corneal USP10

Rabbit corneas were obtained from Pel-Freez Biologicals (Rogers, Arkansas). Rabbit primary corneal keratocytes were derived from the corneal stroma as previously described. (See e.g, Bernstein, A M, Greenberg, R S, Taliana, L, and Masur, SK (2004). Urokinase anchors uPAR to the actin cytoskeleton. *Invest Ophthalmol Vis Sci* 45:2967-2977). Total RNA was isolated with TRIzol Reagent (Invitrogen) or using Purelink RNA mini kit (Invitrogen). RNA was sent to ACGT, Inc (Wheeling, Illinois). The RNA samples were evaluated by Qubit fluorometry and Agilent 2100 Bioanalyzer. First-strand cDNA was constructed using the Mint-2 cDNA synthesis kit. The cDNA samples were evaluated by fluorometry and agarose gel electrophoresis. PCR was performed on first-strand cDNA, using Prime-STAR GXL DNA Polymerase and primers designed specifically for this study. All PCR products were evaluated by fluorometry and agarose gel electrophoresis. The "Rabbit" PCR products were purified using Agencourt AMPure XP Beads, and evaluated by fluorometry. Purified PCR products were fragmented by ultrasonication to an average 250 bp target fragment size. Uniquely barcoded sequencing libraries were constructed from fragmented DNA, using the NEXTflex™ Rapid DNA Sequencing Kit as per the manufacturer's instructions. Appropriate quality control analysis was performed at every step. Final libraries were assessed by Qubit fluorometry and Agilent 2100 Bioanalyzer. Final libraries were combined with compatible libraries from other projects, and loaded onto HiSeq 300 cycle flow cell to generate 150PE reads. Enough sequence was generated to provide at least 0.5 million reads per sample, with Q30 quality (average per read) sequence data. The raw Illumina reads were de-multiplexed and converted into fastq format. Low quality (Q<30) and short reads (N<50) were filtered out. The trimmed and filtered reads were de novo assembled to generate contigs. The contigs were analyzed and identified using BLAST, and a final assembly was constructed. Genbank submission MN927131. The trimmed and filtered reads were aligned to the reference sequence of the predicted USP10 gene based on the results of the BLAST analysis, and a variant report was generated.

The resulting de novo sequence for rabbit corneal USP10 was aligned with predicted RefSeq variants XM_002723256.1 and XM_002723256.2. Common region with 99% identity covering partial 3' UTR and most of the coding sequence, with the exception of three initial exons, was extracted as a consensus sequence for sdRNA design. The regions containing a few nucleotide mismatches with the database variants were avoided.

Self-Deliverable siRNA (sdRNA)

In embodiments, Self-deliverable siRNAs are the fully chemically modified asymmetric siRNA-cholesterol conjugates.

For the identification of the active sdRNAs against rabbit USP10 gene ten lead candidates were predicted by the published algorithm. (See e.g., Shmushkovich, T, Monopoli, KR, Homsy, D, Leyfer, D, Betancur-Boissel, M, Khvorova, A, et al. (2018). Functional features defining the efficacy of cholesterol-conjugated, self-deliverable, chemically modified siRNAs. *Nucleic Acids Res* 46:10905-10916). The designed sequences are listed in FIG. 13. For the primary screening, sdRNAs were synthesized as separate guide and passenger strands (TriLink Biotechnologies; San Diego, CA) and dissolved in sterile RNase-, DNase-free water for injection (CalBiochem, 4.86505) at 200 µM concentration. Duplexes were annealed by mixing equal volumes of the strand solutions, followed by heating to 95° C. for 5 min and allowing to cool gradually to room temperature. The quality of duplex formation was tested by using native gel electrophoresis (See FIGS. 10A and 10B).

More specifically, FIG. 10B depicts annealed duplexes were analyzed in the native gel electrophoresis. Duplexes were mixed with 5× TBE high-density sample buffer (Novex) and loaded in the TBE 4-20% gradient gels at 10 µmol per lane. Samples were fractionated at 150V and stained with SybrGold dye (ThermoFisher) for 10 min at RT. As a reference (M), we used 10 nt-100 nt Low Molecular Weight Marker (Affimetrix). Duplexes were formed in all the samples.

The sdRNA solutions were stored at −80° C. Prior to use the sdRNA stock solution was heated to 37° C. for 5 min, vortexed, and briefly spun down. The selected in primary in vitro screening sdRNA sequence (US09) was synthesized at 10 µmol scale (TriLink), the same sequence with 5'-terminal vinyl-phosphonate and non-targeting control were synthesized at 10 µmol scale by ChemGenes (Wilmington MA). These duplexes were formed at 200 µM final concentration in sterile PBS. Dose response by qPCR, (See FIG. 11).

Figure 11:
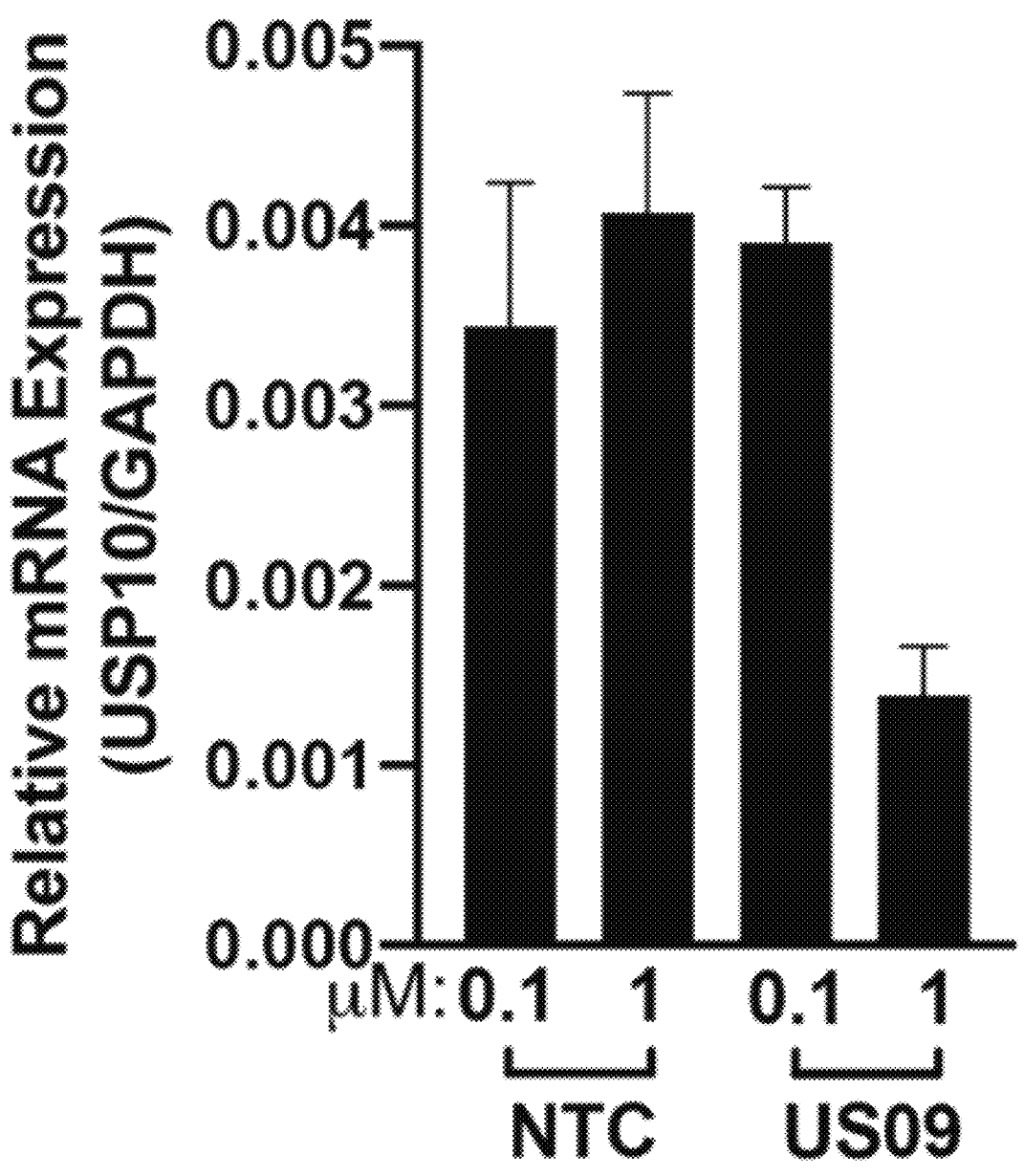
FIG. 11 is a histogram chart showing relative mRNA expression of USP10/GAPDH+/−SD.

More specifically, FIG. 11 depicts rabbit corneal cells were treated with 0.1 µM or 1.0 µM, US09, or NTC and incubated in supplemented serum-free media for 72 hours prior to lysing with Trizol and extraction of total RNA. Relative expression of USP10/GAPDH+/−SD is reported.

TABLE 4

| | Passenger strand | Guide strand |
|---|---|---|
| US09 | fC.mA.fG.mA.fA.mG.fC.mU. fG.mA.fU.mC.fA#mA#fA-Chol (SEQ ID NO: 21) | PmU.fU.mU.fG.mA.fU.mC.fA.mG. fC.mU.fU.mC.fU#mG#fA#mC#fA# mG#fC (SEQ ID NO: 22) |
| NTC | fU.mU.fA.mC.fA.mU.fG.mU. fU.mU.fU.mC.fC#mU#fA-Chol (SEQ ID NO: 23) | PmU.fA.mG.fG.mA.fA.mA.mC.fA. mU.fG.mU.fA#mA#fA#mC#fC#mA#fA (SEQ ID NO: 24) |

Table 4 depicts sequences used in Example 1 includes (SEQ ID NOS. shown above in the 5' to 3' directions). The modifications are as follows: m stands for 2'-OMe, f-2'-Fluoro, #-thiophosphate, Chol-Cholesteryl-TEG.

RNA Extraction and qPCR

Rabbit corneas were obtained from Pel-Freeze Biologicals, Rogers, A R. Keratocytes were isolated from corneas and differentiated into fibroblasts as previously described. (See e.g., Bernstein, A M, Greenberg, R S, Taliana, L, and Masur, SK (2004). Urokinase anchors uPAR to the actin cytoskeleton. *Invest Ophthalmol Vis Sci* 45:2967-2977). Primary rabbit corneal fibroblasts, were maintained in DMEM/F12 medium supplemented with 10% Fetal bovine serum and penicillin/streptomycin solution (Gibco). Cell were cultured for 1-2 weeks and passaged once 24 h prior to transfection. For the qPCR assay in FIG. 1A (sdRNA screening) cells were trypsinized and mixed with oligonucleotides in reduced serum medium DMEM with 3% FBS at a final concentration 1 μM sdRNA. Cells were incubated for 72 h and then harvested. Total RNA from primary corneal fibroblasts was purified with PureLink RNA 96 kit (Invitrogen) according to manufacturer's recommendations and was added as a template into one-step multiplex qPCR assay using Quanta qScript XLT ToughMix with ROX dye (VWR). For that, 1 μl of total RNA was mixed with the reagent and primer-probe mixes for rabbit USP10 and reference gene GAPDH in a 10 μl reaction. The cycling parameters were as recommended by Quanta. The primer-probe mix for GAPDH labeled with VIC was from Taqman (Oc03823402_g1), and the primer-probe mix for rabbit USP10 labeled with FAM was specifically designed for the generated rabbit corneal sequence and synthesized by ThermoFisher. The sequences were as following: primers CTG-CATTTTCGGTGGACACA (SEQ ID NO:25) and TGGCC-GATTCTTTCGAACTCT (SEQ ID NO:26), MGB probe covering exon 11-12 junction of XM_002723256.2-TCAGGTCTGTGGTTTACC (SEQ ID NO:27).

For the qPCR assay in FIG. 3E, immediately after sacrifice, eyes were enucleated and corneas were excised from the globes. The cornea was cut in half through the wound and the wounded section was excised and put directly into TRIzol Reagent (Invitrogen). Purelink RNA mini kit (Invitrogen) was used to extract total RNA. For the dose response qPCR of US09 (Supplementary FIG. 3), rabbit corneal cells were treated with 0.1 μM and 1.0 μM, US09, or NTC and incubated in supplemented serum-free media for 72 hours prior to lysing with Trizol and extraction of total RNA. Further purification of both tissue and primary cell RNA was performed with Monarch PCR &DNA cleanup Kit (New England Biolabs, Inc). cDNA was generated from 1 μg of total RNA in a 20 ul reaction using iScript Reverse Transcription Supermix for RT-qPCR (Bio-Rad). The qPCR was prepared in 10 uL reactions with iTaq Universal SYRB Green Supermix (Bio-Rad) with 1 μL of cDNA and 500 nM each primer. The cycling parameters used were 95° C., 10 min; 40 cycles of 95° C., 15 sec; 60° C., 60 sec. Primers used: USP10 (IDT): AGAGCGCCTCCCTCCCTGCC (SEQ ID NO:28), GGTCCTCGGATGCCGGAACC (SEQ ID NO:29); GAPDH (IDT): GAGTGAACGGAT-TTGGCCGC (SEQ ID NO:30), TTGATGTTGGGGG-GATCTCG (SEQ ID NO:31).

Ex-Vivo Corneal Tissue Culture

This method of ex vivo organ culture has been previously described. (See e.,g Gillespie, SR, Tedesco, LJ, Wang, L, and Bernstein, A M (2017). The deubiquitylase USP10 regulates integrin beta1 and beta5 and fibrotic wound healing. *J Cell Sci* 130:3481-3495; and Castro, N, Gillespie, S R, and Bernstein, A M (2019). Ex Vivo Corneal Organ Culture Model for Wound Healing Studies. *J Vis Exp*). Briefly, after enucleation of the eyes, a 6 mm trephine is used to wound the center of the cornea. The wound penetrates the epithelium and anterior stroma without making a full-thickness wound through the entire cornea as is described below for the in vivo experiments. The demarcated tissue was removed. Corneas were mounted on an agar base and wet with PBS. One nmol (5.6 ul) of non-targeting cy3-labeled sdRNA (MAP4K4-cy3, Advirna) was pipetted into the wound and imaged immediately under a dissection scope (Accu-scope, Commack, NY). Cell culture lids remained attached during imaging to maintain sterility. Four mls of supplemented serum-free media was added to the plate, maintaining corneas at an air-liquid interface at the limbal border in 5% CO2 at 37° C. Corneas were wet every 24 hours with conditioned media. Media was changed every 48 hours. (cy3-sd-RNA was not re-added). At 2 h, day 1, day 2, day 3, and day 7 corneas were imaged by live cell confocal (Zeiss, LSM780). Supplementary FIG. 2.

Animal Studies

Twelve female New Zealand White rabbits (See Tripathi, R, Giuliano, EA, Gafen, H, Gupta, S, Martin, LM, Sinha, P R, et al. (2019). Is sex a biological variable in corneal wound healing? *Exp Eye Res:* 107705) (Charles River) 12 to 15 weeks old and weighing 2.5-3.0 kg each were used. The Institutional Animal Care and Use Committee of SUNY Upstate Medical University approved the study. General anesthesia in rabbits was given by an intramuscular injection of ketamine hydrochloride 100 mg/ml given at 40 mg/kg and xylazine hydrochloride 100 mg/ml given at 6 mg/kg along with an injection of buprenorphine SQ (slow release) 1 mg/ml given at 0.1 mg/kg for pain control. Local anesthesia was also given with two drops of topical 0.5% proparacaine hydrochloride (Alcon Laboratories, Inc., Fort Worth, TX). At euthanasia, anesthesia as above prior to 1 ml of Fatal-Plus IV (Pentobarbital Sodium 390 mg/ml). In each rabbit, the right eye was wounded. The central area of the anterior cornea was demarcated with a 6 mm trephine. The circular area that was demarcated was removed with forceps. This type of wound leaves a bare stroma with the epithelium and basement membrane removed. 1 nmol self-delivery siRNA resuspended in PBS was applied (total volume 5.6 ul). Six wounded eyes were treated with non-targeting control siRNA (NTC, Advirna) and six wounded eyes were treated with sd-USP10-targeting siRNA (US09, Advirna). According to the adherence to the ARVO Statement for the Use of Animals in Ophthalmic and Vision Research, the contralateral eye served as untouched (naive) control. E-collars were used for all wounded animals.

Slit-Lamp Biomicroscopy

After surgery, slit lamp was used to evaluate ocular health, corneal haze and wound closure. Epithelial wound closure was assessed using fluorescein (Flucaine, 5 ml OCuSOFT, Inc., 1 drop per eye) and photographed on days 1,2,3 and 7 using a slit lamp (Nikon Slit lamp Microscope, NS-1) microscope equipped with a digital camera with a cobalt blue filter. Images were analyzed by 2 independent graders for wound closure quantified by the absence of fluorescein staining over time.

Immunohistochemistry-Frozen Sections

Immediately after sacrifice, globes were enucleated and corneas were excised from globes. The cornea was cut in half through the wound and immediately submerged in a plastic mold with OCT compound (Fisher) to be frozen at −80° C. For cutting the sections the Cryostat temperature was between −20° C. and −23° C. and sections were cut at 7 μm. 3-4 sections were placed per slide and stored at −80° C. Slides were thawed and baked overnight in a slide moat at 37° C. Next day sections were rehydrated in PBS for 15 minutes, treated with blocking buffer (10% normal goat serum in PBS, Jackson Immuno Research Labs) for 20 minutes, and then incubated with primary antibodies (Fibronectin-EDA (SIGMA/F6140), Collagen III (Novus Biologicals/NBP105119B), aSMA (SIGMA/C6198), CD45 Thermofisher/MA5-28392) 1:250 for 1 hour in a moist chamber at RT. Slides are washed in PBS for 15 minutes and sections were treated with blocking buffer for 15 min. Tissue was then incubated with secondary antibody Alexa 647 (1:250) for 45 minutes in a moist chamber. After washing with blocking buffer for 15 min, slides were mounted with Prolong Gold Antifade with DAPI (Thermofisher Scientific).

TUNEL Assay

All the solutions were supplied with the kit (R&D System TdT In Situ Apoptosis Detection Kit-Fluorescein 4812-30-K). Slides were thawed and baked overnight in a slide moat at 37° C. Next day sections were rehydrated in PBS for 15 minutes, fixed in Acetone (Fisher A18500) for 10 min at RT and washed in PBS twice for 5 min. The tissue was post-fixed in pre-cooled Ethanol (UltraPure 200CSGP): Acetic Acid (Sigma A6283-100 ml) 2:1 for 5 min at RT, followed by two washes in PBS. The Equilibration Buffer was then incubated directly on the specimen for 10 seconds at RT. The excess liquid was gently removed and the Working Strength TdT Enzyme was incubated in a humid chamber at 37° C. for 1 hour. The Working Strength Stop/Wash Buffer was then incubated for 10 min at RT. The slides were washed in 3 changes of PBS for 1 min each wash. The excess of liquid was removed and the Strength Anti-Digoxigenin Conjugate was applied for 30 min at RT in a humid chamber avoiding exposure to light. Slides were washed in PBS 4 times, 2 min each wash. After washing, slides were mounted with Prolong Gold Antifade with DAPI (Thermofisher Scientific).

Quantification of Histochemistry

Collagen III, FN-EDA, CD45, and α-SMA: Imaging was performed using the Nikon Eclipse Ni microscope using fixed exposure times for each antibody stain. Images were taken consecutively of the entire cornea using the 4× objective and were then processed in ImageJ by the "Apply Threshold" plugin. A fixed threshold was generated using control tissue to cancel background/baseline levels of fluorescence, which was then applied to all Wnd-NTC and Wnd-US09 images, thus binarizing pixel intensity. Signal above this threshold was considered "scar", and signal below threshold was "unscarred". For Collagen III, FN-EDA, and CD45 staining, the number of pixels above threshold was then quantified in each corneal section and divided by the total number of pixels composing the scarred portion of the cornea to generate a "% pixels above threshold" metric of scarring severity. Because α-SMA staining was restricted to small and isolated pockets of cells within the corneal scar (and thus minute portions of the total area of the scar), α-SMA staining was simply reported as the total number of pixels above threshold.

Cell proliferation was determined utilizing Collagen III stained sections to mark the scar-tissue. Quantification was restricted to only the scarred portion of the cornea, which was defined by an abrupt and readily observable increase in epithelial thickness as well as an abrupt increase in Collagen III staining (in the anterior portion of the stroma, directly adjacent to the epithelium). "Inside the wound" corresponds to stroma with Collagen III staining, whereas "outside the wound" was defined as the remaining stroma, posterior cornea beneath the scar to the endothelium. DAPI-labeled nuclei were the quantified in these portions of the stroma using the "Object Counter" plugin in ImageJ software. These counts were normalized by the total area of each portion to generate a nuclei density measurement.

Optical Coherence Tomography (OCT)

OCT was recorded using a bioptigen Envisu R2210 with a 10 mm telecentric lens directly prior to sacrifice. OCT datasets comprise 100 transverse sections spanning 6 mm of the eye (the central wound). Each section has a width of 6 mm (1000 pixels) and a depth of 1.491 mm (1024 pixels). Regions of each image containing cornea are identified using the MATLAB function "imbinarize" with the adaptive thresholding method, and all other pixels of the image are reduced to zero intensity. Corneal Thickness: Corneal thickness was measured at pixel resolution in these thresholded images as the distance across the nonzero region, and thickness is averaged across the entire cornea. OCT variance: Aberrations in cornea (i.e. scarring) increase nonuniformity of pixel intensities in localized areas of the cornea. To quantify this nonuniformity, we first segment the cornea in each image file into 100 equal parts. For each segment the statistical variance (ie . . . [st dev]$^2$) of pixel intensities was calculated. This yields 100 variances for each transverse section. Transverse sections from a dataset are averaged yielding a two-dimensional "Variance by Position" plot.

Statistical Analysis

Numerical data are expressed as the mean+/−SEM of 6 animals. Statistical significance for histological analysis of three groups (UnWnd, Wnd-NTC, and Wnd-US09) was calculated by one-way ANOVA with Bonferroni's test. Statistical significance of all other numerical data was calculated with the Student's t-test. * p value<0.05,  p value<0.01, * p value<0.001.

Example II

Self-deliverable siRNA (sdRNAi) directed against USP-10 of Table 1 were provided. These self-deliverable siRNAs were fully chemically modified asymmetric siRNA-cholesterol conjugates. The modifications to the individual sequence are characterized as:

```
                                            (SEQ ID NO: 1)
5'-[fC][mA][fU][mU][fA][mA][fA][mA][fG][mA][fU]
[mU][fU][*][mC][*][fA][CholTEG]-3'

(SEQ ID NO: 3)
5'-[fG][mA][fG][mA][fA][mA][fC][mU][fC][mU][fU]
[mU][fC][*][mU][*][fA][CholTEG]-3'

(SEQ ID NO: 5)
5'-[fU][mG][fA][mA][fA][mC][fA][mG][fA][mC][fU]
[mG][fU][*][mU][*][fA][CholTEG]-3'

(SEQ ID NO: 7)
5'-[fC][mA][fA][mC][fA][mA][fC][mA][fC][mU][fU]
[mG][fU][*][mA][*][fA][CholTEG]-3'

(SEQ ID NO: 9)
5'-[fA][mA][fA][mC][fC][mU][fU][mG][fG][mA][fG]
[mU][fU][*][mG][*][fA][CholTEG]-3'

(SEQ ID NO: 11)
5'-[fA][mA][fU][mG][fA][mA][fU][mG][fA][mG][fU]
[mU][fC][*][mA][*][fA][CholTEG]-3'

(SEQ ID NO: 13)
5'-[fC][mA][fG][mU][fU][mA][fA][mC][fA][mA][fG]
[mU][fC][*][mA][*][fA][CholTEG]-3'
```

45

-continued (SEQ ID NO: 15)
5'-[fG][mA][fU][mU][fU][mU][fA][mG][fC][mC][fC]
[mU][fG][*][mA][*][fA][CholTEG]-3'

(SEQ ID NO: 17)
5'-[fC][mA][fA][mU][fG][mA][fA][mG][fA][mA][fG]
[mA][fG][*][mC][*][fA][CholTEG]-3'

(SEQ ID NO: 19)
5'-[fC][mC][fC][mU][fG][mA][fU][mG][fA][mA][fU]
[mU][fC][*][mA][*][fA][CholTEG]-3'

Modifications to the sequences are also shown below:

(SEQ ID NO: 2)
[5Phos][mU][fG][mA][fA][mA][fU][mC][fU][mU][fU]
[mU][fA][mA][fU][*][mG][*][fG][*][mC][*][fA][*]
[mA][*][fU]

(SEQ ID NO: 4)
[5Phos][mU][fA][mG][fA][mA][fA][mG][fA][mG][fU]
[mU][fU][mC][fU][*][mC][*][fU][*][mC][*][fU][*]
[mA][*][fA]

(SEQ ID NO: 6)
[5Phos][mU][fA][mA][fC][mA][fG][mU][fC][mU][fG]
[mU][fU][mU][fC][*][mA][*][fA][*][mC][*][fC][*]
[mA][*][fA]

(SEQ ID NO: 8)
[5Phos][mU][fU][mA][fC][mA][fA][mG][fU][mG][fU]
[mU][fG][mU][fU][*][mG][*][fC][*][mU][*][fG][*]
[mG][*][fU]

(SEQ ID NO: 10)
[5Phos][mU][fC][mA][fA][mC][fU][mC][fC][mA][fA]
[mG][fG][mU][fU][*][mU][*][fU][*][mC][*][fA][*]
[mG][*][fU]

(SEQ ID NO: 12)
[5Phos][mU][fU][mG][fA][mA][fC][mU][fC][mA][fU]
[mU][fC][mA][fU][*][mU][*][fA][*][mG][*][fC][*]
[mC][*][fG]

(SEQ ID NO: 14)
[5Phos][mU][fU][mG][fA][mC][fU][mU][fG][mU][fU]
[mA][fA][mC][fU][*][mG][*][fU][*][mC][*][fA][*]
[mG][*][fG]

(SEQ ID NO: 16)
[5Phos][mU][fU][mC][fA][mG][fG][mG][fC][mU][fA]
[mA][fA][mA][fU][*][mC][*][fU][*][mC][*][fC][*]
[mA][*][fA]

(SEQ ID NO: 18)
[5Phos][mU][fG][mC][fU][mC][fU][mU][fC][mU][fU]
[mC][fA][mU][fU][*][mG][*][fA][*][mC][*][fC][*]
[mG][*][fA]

(SEQ ID NO: 20)
[5Phos][mU][fU][mG][fA][mA][fU][mU][fC][mA][fU]
[mC][fA][mG][fG][*][mG][*][fC][*][mU][*][fA][*]
[mA][*][fA]

As shown in the paragraph above, "m" refers to 2'-OMe modification in each instance, "f" refers to -2'Fluoro modification in each instance, "*" refers to a-thiophosphate modification in each instance. The nucleic acid strands are written 5' to 3' in the paragraph above.

Testing of sdRNA complexes targeting human USP10 (US31-US40) was performed. Native gel electrophoresis for USP10 complexes was performed, where compounds were dissolved in sterile Rnase-, Dnase-, free water to the final concentration of 100 μM. The presence of the compounds is confirmed in the gel electrophoresis of FIG. 21.

Reporter screening of USP10 sdRNA compounds of the present disclosure is depicted in FIG. 22. The reporting screening was performed under the following conditions: cell seeding: 10,000 Hela cells/well; 10 USP10 sdRNA were passively transfected into Hela cells expressing luciferase reporter; transfection: 1 μM compounds, antibiotic-free EMEM medium 3% FBS, 24 hr incubation. Knockdown was measured via *Renilla* luciferase expression and normalized to constant Firefly luciferase expression. Data is expressed as the percentage of gene expression of NTC transfected cells (NTC).

Samples US 31, US 36 and US 38 were chosen for dose curves in primary human corneal cells. The dose curve analysis included the following conditions: cell seeding: 5,000 human corneal fibroblasts cells/well; 10 USP10 sdRNA were passively transfected into Hela cells expressing luciferase reporter; transfection: 2-0.016 μM compounds, antibiotic-free DMEM/F12 3% FBS, 72 hr incubation. Gene expression was measured by qPCR (Taqman chemistry), adjusted to the standard curve, and normalized to the reference gene GAPDH, and data is expressed as the percentage of gene expression of NTC transfected cells (NTC). The data from these dosage curves is depicted in FIG. 23, and FIG. 24. Further, US 31, US 36 and US 38 were chosen for dose curves in HEPG2 cells. The data from these dosage curves is depicted in FIG. 25, and FIG. 26.

Referring to FIG. 27 USP10 is upregulated in human cirrhotic liver. FIG. 27A and FIG. 27B depict deidentified human cadaver non-fibrotic liver control and cirrhotic liver (respectively). Sections were obtained from the bioreposi-tory and Pathology Core at Mount Sinai Hospital, NYC. Here, USP10 is increased 2.32+/-0.9. Bar=100 μm. N=3.

Additional Examples

Referring now to FIG. 16, a rabbit model for proliferative vitreoretinopathy (PVR) is shown. Here, New Zealand White Rabbits were injected into the vitreous. The injection of cells creates a scar that detaches the retina. Vitrase "loosens" the vitreous to allow the dispersion of drugs int the vitreous. Retinal images: 10A depict prior to injection, immediately after injection FIG. 10B vitrase only, FIG. 10C vitrase plus cells: 30 Days after injection FIG. 10D vitrase plus cells, FIG. 10E vitrase plus cells and USP10 siRNA. The USP10 siRNA prevents retina detachment in this model. N=2 for each condition.

In glaucoma filtration surgery, 50% of surgeries fail by 5 years because of scarring. The data demonstrate that sdUSP10 prevents a fibrotic response in glaucoma filtration surgery. Referring now to FIG. 17, a glaucoma filtration surgery pilot study is shown. Here, a Pilot study comparing US09, NTC, and the current standard of care, MMC. FIG. 17A) a superonasal fornix-based conjunctival flap was raised behind the limbus. Drugs were injected (pipetted) into the bleb. Referring to FIG. 17B, frozen control section that includes Cornea, Limbus, and Tenon/Sclera is shown. FIGS. 17C-F; a top image of enucleated rabbit eyes after sacrifice and before sectioning is shown. Bottom Images of Tenon/sclera portion of section. Dapi (blue), α-SMA (red). Images as labeled are shown. Of note is that in rabbits treated with US09 compared to NTC or MMC, the tissue remained "thin" similar to unwounded. α-SMA staining was also similar to unwounded tissue. N=3 rabbits in each condition.

FIGS. 18A-18P depict knockdown of USP10 in mouse cornea after wounding. To expand the data on USP10 siRNA from rabbit to another species, mouse, the USP10 knock-down experiment was performed in mice after wounding with 0.15N NaOH for 60 seconds. This is a standard chemical wounding model. Arrows denote separated epithelial in wounded siControl but not siUSP10. Panels are labeled: FIGS. 18A-C) Day 14 Collagen III; FIGS. 18D-F) Day 14 FN-EDA; FIGS. 18G-I) Day 3 CD45+; J-L) Day 14 CD45+; FIGS. 18M-O) Day 1 TUNEL (apoptosis); P) qRT-PCR -Relative USP10 mRNA expression at Day 3. Results are identical to knockdown of USP10 in rabbit cornea.

FIGS. 19A and 19B depict USP10 increased in wounded mouse tendons. FIGS. 19A, 19B; 13-week old male C57BL/6 mice remained uninjured (FIG. 19A) or underwent an excisional midsubstance defect (Beason et al, 2012) in the left patellar tendon using 0.75 mm biopsy punch (Shoney Scientific, Waukesha, WI) (FIG. 19B). Mice were sacrificed 1 week after injury, and their left patellar tendons were dissected, fixed in formalin, embedded in paraffin, and sectioned at 5 µm in the coronal orientation. USP10 is increased 3.75-fold+/−1.26 *p<0.05 in wounded tendon compared to control.

FIGS. 20A and 20B depict USP10 is upregulated in fibrotic mouse liver. The Bile duct ligation (BDL) induced cholestatic liver disease model was utilized in mice to induce acute liver injury and liver fibrosis. Compared to normal mice, fibrosis around the portal vein area is observed in the BDL model. FIGS. 20A, 20B) mouse non-fibrotic liver control (A) and fibrotic liver (B). USP10 is increased 2.1+/−0.5. Bar=100 µm. N=3.

FIG. 28 depicts knockdown of human USP10 with US36 and US31 in human adult dermal cells. Adult human dermal fibroblasts (ATCC #PCS-201-012) were treated with 2 uM each of NTC (non-targeting control), USP10 targeting self-delivery siRNA (sdRNAs) US36 or US31 for 72 hours. Western blot for USP10 and integrin avb5 demonstrates USP10 knockdown and subsequent integrin avb5 knock-down that was first identified in human corneal cells. These data suggest that knockdown of USP10 with US36 or US31 in dermal cells would prevent or reduce scarring in skin, similar to what we identified in vivo, in cornea.

The entire disclosure of all applications, patents, and publications cited herein are herein incorporated by refer-ence in their entirety. While the foregoing is directed to embodiments of the present disclosure, other and further embodiments of the disclosure may be devised without departing from the basic scope thereof.

What is claimed is:

1. A composition comprising a synthetic nucleic acid comprising a polynucleotide sequence of one of SEQ ID NOs: 2, 4, 6, 8, 10, 12, 14, 16, 18, and 20, wherein the synthetic nucleic acid comprises one or more modifications.

2. The composition of claim 1, wherein the synthetic nucleic acid is an antisense oligonucleotide.

3. A composition comprising a synthetic nucleic acid comprising a polynucleotide sequence of one of SEQ ID NOs: 1, 3, 5, 7, 9, 11, 13, 15, 17, and 19, wherein the synthetic nucleic acid comprises one or more modifications.

4. The composition of claim 3, wherein the synthetic nucleic acid is a sense oligonucleotide.

5. A composition comprising a double-stranded self-deliverable siRNA (sdRNAi) comprising a first synthetic nucleic acid and a second synthetic nucleic acid, wherein:
   the first synthetic nucleic acid comprises a polynucleotide sequence of one of SEQ ID NOs: 2, 4, 6, 8, 10, 12, 14, 16, 18, and 20;
   the second synthetic nucleic acid comprises a polynucleotide sequence of one of SEQ ID NOs: 1, 3, 5, 7, 9, 11, 13, 15, 17, and 19;
   and the sdRNAi is directed against Ubiquitin-Specific Peptidase 10 (USP-10).

6. A composition comprising a double-stranded self-deliverable SiRNA (sdRNAi) comprising a first synthetic nucleic acid and a second synthetic nucleic acid, wherein:
   the first synthetic nucleic acid comprises a polynucleotide sequence of SEQ ID NO: 12; and the second synthetic nucleic acid comprises a polynucleotide sequence of SEQ ID NO: 11 and the sdRNAi is directed against Ubiquitin-Specific Peptidase 10 (USP-10).

7. The composition of claim 6, wherein the sdRNAi further comprises a one or more modifications, cholesterol moieties and/or vinyl-phosphonate moieties.

8. The composition of claim 6, wherein:
   the first synthetic nucleic acid comprises or consists of 20 nucleotides, and
   the second synthetic nucleic acid comprises or consists of 15 nucleotides.

9. A pharmaceutical composition comprising the sdRNAi of claim 6 and a pharmaceutically acceptable carrier.

10. The pharmaceutical composition of claim 9, wherein the pharmaceutical composition is formulated for topical administration, intravitreal administration, or transscleral administration.

11. The pharmaceutical composition of claim 9, wherein the pharmaceutical composition further comprises one or more modifications, cholesterol moieties and/or vinyl-phosphonate moieties.

12. A method of treating or alleviating fibrosis in a subject comprising administering to the fibrotic tissue or wounded tissue in a therapeutically effective amount of the pharmaceutical composition of claim 9 to the subject.

13. The method of claim 12, wherein the method fully or substantially eliminates an upregulation of USP10 after wounding.

14. A method of eliminating or reducing fibrosis in a subject after a tissue wound comprising administering to the tissue wound a therapeutically effective amount of the pharmaceutical composition of claim 9 to the subject.

15. The method of claim 14, wherein the method fully or substantially eliminates an upregulation of USP10 after wounding.

16. A method of eliminating or reducing ocular scarring in an eye of a subject after an ocular wound comprising administering to the ocular wound a therapeutically effective amount of the pharmaceutical composition of claim 9 to the subject.

17. The method of claim 16, wherein the method fully or substantially eliminates an upregulation of USP10 after wounding.

18. The method of claim 16, wherein the ocular scarring occurs on a cornea.

* * * * *

SEQUENCE LISTING

```
<160> NUMBER OF SEQ ID NOS: 62

<210> SEQ ID NO 1
<211> LENGTH: 15
<212> TYPE: RNA
<213> ORGANISM: Artificial Sequence
<220> FEATURE:
<223> OTHER INFORMATION: Synthetic sequence

<400> SEQUENCE: 1
cauuaaaaga uuuca                                                     15

<210> SEQ ID NO 2
<211> LENGTH: 20
<212> TYPE: RNA
<213> ORGANISM: Artificial sequence
<220> FEATURE:
<223> OTHER INFORMATION: Synthetic sequence

<400> SEQUENCE: 2
ugaaaucuuu uaauggcaau                                                20

<210> SEQ ID NO 3
<211> LENGTH: 15
<212> TYPE: RNA
<213> ORGANISM: Artificial Sequence
<220> FEATURE:
<223> OTHER INFORMATION: Synthetic sequence

<400> SEQUENCE: 3
gagaaacucu uucua                                                     15

<210> SEQ ID NO 4
<211> LENGTH: 20
<212> TYPE: RNA
<213> ORGANISM: Artificial Sequence
<220> FEATURE:
<223> OTHER INFORMATION: Synthetic sequence

<400> SEQUENCE: 4
uagaaagagu uucucucuaa                                                20
```

-continued

```
<210> SEQ ID NO 5
<211> LENGTH: 15
<212> TYPE: RNA
<213> ORGANISM: Artificial Sequence
<220> FEATURE:
<223> OTHER INFORMATION: Synthetic sequence

<400> SEQUENCE: 5
ugaaacagac uguua                                                     15

<210> SEQ ID NO 6
<211> LENGTH: 20
<212> TYPE: RNA
<213> ORGANISM: Artificial Sequence
<220> FEATURE:
<223> OTHER INFORMATION: synthetic sequence

<400> SEQUENCE: 6
uaacagucug uuucaaccaa                                                20

<210> SEQ ID NO 7
<211> LENGTH: 15
<212> TYPE: RNA
<213> ORGANISM: Artificial Sequence
<220> FEATURE:
<223> OTHER INFORMATION: synthetic sequence

<400> SEQUENCE: 7
caacaacacu uguaa                                                     15

<210> SEQ ID NO 8
<211> LENGTH: 20
<212> TYPE: RNA
<213> ORGANISM: Artificial Sequence
<220> FEATURE:
<223> OTHER INFORMATION: Synthetic sequence

<400> SEQUENCE: 8
uuacaagugu uguugcuggu                                                20

<210> SEQ ID NO 9
<211> LENGTH: 15
<212> TYPE: RNA
<213> ORGANISM: Artificial Sequence
<220> FEATURE:
<223> OTHER INFORMATION: Synthtetic sequence

<400> SEQUENCE: 9
aaaccuugga guuga                                                     15

<210> SEQ ID NO 10
<211> LENGTH: 20
<212> TYPE: RNA
<213> ORGANISM: Artificial Sequence
<220> FEATURE:
<223> OTHER INFORMATION: Synthetic sequence

<400> SEQUENCE: 10
ucaacuccaa gguuuucagu                                                20

<210> SEQ ID NO 11
<211> LENGTH: 15
<212> TYPE: RNA
<213> ORGANISM: Artificial Sequence
<220> FEATURE:
<223> OTHER INFORMATION: Synthetic Sequence
```

```
<400> SEQUENCE: 11
aaugaaugag uucaa                                             15

<210> SEQ ID NO 12
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 12
uugaacucau ucauuagccg                                        20

<210> SEQ ID NO 13
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 13
caguuaacaa gucaa                                             15

<210> SEQ ID NO 14
<211> LENGTH: 20
<212> TYPE: RNA
<213> ORGANISM: Artificial Sequence
<220> FEATURE:
<223> OTHER INFORMATION: Synthetic sequence

<400> SEQUENCE: 14
uugacuuguu aacugucagg                                        20

<210> SEQ ID NO 15
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 15
gauuuuagcc cugaa                                             15

<210> SEQ ID NO 16
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 16
uucagggcua aaaucuccaa                                        20

<210> SEQ ID NO 17
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 17
caaugaagaa gagca                                             15

<210> SEQ ID NO 18
<211> LENGTH: 20
```

```
<212> TYPE: RNA
<213> ORGANISM: Artificial Sequence
<220> FEATURE:
<223> OTHER INFORMATION: Synthetic Sequence

<400> SEQUENCE: 18
ugcucuucuu cauugaccga                                                20

<210> SEQ ID NO 19
<211> LENGTH: 15
<212> TYPE: RNA
<213> ORGANISM: Artificial Sequence
<220> FEATURE:
<223> OTHER INFORMATION: Synthetic sequence

<400> SEQUENCE: 19
cccugaugaa uucaa                                                     15

<210> SEQ ID NO 20
<211> LENGTH: 20
<212> TYPE: RNA
<213> ORGANISM: Artificial Sequence
<220> FEATURE:
<223> OTHER INFORMATION: synthetic sequence

<400> SEQUENCE: 20
uugaauucau cagggcuaaa                                                20

<210> SEQ ID NO 21
<211> LENGTH: 15
<212> TYPE: RNA
<213> ORGANISM: Artificial sequence
<220> FEATURE:
<223> OTHER INFORMATION: synthetic sequence

<400> SEQUENCE: 21
aaacuagucg aagac                                                     15

<210> SEQ ID NO 22
<211> LENGTH: 20
<212> TYPE: RNA
<213> ORGANISM: Artificial Sequence
<220> FEATURE:
<223> OTHER INFORMATION: synthetic sequence

<400> SEQUENCE: 22
uuugaucagc uucugacagc                                                20

<210> SEQ ID NO 23
<211> LENGTH: 15
<212> TYPE: RNA
<213> ORGANISM: Artificial Sequence
<220> FEATURE:
<223> OTHER INFORMATION: Synthetic sequence

<400> SEQUENCE: 23
uuacauguuu uccua                                                     15

<210> SEQ ID NO 24
<211> LENGTH: 20
<212> TYPE: RNA
<213> ORGANISM: Artificial Sequence
<220> FEATURE:
<223> OTHER INFORMATION: synthetic sequence

<400> SEQUENCE: 24
```

-continued uaggaaaaca uguaaaccaa                                                             20

<210> SEQ ID NO 25
<211> LENGTH: 20
<212> TYPE: DNA
<213> ORGANISM: Artificial Sequence
<220> FEATURE:
<223> OTHER INFORMATION: synthetic sequence

<400> SEQUENCE: 25
ctgcattttc ggtggacaca                                                             20

<210> SEQ ID NO 26
<211> LENGTH: 21
<212> TYPE: DNA
<213> ORGANISM: Artificial Sequence
<220> FEATURE:
<223> OTHER INFORMATION: Synthetic sequence

<400> SEQUENCE: 26
tggccgattc tttcgaactc t                                                           21

<210> SEQ ID NO 27
<211> LENGTH: 18
<212> TYPE: DNA
<213> ORGANISM: Artificial Sequence
<220> FEATURE:
<223> OTHER INFORMATION: synthetic sequence

<400> SEQUENCE: 27
tcaggtctgt ggtttacc                                                               18

<210> SEQ ID NO 28
<211> LENGTH: 20
<212> TYPE: DNA
<213> ORGANISM: Artificial Sequence
<220> FEATURE:
<223> OTHER INFORMATION: synthetic sequence

<400> SEQUENCE: 28
agagcgcctc cctccctgcc                                                             20

<210> SEQ ID NO 29
<211> LENGTH: 20
<212> TYPE: DNA
<213> ORGANISM: Artificial Sequence
<220> FEATURE:
<223> OTHER INFORMATION: synthetic sequence

<400> SEQUENCE: 29
ggtcctcgga tgccggaacc                                                             20

<210> SEQ ID NO 30
<211> LENGTH: 20
<212> TYPE: DNA
<213> ORGANISM: Artificial Sequence
<220> FEATURE:
<223> OTHER INFORMATION: synthetic sequence

<400> SEQUENCE: 30
gagtgaacgg atttggccgc                                                             20

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
ttgatgttgg cgggatctcg                                                        20

<210> SEQ ID NO 32
<211> LENGTH: 20
<212> TYPE: DNA
<213> ORGANISM: Artificial Sequence
<220> FEATURE:
<223> OTHER INFORMATION: synthetic sequence

<400> SEQUENCE: 32
taaatgccac agaacctata                                                        20

<210> SEQ ID NO 33
<211> LENGTH: 20
<212> TYPE: DNA
<213> ORGANISM: Artificial Sequence
<220> FEATURE:
<223> OTHER INFORMATION: synthetic sequence

<400> SEQUENCE: 33
tcggctgatg aacgagttta                                                        20

<210> SEQ ID NO 34
<211> LENGTH: 20
<212> TYPE: DNA
<213> ORGANISM: Artificial Sequence
<220> FEATURE:
<223> OTHER INFORMATION: Synthetic sequence

<400> SEQUENCE: 34
gactatcctg tggacttgga                                                        20

<210> SEQ ID NO 35
<211> LENGTH: 20
<212> TYPE: DNA
<213> ORGANISM: Artificial Sequence
<220> FEATURE:
<223> OTHER INFORMATION: synthetic sequence

<400> SEQUENCE: 35
gacttggaga tcagtaaaga                                                        20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
ggagttgcta atggacaaat                                                        20

<210> SEQ ID NO 37
<211> LENGTH: 20
<212> TYPE: DNA
<213> ORGANISM: Artificial Sequence
<220> FEATURE:
<223> OTHER INFORMATION: Synthetic sequence

<400> SEQUENCE: 37
aaatgccaca gaacctatag                                                        20

```
<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
gtggacttgg agatcagtaa                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic sequence

<400> SEQUENCE: 39
gctgtcagaa gctgatcaaa                                                    20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 40
gctgtcagaa gctgatcaaa                                                    20

<210> SEQ ID NO 41
<211> LENGTH: 20
<212> TYPE: DNA
<213> ORGANISM: Artificial Sequence
<220> FEATURE:
<223> OTHER INFORMATION: Synthetic sequence

<400> SEQUENCE: 41
tacttgaggg atggcggtga                                                    20

<210> SEQ ID NO 42
<211> LENGTH: 20
<212> TYPE: RNA
<213> ORGANISM: Artificial Sequence
<220> FEATURE:
<223> OTHER INFORMATION: Synthetic sequence

<400> SEQUENCE: 42
auugccauua aaagauuuca                                                    20

<210> SEQ ID NO 43
<211> LENGTH: 20
<212> TYPE: RNA
<213> ORGANISM: Artificial Sequence
<220> FEATURE:
<223> OTHER INFORMATION: Synthetic sequence

<400> SEQUENCE: 43
uuagagagaa acucuuucuc                                                    20

<210> SEQ ID NO 44
<211> LENGTH: 20
<212> TYPE: RNA
<213> ORGANISM: Artificial Sequence
<220> FEATURE:
<223> OTHER INFORMATION: Synthetic Sequence
```

-continued

<400> SEQUENCE: 44
uugguugaaa cagacuguug                                                    20

<210> SEQ ID NO 45
<211> LENGTH: 20
<212> TYPE: RNA
<213> ORGANISM: Artificial Sequence
<220> FEATURE:
<223> OTHER INFORMATION: Synthetic sequence

<400> SEQUENCE: 45
accagcaaca acacuuguaa                                                    20

<210> SEQ ID NO 46
<211> LENGTH: 20
<212> TYPE: RNA
<213> ORGANISM: Artificial Sequence
<220> FEATURE:
<223> OTHER INFORMATION: Synthetic sequence

<400> SEQUENCE: 46
acugaaaacc uuggaguugc                                                    20

<210> SEQ ID NO 47
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 47
cggcuaauga augaguucac                                                    20

<210> SEQ ID NO 48
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 48
ccugacaguu aacaagucaa                                                    20

<210> SEQ ID NO 49
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 49
uuggagauuu uagcccugau                                                    20

<210> SEQ ID NO 50
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 50
ucggucaaug aagaagagca                                                    20

<210> SEQ ID NO 51

-continued

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 51
uuuagcccug augaauucaa                                          20

<210> SEQ ID NO 52
<211> LENGTH: 20
<212> TYPE: RNA
<213> ORGANISM: Artificial Sequence
<220> FEATURE:
<223> OTHER INFORMATION: Synthetic sequence

<400> SEQUENCE: 52
ugaaaucuuu uaauggcaau                                          20

<210> SEQ ID NO 53
<211> LENGTH: 20
<212> TYPE: RNA
<213> ORGANISM: Artificial Sequence
<220> FEATURE:
<223> OTHER INFORMATION: synthetic sequence

<400> SEQUENCE: 53
gagaaagagu uucucucuaa                                          20

<210> SEQ ID NO 54
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 54
caacagucug uuucaaccaa                                          20

<210> SEQ ID NO 55
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 55
uuacaagugu uguugcuggu                                          20

<210> SEQ ID NO 56
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 56
gcaacuccaa gguuuucagu                                          20

<210> SEQ ID NO 57
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 57
```

-continued

```
gugaacucau ucauuagccg                                              20

<210> SEQ ID NO 58
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 58
uugacuuguu aacugucagg                                              20

<210> SEQ ID NO 59
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 59
aucagggcua aaaucuccaa                                              20

<210> SEQ ID NO 60
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 60
ugcucuucuu cauugaccga                                              20

<210> SEQ ID NO 61
<211> LENGTH: 20
<212> TYPE: RNA
<213> ORGANISM: Artificial Sequence
<220> FEATURE:
<223> OTHER INFORMATION: Synthetic sequence

<400> SEQUENCE: 61
uugaauucau cagggcuaaa                                              20

<210> SEQ ID NO 62
<211> LENGTH: 79946
<212> TYPE: DNA
<213> ORGANISM: homo sapiens

<400> SEQUENCE: 62
tgcgcaggcg cggcggccga tgcgagtgtg tatgtgcggg cgagaagatg gcggcggcgg      60
gggaagcagc gtgagcagcc ggaggatcgc ggagtcccaa tgaaacgggc agccatggcc     120
ctccacagcc cgcaggtagc cgccggtctg cgccttcggc cggaaggggc ccgagccccg     180
ggcgggcgga cgccgcggcg ggcgggcgtc cgcgccctgc ccgagcgag cgtgtgggag      240 tgggggaggg cgctgggaca cgctgcccgg gcctaggccg gagccacccg ccgcctccgc     300
gcccgccgcg ccttcgtccc ctgagccacc cggacccccct agtcccgggg aggtcgaagg    360
gcgggggctc cgggccccgc ttggggaggg cgtggagggc gccgaagggg ttaacctccc     420
tggggctgga ccgcggggcg agcccgggt gtggagtggg gccctccccg ccgcgccggc      480 cggggggaggc ggcccggggg ctccgggagt cccctggagc gcaggggccc cagagcagct    540
caggttgctg cctctgcctg gagcgagcct cagagatttg ggggtgccct gttgcccctt     600
```

-continued

```
tgccccaaga gcttcctttc tcagcttgat tgatgatgcg ggggttgccg attttctgtt      660
ttttagatag aagtagcaga gtagcggcct tgggctgctg ttgcaaagaa aactcgaaat      720
aagtcgcaag gaccgtactt tcacttgcgt ttgagtgaca tcccttgcac gaatccatcc      780
cagccaggct gacaactaac gcaccctgcc tgaacagtag ctaaagcttg ggggcccttt      840
acaataatcc cgtggtggaa agaaagagct cttttttggga gatgtgcgtg tagagttaag     900
ctcttattcc cctctcccac cccttctctc acatcttctc cccctccgc cattataatt       960 attctggaca aaaatcggca tgatgtatta tttgtcagcc ttgctttaga ctgctaattt      1020
gttgacatct ggtccctata aattgttgca cactttaaaa ccatctcatt gtgtatttgt      1080
attaaatatg gggaaatgaa acaaagtagc cattcgggaa actgattgcg agtaaaatca      1140
taacccttca tgagcaattg ggttttgttg cccttctgca gatgaagtca atctgactac      1200
acctcttttg aaacatgatt ttcggaacta ttgtaatgaa tgcgtgttgt ggaatctaaa      1260
atgcgaaaac ttttaaaaa attagatctt acgacaagct tcaattttgt taaattagct      1320
gtagtttagt ttgcatcaga atttccccct ttaacgtttt gttcccttat tcatttactt     1380
ttgtaagtag tgtaggtctt tgcgccaaaa aagggatcag tagttgaata atttttacaa      1440
atgtatagcc caaagatttt aagagatttg gtgtatttag ctttgtttag acctttctgt      1500
taaaaaaaaa gatttgatat ttgctttttt ctcaacttaa atcctaatta actagcttat      1560
tagaattggt atgaacaagt aaaaggctca ttatgaatta atgtgtaata ttccttgtga      1620
ttttgacatg aagaaagcat ctttaggcat agctcacttc ctttatttaa taagcatcaa      1680
tcacaattca aggttgattg aaatgttaat taatggggat ggataatatg taaacttaat      1740
tgtaatttcg tttgcattca ttgtcccagt atttacgttt tatacaacag tctaaagcgt      1800
tatacacatc tttagaaaat tggagtagca aaagttggcg gaacgtaaat gttagcaaca      1860
ctttgggttt attcttttaa agtatgattt aaatgctttt aagtttttagc atggagaaag     1920 tagcaaagga aatagtttga tttctcataa ttttcttctt cttttttttt tttttttttga     1980 gttggaattt ggctcttgtt gcccaggctg gagtgctgtg gttattaacc tataaacttt      2040
tttatttatt ttgagatgga gtttcgctct tttttttttt ttttttttttt ttttttttgag   2100 acgggagtct tgctctgtcg cccaggctgg agtgcagtgg catgatctcg gcccactgca      2160
acctctgcct cccgggttca agcgattctc ctgcctcagc ctcccaagta gctgggatta      2220
caggcgccca ccaccatgcc tggctaattt tttgtatttt tattaaagac gggtttcacc      2280
atgttgatca ggctggtctc aaactcctga gctcaggtga tccacccgcc tcggcctctc      2340
aaagtgctgg gattataggc gtgagccact actgcgcctg gccgatttct cataattttc      2400
attttaaaag aatagtaatg caaacaagta atggaatcat gtatgacagg atttagttac      2460
tggttcctgc tccagtcatt ctgagcgttt taataaattt gttttacttg gttgcctact      2520
gtcctaagag tcttgcagcc ttaatggcca ttcattcatt cagcaaatac tgattgttta      2580
tcagatatta agcgtcatgg tatgtatatt acttgtttat gttgggaata acaactgcaa      2640
attgaaggtc ttattttaaa attgacttgt taaagttaaa tttgtcactg agaataatgg      2700
gaggtggaaa aagttacagt ttaaaaatgt ttacaggcca gcgcggtggc tcgtgcctgt      2760
aatcccagca ctttgggagg cgcaggtggg tggatcactt gaggtcaggg gttcgagatc      2820
agcctgacca atatagtgag accctgtctc tactaaaaat acaaaaatta gccgagtgtg      2880
gtgaagctcg cctgtagtcc caggtacttg ggaggctgag gcaggagaat cgcttgaacc      2940
cgggaggcgg aggttgcagt gagccgagat catgccactg cactccagcc tgggcgacag      3000
```

```
agcaagactc ccgtctcaaa aaaaaaaaaa aaaaaaagag cgaaactcca tctcaaaata     3060
aataaaaaag tttataggtt aataacctta tttccaaata ttagaaagtg ttggttgatc     3120
cctgttacct gtattgaagt gtaatagtga agaatttgga aacattttga gaccggtaac     3180
tcagcatttt agcaaagaca aataaatgaa ctttaacagt tgaagtgtag gtccaagtga     3240
atatccttgt cactgagggg accggttaaa ttatttgggg taattaattt gaagctatta     3300
gttttgcctt acaccgaaaa aatatttgtg attattgatg tcatttatag tgaaatctcc     3360
acaataatgc ttcctacacc caatttgaat gtcatgcagt tggcttctgt ccttgtctct     3420
gcatagactc accccagtct cttttttagc ttgtaatagc agatcctcca cattttacat     3480
gatggaaagt cttggattcc ccctctagca tatggctgaa tgttactgta ttgctgaata     3540
tctgtttcta gccaacagct ggattagtgt taattcttaa aagagataca ttttattag      3600 aatctcaagt aatgagcagc tgaagtaaat acaattgttt gaaatgttga cagggcattt     3660
ggagataaca gttttccttt gcatagtgac agcaagctat ttaaacatgt cctaagagta     3720
gatgttttaa gtttgtgagc cagtggtcac cttagtggtt tgtacagatg gcctgagaag     3780
tttgtgagcc agtggtcgcc ttagtggttt gtacagatgg cctgagcagc cgcgccgtac     3840
caggacctca ccatcatgct cttgagccca tctcattgag agcacagcgc actgaaattc     3900
cagtgaatac taagcgggcc taccacattc taaattcctc actaaagcaa aagttaggac     3960
atgtattcca gtgttctgtt acgtggaact gataggattt aagcagtgat tcacatagga     4020
aaacttaaag gagaaaagga ttacgaagct taatgattgc tgtttaatgc caagcctaag     4080
cggcacgttg cactgtgctg tgctcagaat ataacattca agtaattgag aaaagtggta     4140
tcatctccaa ttgaattagt tacatcaggg tttttgtttc ggtttttttgt ttgtttgttt     4200 gtttttaaag atataatttc agacatgtag gtacttcctg ttaatggttc ctggtattca     4260
ggtggcacat taaacgtggt tgctgaggac acttattact ggtactatac caaaatatga     4320
aacgtagtgg gaagagcttg cttttgaatt tgtaattagg ctgttacttt tctatttact     4380
gccacacatg caagaatcac catcgcacaa aacagataaa tctgtttgca atggaatttg     4440
ctggccttgg gccattggat tactgtcatt tgtcacttta gtgccacttc agcagtgtag     4500
atgttcattt ccagagactt gtatgtgctt ggactgcagt tttcctgttt attgaagtgt     4560
tctcccaaaa ggtctttctt tgaccatttc tgtcaataca ggctggatga agaattagtg     4620
taggaaaata aaggtagccc ttggggtatg tgtatagtat ttgtttcaag gatcagaaaa     4680
tgtagaattt atcataaacc tcgatgtaga atcttcagat cctagatttt ttctgaactg     4740
gctattttct ggctatttga aagctcctgg gccatgatcc cattttcatc agatgacttg     4800
agaacccaga agctctacca gcactgccat tctgtcccgt cttgaaacat catgccctgg     4860
ttgccctctc ctggaatagg gcaggtaagg tgttgagata gaaatgtggt ttggggctgt     4920
tacagcctga attcctcgac tttccctttt gggctcacat gagaattgtt aggagaatgt     4980
gcatgtggag tgcgggccca gcacctgcta ccgtctgcgc tgtaatggtg gctgctccta     5040
agagtcctca gtctcctccc cgttgggctt gtgtgtacag ccttatcggt tgtcattctt     5100
cggatccatt ctcagtttat ttttctggta ttagctggag ggacatctcc ttaagcctgt     5160
actctatggc tcaggagtct caaaaccagt ccattttgaa gtgagagtat ccctaataaa     5220
aaggtgagtg tccccactcc tgtgccttgt ttttttttgtt tgtttttttt tttgagacgg     5280
agtctcgctc tgtcgcccag gctggagtgc attggcggta tcttgtctca ctgcaacttc     5340
```

-continued

```
tgcctcccgg gttcaagtga ttctcctgcc tcagcctcct gagtagctgg gactacaggc      5400
acccgccacc atgcccagct aattgtttgt attttttagta gagactgggt ttcaccatgt      5460
tagccaggat ggtctccatc tcctgacctc acgatccgcc cacctcggcc tcccaaagtg      5520
ctgggattat aggcgtgagc caccacaccc agccactcct gtgccttttg aacctgattt      5580
ttacatctag ctgactcctc cctccgtccc tttccctctt tctttcttcc tgatctgatg      5640
gtgctagatt tttgttttcc catttgtctt tgttttatga agatgtgctc ctttccattt      5700
gtgtatgttg agtacagaca taatcatgcc cttgcttgct tttttttttt tttttttttt      5760
tttgagacag tcttgctctg ttgcccaggc tggaatgcag tggtgcgatc tgggttcact      5820
gcagcctcta cctcccagat tcaagcgatt ctcctgcctc agtctctcaa gtagctggga      5880
ttacaggtgc ctgctaccac gcccagctaa ttttttttgta tttttagtag aaacggggtt      5940
tcaccatgtt agtcaggctg gtgtggaact cctcacctca ggtgatccac ctaccttggc      6000
ctcccaaagt gctgggatta caggcatgag ccactgcccc cagcatccct actcattctt      6060
tgaaaaaaac aatttgttgt tgttttgtag agacagggat ttgctgtgtt tcccaggctg      6120
gtcttgaact cctggcctca agggatccct tctgcttcag cttcctaaag tactgggatt      6180
acaggtgtga gccaccgcgc ctagcctccc tattcattct gcaagtatca gtctttttac      6240
ttttgatagg acatgttgaa gttttggtta aaaatagaag aggatttgaa aatgaagttc      6300
aattctagag gttttcgaga ttcctgccca atataaaaaa cttctgatac attaaaacaa      6360 ttttttttata cttcattttt tagagcagtt ttaggttcac agcaaaattg agagaaaagt      6420
acaaagagtt cctatatacc ccttctcttg gtattttaag taataatttc ccttacgtgg      6480
ctgcaaagac tatatatata tttatatgta tttatttgta tatgtatta tatttattta      6540 tatttttata tttatatata tttttatata tatatatttt ttgagacgaa gtcttcctct      6600
gtcacccagg ctggagtgca gtggcgcaat ctcggctcac tgcaagctcc gcctcccggg      6660
ttcacgccat tctcctgcct cagcctccgg agtagctggg aatacaggtg tgcgccacca      6720
cgcccagcta atttttttgta tttttagtag agacggggtt tcacggtgtt agccaggatg      6780
gtctccatct cctgacctcg ggatctgccc acctcggcct cccagagtgc tgggattaca      6840
ggcgtgagcc accgcgccgg gccaagacta tatatatatt tattcaagac ctgaagtagg      6900
ctttctgggt agatctgatc attggagaag gagaaacata tttattacga gatactaagc      6960
attgtagtag tcatcatttg aagcctataa actctataaa ctgcatagtt tagaaagtgc      7020
cttagcttgt ttgagccttt acagcaactc tgtcctgtat tattataacc atttttacaga      7080 tgagtaagat aagacccaga gaggttgtgg cttgaggtca aatggctgct ggccatcagg      7140 acctttttaaa agcaggtgtt ttgacttcta aatcctttgc tttttctact ttgccagact      7200
ggttttctgg aagagactga tgaaggcata atctttcaca ctgtgacttc cccttagtag      7260
ttcctccata aacatttaca gaatgaatga atgaaatgtg catttagaaa ctttaatgtt      7320
actaattaca aaatttgtta ctataatatg ttactattca ctaaagtttg tgtggggtac      7380
attttaataa agtcgtttat tttatttttct agtataaaga catgctattt ttaagacacg      7440
aaaacagcac agacgtattt aaagtgaaaa gtagaagtca ttcccttcct ctctgatcct      7500
taatcgtcag tttggtgtgt gtcttctatg ctttttttcca ctggagtatt ttgttgttgt      7560
tgttccgttg tttcataata tggtctgttg tatctagtca ctgaacttta ttgagcaaac      7620 cttgtttttca aaattattga aaacatccac tgaagtcagt tttcttaggt ttacctaatt      7680
ttgccaggga atgaagcaga tattctggag attgaagtga cttatcagga tccagtgtgc      7740
```

```
aggggattgt ggaagtgctg ccacaactta taacatgttg tccaaacaat tttttttttt   7800
cttaagaaat attttgggcc aggtgcagtg agtgactcac gcctgtaatc ccagcacttt   7860
gggaggctga ggcaggcgaa tcactcaagc tcaggagttt gggaccagcc tgggcaacgt   7920
agcaaaactc tttctctaca aaaatacaaa aattcactgg gcatggtggt gctctcctgt   7980
agtcccacct acttgggagg ttgaggtggg aggatcgctt gaacctggga ggtggacatt   8040
gtagtgagtc gagattgtgc cactgcactt cagcttgggt gacagagcga gactcttacg   8100
tcaaaaaaga aaagataaga aatattttga agacttccac ccccttagta gtagtcatgc   8160
tgtccggtgt tcatagtgta aaaagaggtc tggctgggcg tggtggctca cgcgtgtaat   8220
cccagcactt tgggaggtcg aggtgggtgg atcacctgag gtcaggagtt tgagaccatc   8280
ctggccaaca tggtaaaacc tcatctctgc taaaaataca aaaattagcc gagtgtggtg   8340
gcgggcacct ttaatcccag ctgctccgaa ggctgaggca ggagaatagc ttgaacccgt   8400
gggggcagag gttgctgtga gacaagatca cgccacttca ctccagcctg gacgaaagag   8460
tgaaactcca tctcaaaaaa caaaaaagga ggtctgattc acattcagat tcttgtccat   8520
ccattgcctt tgcactagat ttatgagagg acaaactttt tattagttgg agattggtaa   8580
gtcacctgcc ctaggaaata atgagaaact gggtaattca cctgaatttt tctccatctt   8640
cttcaaaatc atgttttgt cttctgtcac tttgtttcat cagagtactg caatggcaaa   8700
aaacaaaaca cttcccaact caggtcccac tcctgagaga taaccacatt taagtacttc   8760
tgacttgtaa tagaatgcaa aatcgggggct tccaagtgtg gtttactatt ttgtttagaa   8820
ttaatttgta gaatactaga cactttttc agaaccacat atgaaggact ttatatcttt   8880
tgtgattgtt cacagatttt ggtggccgga cgttaggagt atagagctga agagagaatt   8940 cctgtgctt agaggttcgc tgggtagtga gggagagaag caggctaatg gctgggtgca   9000
tccagtttta gggtggtaat tcctgtaaca caagtgtgaa caacatagtc aagaacattc   9060
attcattcgt ttgttcattc attcagcaaa tagttaccga gtggctgctg tgtaccaggc   9120
actgaggagg gagtgatgag cgaaaacagg cattgtttct ctcgcggagg agtttatggg   9180
tccattgagg aagacagctt gctaatcaga taatcacagt tacgtacacg tcactccaaa   9240
ctgagagatg tttcccaaag gaagggaaca caatctgaag tcagagaacc gttcccgtgg   9300
aagtgacgtg tttacagcat gagacagtgg ggacagcatg tgtggtggac ctttggctgg   9360
agggaatttg gagcacttg gagaactcag caaggagttg tgtgtcttgg gcacagagct   9420
ggaggggagg gacagacgca ccatccaacc ttgcagcctt tgttagatgt tactgtcttt   9480
attctgagaa aagtgtggaa gaggggtgg tacaacattt gaccatggaa cctcataatc   9540
acattgcctt ttgggatcat actctgccca gtgaagaata gactcacggg gtcgcagtgg   9600
ccataaggag atcatttagg gcagggtcct tggactttg actcggaggg tgccgtggag   9660
gtggagagaa gttgcgtgac tcaggagtta ggtataaggt gtttcaaaaa aggaggagag   9720
tgggactgaa tgttgggcaa agctgggaag acgtctcttg tagaacggtg acatttgagc   9780
tggagttttt caggcagaga agcacacgga caagggcatg tggaggagac tgtgcagagg   9840
aactgtctca aagcctgcag cctgtttggg aaacagataa atttgtggct gaaatggtgt   9900
gtagggtgaa gtggttagcc gggagtctgg agaggagaga gaaagaattt ggtaatccaa   9960
gctcaggact gagtgaagtt ggtagcaact ctgtgttaag atagctggtt gaggccgggt   10020
gcgaggctca cgcctgtaat cccagcactt tgggagaccg aagtagacgg atcacttgag   10080
```

-continued

```
gtaaggagtt tgagaccagt ctggccaaca tgctgaaacc ccatctctac taaaaataca   10140
aaaattagcc gggcgtggtg gcgcatgtct gtaatcccag ctacttgaga ggcttaggca   10200
agagaatcgc ttgaacccgg gaggcagagg ttgcagtgag ccagactgtg ccactgcact   10260
ctagcctggg caacagagca gactccatct cggaaaaaaa aaaaaaaaaa agattgctgg   10320
gttgagttga ttgtgcaggg gtcttactta gatgcttcga aagttgtcag ggatttgatt   10380
ctttaggctc tcctccatag ctgggactct actctctgct cattttggca tcttaagcct   10440
cataactttg aggggaaaga agtagggcat ttcttttggg gactttttgag acagattaat   10500 gtgaggcagg tagcccttca gtgtcctcag tggtaattgg atagagtagt tagggaaggt   10560
catttaggga catattccct ttattttgag ggggaggcac ctttaaaaac aagcatctgt   10620
cccttgatta tattcgtaga aaatattaag gaaaacttag gtgacttgtt accttatttt   10680
aaatgtttcc tgtagtactt ttggtagtaa actttagaaa tttggaatca ttggatttaa   10740
cagcgttttt aggtttgtga tcctcgagtg ccctcttcta ataccagaat cacctggcac   10800
cctgggtgcc accaagagac actgagtaag gatccctgtg agcaggtccc caggccgtct   10860
gagccaggct caggttgcag gtcgtccgca tgggtttgtg tacagctttt tttgtttttaa   10920 cttgttgagc cctttcgcat gaatagcaat aacgaaatcg tattttggac aaagtgttac   10980
atctccagtc taggttaggc gtgaacaaca acaaaaatat gaattgtgcc cctccctctg   11040
agtgtgatac tcacttattt tagcgccgag tggaatggtg gaacagttgt gagcagatga   11100
gaaacctgac attttgccac tttgaagagc tgtcatgtcg tgtcttcaga acgagatttc   11160
agtttggctt ggcattcatt aagtccatga ttatgccttt taagcaagca tttacccagt   11220
acttgctctg tgccagggcc cgtgttggga tttataagtt gcaaaaaaac atgtttttaa   11280
aaatgtaagt acacatgtgt tccccagaac cttaagagct gctctggctg ttgctctgca   11340
ccccacatct tgaaatagga cctttgtgga cagcatggga tcagcacact cccccacagc   11400
tcagtgtaac tgtgagcatc tgatgtccca gagaactgga actttataat tcatcctgaa   11460
gcctggttgt caacatctct gaggatgtgt gcatagcatt aagccaattt accatcggga   11520
attcctgctc tcttttgctg ttgttgctca tggattcgtc aggtgaggaa attctagtct   11580
ctagtttttc ccaaactggt gctgaaataa ttacgcttgg ttctctgttg cttcttacct   11640
ctttgctctt ctgtgccaca acaatgtatt ctaagttagg tgccagcagc agaaactttt   11700
cttccaccta taactagagt tttaggcgtg aggaagggct agcttttttt tttttttttt   11760
tttttgtctg agatggagtc ttgttctgtc acccaggcag tggcaagatc tcagctcact   11820
gcaacctctg cctccggggc tcaagtgatt ctctggcctc agcctcctga gtagctggga   11880
ttacaggtgc gtgccaccat ggctggctaa ttttttgtatt tttagcagag acggggtttc   11940
accatgttgg ccaggctggt cttgaactct tgacctgaag tgatccgcct gcctcagcct   12000
cccaatgtac tggggttaca ggcatgagcc accgcgcccg gtggcttttg ctttttaagg   12060
tggacagaaa caccttgcag ctgtgcttcg ttgcccttgc tgcttttggg tggaaacata   12120
gacttaagtt agcatattca tcagttgatc tcttttctgt gagaagggaa agaaatcgca   12180
gtattttgtg tgtatggcag gctttgaggg cccttatact ttgattctgt agatgccctg   12240
tccttcctca ggaggcagtc agctgtgtac agaggcccct gtggtcctgt cctgagagta   12300
gcggaaggaa gacatggctc tgcctgggga gactgtgcct tatgcagagg ccaacaccac   12360
atggatgagc cggaagcagc cgctggcctg gctgctcttt cgggtcagga aggctttctt   12420
gagtctggta tggtctggct gccccagtgt ccccactgcc tagcacagtg ggcactcagg   12480
```

-continued

```
tgtttgtctg ttggatcggt taattggcag ggaccagttg aagcaaacag agaacagctg   12540
gttgtcattc actgttttca ggactgctta tggttgtttt tggtgtttct ataatagttc   12600
taggcatgaa gttcaggacc acagcatgca agaccccgag gggcagattt gccgtctata   12660
gaaatagtaa tgagagctga tgaagaagag gtggctgctt cccacagtat caccttgatt   12720
gtcatttctg catttagaat gcatgagtga cccctaagct gctcttcagg ttcttcagtg   12780
ctctctttac ctctgttgtg tagtttcttg aatccaggtg actgacccgc acgtcacata   12840
taagttattt ggttttattc cttggtctct ttctcagcaa gtgtagtctg gagatgatag   12900
gacacttagc aatgcagaga gaatgccttc accagagtta ccagcaagtg cttggctgtg   12960
ggggctccgt gtactaaagc tcttccagga ttgttagtgg gcatgccagt gatctatctt   13020
cgcaggcctg cttacagcaa atgcagctgt cccccaaatg caagaaccat ggagcagcca   13080
gcctttccag tacagggccc aattatgtgt caccagtgaa catggaaaga gcttttcggt   13140
tggtttgcca cagttagttt atctttcccc cacctttgtg accttagata tctcagccaa   13200
tgccaccatt cacccactag ttatttattg aactcagcta tgtgccaggc attgttggta   13260
cagaaatgga ggggaacaca ttgtctgtcc ccgagaccct ctgtctgtag acaggctcgc   13320
cccctttgtc cctgtggttt gctcccctac tttcagtgag tctctgtgcc tgggccatct   13380
tcttacaccc actttaccca cctttaaaat tgcgccctcc ttcacacttg tcaccctgtc   13440
tgcttgctcc ctctccagag cacttcacac ctaataccct acatacccgc tatcctgacg   13500
tgtgtgtctg gttcactctc tcgtcctccc ccaatgtaag ctccttgagg ccccaatgta   13560
agctccgtga gggcagggt ttttgtttgc tttgttcact gctggggccc ctagtcctag    13620
aatgtggtga gtgctcagta aatatttatt aacaaacacc ttcatgaaag acataccaca   13680
gtggacatat tcagaagccc acagtcaggt gtgggaaaga agctagagaa tcaactgtta   13740
ggatccagaa ttagagagac catcacagga gagtccccgg ggacaccttg gctcatgttt   13800
gtgaggaaaa tagttcacaa agatgagcct ttggaactga gttctatagt ttgcagagtc   13860
agccaggcca gcagggtccc aagagaaggg cgcccaaagc agaaagacct ggcgtgtgcc   13920
gtgtcgctga agtgcatttg ggacgtggag agttgtcggg gctgcagcac tgggggttgg   13980
ctgggaaggt ggatgggtgc gtcttgtagg ctctgctaga gcctttagc ctgaaaagtt    14040 ctgggagact agaaaggctt ttcctgggca ccagaatagt aaggttcagt tgagagacag   14100
ctctgtggtg gccacatgca gtttggaggg tgaggggtga gcacagaggc ggaggtagat   14160
tgttgcagag acccagttga gaagcgtgga gggcttgaac agtgcctaga ggaggggcag   14220
gccttagggt ggcgggaggt gggtggctgg cgggagccag ctcgttgtgg tttgttcatg   14280
gtatagtagt ttcttcctta aaatgtggaa tgacacttgt ttagtaaaat gttttttccca  14340 cttcttcctc ttttttagag atggggtctg gctctggcat ccaggctgga gtgagtggca   14400
caatcgtagc tcactccctg caccatctaa ctcctaggct taggccatcc tccctcttta   14460
gcctcccaaa atgctggggc tacagacgtg cgccaccgtg cacggctttg catttcttat   14520
attgttgaat gtttttccat taaatatttt cctttgcgat tgtttttttt tttagatctc   14580
aagagcctta acttaatctt cagcattgtt ttttaaggac tgcagcgtat tcacaagtta   14640
tagtttatgc atactaaaaa tggtaatgtt tggcaggttt ttttggtcca atttttagtt   14700
gttacttgtg aatttatctt atttcctaga gcaaattaag cacattattg taaactggaa   14760
gatgaacgtc cttaattcat tgattatttt tggggtgaag ggagagagat attttgctaa   14820
```

-continued

```
gggatattaa gaagatactt agtggatatt taaaacatga atttttttaa attttaaaag   14880
taatatcaaa aacaagttct acatatgaaa tgtttgaaaa atatttaaaa agttctgatt   14940
attattatta ttattattat tttttttttt tgagatggag tcttgctctg tcgcccaggc   15000
tggagtgcag ttcgcagtct cggctcactg caacctctgc ctcttgtgct aaagcgattc   15060
tcctgcctca gcctcctgag tagctgggac tacaggcatg caccaccatg cctagctact   15120
ttttatattt tttagtagag atggggtttc accatattgg ccggtctggt ctcgacctcc   15180
tgacctcaag tgatctgccc gcctaggcct cccaaagtgc ttggattaca ggcgtgaggc   15240
accactcccg gcccatttat aaaatatcaa taagctgact tatgtttggt gaaggccaac   15300
tatttcagct attgctgtag atatccagga agataaccaa agcatcctta cctttgtgta   15360
taatggatag ctaaggcata agaaacaact gggcacgtta caagatgtgt aattaagtgc   15420
tgaattatgt ggtgcatgtg gcaggttctt ttgtagtaat tcagagaatg aagatgggta   15480
atgagctagt cttgagaagg aataggatct ccgcctccca aagtgctggg attacaggca   15540
tgagccagtg agtccacctg ggtgacctta ctactttata tgaatcctct ggtcactgct   15600
gcccaactat cctttatct ccttttttgc ttaccccatt tatgtgttag ggtgccctcc     15660
cttttttttt taaaaaaaca aacaagtaga gctcagcttt ctaactggct tacaccataa   15720
actagagatt tagtggctca tgtaactaga aattccagag gtagatcagg cttcaaagtt   15780
ggtttaattc agccgtttag ttacagtttt gaggacgtgg cttcttttca ttttttcact   15840
tttcatttct tcatcttttc attctgcctg tcagtattat cccagggcta gtttccccca   15900
cgatggcgga atggccacag cagtttcagg cttcacattt gggcacagcc tccgtcacac   15960
cagcctgacc aagagagtga gtgtgcatcc cagaattta ggcagtgtcc tgagcttctt    16020
gccctttggg tcgtccctca accagagcac tgtggcgagg agggtggtat gccaagcagg   16080
gctcccatct ggcctggggg tggggtgtg ttgacttctg aactgggtga ctactatccc    16140
acagggtagg aagggagct ggccagttcg ctactgtccc acatgagcgt aatgtctctc     16200 cccctctcc tttccagat atgccagttc ctcctggact cctcagactg gaagattgtc       16260
ctttctcctt ggcaaatcat ctgtactatc tgattgcatc ttacagtctt ctttaaatat   16320
tattgttcct taactgttaa tgtgtctgtg ccttgaggtc agcctcaggt tccaatcctg   16380
ttccattttg tttgtggaat ctcaggcaag gttggtttct ctgaactttt aaagtttttt   16440
catcttcatt cagcaaatct ttattagatt ctcagtattg tgcttcagtg gacgaaatac   16500
agactgacac aaggagataa cagttcattc acagagacat aggtaaatga gaattactat   16560
gaaatatgaa cagtgctttg gcagaaatag ggtttagaaa cacttcctga ggaggtgatg   16620
cctgcgttga gctttgaagg acaagtagga cttcttcaga gcatggggga agagggagct   16680
gcctgcacga aggctgatca gcagaataat gaataaatgc agagttactg ggatcttagg   16740
tgcacgacct tcggcaaggt tggtaggcag agacgcccat tacaccaagt tgaagagtga   16800
agattctacc tttatataca ccttacaatt acatggggag tgaccgcatg tcctggtcta   16860
aacttatccc agcataattc atcataatga tcctttcact ctgagatatg cctctaattt   16920
ggatgataaa tggttacgca acttaaaata gaagtccaga gccatagga cagtcactgt     16980 gatagcagtg tgcttgcttc atagtagagc ttcgggatta catgagatag agcatagcag   17040
tgcttctcaa acttaaaagt ccgttgagaa tcagctgcgg gtcttgtgaa tgtgcacatt   17100
tagattcagt acacctgggg tgggccctgt gcgctgtctg agctcctagg taattcctag   17160
gctgctggcc tggtgacctc actttgagta gcaggtcgta ttgggcttcg ggagcttcag   17220
```

```
agggtctgtg aagttctgaa atcatacgca gaaatgtgtg tacatgcatt ctttaggggg  17280
tgggcctaat tcccttacat cagtttctcg ggaggtctgc tgccacccaa aaaagattag  17340
gaatcctccc ttttagaaat tttgtgcaga ttaaatgaaa tatgttgatt aaatgccttt  17400
aacattgtct agagcataat ggacattcag tacacactag ctgtatgtcc tccttccctg  17460
accccagttc tttgaaggca ggacacattg cttaaacatt ttaaactgct ttttaatgtc  17520
ctttttatgt cattggtgct caataagtgt cgatttagct tggtgacaag ctgtttggtg  17580
actgtgagcc attctgtcag catttgctag tctcttaggt gccaagcatt ttactaggta  17640
ggtaggagga ggccactacc taggttattg cagataccca ggcataggtg gagtcatcag  17700
ggcctgtgct ggatagtaac tgtagagttg aagaggagat gcatcacttc ttagtaatct  17760
tcctgagtta tgtgtgttca ggaaagtgct tctactgcct ttgattcatt gaggtcctag  17820
tctctggtcc tcaggtgtat gtgatttcag tacggattaa tttactgtaa tgcttaattt  17880
aattcattca gttgctattc ttgccaaatg cagttttttct gaacattttg atattttgtt  17940
gagatggtcc cagaaatttg ggattcgtga tcacgttagg gtatttgtga tggaaagggt  18000
atataattta tggtattttc aaagttcctt acctaagaga ttggaagaac aatgatgaga  18060
gagagattgg gagattactt gtcttataga gttgtagatg cttcagagaa cttgactaca  18120
ttgcgaaggg aaaatcttgg attggaaggt tatttttgag aaagtggagt gttggtagtg  18180
aaagttagat ttcagtgaat taaaagcaaa tgagagatga gtttaattac aaaagaaatg  18240
tcttttgttc agaagacatt tctgaagagt tgcttgtgag ttcatttatt ttattgagac  18300
aggattgtac tctgtgaccc aagatagagt gcagtggtgc aatcatggct cactgcagcc  18360
tcaaagttat tggctcaagg gatcctccca cctcagcctc ctgaggagct gggactgcaa  18420
gtgtgggcca ctgtgtttgg caggagttta attttttctgt catattactt ctaatttagt  18480
tgcattatag ttttttcttct ggccgggtgc ggtggctcac gcctgtaatc ccagcacttt  18540
gggaggccaa ggcgggtgga tcacctgtca ggagttcaag accatcctgg ccaacatggt  18600
aaaaccctgt ccctactgaa aatacaaaaa ttagcccaga catcgtggca catgcctgta  18660
ataccagcta ctcggaggct gaggcaggag aattgcttga acccaggagt cggaggttgc  18720
agtgaactga gattgcgcca ctgcactcca ggttgggcaa cagagcaaga ctgtctgaca  18780
aaaaaacaaa aaaaaagttt ttcttctttt agttttgttg ttgttgttgt ttttgagaag  18840
gagtctttct ctgtcaccca ggctggagtg cagtggtgca gtctcagctc actgcaacct  18900
ccacctcctg ggttcaagcg attctcctgc cttagcctcc cgagtagctg agattacagg  18960
cgcccgccac cgcacccagc taattttcgt attttagtag agacagggtt tcactatgta  19020
ggtcaagctg gtctcgaact cctgacctca aatgatccac ccgtctcggc ctcccaaagt  19080
gctgggatta caggcatgag ccaccgcgcc cggccagttt agttgttgtt gttgttgttg  19140
tttttgcctt tattaacttg ttaatgatca gtaaaccctt aaaagcacta aaagagttcc  19200
cattttaaag acatctggat gttgttcatc aactttatat agtgagtaat tatctcaaat  19260
tattttataa tttctttttt aactgggagg cataactgaa tggagaagta gctcccctca  19320
tcctcctgtt ttctgcttag tttctcccac ctcctcagtt gcctgtagtg atggagcttt  19380
tacttggatc acgggaatgc ccctacacag tgattctaaa ctccaactgt aagtcagaat  19440
cacacaggaa gtgtttaaaa tgctaaatga ggcctggact ccaccctaga ccactgaagc  19500
cagaattgtt gcaggtgtgg cctgaggatg ctctgattct aaggtgtggc caggttcgag  19560
```

-continued

```
gactgttgtc ttaggccttt gtccaatatg gtttatgctg ctcccctgct aggtgagtac   19620
caccgcggat tggttacctg cttttatgtg gaaaatagaa tataggaagc cgattgggtg   19680
gaaaacatct cttctagtgt atgtaggtcc cataaggggg actttgaagt ctggagttaa   19740
cagttttcta ataaaagatt tcagaccata tccaggaact taaatacata attaaagagt   19800
ggaatgcaaa ttattaggat ttttgctggt aaagcaagct atacttgcat aatttaaatc   19860
tttggagggc atgtttcgac agatcattag gtgaaggtta aactgagaca gcaaacagtg   19920
gattccttcc ttagctagta taccactttt tgcattcttt tattttcaac agatagtaat   19980
tttgcagctt tttacttctt caaccaaacc ttctaagtaa ctttgctttc cattaacaac   20040
aaagccgctc attaaggtgg aagttctgtg cttgatctta acaccggaag gagaggagtc   20100
tatttaccag ctaatgtaag tacttcttat tagacagtcc tagattttct aggagatttg   20160
aagagtctgc tgacagtggc cagcaaatca gaggaaaatc atttctgtag ctaggttctt   20220
ttttcatgga tgtcctttaa gaggaagctc tgccgtggcg atgtgcgttc cttcctggcg   20280
ggtggcctcc agtagctggc cttctgttgg tccggttcca gcgtatttta ttaagtgaaa   20340
aatcctgtag aacagatggc acttacaagt ttctgcccat gtagcactct gtttaatgaa   20400
atactatagt tttgcttcat tgtttttggc agtaattgtc tttgtgtgga gtttgagtac   20460
atggtccgag aagctcggca gtaataaagg ttgagccagg caagaataat ctgaagtgac   20520
tgagtaatga tgggacagag gcttcagagt ggtgcacagt taaattgaaa acagatgcag   20580
aataaaaaga tgatgcccaa ttttttttt tttttttttt tttgagatgg agcctcgctg   20640
tgttgcccag gctggagtgc agtggtgcga tcttgcctta ctgcaagctc cacctcctgg   20700
gttcacgcca ttctcctgcc tcagcctcct gagtagttag gactacaggt gcccgccacc   20760
acacccagct aatttttttgt attttttaat agagacgggg tttcaccgta ttagcgggga   20820
tggtctcgat ctcctgacct catgatctgc ccacctcgac gtcgcaaagt gctgggatta   20880
cagtcctggg ccaccgcgcc cggccaatga tgcacaattt tttttttttt ttttgggaa   20940 ggagtctcgc tcttttgccc aggctggagt gcagtggcgc gatctcagct cacggcaacc   21000
tccgcctgcc gtattcaagc tattttcctg cctcagcctc tcgagtagcc gggagtacag   21060
gtgcccgcca ccatgcctga ctaattttg tattttagt aaagacgggg tttcaccact   21120
ggccaggctg gtcttgaact cctgacctca ggtgatccac ctgcctgggc ctcccaaagt   21180
gctgggatta caggtgtgag ccaccatgcc cggcaatgat gcagaatttt taagatgatg   21240
ttgtgtagca ctgggaggtc tttggaccaa ggaatgtgaa actaaaaatc ccagagtgtg   21300
gatgcctaca aatagggtgt actgaagaat tcttcttccg tagatgagag attaacaaat   21360
agagcgtact gaggaattat tcttctgtaa atgaaagatt acaactgtgg ccattggtct   21420
tcaagagctt tgattatggt actgcttcat ctgctttaca tagattgtgc ataacaattt   21480
ttaaaaagtc aaccttattg aagtataatt taatacaata aatgtaccca ttttaagttt   21540
gcagttcgag gttttttgtc tttgtttttc agacgaggtc ttgctctgtc tcccaggctg   21600
gagtgcagtg gtgtgatcat agctcactgc agccttgacc tcctgggttc aagccatcct   21660
cctgcctcag ccctcccaag taactgggac tacaggcatg tgccaccaag tctggctttg   21720
ttttgttttg ttttgtttta gagattgagt cttgctctgt tgccaggctg gagtgcagtg   21780
gcgcgatcac agctcactgc aacctccgcc tcccgggttc aagcaattct cctgcctcag   21840
cctctcgagt agctgggact acaggcacac gccgccacac ctggctaatt ttttgtgttt   21900
tcatagagac agggtttcac cgtgttgcct aggctgatct tgaactcctc tcaagtgatc   21960
```

-continued

```
ctctcacctt ggcctcccaa agtgctggaa ttacaggctg ggagccatca cgcccagccc   22020
agtttgagtt ttgacagatg tatacaccaa agtagtaact actaccacac tccatatata   22080
gaacatttcc attgctcaga gagtttcttc atgccccttt gccatgaatc cccaccttgt   22140
ccaggcagct agtggtctgc ttctgtcact ataggctaag aaagtttgcc ttttctagaa   22200
ttacattggc ccagaattac acaaactgta ctcttttgtt tggttacctt cacctgaccc   22260
aactatttag atttagccat gttgagtgtt gagttccagc cttttcagta ctgggtagta   22320
ttcctttgtg gatgtcccac agtttgcttg tctctttcct cttgatagac attttttgttg   22380 ttcccactgt ttgaatctgc tgttcacatt catgtacaag tgtctgtgtg gacataggtt   22440
ttcatttctt gtgggtaaaa tgtggtaagc gtatattcta ttctgtaaga aactgcaagg   22500 cttttttcaaa gcggccatgc cgttttctat ctgcaccagc agtgtatgag aatgcttctt   22560
ctctgtcctc accaacattt gatattgtca gtcttctttt tttgagacag agtctcactc   22620
tgtctcccag gctggagtgc agtggtgtga tcttggctca ctgaaacctt cacctcccag   22680
gtttaagcag ttctcctgct agcctcccga gtagctggga ttacaggcag actcccccac   22740
gcccagctaa tttttgtatt tttagtagag atggagtttc accatgttgg ccagtctcga   22800
actccctaac ctcaagtgat ttgtccgcct cggcctccca aagtgctggg attacaggtg   22860
tgagccactg cgtccggctc agtcgtctta atttttatagt acatcaattt aaatgataat   22920 ttttttgtccc taggaacatg agttcctgtc attgacagca aagtgaaact gagtacaaat   22980
aggtggttct tagtgaaatg tgcccagaaa gacagtttga gcagaaagga gggaccaaga   23040
aatacaggat gcatgcctgc ttcacactgg aaaccggtgg tcttatttga gggtcaaaga   23100
tggggggtgg ggaataaagt cgattttaaa aggattgacc ggctccgata ccttctgatc   23160
acatccaggg tttttttttt tttggccttt tttcccccctt atacacttaa gattttgaaa   23220
agtggtttct ctttagcttg ggaaatggat cacatggtaa ttgttaatga tttttctttta   23280 ggtcaaaata ggtgttcctt taaagtgttc tgtgaagctt aattcactta cgttgaataa   23340
gtcttatatt ttaaaatata agtttaagtg ttatactttta aaaataagtg ttatttcttg   23400 attgtatttta tttgaagatt atatttgaga atgaaagatg tactcctagc tggaacatct   23460
ctggtgataa taaaaacatg agaataaaaa ccattcagag tgatcaagtt aagactgtca   23520
gcccactgac gcctgggaag tcacaatgat tgctatgtag tttggagaaa ttattcctta   23580
tccttagata agcttttttat ttgtgtgggt tttttcatct tcctcttcct gaattcattt   23640
gttcaacaaa gctattttga gcacctactc tatgccaagt ctactgcatt aacttctggc   23700
taaacaaaga tggatctaac tcgattcttg tactttaaag aaatcagctt tatggaggta   23760
taacgtatgt gcggtgaatt tcacccattt aaagtgtata tttccatgaa ttttaacaga   23820
tgtattcatt tgtgtaatca cctccacaat caagacacca gttctgtcat tccccagaat   23880
gacattgagc ccccttgcag cctcttcttt tgttcgtcct tggccccagc aaagatagaa   23940
ctgcttctgt tacagtttct tttttattgg tttcatcttc catttctttt tttcttaagg   24000
tcagcaccaa ggtgattgta atgaatatga aagttggtgg aatcttgaac ttctactagg   24060
gctatcccag ataaagttga ctgaatttac tccctaattt atctgctgtg tttcatacaa   24120
tagcaatttt acacaggaag ttattcaata atgagggcta tctatattac cttgctattt   24180
agtactagtt aagagcaaag cgagttaaaa tttaatggcc attttgtaat acagttctaa   24240
tatagacaca ggactggaaa gttggtaaaa gtgggtttct gttaagtgaa tcatgttttc   24300
```

-continued

```
taatttggag attcaatctg aattcaatct aaaatttctg aaggaaattt tagctcggaa   24360
tctccatgaa agcacttaat atacagccaa cctgttaaaa accatacttt gagaggtaaa   24420
atgattactt tttgatagca cttttaatagt agaaatagaa tatacaaaca gggaagtaga   24480
cactcaattg cagtactttg acatttgagt ttcaaggaga gaggctgcct gtgagagtga   24540
ctttgtgata gtttgtctac tttgttcgct tctcaggacc tctttgcccc aagaaagtaa   24600
agcaaaattt tgctatagcc ctattagtga gggaacaaaa cttctcttcc tccttcttcc   24660
tttgtctgct tctgccattt gtaacactta gttcagcttg cagttggctt gcactgtaat   24720
aaaactgtaa atgtcaccat gccctgaccc ctgtgtgtgt tgtgttcaaa gttttactct   24780
cgtagtctcg catagttgag tgtggattgt tgatgctcag tgcatattgt taaattggcg   24840
aacttcctgg tgtgcattca ctagttgatg atagtgtcat ctccagatgt cctcagaacc   24900
acccacacca ccttctgaag ttgaaagcac acaatgattg ttcagtagat atcagctagc   24960
acccataact tactgggctt tgattcataa agcctagtaa agaaattaaa atttttattt   25020
tgatataagt actgaccttt tttaaaactt tattgagata taattcacat gctgtggagt   25080
ttgtgtattt gaataaatat gcatttcagt ggttttagt gtattcacaa agttttgcag   25140
ctaacaccgt agtccatttt agaacatttc atcatcccca aaagaaagct catgttcatt   25200
agcagtcacc gcctcccgct cccccattct cctctcctcc cagcccttgg caaccatgat   25260
ctttctgtgt ctggtaattt gcctattctt ggcatttcat atgaatggaa gaaacaattt   25320
atggctcttt gtgtgtggct ttaacttagt ataatgtttt caaagtcatc ctgttgtagc   25380
atgcattagt ctgatgacat tttcttttc tttttctctt tcttttcttt tttcttttt   25440 gagacggagt tttgctcttg ttacccgggc tggagtgcaa atggcacgat ttccgctcac   25500
tgcaacctct gcctgctggg ttcaagcaat tctcctgcct cagcctcctg agtagctgag   25560
attagaggcg cctgccacca tgcccggcta attttttt gtgtttttag tagagacagg   25620
gtttcaccat gttggcagtc tgttctctga ctcctgacct caggtgatcc acccgcctcg   25680 gcccccccaga gtgctgggat tacaggtgtg agccaccgtg cccggcctgt ctgacgacat   25740 tttcaaacccc gtgtttctta atccttttta gatccaagag atccttttgg agatgggaag   25800
aattttagaa gttgtctggt ccaacatacc ttcattttgt agatgagatt aaggctttaa   25860
tcatgccaaa cagtctattg ctcttttcat gtttccccaa attgagctta tttggatcag   25920
gagaagaggg agaatacttt atacttctca gcttcttgtg tatttgactg tgacctggtt   25980
ataccatttg ccactgtgag gcttagctgt gcatctgtga atgggagatt gttcttagag   26040
attggtcata gttgtccacc tgcctcggaa actgcaggta caaatgcagc agcaaagtat   26100
ttacattctt acttcagggc tgatctccta tttctatcag tccttttgaa ggcagagaat   26160
gttaatttgg aacaacctgc atatttattc aaatttccag agagatgaaa ctttcagaat   26220
gctgtgctgc agcgcccccct agtgccgtgc tgtactgata gtcccagcg tctcctgaag   26280 ccgaaagtgg cgtttcccgc agttccggcg ggagagctgt agccagcagg ttgtgcaagt   26340
gaacattaga catcttttct ccttctcgcc ttccttgggc tgagatggag gaatgtgtct   26400
ttattgctga gggcaaggtc tttgttttc ctttagcagg aacactggtt ttcccacttc   26460
gtctaaacct ttgcccaggg tttctcaact caggcccctc gagggccgta gtggcctcca   26520
cacacctcca gaaggtaaac tgagccagct tagccaacag gctatgcttc agggaggaag   26580 gtgtctttg ttcccatccc tgctgtggtg tgggcttgcc ccctttct cgaagtgttt   26640 cttgtatatt tttttccaca tcctcttgag aaaggatcag aaagtaaaga tgtgaacagt   26700
```

-continued

```
gagagttttg aaagcccggg atggaggccg gatgggatat gaggggaagt ggtggagggg   26760
aataaatagc ttctctagtt cacagtctta cttcccctaa aaaggggaag aaatgcctga   26820
agcccttgta ctttgctccc ccgaatcgca ggcatttctg tgccgtcccg cccctgggca   26880
tttcctatgc aaccacagga cgcgggaaag gagcgtttgt tactgctttc tgatacctcc   26940
ttttgacccc agtgttctga ctctggcaga gttgctgaaa ccttaggggg cttcccagtc   27000
tttcctgatg gtatttggtg tagctgtggg aagggcagag ttagccgcag cagtgtcaca   27060
gtttctgtgg tgtggcatgg ctgacagggc ctccaggtac ctgcttttat tttaatgaca   27120
gccaccaata tgtcctaagc tctgcacttt cttggaaatt acaagaaacg atgaacttac   27180
tcgtgctttt tagtctcccg tgtgaactga attgttctgt attttatctt gctctgttat   27240
gggcaaaact aattcatgtc atcagtggca tttccctctt cactaggttg taaatcctgt   27300
gaagtcagac acagcgttat tttcatcttt attttaccca aacacctaca attttccccc   27360
ctcatgtgac agcctttgaa ataagttaat cttccagagg agagaaaaca ctaaacagtc   27420
aaacataagg agagggtaaa ggttttcctc ataacctcac aattttcagt gttagcttta   27480
aaaaaacaaa caaacaaaca aacaaacaaa caaaaactct ttatttgcaa atagtttgaa   27540
acttgaaaag ttgcggaaag aaaaatagta caaagaatcc ccagatggtc ctttacccag   27600
atccacctgt tgttaagatt aaatccattt gcttaatcat ttgtgtgtgc tggaattctc   27660
tgtctgcaaa tacacactca tacggataca catacagaca cacagacatg ggctaacaaa   27720
tgcaaatata cagacataca atatttttcc aaaccctttg agatttcagg gaagattaca   27780
tacactgtag ccacttaatc ctaaattctt gaatgtgtat ttcctaagaa taggcatatt   27840
ctcttaaata accacagtaa tacgttacca cttttcacaaa tttacattga tgcagtactt   27900
ttttctaacc tgtccatatt ctaattttgg gagttgacca tataatgtcc tttctagaat   27960
tttcccttcc agcacaggat ccagtctagg gtcaggaaat gtatttagtt atcatgtctc   28020
tagctttttg tagtctggaa gtttcccaca gcctttcagg atattgactt ttttgaacag   28080
cagtttctcc tcccctcttt tgataacatt cctcatttta ccaaacacct aaaataacat   28140
ttgattggaa gttaggaagg cttttggaga aggagatggt gaaaccagaa cattttaata   28200
gcagttggct gtcctgaatt tctgtgataa acttttttggt gtcacaaaca tgccttgctt   28260
caacatttag tcagatatca tttttagttaa ataattgtca ctcactggta tttgctataa   28320
atatattgaa taaattgaat aaataattga aatatattga ataaatattt ggcctttttt   28380 acttttttttt tttctcgctg ttgcccaggc tggagttcag tggtgcgatc tcggctcact   28440
gcaacctctg cctccccggt tcaagcgatt cccctgcctc agcctcccgg gtagctggga   28500
ctacaagcat gtgccaccac gcccggctaa ttttttgtatt tttaatagag acggggttta   28560
gccaggatgg tctcaatctc ctgacctcgt gatccgcctg cctcggcctc ccaaagtgct   28620
gggattacag gcgtgagcca ccgtgtccgg cctccttttg tagtttttatc aaaattataa   28680 tttatgtccg tccactcact ggtatttgct actgaataag tatttggcca ttttcccttt   28740
ttgtagtttt atcagcatat gcaaaaatta cctttttttcc tcccaataaa gttgtcatat   28800
tctgttttat aagcagcacc tcttctttttt tcttttttttt gagacggagt cttcctctgt   28860
cattcaggct ggagtgtagt ggcaccatct tggctcactg cagcctccgc cttccaggtt   28920
cacgtaattc ttctgcatca gcctcccaag tagctgggat tacaggcacc caccaccatg   28980
cctggctaat ttttgtattt ttagtggagg tggatttcac cattttggct gggctggtct   29040
```

-continued

```
tgaactcctg aagtcaagtg atctgctcgc ctcggcttct ggaagtgacg agattacaag   29100
cgtgagccac cgtgtctggc caagcaacac tttgtctttt ggaatagtgt tgataataaa   29160
tgcttcttca ttgtagtgct ttgaatgatg catatgattt tgttaaatac aaaaatgatg   29220
tcttaacctt cacatttgta tggattattt tatcacatca ttcataatcc atgtttgaat   29280
ggttaccatg ccagcttact ttgccaagaa agaaatattt atcgtttttc aaaatgtgca   29340
ttgcaattct aagaaattcc gttttattct taggattccc ctagcttgtg atatcgatga   29400
cttgtctttt actgacattt gatagttaac tccccaaata gaggattcct ttatatgtgg   29460
ttattgggtt gtatcagaat tcctgcttga gtataagtta tatttgtatt gacacatagg   29520
aaaaagatac atgtagttta tctgccatga gcatatgggg aatactcatt gtatgggaga   29580
tggaaattct aatcaagttc cccgggaggc tgagcgcctt gcagagatgc tcttaaaccc   29640
ttggcactga cttcttagcc cgttccttta tttcagttat aaaatcgaaa ggaccggttt   29700
taaatattgc tgaagtgtaa ctgctcactt ttaaaagctc atgcatttaa ggattaaaat   29760
gtgattcacg tgtattttga tggagttgtt ttttgagcta tgtgagccag tgttaaggaa   29820
attaagttgg agttcaaaac agccgtggct agtgatttgt caagtgttaa atgatagttc   29880
agtgttgcat agctggtaat cagcagttac ttatggtgta ttttttttgcg tgacatgttt   29940 tcatcaagtc ctaagctgtt gtcaatgagc tcttgaaact aacatgctta tgaaattatg   30000
tctgtgcaaa atgggtgtat ttgaagagtt gtaaggtgat ttctgttgtg tttacttttt   30060
atgattaatg ttttgaataa agtatgtagt cccctcccaa gaaaaccctc caaaaaacgt   30120
gctaggaaat cccctccact cctgtctgcg tccactcagc gtccactcag tgctactgtc   30180
ccaaaggtga agggccacat tttttcttgt tgatctttcc agtgtctctt tatgcagaca   30240
caaatatcta tattattaac aaacacaaat atgttattat atagcaacac agatactcta   30300
ttttcctacc tttttttacac cgagagtgct ttcttctttt aatagtattt tgaagatctc   30360
tcgctgtctg tacctaaagt tcttcctcat tttcccctag ttaattctgt aatttgattg   30420
aaggtacata tctgtggaga aattattgac atgaagttat aataaaaaca cgcttaaaat   30480
ctataacatt ttctcagata ctttaaaaat aattaagtaa aactaataaa tttgaaaata   30540
ataggagaaa aaaaactcag tgaaccgttt ctgagcgttc cagctcatga cttgagggtg   30600
tttgccgctg actcatgctg aagccacttg gtgtctgcgt ttgaaacagg aagtgtgtgt   30660
tagtggcttg gaatcttgtt ttctcctcct ctcctcctct gctgccaaga tttttatcaa   30720
atcatttgga tttgtagtgt tcttactgga ttgaccagct ctaaaaactt taggctgtat   30780
atgaactgaa ataagaaagt gtgcttagaa gtatgattta aataaacatt tttattttcc   30840
attgtctagg aagaaaacct tcctaaagaa aatacctgat aatcctgcag aacattctga   30900
tttcttatcc ttaggtatct tccccacatt ctgaagtaaa aggcctttct tgttagtcat   30960
aagataaaat ggataacttt taatatatag catttctacc tttttttttt tttttttttt   31020
ttgacacgga atctctctct gtcagcaggc tggagtgcag tggctcattc tcggcttgct   31080
gcaacctcca cctcccgggt tcaagcgatt ctcctgcatc agcctcctga gtagctggga   31140
ctacaggtgc atgccaccat gcccggctaa tttttttgtat ttttagtaga dacgggggttt   31200 caccgtgtta gccaggatgg tctcgatctt ctgacctcat gatccgccca cctcggcctc   31260
ccagagtgct gggattacag gtgtgagcca ccgctcccgg cctctacttt tttttttttt   31320
ttaactgctc gttgcagagc agggctacgc cataggcaat gtgcacagag tagccacgtt   31380
tctactattg atattaaaca aaacagcatg attttagttt atttattctt aatatttgca   31440
```

```
ttaaacttca cagctgccgt gtgtttcttg tattttactt ctttatcatt cttgtatttc   31500
tcgaattcat tttctggaat tcttaagcag tttcctttcc tccccccaag aaaaaggtgt   31560
atgtgacaga aagtgttctt tctcttttgc acttgaaaag tagtttatag aattctatga   31620
aaaaatactc tggcattcta ggaacaaaat ccttttttct cgaaactttc aaaatgttgc   31680
cccattgcct tccatagcct tgttgatttt gctattaaga cgttctgttg agtttttaa   31740 tttagtgatt taaaattagt aattaatttc cgcgaacact ttcatgatct ctgatagctc   31800
tttttttttt gtgatagtct gtgctaattt tttctgcttc cttttagcct atagaatttt   31860
cccttccatt gctttgaggg tttcttagtg aaattcatat catcttttcc cagtgttggt   31920
gatgagaaga aggtgtaacc ttctatattc ttcactgaaa agtgacagta tttcagaaga   31980
tcatttctga accattttga ggctctgttt attttcactg ttactgtcaa tacataattt   32040
ctttgttgac ttttgcaagt atatgtaaat attatatgaa aactttttg ttcttaatgt    32100 atatttatag ttttggtaga tgttgtcaaa gagctctcca gaaacgtttt ccctgtgcat   32160
tcttaccagg agggtattac atttagtggc catttattca catttacaat aataatgagt   32220
attattcatt tatgtaatat ttagttactg gttatttttg aatcacttgg cttgtaaatt   32280
tccctggaag ctactagact gtttagttcc attagaacag aggaaccaca ctctgcttac   32340 cattttata cccagtactg atcatacgtg ggcatttgta ggttctaaat aattattgat    32400
taaatgaatg aatcattgct tctccgttgt ggaaattgct aattcttctc aatgacttct   32460
tcttcttctt tttttttttt ttcttttttga gatggagtct ggctctgtcg ccccggctgg   32520
ggtgcggtgg cgcgatctca gctcactgca acctcggcct ccctggttca agcaattctc   32580
ctggctcagc ctcccgagca gccgggacta caggtacacg ccaccacgcc tggctaattt   32640
ttgtattttt agtaaagatg ggggtttcac catgttggcc aggctggtct cgaattcctg   32700
accttaagtg attcgcccat gtcagcctcc cagagtgctg ggattatagg cgtgagctac   32760
tgcgccaggc ctcaatgact tgtttcttga agctccatgg agaatatgaa ctggtaggca   32820
cttgccagac tcacatccgt gcagtttaac cacttcgttt tccagaaaat cacattctga   32880
attccgtgaa atcaggcttg caacaagggc tgtgtctgtc tgataatatg tgtatctgtg   32940
tatcctatgg aaatgcattt ttaaactaag aagttatata gatatttta aagatcatta    33000 atcaggatca ttaacatttt ccttttttgg atttccttgt cttcccattt gaaccacgtt   33060
ttctgctttt ctttagtatg tttggcagag aaagcggaaa tggaggtagt ggcatgagtc   33120
agcagaaagg taaatggaac aactggcagt atttgtgaac caataaaaat ctcctgcaag   33180
caggactcga caagtttggc atacaaaatt gatttgtttc aaaataagct ttatcagttt   33240
catagtgttc tttgacaatt tgtaggaaag gttcagtagt atttctttta tataaacaac   33300
ctagaactct gagttgcaga tcctctgttt aattgagaaa ggatcttggg ggttatggcc   33360
caaatgttgc ataggattgt taaaatatgt agcatttttt ctgaaagtat ataatttgta   33420
tattttatgt gatcagtgac tctcttattt tttttcagta tattttttgga gattttagcc   33480 ctgatgaatt caatcaattc tttgtgactc ctcgatcttc agttgaggta agacaaaact   33540
ttgttttagt gagtccgtgg gtagatacaa ttaatagtta tgtttctatt ttaatttgtt   33600
tttttaaata aagaattcca atgtagagaa aagtatggag actaatatga gaaatgcctc   33660
aacccaccaa ctagatttga ctgacatttg atttgacatt ttgctgtatt tactttatta   33720
ggctttgaaa agcaaataaa acattacaga tgcaactgaa gcctcctttg gacctctctc   33780
```

```
ccatctctcc ccagaagtaa ctactctgct gaaattggga aatattggtc ctgactggtt   33840
ttcacctttt atcatatacg tgtatatcac catagtcaat cgtagtgttt tatgtgcttt   33900
aaagtgtcac gtaaatggta tactatattc agtttgtcgt ttattttaag ctaacgttgt   33960
attctttatg ctaagaaatt tgtccttgtt ctttgatttc cagtgctcag taccactgat   34020
tgaacacact gcaatttact tacatatttt cctgtcgagg gccatttagg tctctagttc   34080
agccgttaaa aatattgcac tcaatgtatt ttatcatgtc tcctggtgcc cctctgtggg   34140
ctcctccggg acacagacct gggaatggaa ttactgggtt ctgtggaccg agcctcttta   34200
gtttcactag agactgctcg tttgctatct aggattttaa cagtcttcat tcccatcagc   34260
agtgcatggg agttttcttg ctcgtattaa aaaaaaaatc ttgctaactc ttggtgttgg   34320
catatttaaa attttgtgaa tctgatgtgt gtagtaaatg gactctcatt gttttaattt   34380
acatctccca gattacaaac agctgggtac tatttcattc tcttcacgtc tgctggcaat   34440
acggatgtcc tctgctgtga attacttggt ttatatccct tgtccatatt tttaaatcaa   34500
gtagcttgtc ttttcttac tgattttagg attaatcttt ggttttacag gcatctgttc   34560
ctagcatgag ggctttaagc ttcacatgtt aggtgaaccc tttttggggt tgggtttttt   34620
tgttgttgtt gttggataag aggagtacac tttcaacttt aatgtcaact gaattgattt   34680
ttttttcctt atagtttgtg gatttttagt tttaaaaata tctttaggaa attcttccca   34740
tcctttagat aacgaagata tttgtctgtt ttcttctaaa agttttcaga ttttgttttc   34800
acgcttcagt gtgtaataag ctgaaattga ggcactgaat tttgtatatg tgtgaggtgg   34860
catcgaactc cctgcccctg tggccctggc aggtgcctcc tcaccattca ttgggaactc   34920
ggcccttagc tgtcctgtca gccccgttgg gcagtgcatc tcccctggtt ccgagtgtgc   34980
tattctgtgg gcctattgct tatctctgta taaacaccac acgttttatt ttattttttt   35040
atttctattt tttcttttct tttctttttt tcgagacagg gtctcactct gcccaggctg   35100
gagtgcagag tgcaatcaca attcactgca actttgaccc cccgcccgc ctcaggggg    35160 ttctcatgct tcagcccctg aatagctggg attacaggtg tgtgctgcca ggcccgggtg   35220
gtgtgtgtgt gtgtgtgtgt gtgtgtgtgt gtgtgtgtgt ggtgtgtgtg tttttaagta   35280
aggggatttt gtatttttc ccacatcaca ctgatgtaac catacgtttt agttgctaca   35340
ggttttctca agtgtgtaca catgtggatg ggtgggtacc tgtttgcaag tgagtagaca   35400
aaaacttgag ttttcatgtg ataggaaagt gaaaagtgca ccgtatttca agtctgaagg   35460
cctggggtcg cttcagttct gccacttcca caggctcgga gggtttgggc acgttctttc   35520
cttttgggcc tcccatttct tttctctttc ttttgttttt taaattgaaa aaatgcagaa   35580
tgcttattca cgtcacagaa atgttgggaa atcagctaat gtatggtccg ataactagtg   35640
agtaacagat gttagtagaa atggatgaaa agggtacaga tggtaagtta tgccaaacct   35700
tttattcaca gaagacgtga ctgtgtctca tgaaaatgag ctcaagcttc agaactcgta   35760
gtgtgtgtgg gcttatttgg gcttttctgt ttttcttatt ttttaacata cggtgaagtt   35820
tggaggggta taaaaagagt ttatcaaaat cacagtaacc tgcaaaaggg aaatgcaggc   35880
taattaacat aatcggatgg agttgttttc cccaatcttc aggaatctga attataatag   35940
cacatgatta cacaggaact cactttcatg gggcggcatg tggttgggcc tgtgggtgtg   36000 tgagtgcga gggcgtgtca cttggacctg tgggtgtgtg agtggcgagg gcgtgtcact   36060
tggacctgtg ggtgtgtgag tggcgagggc gtgtcacttg gacctgtggg tgtgtgagtg   36120
gcgaggggag ggcgtgtcac ttctacagca cagtttggcc ttttatctct caggtaacat   36180
```

```
aattgccgct caaacatgca gtgtttctac catgtggctg tggcatgagt tacaatctag   36240
tcgaattttt catatgcttt ttctccgttg ttaggagctt gataaaatat tgttttctct   36300
acttggggcc atgaattgaa aaaccaaaat taagaaatgt gggatgttaa gatgaaagag   36360
cattctgcct tcctgcagaa gcgcctcctg ccagcggagg gctgctttgt cttttagttt   36420
gcttgcttgg cagcttgcca ctggcaagat aaggtggcta gtaatttagt ggcatcagga   36480
gaaacgaatt caggtgaaag gtagctggca tcttttctag agttgtgctc cagtgattta   36540
aaaattattt tctccagtgg aaaaaatgca gtcaccttat ttaataagca tgtttaaacc   36600
tcagtcgtaa tcctgttatt tatgttcaga aagaaagaga aaatgctcac cattctttag   36660
tttccagaat ctcagctttg gaagtagcac acatcccaac catgactgag tcaataagcc   36720
cccgatgaca tagtgttggc agtgggcagt gtgtgtggtg tgggtgtgtg tgggtactca   36780
tggagagtag agagtagaga cagttcttaa tttggtgtgt tttctttttt gagagggagt   36840
ctcgctctct cgcccaggct ggactgcagg ggcgtgatct cggctcactg caagctccgc   36900
ctcccgggtt cacaccattc tcctgcctca gcctcccgag tagctgggac tacaggcgtc   36960
cgccacctcg cccggctaat tttttgtggt tttagtagag gcggggtttc accgggttag   37020
ccaggatggt cttgatctcc tgacctcgtg gtctgcccgc ctcggcttcc caaagtgctg   37080
ggattacagg cgtgagccac cacgcccggc ctaatttggt atcttaatgg gattttaaag   37140
gagggctttg tggttcagga gagtctttga gacggaaagc agaacacaca ggtagcccag   37200
agggagactt cagaacatga ccttcctata gccacgggcc caggtatcct tttcacaagg   37260
ccgcagcact gttttcacac tgtgcgttta gcataactat taatagatga cagttttttc   37320
ccttgctcac tttgcatttg tctagggaat tttatgtctt tgctttgatt tttgaacttt   37380
gtattcttac aaatagttat atagttaatg agtgaacttc gaaccatcct ggcacttta   37440 ttctgttgtg tatttagata cccagttacc acagactaag tgcatctgat gtgtgaggga   37500
ggtttgctga atgaaaggtg ctgtgtgcct gtggaataaa acacacacat ttccacagtg   37560
ccacaaccca tctggcattc ctgcaggtgc gctcttttat cagcttagca aatcaaagta   37620
agtgtgttga gcatgcttac tgaaggtggc agtgtcatct gggagtttgc tggtggtcgt   37680
ctcaccagat ccctgctgtg cctcttactg gcagtgtcac ctgctggcac tgtcacctgg   37740
cttcctcatc tgaagctggc agtgtcgcct ggcttcctca tctgtcagag ggccacagta   37800
acaggacctc ctccccagag ttgttgagga gcaggatgtg tgcctggcac accctgagtg   37860
cccagtcagt gccacctggt gtcactggtc cagcctttcc agcctctcca ccctcagtca   37920
gcgccacctg gcattaccgg ccccgcctct ccacttggct tgtcctcagc gtcatctgtg   37980
tatttttccc gattgctggg gtttttcttct gcatgttgtg ggagtggctg ggagttgagt   38040
gagtgttcac accccgtggt tgaatgttga ggaaggggac agccggaaga tggtgagcag   38100
ggttctaaca gctctctgcc ttgtgaagtg gatgggtgaa gaggtccctt ctctgaattg   38160
tgcgtcttcc cagcctgctg cagtctctcg ggtctggagg tttccttcag cattctctct   38220
tccccgagca gaacagaata ctgggaagtg tgaagagaac attgatataa tagtgatgaa   38280
actgttttga ctcagaaaaa gatgatttct tgatgttaca ataaattttg tgtaaaaata   38340
gagtgattca aaacactttt catgcctcaa aataacacag ctttctgtca ccaggggca   38400 tcctagtgtc attaacagaa aaagagggca ttctatgtat cagtttctaa actgtcttct   38460
ttgaccacag agggtttga acgagatgga ggcttcctga gacacacatg gccgctgtgt   38520
```

```
ccactgccct tatagaccca cctctctgct ccaggtgcct gccagcatca atgctggtgt   38580
gtggaatggt ctttgccttg cgggtgccaa ggctagtgta gcccatctca gcatacagaa   38640
tgctttcttc tgggtgtcaa cgtgatgcgt actaggttgc cccctggtgg tggagataag   38700
tgcagctgtc aactcctgaa ggtgttggct tcttttgaat tgccctgtgt tttcctgttt   38760
gtcataattc tctgggaaga gaacttactg cgttactagc agagagaagc ttttattgct   38820
gtgattattg aattggtgtg ctgagatctc attggagaac tcagctgagg aagccaatca   38880
agcagcagct ctcatacagt attgggcatg agacttacct aggagcctct gaactttgcg   38940
gccctagggc cgttcctgca ctggcctttg tactgcagtg aacagacttt gggaagtgct   39000
gcaccagaat gtcttttttgt tcttttgttc tgccctcagg tagcagttta tctctctgct   39060
taccttaccc ctttttcttcc taaacctttt tttttttttt gagacagagt cttgtgctgt   39120
tgcccaggct ggagtgcagt ggcactatct cggctcactg caagctccgc ctcccgggtt   39180
cacgccattc tcctgcctca gcctcctgag tagctgggac tacaggcacc caccaccatg   39240
cccggctaat tttttgtatt ttttagtaga gacagggttt gttttttttt tgttttgttt   39300
tgttttggtt tttgagacaa agtcttgctc tattgcccag gctggagtgc agtggcgcga   39360
tctcggctca ctgcaacctc catccccag gttcaaacga ttctcctgcc ttagcctccc   39420
aagtagctgg gattacaggt gcctgccacc acgcccagct gattttttgt atttttagta   39480
gagatggggt ttcaccatgt tggccagact ggtctagaac tcctgacctc aagtgattca   39540
cccacctcag cctccctcat tgctgggatt acaggcatga gccaccatgc cctgcccctt   39600
cctaaacttt cttacaccca atgtgtccat tggaagcatt tccaactctt aaataaaatgt   39660 tatggaatag ctaggaagaa gaaaaattta agttattttt gagataacct ttcagcttttt   39720 tacaaagaag tcagacagtt cccattctgc tttctgtctg ccaaacaagg aatgtgactt   39780
ctagctgtta atgtagttaa ttaaggcact gtgttaaaaa gggagctgca gtcaccaggc   39840 ttttttgttta tagtgcgctt tcctctgctc tccgaccatg gacctggtcc cagcctctac   39900
tggctgtgtt gcaatgtagt gatcgtgaat aagaggtgca gtcaggaaga gtcatcttcg   39960
ctagtgcaca aacaaaagtg tctgtggtct ggatggtcag tcactgacat cctgtggaaa   40020
gaaggatgta tcataagcat ttcattgtag ctgatttaca tgtccattgg agttcatttt   40080
tattcctttt ggcttcattt tcggatctgt ttaatagtga taaatatttg aaagcatttc   40140
tattgtgttt ttttcgttaa atgaagatga tttagattgc actgactctt catgtatgtt   40200
attctgctag aagtaacggc atgcaaagtt gtatggatta agagtttttaa tgaattgttg   40260 ccttaattaa atggtaagcg ttggttttaa cattttgttg aattaaaatt tgttttctga   40320
ttccttgtgc agcttcctcc atacagtgga acagttctgt gtggcacaca ggctgtggat   40380
aaactacctg atggtaagct agttctctcc ttatttccct gaagggaatt tggccatacg   40440
tgctgggtgg gcaggctacc tgtaaacatt gtttcccatt tgaataaaca tttctttgta   40500
gcttgaagtt tttgctgtaa actgtaatgt atttaattgc tgaatcactt tgactagtga   40560
attggtttta aagcgtatcc tgtgcttcgg agtgccagcc atgtaagatt tagtttagga   40620
aatggttgtt gagttctttt tttcctaaca gttctgagtg caacaggtat gttactcttc   40680
atcagcacat gctggagttg aagcgaactt tgggtcttgt tgctaagcag cctgctggct   40740
ccagcgccag ctagcttctg agcctgtgtt ctttgtaaac taaggggcag ctggcatctg   40800
ttgttcttgc agttcacatt catgtcctgg tctgtcgctg actcttggga actcaggtca   40860
actcttcacc tcctggtctg ttactttttt gggtctccat cacaggcact aagctgattg   40920
```

-continued

```
ccagagatgg tgcttatgga gatgcaatga ttttgtattg cttaagtacc cagcgttgga  40980
ataccaacaa ggttgtttaa ttattgattg caggctgccc ttgcacaatt caaacttgtc  41040
gagatcattt ttcaatctga atcactttaa aggcccttac tggcctccag gaaactgatg  41100
ccaaactttt tctttgagag ttagaggttt ggattccctg ttcagttagc atggtcagac  41160
ttatgaaagg ggttttaatt acaatttagg cttcaataga agccttgaaa agactaacca  41220
aacgttttat ctccagtaac atcagggagt gattatatct aaaattttag atttataaga  41280
aatgtgggag accataaggg aaagagcaga tctaacaata gcttaggaca agtaataaaa  41340
tgaatgaagc ttgagggacc gggaagccgg gctgctcagc ctcctgagcc accttttaat  41400
tggctgatgt caacctctca gacatctgag tcagtgggac ttcctctgtc actgtgtgct  41460
ttgcacgtgg tgagcatgct gctcatgttg aaccagtgct tacaaatgcc ccatgatgtt  41520
cccatgcaca tcacttcttt gagttcaccc tcctccctgt gcagtgggca ccaccagctc  41580
ccccagcctc tggagttctg cttccccctc cctccttcca gcctgcctgc cctttttcagt  41640 gactgcttct tggcccttttt tctccattct ttactctgtt ccctctaagt cctgccttttt  41700 ttctgccaaa aacacgactg gaatcttgcc accagtttgc acagttagtg acaggcctgc  41760
ttttctctgc agcctttctg ggtatcttgt gtttccatga cattagtttc tcttccagtg  41820
cctgttcgac tgtacagagc ctgtgggcac tgtcatggac ctgcctctct ttccagcctg  41880
ctcagctgct gatggcagga tccatttctc tgtgtctgtc actgcgcctg tagtatctgg  41940
aatgttgtaa gccctcagta catttgttgg atgaatggtt taggatgctt tattctgctc  42000
cctcccacta cctccagctg cagcaagccc tttgcagagg cacctcatcg tggcttccct  42060
tttagatctc ggcctttttct atttttgtgt tttttaattt ttttatattt taatttttgt  42120
aggtacataa taggtgtata tatgtatggg gtacatgaga tattttcata caggcataca  42180
acaagtaata atcacatcaa ggtgaatggt tgtccttcac ctcaagcact gcctgtttta  42240
gatgttccta aagcttgaga taccactcct tcaccctgcc cttagcaatt cagtgatcca  42300
tcaagttcca ctgacctctc tagtttctga tagaagttga tcactgtttc ctgcatccag  42360
aagaatcctt tttctaaagc tattcacagc tttctctccc ctccctccat gttttcattc  42420
tcagttgttt gtatttgtct ccctaataaa tgtgaactct ctgagcaggg cccttgtgtc  42480
actaatctct gtatatttcc ctccctcgcc ccctgccttg tagtccagtc ctctctactg  42540
catgtactgc agtgagcagc cttggagaaa tgctgtgtta ggattcgtgg ttttaagagc  42600
ctctgcctgc attacctgag tattgagttt ccatcttcct aatgtattga ttgggttgtt  42660
gaagccaagc gtgcaggccg tcctgcactt cgtctgcctg gcacattggg ctctgagctc  42720
tctgccatgc ggtgcaaggc acatggcgtc cattgtgagt gttcctccat aagaagagga  42780
actgtgctgg ctaggaatct gccttctagt gagatgatca aacatggtat tgagtaaatg  42840
tttgatacta attataacat actgaaatgg ttctgttcac gttacatcac attctagaat  42900
gttttatgtt ctgataagat tgagaattga gatgtgtaca gcacatctgt gtcttagaaa  42960
taatcagtct tgcataagct gaatgacaca acacgttcta gtttctaatg tgatttcaca  43020
gccttcaaag ggcaggctcc acatggagcc ttccgcccca ggcacacccg tttcaatctg  43080
gggagccttg acggccccag aacatcaggg aatagggggat gtatggaacc aaaatgaaca  43140
gccagcccct acatatgata ataaattcat ttccccttga tattcttttc aaagtaagga  43200
aacaaaaaat aaatagtagc caaaggaatt agatggtcgt gacttcatgc ataaacttgc  43260
```

-continued

```
tgttaggtgt aatcgtcatc agtgttcttt tccaggaact ttctcttgtt ggggcaggat   43320
tgtgctgcca ccacccttca cccccacag tcggggctg tgattctaaa gcatacgaag       43380
attcaggagg cctcgggagg ctgtgtagct ccagcctcct gcacactcac ttgcacgtaa   43440
ctggcccctc tcagcgtctg tattttttct tctacaaaaa gatttctagg ggtcctttca   43500
aggtaaaata tattcagttc tccgcagtag aacaccgttc tttgggtatt agtttctttt   43560
cttaagatag atgccttgaa aaaaaaattg gcccttaat gctagcctgg aagaaatctt     43620
catgcattaa agatgaaata taaggcatgt gtccttccct taacttcaaa atgtgtaact   43680
ttttatcaaa tataaggtga cattgatgct tgatttctgt tgaaagacac aattgattct   43740
aaaacttaac ctgatttcag aggtgtaaac tataaaaata cgtctgtctt agcaggaatg   43800
aattatgtgg attgtggtta actgggaagg aagtattgaa ggcttcccaa gagatattta   43860
aaagttcaca attctaactt tttcttttgg tattttggga aggctttacc acccatgggg   43920
ttaatccagt gtgaatttat ttagaggacg tttgcatgtg ttcatgtcag ggccattttt   43980
cagacttaat tgaaggttac cagcggagga gaccaagaga tagagaattc agaagagtgc   44040
tctgaagtgc gcttttatat ataggattct ttgttgttgt tgttgttgtt gttgaatctt   44100
tttttgacat cttttttttt tgtttttaaa tttatacttt ctaatttctc ctatccagta   44160
tgtataggat tctttgcgta gttcatgttt ttggaattaa tcaaatcacg ttaactacag   44220
aagctgattt aaccatgttt taagtcccta agttagttgt catgatcttt taaaatttaa   44280
gttgtccaaa atacatattc ctttatctca ggcataaggc agctataaga aagtcagatt   44340
ccactggggg gtatttttaa aattggcaaa atattacttg ctttttatta caaatttatt   44400
ttaatttcta ccttctgaaa gccttcctta gctagaaaga taagtacagg cttctgcttt   44460
tcatatcccc aaaattaaata ataattttat agttgtttca ttttccgcaa attgttcagc   44520
gtaagtaaag gacgtaatag atttgttgat taggaagaga acttaaggtt tttattttca   44580
aagagaaagt gagtaattac tggtacttag agtttgtaga actgggttct taactaatag   44640
ttttctttct aaacaggaca agaatatcag agaattgagt ttggtgtcga tgaagtcatt   44700
gaacccagtg acactttgcc gagaaccccc agctacagta tttcaagcac actgaaccct   44760
caggcccctg aatttattct cggttgtaca gcttccaaaa taacccctga tggtatcact   44820
aaagaagcaa gctatggctc catcgactgc cagtacccag gctctgccct cgctttggat   44880
ggaagttcta atgtggaggc ggaagttttg gaaaatgatg gtgtctcagg tggtcttgga   44940
caaagggagc gtaaaaagaa gaaaaagcgg ccacctggat attacagcta tttgaaagat   45000
ggtggcgatg atagtatctc cacagaagcc ctggtcaatg gccatgccaa ttcagcagtc   45060
ccgaacagtg tcagtgcaga ggatgcagaa tttatgggtg acatgccccc gtcagttacg   45120
cccaggactt gtaacagccc ccagaactcc acagactctg tcagtgacat tgtgcctgac   45180 agtccttttcc ccggagcact cggcagtgac accaggactg cagggcagcc agagggggggc   45240 cccgggggctg attttggtca gtcctgcttc cctgcagagg ctggcagaga caccctgtca   45300
aggacagctg gggctcagcc ctgcgttggt accgatacta ctgaaaacct tggagttgct   45360
aatggacaaa tacttgaatc ctcgggtgag ggcacagcta ccaacggggt ggagttgcac   45420
accacggaaa gcatagactt ggacccaacc aaacccgaga gtgcatcacc tcctgctgac   45480
ggcacgggct ctgcatcagg cacccttcct gtcagccagc ccaagtcctg gccagcctcc   45540
tttcatgatt ctaagccctc ttcctcctcg ccggtggcct atgtggaaac taagtattcc   45600
cctcccgcca tatctcccct ggtttctgaa aagcaggttg aagtcaaaga agggcttgtt   45660
```

```
ccggtttcag aggatcctgt agccataaag attgcaggta tagttgaaaa gatacaaatc   45720
tagagtgaag atgggagcag acctcatcaa ctgggcttat agactgtggt gttacccata   45780
acaatggcag attacctgtg tgttaatagc aacgtctgaa ggatgcctat gtcttaaatg   45840
ttctctaaaa gtaagataat atagaaacaa atgggaggag agggttgtcg taactttatg   45900
ttaagtgaaa gatccatgtc tgttagcagt tcttttctgt tgacaagtta catttccatt   45960
tcttgccttt tgttcaagta attctgctcc acggtatgaa tgtataatgg actttttctg   46020
tgatatacct ttggtatgat aatcctgatt tgtactcact gtgtgctcct tttttatatt   46080
tcttaagata caagaaatca ttttgtgaaa taacatggtt tttttttttt ggattgagta   46140
aatggatttt attcagaatt ttgatacacc aaggtcagct cttgaagaga aaaaaaatgt   46200
taagggttca gcccaaagtt aatgttttat tttagagtgc taaggctcca aagtagaaac   46260
aattcacaat aaaaatagaa agctgcataa ttcacagatt gttttaaaa agttacagta   46320 ggaagtcaga aatgcagcag ggtatgaaag aggtatgtgt cctcacatag ccacgtgttg   46380
cttaactaag atggatatgt gttccgagat gtgcgtgtta acatcagaga gtactacaca   46440
aatacaggtg gtagagcctt aggctggtgg tgcagcctat tactcccggg ctgcaaacct   46500
gtccagcgtg ttactactga atactgtagg cagttgtaac acagtgctaa gtatttgtgt   46560
gcctgaacac atttagacat agaaaaaata tagtacagat atggtataaa ggatgaaaag   46620
tgcttcacct gtatagagca ctcaccgtga atggagcttg caagactgga gtggctctgg   46680
atgggtcagt gatgagtgct gagtgaatgt gaaggcccag gacagtactg agcaaagccg   46740
agttttataa acagtcaaca cttaggctgt actacgttga tttacaaatt tttcctcaat   46800
aagaaattaa ccttaaccta ctgtaacttt tttacgtttt attttacttt taaattaaaa   46860
attctaaact ttttgactct ttcatgagaa catttagctt aaaacacaca ctacagctat   46920
acaaaaatat tttcttcctt tttattctta cttttcctata agcttttca tattaaaaat   46980 tgttttttaac ttttttaaact taaaaagtaa gacacaaaca ttagcctggg cctgcacagg   47040
gtcaggagca tcaagacgcc actaggcggc aggacgtttc agttccacta gaatcttgtg   47100
ggaccatcat acgtgcggct cattgttgac cgaaatgtta cgccgcgcgt gactgtacgt   47160
acctaagaag cagaagctgt gtcatcaggt tggattccac caagcctggt gaccagatct   47220
tcagattgtc accctagtag ccaagttaaa ataagctgtt tggtttaggc tttctgtaat   47280
actttctgat gtgacctttt ggaacacctg acacccttca ttaccaggat gtagcagcaa   47340
gctgccaaat gcacacccct cgatggatgg tcagaattgt gtaaaaaata aaacacattc   47400
tttgggtggc aatagggtga tagcaagcaa tgtatatata tttttaagag tattttattc   47460
cttatacaaa atacattatc tcaggtactc ttgttgttct gaagttctct taaatgagca   47520
aatgataggc cagacgtcgt tattttgggc ttcatatata ttttttaaag ccaggtgatt   47580
tttttttttt tttttttttt ttttgagatg cagtctcact ctgttgctca ggctgtagtg   47640
caggaggcac gatcttggct cactacaacc tccgcctcct gggttcaagt gattctcctg   47700
cctcggcctc ccaagtagct gggattacag gcacatgcca caatgtctgg ctatcttttt   47760
ttgtattttt agtagaaatg gggtttcacc atgctgccca ggctggcctc aaactcctga   47820
cctcaagtga tctgctcgct tcagcctccc aaagtgttgg gattccaggt gtgggccacc   47880
gcactcaggc caggcgattt cttgaataca gctttcagaa tgtatttatt gcaaggactg   47940
atactgtagg tggatgacaa ggtcaggaga tcgagaccat cctggctaac acggtgaaac   48000
```

-continued

```
cccgtctcta ctaaaaaaaa cctaaaaatc agccaggcgt ggtggcgggc gcctgtagtc   48060
ccagctactc aggaggctga gacaggagaa tggcgtgaac ctgggaggcg gagcttgcag   48120
tgagccgaga tggcgccagt gcactccagc ctgggcgaca gagccagact ccatctcaaa   48180
aaaaaaaaaa aaaaaaaaaa agatagattg tgtaagcctt tatatagatt actaagttaa   48240
aagtttattt ttaacctata atgagaaatg catggtgggg tcctgttaaa aatgtgcatt   48300
ctaagttcga agtcatgaga attttatttt cttttcttta tttttgagag ggggtctcac   48360
tctgtcgccc aggccggaat gcagtggcgc aatctcggct cactgcaacc ttctcctcct   48420
gggttcaggc aattctcctg cctcagcctc cctagtagct gggactacag gtgcctggca   48480
ccacgccagg ctaatttttg tattttttagt agagaccgag tttcaccatg ttggccaggc   48540
tggtcttgag ctcctgacct caagtgatcc tcctgcctca gcctctcaaa gtgctgagat   48600
tacaggcgtg agccaccgcg cccagctgag aatattatag tttcgtttct aaaattgctc   48660
cacaaaggaa aacctcccat cttagggaga ttttctctat ctttatttaa aataaccaag   48720
aaaagcttca tttaaaatgt tttagaacat tctacttagt catatgactt taaatatagt   48780 ttgataaaata gtttgttatg ttctgtatat gttaaagtct aattgaagta gctttgtcaa   48840
acactgaaag taagggcctc ttaatgactg gtagtagagg aaagccttgc cacacacagt   48900
ccacgtaatt attttttgtgt ggacatattg taaacccta ccaaacagat tattttttta   48960
atcctatttg gttaggtcag ttatgaagat gttttaattt tctgagcaaa agtgtagttt   49020
ctttaaaaat atataattct tttcagcctg tttgttgagg cttcgataga cagaacgtag   49080
ttgttgacag tttcaggagt ctcgtgagat agtagagcaa tagagtcaca ttgaataacc   49140
cttgggatca tatagggctt agggagaatg gcattgtttg aaattttttt tgttgtttta   49200
ttctcctact tagggattta ctttataaaa gtggtaaaac atactcagtt tgttacaagt   49260
cagatccact accacaaatt ccctttagtg ggcacacttt taagtgtagg cccacttatt   49320
ttaagcagcg tttaactgag tgaaagtcta gtttcattaa aagatctgtt gatgtggggtt   49380 ataatagagt ttgacttgca ttagtatcta actgtttcta ctgagacagt ggtatttgtg   49440
ttattaactt ttgggaaaga gggagtaggg aatgatttag acattaaatg tattcctttc   49500
tgccaggcat gatagtgtgg agattgaggc ttgaggctcg ataacttgag cccgggagtt   49560
cgaggccagc ctgggcaaca tactgagacc ccatctttaa aaaaaaaaaa aattatacac   49620
acacaaaatg cttggaataa tttgtgtatt ttttatctca agtttgtttc aaatactcac   49680
atttctggac tatttcccct attgttaagt ctgcttaata aatgccagct agttttatg    49740 ccatcagaag tgaaattaag aaggcagatg gactaaaaga atcacgtata agggattttg   49800
aagtgaaata cattaaactc ttgattactc ttaaactatc cactttaacg ggttctactt   49860
ggaccttctt ggtggcaagg ccatctcctc ggtgtaggtt atgtgtcaac attttgttcc   49920
attggctgtt tttcaagtgt gaactgttat ttgaaaggag aaggacacgc caggggagag   49980
cgtgtgaact gaatactcag tgatttcctt tagccccaag ggaaggatgt atctaaacac   50040
aaaagccctg tcttgccgag ggttggagag ggatctgtgt ttcagtgact ggtctgagag   50100
gagatggttg ccatttatca gtaggagtca acaaaaggaa acttaataca gcccggcaca   50160
gtggctcacg cctgtaatcc cagcactttc ggaggttgag gtgggtggat cccttgaggc   50220
caggagttca agaccagcct ggccaacata gggaaatccc atctttacta aaaataaaaa   50280
aattagatgg acgtggtggc tcatggctgt aatcctagct actgaggagg ctgtgtcagg   50340
agaatagctt gaaccgggga ggtggaggtt cagtgagccc agatcgtgcc actgcactcc   50400
```

-continued

```
agcctgggcc acagagtgag actgtctcaa aaaaaaaaaa aaaaacccaa aacttaatag  50460
cttgtgtttg aaagtagttg caaaacgcga cacccttgtt aagagtgagt atggcagaca  50520
cgtggggagt gcctttgctg ctgcttccct cattagcaca gatactttgg agttgacgaa  50580
catgtgacgt ttgaaattga acgtatgctt tcattgaaca ttgtactttt cctgggtctt  50640
tactaaggaa cattcctcat atactagacg aaattgtatc agatgctttc acatcacaaa  50700
tagagccatt ttgtatttga tgttttgctt tcaaaattat gcaacagtat attttgtttt  50760
aacagaatat aaataatgct gggtaagaag agtggccaac tgcccgataa gttaaaattc  50820
cagtgagaga gaactaggaa aactgagctc ttgaacagct ctgaaaacat tgcgttgagg  50880
tatctagcaa tgtcatttat tatgaattgt tagtcaaaac ctgtttatat gattttttcac  50940 agtggtttta tacctaaaag gcattggatc aagaaacaaa gttattacaa tttgggtctt  51000
ctctaatgaa ttaccctgtc cgtgtttatt taagtgtaaa tgaacataca gttatgtgct  51060
gctttaatga tgtttcagtc aacaacagac cgcatgtacg acagtggtcc cataagatta  51120
taatggagct aaacaatttc tagtgaccag tgagttgtgt tacagttgcc tacggtattc  51180
agtacacaac atgctgtacg ggtttgtagc ttaggagcaa taggctctag catatggccc  51240
aggtgtgtag ttggctatac catctaggca tgtgatccca caatgacaaa attgcctaat  51300
gccacatttc tcagaacata tccccatcat taagcatggc tgtgtatcct aaaactgatc  51360
tttattttgg cagtttataa atcatgcata tatttccccc cgctccttgg gggaaatggt  51420
ttctcagata ttttgcactt cctcttcaaa ctctgaagta cacaggcagt ggtcatgcgg  51480
cgtgatctaa gttaaaaagg cgtggcacct gtttaccggg atccacccct gtggactgag  51540
agtttagtcc acatctgatt cgatgtttgt agcctcacat ttattataca tctttccact  51600
tcagaaacat aagttgatct gtagtcaatg ggtagtggta cattttggtc actttgctgt  51660
cctccacctg gttagataac caagatagtg tgtgttcttc caaattgatg gtaatgagga  51720
aaagaaaagc acttggagaa tgttctggac agttagaatg atgacagaaa agcaggtcaa  51780
caacaccaga atgtcgatta cgggccagtt attgagccct aagaatcaga gttctgtacc  51840 ttgcatttc agggattttc aatgttaata tgacccctaa gtcctaattt taggaaaaca  51900
gaatttgatg tgtaaaatat gtgtaagaat aatcatagct tatgatgaca taaaagttta  51960
cgatgctggt attgcctttg agttgataaa caatttcagt gggctgattt gtggcagccc  52020
ttgtgagcta ccatctagca tgtatgtctt aaaatttgaa aaaaggctat taagcaactc  52080
cattttctgt tatgtcagca gatttcataa gagtgaaatt tcagttcagc cttttcatgt  52140
gagttattac aaaagtgaac tacaggtttc aattttgtgt cttttatgag tcattctggc  52200
attttgtgcc ttttctcaca cattgttcta ggcagcccca ccaactcctg tgacaaagat  52260
ggactggggg aggccatctt cctaaagttg ctgtctgaac agttaagtag taaattatac  52320
caaccatgat gaattgaaaa gaaggcttct ggggaaagtt tgttattaga gccaacttct  52380
attatatgcc cttaaagaag gtaaaataga tacaccaatg gcaatgactt tggaatgcag  52440
gtcaagtttc aacctagaag ttgcctgccc tctatccttg gtggcccgcc ttcctcattt  52500
ttattctttt agcctccata attggaatgc gtattggact ttaggctagg aataacattg  52560
taaatgaaaa tgttgatgtt gaaagaggaa tttaaataga gcgaagagtg atattagaaa  52620
tttggaagtg gtattagttc tggccttgtcc gtaagacctg acttttgcat gataacaata  52680
ggattcattc acttgaacat aattcggtct ggtcttagga ggaattagaa ctgctttttgc  52740
```

-continued

```
accccctgttt ttttcactgc gaggaagaag aggagctcac gaacttcata aagcgttagt   52800
gtctcctcca gttgatggtt atcgaaatga gtcaggatgg aaggcttagt gtacgtgtga   52860
gatgttacaa aagtggacct taaatgtttc ttgagtgttt ggatcttaag agaaaatctt   52920
tgacaataag tatttaatct tcatttctta caatcattcc tcttaaaatg gagctttatt   52980
ttttaaaaac gtattttttt tttcttaaga aacagggtct tgctcattca ttcaggctgg   53040
agtgctgtgg catgatcata gctcactgca gccttgatct ctcaggcgca ggtggtcttc   53100
ctgccccagc ttcctgagta gttgggacta taggcaggca ccaccatgta cagctaattt   53160
ttttattttt tattttttat ttttcatagc aacagagtct cactgtgtgg cccaggctga   53220
tcttggaact cctggactca agtgatcttc ctgccatagc ctcccaaagt gttgcctgaa   53280
atagaacttt attaatatat ctttaatatg tcaagatgtt taaaacttgt caagatttta   53340
aggaagttgg gctaacattt cctcttggga tgctgaaagt tgttggtttt ctcagactct   53400
cacataaatt catttgcttt tcccttctcc ttccacctct attagctctt tattttctag   53460
gggggattct gatgtctgta ttgagctggc cgtcatgccg ggagtggtct gcttatgtat   53520
ttacatgcgt gctcatcttt gctatagctg agcgtggtgc agctccttac ctgttccagg   53580
tgcggagtga tctgccgcac aatgaatgaa gtggcagagc cagggcgcga acccccgtct   53640
tcctggtttg tgtgcctggg cccttgccct ttactgtgcg tcttctcagg agctgtcatt   53700
tagactttct ggaccaggag ctaaatgacc tttaaagtct gttgagtcat ttctaacaaa   53760
tatgagtgga gtcatttgcc gtaaccaaca actttaatct ccagatgttt aattgatcct   53820
gtattactgt ctaatgagaa cttactgtat gccatgcact gtctagttgg agtaatgatt   53880
ggccttgcct tcagggtagt ctaaggcata agatcagaaa ggaacagatg gcagctgttt   53940
gtagggagaa gtgatcattg gcagaggggt gttgagggga aaagcaagg aggggaggcc   54000 tcatgcagct agtagggatg gcagtaacag gctgaggaca caaaaggcca ccaagtcctg   54060
ttaccttaga tggtgcggac tttgttgagc agttgaagtg tgagagtctt gtctttaagg   54120
agcctcctgt ccagagaagg aggcacacag cactaatatc aggtaggcag tgatgaggtc   54180
agctactgtg gagacagtgt ggagaatctt gagtgccttc tgtcggtctt actctgagat   54240
taggatttag gatcattata agagattaat aacagaatga tacggtattt tagtttatga   54300
aagacttgcc actagataaa attttttctac agtaacagaa taatcattaa gaaaaatcta   54360
ggttgttcgt gtctcttctg tattttccaa gtctgaaaag gtttattctg cgtttaacga   54420
cgtcgtacca gaatggcctt tcaaagactg tcaaaggctt gaaggaaagc ttggtggagt   54480
acatttccta gtacacgtcc caagggcccg tacgtatgtt ctgctgttgc agaggttgtg   54540
ctcgttcgct tttgtaggtt ccttgcagtt attgaacaaa ccactgggtg gtgctagaag   54600
acttgatttt aatactgtgc aagaaaaact gaaactgctt tttaacctgc ctgcgcctca   54660
aaataagcaa actggaagct ggtatcgatt taagggaatg gctgatgtag aaactaaagg   54720
tttctgtctg actagttcat gctgtctcac aaataaatgc tgggaaaaaa gtcggtttat   54780
agttgattta tgtatccttt gattgcatag agattgaatg gtcaagcctc caggccatgc   54840
agattattct gggcccctaa ctcagttaag aacatgaaag gaggccaggc acagtggctc   54900
acacctgtaa tcccagcact ttgggaatcc aaggcaggcg gattgcttga ggccaggagt   54960
tcgagaccag cctggccaat gtggcaaaac cctgtctcta gactttgtcc cagaaaaaaa   55020
aaaaaaggag ctgtgttttc agacagagct tagtgcagcc agttcttgat ggctgtgcaa   55080
tgctttcctt ttaagagtgg agttagcctc gtcataaagc gtgttttttga gtctgttcga   55140
```

-continued

```
acgggtcaac aacgaaggga agtttcaggc agatcttgta tgcctggccc tggtggctgc   55200
tttcatttcc ttccagtatc agtgctaaac aggaatgaac atgttcaagc cccgtctcac   55260
ccacctctgg catcttcgcc ctaactctgc cctagaagac ctttccttcc gtatcgtcaa   55320
gaaaactgaa gttgctgttt cactccttct cccacccaga aacttcgctg catcttcctg   55380
gatccctagc tccttgcacc catgatcctg tctccttcct cagcccggct tctggctgag   55440
cagcctgcac ttgctgtctt cactcctaca cgctgccccc actcctacac gctgccctg   55500 cgtgcttctc acttctctac ccttccagcc ctgcactctg gggacctgtg cgtatgtttg   55560
tgtgattatc aatctgttga acccaggagg tcgaggctgc agtgaggcat aatcacgcca   55620
ctgcactcca gcctgggtaa tagagcaaga tcctgtcttt aaaataataa ttatgattgg   55680
gtatggtggc acacatctgt agtcccagct actcgggagg ctgaggcaca agaattgctt   55740
gagacccaga ggcggaggtt ggagtgagct aggatggtgc cactgcattc cagcctgggc   55800
ggcagagtga gactgtctca aaaaaaaaaa aaaaaatcag tcacttgctg gtcttttaat   55860
atacatatac gatttactgg tgtcatctgg gtatctttta ctaacatctc taaaactgag   55920
ctcattacca cactaaacaa aaaataacct gctcatctgt tgtattcctc ctctagttgg   55980
atagcactgc tgccccagtc agtgagaacc ttctagtata tctgttcttc ctcagcttcc   56040
atttggtggc ttcaacccct gaccttccca gagtttctgc agcccttgga ttgggctaag   56100
catccttccc caccccccgc cccccatctc ccaacacccc ttcagcttag cctgtacagt   56160
gtgtgtttgg agccagggac atcacagttc gtcccttcac tggtctgcga gcttgcctag   56220
ggcaggacca ccttgcattc atctctgtgc cttccttacc cggtgcctag gcagggctca   56280
gcaggggttt actcgccttc agcgaaaggc agcatgttat ttaacaaagg tttcagccac   56340
acaccatggc tcatgcctgt aatccaagca ctttgggaga ccaaggcagg tggatcactt   56400
gaactcagga gttcaagacc agcctggcca acatggtgaa atcctgtctc tcctaaaaat   56460
acaaaaatta gccgggcgtg gtggtgcacg tctgtaatcc cagctacatg ggaggctgag   56520
gcaggaaaat cacttgaacc caggacacag aggttgcagt gagccaagat tgcaccactg   56580
cactccagcc tgggtgacag agcaagactt gtctcaaaaa aacaaaggtt tctatgttag   56640
aaagatagca ggctttgagt cttaaggtta ggtttaaaaa aaaagtcat ttgatataaa   56700 aatactatgg caaagccttg ttggaatcat gctggagttt tcatttgaga cactatgcct   56760
ttacgtcatt gatggttatt tgaaaatgca ccttttttaac actgcaatga cattagttgc   56820
tgttctgtgg cacacactag aaatgataga ctgttgtgat gatatggttt aaagacaaat   56880
gtaaaaatcc actgtcaata gactttaagc ctgtggggaa aagtaagtat ctgaaacctt   56940
ggaataaaag ggatttttaa gtgaagcccc ttatatattg aggaaagggc tcaacctctt   57000
gagtcaggtg gacccaggtt cacaggtcat ttcagctgtt atgtgacctc agttttctca   57060
tctgtaaaat ggggttggta actatctctg acagtagggt tatgataatt atgaataata   57120
tacacaaagc ttctagcaca gtgtccctca catgacaggt gctatctctg ctgggtgtca   57180
tcacatgcag gcttgggggtt cagttcgtaa ctgatccatt attcatttat ttcaaggccc   57240
agttcggtat tccatattaa gagagagagg agctttgcaa acttagtcta attaaacaga   57300
ttccacagaa tctgtaatat tttactttct acagaagaag agctagcaga aattattccc   57360
tacgcttctt cagttagaag gaagaggaca tttattcata ggaaggaggg aatgagaggg   57420
gtgggggtgt gtgtgtgtgt gtgtgtgtgt gtgtgtgtgt gtgtgtgtgt tttgaatttt   57480
```

-continued

```
gtaaattaat ttttcattt gattagtgcc gaagtctggg atctgccagt acaatgtagt   57540
ttagaaaaga aaagcttatt tttgagcgat gccttagatg gatgctacta tcaaatgtat   57600
gtatgccatt ttggtttttc tttcctatat acaatttgtt tatttattat actttatttt   57660
taaatgaatt tttgattttt gttggtacat agtaggtgta tctatttgtg ggttatatga   57720
ttagtataca atttaaaagt aaaggagaca gtgtggattg gctgcagatt atggagttga   57780
ggccctggct atgctacctg gctcctgtgt gatcacaggt gagttagtca gtctttggga   57840
gcctcatttt ccttattggt gaaagggtca aagtggtggt actcctagat tactaaggat   57900
taagtccagc caattaacat ttgtcaattg taaagaacgt gctaagtgta gaagggttta   57960
taaattgtag ccatcaccat tagaagattc atagtgggac aggggagagac cttgtcttgt   58020 tttcaagcat ttctgatggt taattctata aagatggcat tcacagctgt tttaatacac   58080
agaaagagtg atgtccactc agggtgaacc tgaggctgag cagcgtgttt gtaaatggaa   58140
taagggaatt acagtttata aaacagttgc taaattggat ttctagtgga cggtttaatt   58200
tgtaggagac cgctgtctct gaaaggagta ttttttactca ctgaacagcc attgaacaca   58260
cacagtgatg tgtagggtca gcattagatg ctggggatgc agagaggaat gagacgtggg   58320
ttctgcaaga tatctttcta tctagtgtct gaggcgcctt gctgctgatg agacacacct   58380
ggctaatggt gtttaaggaa gaaaggctgt atctctcaaa tctattctct aataatgata   58440
ctgtgttaac attttttttgt ttctcattaa aataggtagt tcttgtgttc cctaattctg   58500 ttcccccag gaagattaaa tgttgctatt tgagggaaaa gattagtttc aaaaatgttc   58560
taattgaata atgtacttga tgttgaactg aatgaagcct taacagtatg cattttcttt   58620
ggctgtgtgt tttactgaag ggattttaaa tgctgtccca gagtagagca tgtgaaatga   58680
tttgaatgtt cttcactaga tgtcatcaat ttctgaaata tgcttcttca ctctttcaga   58740
gttgctggag aatgtaaccc taatccataa accagtgtcg ttgcaacccc gtgggctgat   58800
caataaaggg aactggtgct acattaatgc tgtatccttc ctggacgccg tccgcaaggc   58860
cagcttgttg cagctgtccc tcctttgggt gcatgtgact tagctcagct tccgtgggcc   58920
atctagctct ccatttgaat ccctaagtct ggtttattac ttggtctgcc taccttgctt   58980
ataaacagga ttattcctga ccccagtcca tctccctcta aaagagagga tatgttggca   59040
cgtgaatgag ggctgcagac aagctggctc tcattagaat agtcacaaat aatagggcag   59100
agcaaccact tacaactgga aatttggttt taactgattg aactgtcttg gttaggtcaa   59160
gttcttgaat acaaacgact gactgcttcg tagatcctta tatggacatc acaggacact   59220
taccctagta actatttggt ttattccttt tcgtggtgac atatctaagt agttcaacgt   59280
ccttagcttc cttgtgtttt tataaacatt cttgtgcttc atgtgccttc aggaaatgtg   59340
gtgtgtctgt tcatttcctt tacgcttcct tactgccact acatagacac tgcaggcatt   59400
ggttgcttgc ccgccgatgt accacctgat gaagttcatt cctctgtatt ccaaagtgca   59460
aaggccttgt acgtcaacac ccatgataga cagcttgtaa gtaaggtggt gaaagatgtg   59520
ttaagtggtg gggtttttcc cgtctgataa ttagaattga aatagtttag taaagctctt   59580
gatttcctgc aaatgagtcc tataattctg tctttttttta aaaatagact gttggcgatt   59640
ttatatggaa gttaaccaga aatggaattg gagcattgat gatctgtgtt ctttagattc   59700
agtagaaaat attttagcgt ttaccagcat atatcacttg aaatagacca aaaatgcata   59760
tagaagagac ttgagttcac tagctgttac agcattggtt acctaaaatc tactatactc   59820
gtatagctga tattctactt agccatcaaa gctctttagt aaaagtatat attgtttaaa   59880
```

-continued

```
actgcactat ttaacatttt ttccccatgt ttagtgttcg gctaatgaat gagttcacta   59940
atatgccagt acctccaaaa ccccgacaag gttagtaaaa atgagttttg ttgatgctat   60000
tacatattgg gagttatgga gacagatgac ttaaatttgg taaattcagt cttgttggga   60060
agatagtgtc tttacaccta tgccattctc aacattcagc caggtgggag gtgggggagt   60120
tttgatgatg ttgctttttt catcatttat gagttcattg tagttaggaa aacctgtgtc   60180
ctctttccat tgcagctctt ggagataaaa tcgtgaggga tattcgccct ggagctgcct   60240
ttgagcccac atatatttac agactcctga cagttaacaa gtcaagcctg tctgaaaagg   60300
tttgagactt ctctgttgtc actagtatca agtgttgcct tttgttccag tgtttgtgtg   60360
gtaactgttg cttattgata tttgccctct gtctccagcg ctataagtag atgtaggttt   60420
ataagagtcc attgcttgga tgatatggtg caccaagcac tgctctcagt actttacata   60480
tattaactta gttgactctg aataaagtat gattatggtc tccttgttac ggttaagaga   60540
agtgaagcca ctgtctgagg tcaggtagct aatgtacatg gcagaaccca gctttcaagt   60600
cagttctctt aaccactgca ctatatgcca ctggggtaga atggagtgca ctgggcctgg   60660
aatgatggca gtattcagaa gagcttatgt cttcatcata cttacaggct ttagtagcta   60720
tttgatgtac ttgattcctt tacctaattt tttttttaatc acatactttg ttactaaagg   60780
catgagacca aggggccagg gagcccttat aaaaggccct ggggctgttg agagtgactt   60840
gggccgccct tagcaccgtt aactggagca tttctttcct cccagattga gtttgtgatg   60900
aatcagtaca agcagttgaa atgatgctta gggaaatgta ttcagagaga aaaatagttg   60960
agaaaatgcc atttaagtca agtttacttg aagcttcatt gctttgaaga agagtgaatg   61020
tcgagggcat cgttgcagga taccaccagg ggtagcatag ggtcttaagc tttttaaatg   61080
cttataatgc agcttttggt attggcttgg aatttgcact tcccaagtaa tgggaacatg   61140
gtgttaggga tgcagaaatg gaatgaagtg cgccctctgc cctcagtgag ggaatgagtt   61200
aatgaatagt caacaagaga agcacaaaga tacagagatg ccttagaacc cagaggggcc   61260
cacctagcac aggtggaggc aaaataaagt gggtgctcag gaacccctct tggatcgtgc   61320
acagagataa tgctatgaac aaaagcatct tctaaaggtt acattaatag gggatgtgtt   61380
gggctcccca agaccaccct gaggttgggt gattcactgg aagaactcag aaaatgcaga   61440
agctggtata cccgtggcta tggttgctga cagcaaaagc atgcggagca gagtcaggaa   61500
gggaaaggac aggtgaggca gggcctaaag gaaacttcca gactcctctc ccagtggggc   61560
cacaaggcta cgcgtaacta ctccagcacc agactgtgac cacacgtgaa atgctgccaa   61620
ccagggaagg tcattacaga ctccgtgtcc agagttttta ctgagggctg gtcccatagg   61680
taccatctgc ctggcttgaa ccaaaagtcc aaactcccaa aacaaaagca aagtgttcag   61740
cagaaagcac attgcttgcg caaacggttt aggcagaatc ccgtatcagt tattggaccg   61800
atgggaacct ttctgaaatc caaattccca gacaccagcc aagggcaac cttgcaagca   61860 ggcctttcca aggagagcca cccaggcctg ctatgaaaag tcttcagcac actttggctg   61920
tgccagtttt tgcccttttc tgcacacgtg cagagcatgc actcacgtga acagctgctg   61980
tccacgtcta ctatctggag agggcaagta aactttgcag tttacctaga tgcttcaaac   62040
agaacaattt gcagggcctt ggaataggca gttgtgctgt gaagaatgaa atatgaactg   62100
atgataagta acagaatcaa acactcgtga tgtgggatta ttaaactctt gggtgactcg   62160
tctgtgaatg attttgctga tgtatgtgta acacagctaa cgctctaaat cagtggagtt   62220
```

-continued

```
tttccacatg tagtttgagt tctttcccat gtagttgtcc atcatcaaag acagacagaa   62280
gcagacatag ggctgcttag ctcattgctc gagtggtgac ccttgcagtt gaacagtgaa   62340
ctggccctag acatctagtt cttcgtcttc tattttgttt acccaagaca gaaacttttt   62400
tttaaataac ttttttgtga taaaggtaat gtggccaggt gtggtggctc atgcctgtaa   62460
tcccagcact ttgggaagcc aaggcaggca ggtcacctga ggtcaggagt ttgagaccag   62520
cctggccgac atggtgaaac cccgtctcta ctaaaaatac aaagattagc caggcatggt   62580
ggcacacacc tggagtccca gctactcggg aggctgaggc aggagaatcg cttgaacccg   62640
ggagctggag gttgcactga gctgagattg caccactgca ctccagcctg ggtgacggaa   62700
tgagactttg tctcaaaaaa aaaaaaaagt atatttattg aagaaaattt caaaaataca   62760
gaaagtataa ataataaaaa tccccattag tccacccatt tagagatatg tgtttagtca   62820
gtttctcctt ttcctcctac tcttgggatt tcagctatgc aagggaaacc catgtcatca   62880
tgtcattgtt tggaaatact ttacatcttc catttcagag gaggcatggt tggactttgc   62940
aagtactgca tgtcctgcag gcctttgaca gtgatcagtt cacagtaacg tgattatatt   63000
tgaccttttc agggtcgaca agaagatgct gaggaatact taggcttcat tctaaatgga   63060
cttcatgagg aaatgttgaa cctaaagaag cttctctcac caagtaatga aagtaggtta   63120
tggtccactt gccgcagagt tgtgcaagag ttcgctgtaa acaggtgttg catactcata   63180
tgttatgttg cttccctgcc cctcagtcgt tttcctttca aatagcattt attccctacg   63240
ataacttaca ccatcgagaa ggttatattt aggtaaatta cagtttatcc cgaacctctg   63300
ccattttcct ttaacttta attaggaaaa tgatcaagcc tataaaaaag ctgaaagaat   63360
cgtttgatga atacctttat aattgccgag tgtacagttt taaacatatt ttctgatgct   63420
atacacacac tgtgtatata tatatatgtc ttatctgtcc atccatatat acatacatac   63480
gcatacattt tccctgaatg attcaaagtt aagttgcagc taacagttta gttcatctca   63540
ggtgctaaag catctcctgc gtaaccacag tcccttatct aactgagaaa aacaactgta   63600
atgacacggt aataccgact ttgcagagca tcttcaaatt tcgccagttg tcccagggat   63660
gtcatttcta ggagttttatg taaacaagga tccagtggtg gtgcacctgt tgcgattggt   63720
tgccgtggat caagtggcat tgcaatgggt tgcagtggat ccagtggcat tgcgcctgtt   63780
gtgattggtt gccgtggatc cagtgacgtt gcacctgttg cgattggttg ccgtggatcc   63840
agtgacgttg tgcctgttgg gattggttgc catggatcca gtgacgttgc acctgttgcg   63900
attggttgcc gtggatccag tgacattgtg cctgttgcga ttggccgtgg atccagtgac   63960
gttgctcctg ttgcgattgg ttgccgtggc tcctaatgta gaccacaccc tgatttcatt   64020
tttaaaactg caatcgacag atctgtgcct tttttttttt tgctgttctt gtcgtaaata   64080
gtagtgtaag cagatgctct ccttttcaga acttacgatt tccaacggcc ccaaaaacca   64140
ctcggtcaat gaagaagagc aggaagaaca aggtgaagga agcgaggatg aatgggaaca   64200
agtgggcccc cggaacaaga cttccgtcac ccgccaggcg gattttgttc agactccaat   64260
caccggcatt tttggtggac acatcaggtt tgtgcttttc tggaataact taatatttgc   64320
cttttctagg gttttgccat gttggtgaag ggggaaggtg tgaggcttgt tttgagactt   64380
cttggacgta atggtttgca tcttgctccc ctgcctgctc ttctcttgca cttcctgatg   64440
cttcccttgt cagcccccgt ggcttattct ctccctgctg gcgcatgtct gcaggggaca   64500
gggagctcct cccttctact ctgtcaagtt cagctgctca ctgctaggga gtaagagaaa   64560
agccagctaa ttggccatac gcggtggttc atgcctgtaa tcccaggact ttgggaggcc   64620
```

-continued

```
aaggcgggtg gatcacctga ggttagaagt tcgagatcaa cctgatcaac atggtgaaac    64680
cccgtctcta ctaaaaatac aaaaatcaac caggtgtggt gacaggcacc tgtaatccca    64740
gctattaggg aggctgaggc aggagaatcg cttgaaccca ggaggcagag gttgcagtgg    64800
cccagatagc gccattgcac tccagcatgg gtgacagagt gagactctgt ctcaagaaaa    64860
aaaaaagaaa aagatacagg agaatgtcat catgacttag gggtaggcaa aggtttcata    64920
agataggtca taaacaataa ccacgagaga gagagaaaaa aaaatatata tatatatatt    64980
agacttcatc tgcatttaaa acttgcaaca taaaaccacc tccgggaggc agaggttgca    65040
gtgagccaag attacaccac tgcactccag cctgggtgac agagcaagac tgtcttcaaa    65100
aaaaaaaacc agctaaccaa accatgtgtt ttggtaagag aagacagtgt atctggagga    65160
attttattta tgttaataaa ttgtgtatat ttaaagtata cacagatgtt atgaaataga    65220
gatagtaaaa tagttgctac agtgaagcag ataaacatat tccccatcac agttaccctt    65280
gtgtgtgtgt gtgtgcacat ggcaagagca gctgcagttt tactcatttc acaaaagtcc    65340
caaatacagt gcactatgag tagctcttgt ccgatgttcc acatcagatc tctagacctg    65400
ttcgcctgtg tggctgccct tggtgtcctt cgaccgacat cttccattcc cactcgccac    65460
ccctaggaac cactcttttc cctatctctg tagtttcgtc tttttttttt ttttaataaa    65520
gattccatgt ataagtgaga ccatgcaata ttttctcttc tgtgtctgac ttctttaact    65580
tagtataatg ttccccaggt tcattcctgt tgtggcaaat ggcagggtct ttattacagc    65640
tgaatagtgt tcccttgtct atatatacac accacagttt ctttatccat tggcccatcc    65700
acagacagtt gtttccctgt cttggctgtt gtgaactgat tggaagcagg tgaggtagaa    65760
agtgaagaga gtgtgaaggg aggtcttttt tacacagaca gacccgtgac tgggctggag    65820
tccctgggca cctggctgtg tgccagttcc cttaagcagc tttttgctca ttcacaaagt    65880
ccttcggaaa ggtttttctt tatttacctg agagcttttc agtaccactg tgatgtggaa    65940
ttcagcaaaa cttgtaccat ctccaagaag gtttacccat cgaaagtact gaagaggcct    66000
cattggagcc taatttcctt tctgaggcct tgcggcataa ccccccaggct ggtatttcag    66060 tgacactctt agtctgttgt tgtcccaaat gctgcgtacc tgaaagaaag agcacccctt    66120
ttgaggcatc aagacttgat tcagtctcag ttctgagact gaatcaacaa ctttcaacag    66180
gtgaataata agaacctcag aaacctgcgc tgacgccctc agaagctggt ttcccgtcct    66240
ctgtggaagt ggatttagaa gccagttgag cagccatgtg accttgaaca agtcacttct    66300
gtgttctgca ctgtgagctc tattccactg gcccctttct attctggtgc tctgtggagt    66360
gtccacggca gctgggtggt cagttgtcac ctgggaaaca cccagccctg accactgtct    66420
gtggttcctt gggacacgtc gtgttgggag ggagacgctg aggtccaggt tggcgcgcag    66480
cagcgaggga aggctgtgcc ctttgctcct tcagcccagc agcctggttt aggattgtga    66540 ggacacccc tcgggatggg agagaaagat gaatggacac ctcaaatgga ggcatcggga    66600
acatggtttt tgtgcagagg ccgggtatca gaatttcaag gccacagagg gtcagcatac    66660
tcaaagatcc caaatttgtc taagagtaac cagtggaaaa taccagcgtc catttggagg    66720
acttgctggc tcagattgaa cagctctgtc acagctgcta gccacatcct ctgaggggtc    66780
tctgtgttga aattggttgt tgatgtttct ttttgaaaaa cggtaaagca aagatagggga   66840 attcttacaa cgtaggaact tcttttcagc cattgttaag catgattctt tattcacacc    66900
aattgaaaga tttacttcta aaactcagcc tcttcagatg ttttttcagtt tccccaggaa   66960
```

-continued

```
gacttccccg cctttcttcc ccggtgccac ctttgctaaa acacaggacc actgaatcaa   67020
gagggcttct tgattctcca ccagctctca tgagcggttt ccccactact gtatccctct   67080
ccagaaccag gggaactgtt gtcactgaag tcttcaaact gtaaaggagc atggagatgc   67140
gtaattaaac cctggacaga aaagctttta gcgagctctt caccgcatct gttctggaaa   67200
gcctgagtac ctgtccacac ccattttatt ccgttgagaa actaggtcac cgagactgca   67260
gaaatagaag cccttgttga acccctggaa tgtttccttg ctgaggctaa atgagagatg   67320
ggccgaacac acaattttta ctcagaaaaa cttagaaaaa ggaaaaaaa aatgaaatga   67380 aaaaccagct aagaaaacaa ggtcaaattg gcgcccttct tggaagggtg gcagcctttt   67440
ttcctggaat gttaacttgt tttttattct acacacccta ctcccctct tcttttgta    67500 agacatcttt ataggaggaa aatgccatta aaaatcctct atttaccttg ggatttcctc   67560
tattttatta gaacaggcta tgatacttgg agaaaatgga aagcagcagc gttttgaggc   67620
catggcaggg tggctgcctt tatgaaccgg tgcagtaaat aacagtgtgg agaggaagtg   67680
aaagaatttg gaaaatgaaa tatgttttct tccagagcac tggcgttggg aacatttatc   67740
aactggtaga tttagttgtt agaaatacta aggaggtgct attcagcaga attattatta   67800
ttttttttaa tttatttttt tattgataat tcttgggtgt ttctcacaga gggggatttg   67860
gcagggtcat gggacaatag tggagggaag gtcagcagac aaacaagtga acaaaggtct   67920 ctggtttttcc taggcagagg accctgcggc cttccgcagt gtttgtgtcc ctgattactt   67980
gagatcaggg attggtgatg actcttaacg agcatgctgc cttcaagcat ctgtttaaca   68040
aagcacatct tcagcagaat tatttttaaa ttcagtatat ttttggcttt tctctgtggt   68100
cttttgaaag tgatattgaa taatcttatt ttcagtgttt attcccttgg ttaatcttaa   68160
gggaaagtgg caaggagtgg tctcttaatt tttttgtttt tgctttcaat tcttaggtct   68220
gtggtttacc agcagagttc aaaagaatct gccactttgc agccatttt cacgttgcag    68280 ttggatatcc agtcagacaa gatacgcaca gtccaggatg cactggagag cttggtggca   68340
agagaatctg tccaaggtta taccacaaaa accaaacaag aggtatgttc acacttgatt   68400
ttgaaccttt ctactaaggt gctctggttt ggtggaaaga acacaaaatt aggaatgagg   68460
ggaaatgggt ttgagttatg cctcttaaat cagttgctta accattttgt actgaaagtt   68520
tttatggttt tacaatgaaa tggttgaaac gtgatcccaa gggcctcttt tagctctaaa   68580
tcatattaca caaggtaatg atctcctttt ggattgttta tcttgagcta catttaattt   68640
tctggcaatc taatgatgat atcacaacat caatactacc tctgacagag gccaaatagc   68700
ttatttatgt tcatgatacc gtagggtaca actgtcatta gattagttag gatgtcagag   68760
agattccaga cacatctgtt ttgcatttga ttgtagatct tccaggtcat tgtaaatata   68820
atatagtcat tgtaaatata atatagtcat tgttctgatg cttgttactc tttgatttga   68880
tctggaaaag gtaagattct tgagtctttc agtcttcatg aatttaagag tatcacatta   68940
tagcttggtg gagtccttgt caactcagtt gggcgagacg gatagcattc tgccctgtga   69000
gagcttatta gttcctggct gtccagatgt gccagcttat agctattttg tactctgcag   69060
cagagagtgt cttctctgtt atatatctta ggttgtggca gtgaattcat aaaaatgcac   69120
tggggagatg aatgcaggct gataattatg gacggtccat agcattcctg caaagcgata   69180
tttgaataat gggcagtgga tggcagctac aaggtaaaat aaggtgcccc aacgtagaag   69240
acctgtcatc acattgcatg actgggatgg atctatcctt ggcttatctt gtgtgctctg   69300
agtcagaaag agcaaagtag gacatageggga ccccttagcac cttcggggtg tcctgctgtg   69360
```

-continued

```
gactggttca cccaggctct gggggggatca gtagaagtta tgcctaatct tctaccgtat   69420
ttgcagactt gcatctcatg ggtgattttg tttaaaaaat agaagcagta ggagccagag   69480
gcagaaactt ggtagttgac ttcagtgaat gagctaagaa gagtctggcg gtggacctcg   69540
tggaagagag agagggaaaa agtggtattt gtgttgggga ggttggttgg gtggttcagt   69600
tgtgcattgt gggtgactgt cggcttggct cacttctgtg gcagctgcaa ctccagagat   69660
agctccctgg ccctggctgc tggtgcactc tgcttatgct gtttcttgag ccagctatgg   69720
gagtctttgg ccacccatgc tgttggggag gtggtcagcc tttccatggg ctgcctaggg   69780
aagacccttt tgtgatgtgt ctgtttttct cttttgcttc tgctgcaatt acagtttgac   69840
tttgctgggg tgggctggta ggggtggcgg tgtgggggca ggggttgagg cgcaggtagt   69900
tgttagcctg ttgttagacg gtagtgaaga aagaatggtt tatcctaaat agcaggtttg   69960
gatgaaggct tccagaaaga aggcgggcca ggtgtggtgg ctcacgccct tagtcccagc   70020
actttgggag gctgaggcag gaggattgcc tgagcccaac agttggaggc tgcagtgagc   70080
tatgatcacg ccactgcact ccagcctgtg cgatagtgaa accgtgtctc taaaacataa   70140
gaagaaataa aaataaagga aagctggcat tttggtggac tccggaagat aaaaaggatg   70200
ctgccagccg ttctgggtgc gtggttgtgg tggtgtgtta ccagatgagg ccaggaccac   70260
tttcaacagc agatgtttca ggaagatttg ggacagcttg tatggaagta tctataagga   70320
gcaaattaca tattttcttg aatgtgtttt tttttaagtt tttaaaatgc cacctttaac   70380
tttattatgt tttagatcag aagtattttt ctgtgggaac atgtgaaggt tttggggaaa   70440
ataggattat atgaaatatt tgctatatag aaaatgtctg cctttgttga gtgattagaa   70500
attaagcctc agttggctgg gcgaggtggc tcacacctgt aatcccagca ctttgggagg   70560
ccaaggcggg tggatcacga ggtcaggaga tcgagaccat cctggctaac acggtgaaac   70620
cccgtctcta ctaaaaatac aaaaagttag ccgggcatgg tggcaggcgc ctgtaatccc   70680
agctactcag gaggctgagg caggagaatg gcgtgaacct gggaggcgga gcttgcagtg   70740
agccgagata gcgccactgc agtccggcct gggcgacaga gcgagactcc gtccccaaaa   70800
aaaaaaaaaa aaaatctcca gtggctgatg cctgtaatcc cagcattttc ggaggctgag   70860
gcaggcggat cacaaagtca agagatcgag accatcctgg ccaacatgtt gaaaccccat   70920
ctctactaaa aatacaaaaa ttaactgggc atggtggtgt gcacatgtag tcccagcctc   70980
tcaggaggct gaatcacttg aaccctggag gtggaggttg cagtgagctg agatcgcacc   71040
actgcactcc agcctcgatg acagagcgag actgtctcaa aaaaaaaaaa aaaagtgtta   71100
tccaaatgaa tatgggaagc atcaaagact ttgtaagtac agagaatgat aaagggattg   71160
ttatttgtaa agatgcatct tagtgacaaa aaacctggct ttatttaaaa gcagcattca   71220
tcagacctgt gaaagtactt caggaacaga ttacattgat aaaactcatg attagaataa   71280
atagctttaa aggttatta aaacatctaa ttggcctgga atcccagcac ggtgggagac   71340
tgaggcgagc aggttgctta agtctaggag ttcaagacca gctgggctca tggctgtagt   71400
cccagctact tgggaggctg aggtgggaga atcacctgag cccaggaagt caaggctgca   71460
gtgagtcctc atcatgccac tgcactccag catgggcaac cagagtgaga tcctgtctta   71520
aaaaaacaaa caaacaaaaa aacccaccta atcctactgg tatcagtttt atcaatacta   71580
tcagagttat tttaaaatgg gtcaatacta ggcctagcgt ggtggctcac gcctgtaatc   71640
tcagcacttt gggaggctga ggcaggtgga tcacctgagg tcaggagttc aagaccagcc   71700
```

-continued

```
tggccaacat ggtgaaaccc cttctttact aaaaatacaa aattagccag atgtggtggt   71760
gggagcctgt aatcccagct actcaggagg ctgaggcagg agaatcgttt gaacccggga   71820
gacggatgtt gcagtgagcg cagatcgtac cactgtactc cagcctgggc gacagagtga   71880
gaactccctc cccccaaaaa aggcggggga gtcagtacat aaataaggtg gtactaagtt   71940
agctttttaa tttttatgct aatttgtcag taatgccaca gagtaaagtt cttaactttg   72000
agtttacgac tggacttcag ggacccaaga ggctctctgc agttgtgctt atgggaacgt   72060
atgcattttt cttcttcttt tttctttttt tctgagacaa gatctcgctg tgttgcccag   72120
gctggggtac agtggcgcga acttagctca ctgcaacgtc tacctcctgg gttcaaggga   72180
ttctcttgcc tctgccaccc aggtagctgg ggttacaggc gcccaccacc acgcctggct   72240
aattttgtat ttttagtaga cacgggattt caccatgttg gccaggctgg tctcaaactc   72300
ttgacctcag gtgatccgcc tgtctcagcc tcccaaagtg ctgggattaa tgggcatgag   72360
ccactgcatc tgggtatgtg cattttctta agaggagcat tggtagatct cagagcttct   72420
gtggggcagg aaaagccatg aagtcctgcc acaggactct tgggcctcac ctctcagagg   72480
acgtctttga gcggaaggtg gatgtggtgt tagctgttgc aagtaagaca gggacggtgt   72540
gtcctggtgt gctttgtgtc ttaggttgag ataagtcgaa gagtgactct ggaaaaactc   72600
cctcctgtcc tcgtgctgca cctgaaacga ttcgtttatg agaagactgg tgggtgccag   72660
aagcttatca aaaatattga atatcctgtg gacttggaaa ttagtaaagg taatgcatac   72720
ataaggtcgg gagtgttcgt ggtgacacac tcctgcacat cagaagctca accctgtagc   72780
atttctttat gatgtcaaga gtgaggacat tctcttgctg gacgtggact tgttttaagt   72840
ttcttgactt gtaatagacc ttaatactaa aattctcatg aaaatggcct gttgaaaata   72900
gaggcaaaaa taactaaact ctataatctt actagattag aaaaatagca gcttttgtct   72960
atcaaaaaga acatcacttt tctgtgaata tttcagggat gaatggtgca gtttgccttc   73020
caccgagtat taacagctgt gttgactagc ccagttaagt ggttttttagt gaagtaagaa   73080 tgatttctca taggcagtga gagtcccttc taacctctag ttgtggtggc gcacaaataa   73140
gacgtggcac ttaccagcct caagtctctg tcaggtcacg ggctcggcac tttttgaaag   73200
caattttaaa gagccccagg ttaaaggcat cttgctaaaa gcacagcttc aagaagactt   73260
ttcttgaaag ctttagaatt tgtgaaaacg tatagtacaa cactgaggct tgattgggac   73320
tgtgattagc tagagaggat tctcagaata tcgaggtgtt tgggaagcag aaaagaggac   73380
actgggcctc actcctgggt cctgcagagg aacaaacctg aaccgagagt cctcttctct   73440
ccgtcccctg gcacagcaac cccacctcat acctccttcc atatagatga cccaggaact   73500
gtgggcatgg ctggcttcta gccggctccc tgtctaccct aggggcgccc tataccttcc   73560
cgtgaagact cagacactgt ctctcccagg cctgcacaca agagctgtgc tttctgctga   73620
cgggcttggc tgctgtgccg ggtttagtgt ccgttgctcc tctcacactt ctagctgcct   73680
tatcactcat cagccgattg cttttttaatc ccatttgagg accagcaaga ggaagaaaga   73740
tgccagtgag aatcatgtaa cagatcctcc tccccatttt attctatcca tcgggaaacc   73800
tggaatgccg gctaagtcaa agaaggcatc ctcggcctct gctcctgcat cttcactcgc   73860
ctccagatca gctgtctgag ctgacttgga tgttttgcta cagtgatttt attttttatat   73920 cttttcttgc ttgctgtatt tttatatccg ctgccacctc caatacatta tcaaaatatg   73980
acataaatgg gggctgggcg cagtggctca cacctgtaat cccagcactt tgggaggccg   74040
aggcaggcag atcacctgag gtcaggagtt cgagaccagc ctgaccaacg tggtgaaacc   74100
```

```
ccaactcttc taaaaacaca aaaattagcc tagcatggtg gtgggtgcct gtaatcctag   74160
ctacttggga ggctgaggca ggagaatcgc ttgaacctgg gaagcagagg ttgctgagat   74220
catgccactg cactccagcc tgggcaacag agcaagactc catctcaaaa aaataaataa   74280
ataacataaa tgggggacaa gaggacctca cttgggtcat gggtcagaag tacagatggc   74340
tgcctcgaac agcatgcctc cgacggactc ttgtgtcggt gtaagtggta cttctgcgca   74400
cagtaagagc agggagttcc cgcctcgtag cagctggtag actggttcct atttggagaa   74460
atcatgttac tgttctgtaa ctgaagtttt gttttgtttt tttttttgttt gtttgttttt   74520 ttcttgctct gtcacccagg ctggagtgca gtggcgcgat ctcggctcgc tgcaacctct   74580
gcctcccggg ttcaagtgat tctcctgcct cagcctcccg agtagctgag actacagccg   74640
cgtgccacca cgcccgggta atttttttgta tttttaatag agacgtggtt tcactgtatt   74700
agccaggatg gtctcgatct cctgacctcg tgatcgcccg tctcagcctc ccaaagtgct   74760
gggattacag gcgtgagcca ccgtgcctgg cctgtaattg aagttttatg atctgacgca   74820
tatgtaaaat tttaattctt gccttggatt tttcacaact gtttttgttt ttaagtcagc   74880
agcttttttc ttttccattt tgtagagcac ctgtttttaa ggggcctccc acaggagcat   74940
cacagcctcg gccgttgctc ctgtttcttt agtgagctgg ctgcacattt tgtgtcctat   75000
tacgtcacat ggctcatttc cttcatgagt caattttttgt gcaactgaag ggatagagtg   75060
ttgttttgtt cctggtctga caggcagttt acttgctggg gagaatgttg ttagccattt   75120
tctgctgctg ttaccctgaa cctttctaaa agtgcttcaa gccattgata ttttgttttc   75180
cagaactgct ttctccaggg gttaaaaata agaattttaa atgccaccga acctatcggc   75240
tctttgcagg tgagtaaatt tgtacgacat tacttcttca ttaaaacact gatgaaggggg   75300 tttacagctg ggcacaggtt tgctgcaact tagcatagcg accagatgct gtactcaggt   75360
atccctgtgg ccttgtgagt cggggagtca cgtgagagtt ttacctgaaa ctctgcgtag   75420
atgacggatt atcatcttgg ccctgaggac agataacaga agaccttgct caaagcgaac   75480
atttctgtct ttgagtcaga ggagggagtt tcaggctccc aggctggctg tttgagaatg   75540
tgacctctcc cggctgtgct tgtggcacct gtgggtgaca gtgctgtgga gtttccacga   75600
cacctggtca cccagccagg ttgggtgagc gcgcccccag ccggtgatcc ctgcgtcctc   75660
ccccacaggt attgttaggg ctgcttgaga gggtgggccc gattacacaa gctcctcggc   75720
tgccaggccc tcagtcagtc atgagaaatc tcccaacagg gtgaatggca ccccctgttc   75780
cctcatgggt ggaccttgag acctcttctg tctcctggct taggctccct gcagtatcat   75840
tttttctgcc acatcatctt cccttttcctt tctgccttcc cttttatcct tctttctctt   75900
ttatagcgtc atcttttatg cctctgagtc tttacctctt tggattgttg ctgtttgccg   75960
cacttttgtt tgcttcccag gctgttttta ctacatgttt ctagcttctg tgtcttccct   76020
cctctggtgt ggcctttggt gaacctgttt gtatcgtaac ataacactgc catttattga   76080
ccttcacaca tgtattgaac ctcttcccaa gatattcttt catttcctta catgtgtcct   76140
aggagatggg aggtgggatc cctgttttat aaaagaataa accagaactc aaggaagaaa   76200
actcaccact ctggcctgca gtggcagagc agggcttcaa gctcctgtcc acctcagctc   76260
acgcccgatg ttttaggaag tttggcgagt gggtgagggc ccaggatgg gggcccaggg   76320 gtgagggcct agcggtgggg gcccaggggg gagggcccag tgggtgaggc ccagagccac   76380
actgcaaggt gccaggcttc cctctcttcc tctcactatt cattgttcct tttgactctc   76440
```

-continued

```
ttcttttctc cccccgatca caattcctcc tcaacttgct gggcctcaga tgggacggcc   76500
atgggcacca cgcgcttgtg ggtgtctcca gccctgtctg gaatggaagg tctgagtcct   76560
cagactctgc agccagccat tatcctgcct ggctccttgg agtgtggcac ccaggtccca   76620
gtgggtggcc agcagtttct ccgccttctc cctgcacctc ttcccctgga ggctcttgcg   76680
ggggacatca ctgggcaggg gcaggggcta gggattgctc ctctcctggt cagggcccca   76740
gtgtgagcac acacacccct ccccgactct gcaacctgcc tcgccccggg acctgggcct   76800
gggttgctct cccctgccct cctgaatcct catcccctaa cccattattt ttttgagata   76860
gagttttgct ctgtcgccca ggctggagtg cagtggcaca gtctccattc actgcaacct   76920
ctgcctccca ggttcaagtg attcttgtgc ctcagccccc cgagtagctg ggattacagc   76980
tgtgcaccac cacatccagc taattttttgt attttgaata gagacgaggt ttcgcccttt   77040
tggccaggct ggaagcctat tctgatcttg gaaatgaggt caccggactg gttagaatta   77100
cctgtagagt gagcaaagga acacttttta agaactgctg tgattgtggg gcctgggaga   77160
agcaatctcg cgcacaagct tttcaggcgg ttctcagcgc tcctgtcagg ggggcttgca   77220
ggtgtgagtg acacacggct cagcccaggg tagttaactg ggctgctgct tatgaaacta   77280
gaatggtgac atgcagtccc ccttgacatt ttagaatgga gatgtcttgt gggaaagaca   77340
agttagtaaa accccccaggc cctgcagatt ctactgatgg tcgctttgaa gcaaaactct   77400
tagcccagtc agttaggtct gtgaggtgaa gatctaggac agaagtctca aagtgaactt   77460
gggatccagg ggacatgctg ctgtcatggg tgcttcctgc cctttcacaa gatggctgtg   77520
acttgtgcag cacaggatga agctatgccc ttggattggc tgtgtccctg gctctccgaa   77580
gtacgggccc cacagtcttg ctgtccctat gctgttcagt ctcctccggg gtccctgcac   77640
agaggatttc tttgtgcaga gcccaggagt ctgactggtg gcctcagtca taagcactgt   77700
cctctagcca gccaaggtcc ctggcccaga gaggactgag gcctcctgct gtcatttagc   77760
ccctccacgt gacaactgcg actagaacct ggtgatgttt ggtcttgttt tagtgctgaa   77820
attccctacc agccaagtct tgcatctctc ctggttcctt ttcttttgtg ccactgatgg   77880
tgggcgcagc ttagcaggct gccctgtcat tccccgcgga atgctgccgg acagccgcct   77940
tcccgaggct ggtgtctgct gctggccagg cagacctgtg cccctctgct ccatagaagt   78000
ggaggatgtg ttctgtggct gtcttaatgt tttcatgaca tcttctacag attttttgtt   78060
ttaggccttt gactaaggct tcttggttat aggattttt ttttaagtaa ataactgtgt   78120
gtgtgtgtgt gtgtgtgtgt gttttgttct gttaaaacat agaaaaatgg gtaattttt   78180 ttaaaggcaa atgcgtaact accagcacca tctccgcagt gccccaccac agctccacgc   78240
tcaagcaacc gtggttagca gtcccagggt ccctcctgcc atgtgggccg gcaccgggag   78300
attgtgtccc gtgtctttag gatagatggg ccacagaagg cctaaggacc ttgttttctc   78360
atttaatata ccataagcgt attcccgcat caccattctt aatctattcc acgaaaaaat   78420
aaattgtgtt attttaatat aatttactca tcagtcattt cttctagtgg ctattgaggt   78480
tttccgtttt ttcactgtta taaatgacat cataatctct gtccaagatt cagataatct   78540
cttcaggaca gtctagaagt agagtcagcc acatccaagg gcatgagcca ggtctgtagg   78600
cctgtacagc tgatggctgt gtaggagtgt ctgtgtgagg cgtgggacat tttaaatatg   78660
tggttaatat gcgtacatgc acacatgtac ctatctgact tacccttacc ttgcagttat   78720
agaaaagttt ttattatgga ttgcttgcgt gttttgagttg aaatagcatt ggtttgtgtg   78780
atgacatctc tctgtcccac ctgctttgga gaggggtttt acacatagga tgcatccctg   78840
```

-continued

```
gagggaagtc ggcggagacc tgtaatgatt cgtgtgcagt gctgttctca ctctgctgcc  78900
tgctgggctc tcttccagtg gtctaccatc acggcaacag tgcgacgggc ggccattaca  78960
ctacagacgt cttccagatc ggtctgaatg gctggctgcg catcgatgac cagacagtca  79020
aggtgatcaa ccagtaccag gtggtgaaac caactgctga acgcacagcc tacctcctgt  79080
attaccgccg agtggacctg ctgtaaaccc tgtgtgcgct gtgtgtgcgc ccagtgcccg  79140
cttcgtagga caccacctca cactcacttc ccgcctctct ttagtggctc tttagagaga  79200
aactctttct ccctttgcaa aaatgggcta gaatgaaaag gagatgcctt ggggttcgtg  79260
cacaacacag cttctgttga ctctaacttc caaatcaaaa tcatttggtt gaaacagact  79320
gttgcttgat tttagaaaat acacaaaaac ccatatttct gaaataatgc tgattcctga  79380
gataagaaag tggatttgat ccccagtctc attgcttagt agaataaatc ctgcaccagc  79440
aacaacactt gtaaatttgt gaaaatgaat tttatctttc cttaaaaaag aaattttta   79500 atccatcaca cttttcttcc ctacccttta gtttttgata aatgataaaa atgagccagt  79560
tatcaaagaa gaactagttc ttacttcaaa agaaaaataa acataaaaaa taagttgctg  79620
gttcctaaca ggaaaaattt taataattgt actgagagaa actgcttacg tacacattgc  79680
agatcaaata tttggagtta aaatgttagt ctacatagat gggtgattgt aactttattg  79740
ccattaaaag atttcaaatt gcattcatgc ttctgtgtac acataatgaa aaatgggcaa  79800
ataatgaaga tctctccttc agtctgctct gtttaattct gctgtctgct cttctctaat  79860
gctgcgtccc taattgtaca cagtttagtg atatctagga gtataaagtt gtcgcccatc  79920
aataaaaatc acaaagttgg tttaaa                                       79946
```